United States Patent
Pan et al.

(10) Patent No.: US 11,404,644 B2
(45) Date of Patent: Aug. 2, 2022

(54) ORGANIC FUNCTIONAL COMPOUNDS, MIXTURES, FORMULATIONS, ORGANIC FUNCTIONAL THIN FILMS AND PREPARATION METHODS THEREFOR AND ORGANIC ELECTRONIC DEVICES

(71) Applicant: GUANGZHOU CHINARAY OPTOELECTRONIC MATERIALS LTD., Guangzhou (CN)

(72) Inventors: Junyou Pan, Guangzhou (CN); Mingquan Yu, Guangzhou (CN)

(73) Assignee: GUANGZHOU CHINARAY OPTOELECTRONIC MATERIALS LTD., Guangzhou (CN)

(*) Notice: Subject to any disclaimer, the term of this patent is extended or adjusted under 35 U.S.C. 154(b) by 395 days.

(21) Appl. No.: 16/472,369

(22) PCT Filed: Dec. 22, 2017

(86) PCT No.: PCT/CN2017/118066
§ 371 (c)(1),
(2) Date: Jun. 21, 2019

(87) PCT Pub. No.: WO2018/113784
PCT Pub. Date: Jun. 28, 2018

(65) Prior Publication Data
US 2019/0363258 A1    Nov. 28, 2019

(30) Foreign Application Priority Data
Dec. 22, 2016   (CN) .......................... 201611200091.9

(51) Int. Cl.
*H01L 51/00* (2006.01)
*C07C 15/60* (2006.01)
*C07D 209/86* (2006.01)
*C09K 11/06* (2006.01)
*H01L 51/50* (2006.01)

(52) U.S. Cl.
CPC .......... *H01L 51/0061* (2013.01); *C07C 15/60* (2013.01); *C07D 209/86* (2013.01); *C09K 11/06* (2013.01); *H01L 51/006* (2013.01); *H01L 51/0058* (2013.01); *C07C 2603/24* (2017.05); *C09K 2211/1018* (2013.01); *H01L 51/0052* (2013.01); *H01L 51/0072* (2013.01); *H01L 51/5012* (2013.01); *H01L 51/5016* (2013.01); *H01L 51/5056* (2013.01)

(58) Field of Classification Search
CPC ............. H01L 51/0061; H01L 51/0058; H01L 51/006; H01L 51/0052; H01L 51/0072; H01L 51/5012; H01L 51/5016; H01L 51/5056; C07D 209/86; C09K 11/06; C09K 2211/1018; C07C 2603/24; C07C 15/60
See application file for complete search history.

(56) References Cited

U.S. PATENT DOCUMENTS

| | | | |
|---|---|---|---|
| 3,567,450 A | 3/1971 | Brantly et al. | |
| 3,615,404 A | 10/1971 | Price et al. | |
| 4,720,432 A | 1/1988 | VanSlyke et al. | |
| 5,061,569 A | 10/1991 | VanSlyke et al. | |
| 6,121,495 A * | 9/2000 | Babb ................... | C07C 43/285 568/17 |
| 6,252,001 B1 * | 6/2001 | Babb ................... | C07C 17/263 525/202 |
| 7,592,414 B2 | 9/2009 | Meerholz et al. | |
| 8,679,644 B2 | 3/2014 | Parham et al. | |
| 9,099,655 B2 | 8/2015 | Pan et al. | |

(Continued)

FOREIGN PATENT DOCUMENTS

| | | |
|---|---|---|
| CN | 1947274 A | 4/2007 |
| CN | 1970551 A | 5/2007 |
| CN | 101055887 A | 10/2007 |
| CN | 101220112 A | 7/2008 |
| CN | 102449796 A | 5/2012 |

(Continued)

OTHER PUBLICATIONS

B. Gómez-Lor et al., 48 Chemical Communications, 5012-5014 (2006) (Year: 2006).*

(Continued)

*Primary Examiner* — Alexander R Pagano
(74) *Attorney, Agent, or Firm* — Kagan Binder, PLLC

(57) ABSTRACT

An organic functional compound, having a general formula of A–$(SG)_p$; wherein A is an organic group having an optoelectronic function; the structural formula of SG is selected from the group consisting of

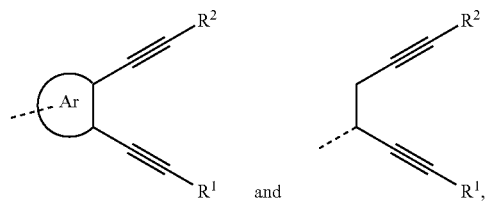

wherein

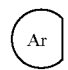

is selected from the group consisting of an aryl containing 5-40 ring-forming atoms and a heteroaryl containing 5-40 ring-forming atoms; R1 and R2 are each independently selected from the group consisting of H, D, F, CN, an alkyl, an aromatic ring group, an aromatic heterocyclic group, an amino, a silyl, a germyl, an alkoxy, an aryloxy, and a siloxy group; and p is an integer greater than or equal to 1.

12 Claims, 1 Drawing Sheet

(56) References Cited

U.S. PATENT DOCUMENTS

| | | | |
|---|---|---|---|
| 2007/0241664 | A1 | 10/2007 | Sakamoto et al. |
| 2009/0134784 | A1 | 5/2009 | Lin et al. |
| 2018/0312522 | A1 | 11/2018 | Pan et al. |
| 2018/0312531 | A1 | 11/2018 | Pan et al. |
| 2018/0354934 | A1 | 12/2018 | He et al. |
| 2019/0006609 | A1 | 1/2019 | Pan et al. |
| 2019/0292309 | A1* | 9/2019 | Pan ............... H01L 51/0054 |
| 2019/0372008 | A1 | 12/2019 | Pan et al. |

FOREIGN PATENT DOCUMENTS

| | | | | |
|---|---|---|---|---|
| EP | 1009043 | A2 | 6/2000 | |
| JP | 2004203770 | A * | 7/2004 | |
| TW | 201406810 | A | 2/2014 | |
| WO | WO-9710193 | A1 * | 3/1997 | ............ C07C 22/08 |
| WO | 2010135519 | A1 | 11/2010 | |
| WO | 2011110277 | A1 | 9/2011 | |
| WO | 2011141110 | A2 | 11/2011 | |
| WO | 2018113785 | A1 | 6/2018 | |

OTHER PUBLICATIONS

CAS Abstract and Indexed Compounds, B. Gómez-Lor et al., 48 Chemical Communications, 5012-5014 (2006) (Year: 2006).*
J. Wang et al., 142 The Journal of Chemical Physics (2015) (Year: 2015).*
Chlorophyll Captures Light with its Conjugated Bonds, from Organic Chemistry, Prentice Hall (1998) (downloaded from http://web.missouri.edu/~glaserr/210w99/group_15_project1sub1.htm) (Year: 1998).*
T. Seri et al., 3 Chemistry—An Asian Journal, 388-392 (2008) (Year: 2008).*
D. Sepulveda et al., 15 Organic & Biomolecular Chemistry, 6042-6049 (Jun. 21, 2017) (Year: 2017).*
D. Smith et al., Journal of the American Chemical Society, 9078-9079 (1998) (Year: 1998).*
CAS Abstract and Indexed Compound, D. Sepúlveda et al., 15 Organic & Biomolecular Chemistry, 6042-6049 (2017) (Year: 2017).*
S. Chow et al., 2 Organic Letters, 961-963 (2000) (Year: 2000).*
R. Martin et al., Journal of Chemical Theory and Computation, 2816-2825 (2013) (Year: 2013).*
M. Noto et al., Molecular Crystals and Liquid Crystals Science and Technology, Section A: Molecular Crystals and Liquid Crystals, 27-30 (2001) (Year: 2001).*
CAS Abstract and Indexed Compounds D. Babb, WO 97/10193 (1997) (Year: 1997).*
Chinese Search Report, English Translation of Chinese Search Report, and Chinese Office Action for Chinese Application No. 2017800595042, dated Jul. 28, 2020, (9 pages).
Tang et al., "Organic electroluminescent diodes", Applied Physics Letter, vol. 51, Issue 12, pp. 913-915, 1987, (4 pages).

Burroughes et al., "Light-emitting diodes based on conjugated polymers", Letters to Nature, vol. 347, pp. 539-541, 1990, (3 pages).
Grimsdale et al., "Synthesis of Light-Emitting Conjugated Polymers for Applications in Electroluminescent Devices", Chemical Reviews, vol. 109, No. 3, pp. 897-1091, 2009, (195 pages).
Zhong et al., "Materials and Devices toward Fully Solution Processable Organic Light-Emitting Diodes", Chemistry of Materials, vol. 23, No. 3, pp. 326-340, 2011, (15 pages).
Huang et al., "Crosslinkable hole-transporting materials for solution processed polymer light-emitting diodes", Journal of Materials Chemistry, vol. 18, No. 38, pp. 4485-4592, 2008, (16 pages).
Veinot et al., "Toward the Ideal Organic Light-Emitting Diode. The Versatility and Utility of Interfacial Tailoring by Cross-Linked Siloxane Interlayers", Accounts of Chemical Research, vol. 38, No. 8, pp. 632-643, 2008, (12 pages).
Zeng et al., "Polymer Light-Emitting Diodes with Cathodes Printed from Conducting Ag Paste", Advanced Materials, vol. 19, pp. 810-814, 2007, (5 pages).
Huang et al., "Water/alcohol soluble conjugated polymers as highly efficient electron transporting/injection layer in optoelectronic devices", Chemical Society Reviews, vol. 39, pp. 2500-2521, 2010, (23 pages).
Jiang et al., "Perfluorocyclobutane-Based Arylamine Hole-Transporting Materials for Organic and Polymer Light Emitting Diodes", Advanced Functional Materials, vol. 12, No. 11-12, pp. 745-751, 2002, (7 pages).
Muller et al., "Multi-colour organic light-emitting displays by solution processing", Letters to Nature, vol. 421, pp. 829-833, 2003, (5 pages).
Domercq et al., "Photo-Patternable Hole-Transport Polymers for Organic Light-Emitting Diodes", Chemistry of Materials, vol. 15, No. 7, pp. 1491-1496, 2003, (6 pages).
Ma et al., "New Thermally Cross-Linkable Polymer and Its Application as a Hole-Transporting Layer for Solution Processed Multilayer Organic Light Emitting Diodes", Chemistry of Materials, vol. 19, No. 19, pp. 4827-4832, 2007, (6 pages).
Jones et al., "p-Benzyne. Generation as an intermediate in a thermal isomerization reaction and trapping evidence for the 1,4-benzenediyl structure", Journal of the American Chemical Society, vol. 94, No. 2, pp. 660-661, 1972, (2 pages).
Kipphan, "Handbook of Print Media: Technologies and Production Methods", ISBN-10: 3540673261, Chapter 1.3, pp. 40-67; Chapter 1.5 pp. 117-144; Chapter 5.5, pp. 711-730, 2001, (76 pages).
Bulovic et al., "Transparent light-emitting devices", Nature, vol. 380, p. 29, 1996, (1 page).
Bulovic et al., "Transparent organic light emitting devices", Applied Physics Letter, vol. 68, Issue 19, pp. 2606-2608, 1996, (4 pages).
Niu et al., "Crosslinkable Hole-Transport Layer on Conducting Polymer for High-Efficiency White Polymer Light-Emitting Diodes", Advanced Materials, vol. 19, Issue 2, pp. 300-304, 2007, (5 pages).
International Search Report, and English Translation thereof, for International Application No. PCT/CN2017/118066, dated Mar. 9, 2018 (3 pages).

* cited by examiner

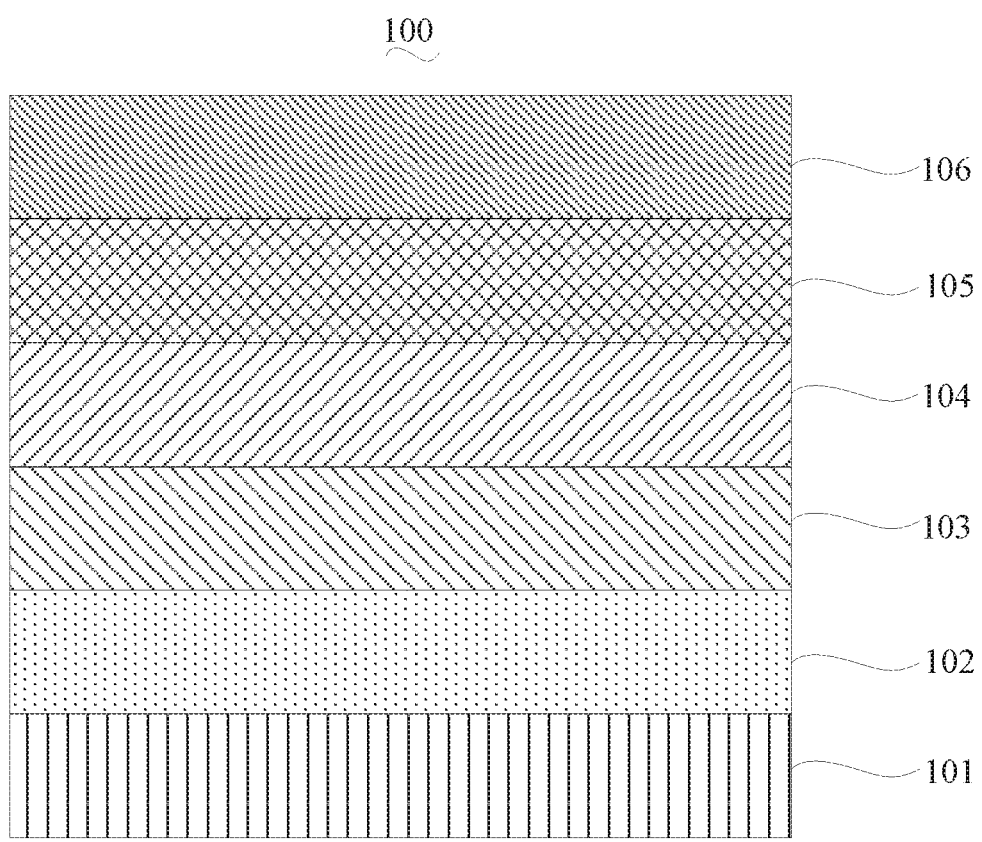

ORGANIC FUNCTIONAL COMPOUNDS, MIXTURES, FORMULATIONS, ORGANIC FUNCTIONAL THIN FILMS AND PREPARATION METHODS THEREFOR AND ORGANIC ELECTRONIC DEVICES

CROSS REFERENCE TO RELATED APPLICATIONS

This application is a national stage for International Application PCT/CN2017/118066, filed on Dec. 22, 2017, which claims the priority benefit of Chinese Patent Application No. 201611200091.9, titled "ORGANIC FUNCTIONAL COMPOUND FOR PREPARING ORGANIC ELECTRONIC DEVICES" and filed on Dec. 22, 2016. The entireties of both applications are incorporated by reference herein for all purposes.

TECHNICAL FIELD

The present invention relates to the field of organic electronic devices, and in particular to an organic functional compound, a mixture, a formulation, an organic functional film, a preparation method thereof, and an organic electronic device.

BACKGROUND

Since organic light emitting diodes (OLEDs) have been invented (Appl, Phys. Lett. 1987, 51: 913-15; Nature, 1990, 347: 539-541), they show great potentials in the application of optoelectronic devices such as flat-panel displays and lighting due to the diversities in synthesis, relatively low manufacturing costs, and excellent optical and electrical performance of organic semiconductive materials (Chem Rev, 2009, 109: 897-1091; Chem Mater, 2011, 23: 326-340).

OLED devices mostly use a multilayer device structure, that is, one or more layers of hole transport/injection layers or electron transport/injection layers are comprised in addition to the light emitting layer. Therefore, in addition to the development of excellent luminescent materials, the development of excellent electron transport/injection materials and hole transport/injection materials is also the key to achieving high-performance OLEDs (J Mater Chem, 2008, 18: 4495-4509; Acc Chem Res, 2005) 38: 632-643; Adv Mater, 2007, 19: 810-814).

Although it is easy to obtain multi-layer, complex and highly efficient OLEDs using small molecules by vacuum evaporation method, there are disadvantages of being expensive, time consuming, wasteful of materials, and difficult to achieve large area applications. In contrast, solution-processed OLEDs have broad application prospects and commercial value because they have the advantages of being able to prepare large-area, flexible devices by low-cost inkjet printing, printing and other solution processing methods. Since organic optoelectronic materials generally have similar solubility, that is, organic/polymer luminescent materials, hole injection/transport materials, electron injection transport materials have good solubility in organic solvents such as toluene, chloroform, chlorobenzene, o-dichlorobenzene, o-xylene, tetrahydrofuran, and the like, there are problems such as interface miscibility and interface erosion when using the solution processing method to prepare a multi-layer, complex OLED. For example, the solvent used would dissolve the underlying hole transport layer when using the solution to process into a polymer or a small molecule light emitting layer, causing problems such as interface miscibility and interface corrosion (J Mater Chem, 2008, 18: 4495-4509; Chem Soc Rev, 2010, 39: 2500-2521).

The crosslinking-curable polymer HTM has been used to solve the above problems. For a conjugated polymer modified by the conventional cross-linking group such as a perfluorocyclobutane group, a styryl group, an epoxybutane group, a silicone group, an acrylate group, a benzocyclobutane group, and the like, the cross-linking group on the polymer initiates cross-linking reaction of the crosslinkable groups such as the perfluorocyclobutane group (Adv. Funct. Mater., 2002, 12, 745), the styryl group (Adv. Mater., 2007, 19, 300), the epoxybutane group (Nature, 2003, 421, 829.), the silicone group (Acc. Chem. Res., 2005, 38, 632), the acrylate group (Chem. Mater., 2003, 15, 1491), and the benzocyclobutane group (Chem. Mater., 2007, 19, 4827.) under conditions of light, heat, and the like, forming an insoluble and infusible interpenetrating network polymer film with excellent solvent resistance, avoiding problems such as interface miscibility and interface erosion (TW201406810A, U.S. Pat. No. 7,592,414B2).

However, the crosslinkable polymers reported so far are based on conjugated polymers. Most conjugated polymers have lower triplet energy levels, which will quench excitons with higher triplet energy (with relatively shorter wavelength) in adjacent light emitting layers such as green light emitting layers and will not act as exciton blocking layers. These all limit the performance improvement of solution-processed OLED devices.

In addition, up to now, the materials of the light emitting layer, including soluble small molecules and light emitting polymers, are mostly non-crosslinking-curable since cross-linking curing has a great influence on the performance of the light emitting layer. Thus, the electron transport layer and/or the electron injection layer must still be prepared by a vacuum evaporation method.

Therefore, there is an urgent need to develop an organic compound capable of being used for preparing a functional layer by the solution processing method, and problems such as interface miscibility and interface corrosion can be avoided by using this organic compound.

SUMMARY

Based on this, it is necessary to provide an organic functional compound capable of being used for preparing a functional layer of an organic electronic device by a solution processing method, and problems such as interface miscibility and interface corrosion can be avoided by using this organic compound.

Further, a mixture, a formulation, an organic functional film comprising the organic compound, and a preparation method therefor and an organic electronic device are also provided.

An organic functional compound has a general formula as follows:

wherein A is an organic group having an optoelectronic function;

the structural formula of —SG is selected from

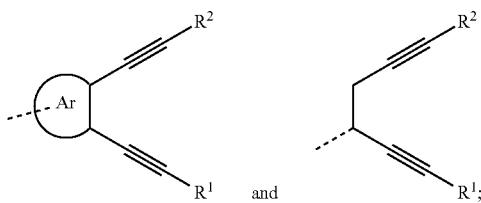
and

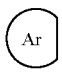

is selected from the group consisting of an aryl group containing 5 to 40 ring atoms and a heteroaryl group containing 5 to 40 ring atoms;

$R^1$ and $R^2$ are each independently selected from the group consisting of H, D, F, CN, an alkyl group, an aromatic ring group, an aromatic heterocyclic group, an amino group, a silicon group, a germyl group, an alkoxy group, an aryloxy group, and a siloxy group; the alkyl group is selected from the group consisting of an unsubstituted alkyl group, a fluoroalkyl group, a deuterated alkyl group, and a deuterated fluoroalkyl group; the aromatic ring group is selected from the group consisting of an unsubstituted aromatic ring group and a deuterated aromatic ring group; the aromatic heterocyclic group is selected from the group consisting of an unsubstituted aromatic heterocyclic group and a deuterated aromatic heterocyclic group; the amino group is selected from the group consisting of an unsubstituted amino group and a deuterated amino group; the silicon group is selected from the group consisting of an unsubstituted silicon group and a deuterated silicon group; the germyl group is selected from the group consisting of an unsubstituted germyl group and a deuterated germyl group; the alkoxy group is selected from the group consisting of an unsubstituted alkoxy group, a silylalkoxy group, a fluoroalkoxy group, a deuterated alkoxy group, a deuterated fluoroalkoxy group, and a deuterated silylalkoxy group; the aryloxy group is selected from the group consisting of an unsubstituted aryloxy group and a deuterated aryloxy group; the siloxy group is selected from the group consisting of an unsubstituted siloxy group and a deuterated siloxy group; and p is an integer greater than or equal to 1.

A mixture is provided, the mixture comprising the above organic functional compound and an organic functional material selected from the group consisting of a hole injection material, a hole transport material, a hole blocking material, an electron injection material, an electron transport material, an electron blocking material, an organic matrix material, a light emitting material, and an organic dye.

A formulation comprising one of the above organic functional compound and the above mixture and an organic solvent, is provided.

An organic functional film prepared from one of the above organic functional compound, the above organic mixture and the above formulation, is provided.

A method for preparing an organic functional film is provided, the method comprising the steps of:

using a ink to form a film layer on a substrate, wherein the ink is the above formulation, or the ink is prepared by dissolving one of the above organic functional compound and the above organic mixture in an organic solvent; and subjecting the film layer to a Bergman cycloaromatization reaction at a temperature of 100° C. or higher under anhydrous and anaerobic conditions to obtain an organic functional film.

An organic electronic device is also provided, the organic electronic device comprising a functional layer, wherein the functional layer is the above organic functional film, or the functional layer is the organic functional film prepared by the above method.

The details of one or more embodiments of the present disclosure are set forth in the accompanying drawings and the description below. Other features, objects and advantages of the present disclosure will become apparent from the description, the accompanying drawings, and the claims.

BRIEF DESCRIPTION OF THE DRAWINGS

FIG. 1 is a schematic view of an organic light emitting diode according to an embodiment; the organic light emitting diode includes a substrate 101, an anode 102, a hole injection layer (HIL) or hole transport layer (HTL) 103, a light emitting layer 104, an electron injection layer (EIL) or electron transport layer (ETL) 105 and a cathode 106.

DETAILED DESCRIPTION OF THE EMBODIMENTS

In order to facilitate the understanding of the present disclosure, the present disclosure will be described more fully hereinafter with reference to the related accompanying drawings.

In an embodiment, an organic functional compound has a general formula (I) as follows:

$$A\text{-}(SG)_p \qquad (I);$$

wherein A is an organic group having an optoelectronic function (hereinafter referred to as an optoelectronic functional group);

—SG is represented by a structural formula (II):

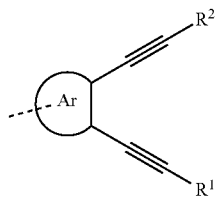

(II)

Wherein, in the general formula (II),

is selected from the group consisting of an aryl group containing 5 to 40 ring atoms and a heteroaryl group containing 5 to 40 ring atoms; further,

is selected from the group consisting of an aryl group containing 5 to 20 ring atoms and a heteroaryl group containing 5 to 20 ring atoms; further,

is selected from the group consisting of an aryl group containing 5 to 16 ring atoms and a heteroaryl group containing 5 to 16 ring atoms; further,

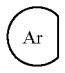

is selected from the group consisting of an aryl group containing 5 to 12 ring atoms and a heteroaryl group containing 5 to 12 ring atoms; further,

is selected from the group consisting of an aryl group containing 5 to 9 ring atoms and a heteroaryl group containing 5 to 9 ring atoms.

Further,

comprises at least one of the following groups:

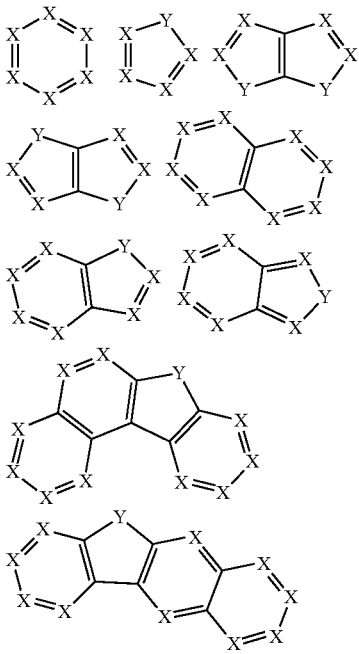

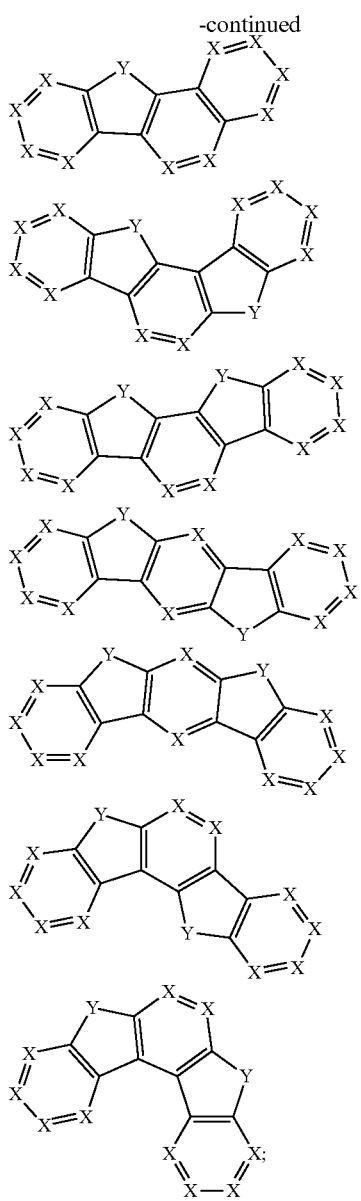

wherein X is selected from the group consisting of $CR_{13}$ and N; further, all Xs in the structural formula are $CR_{13}$;

Y is selected from the group consisting of $CR_{14}R_{15}$, $SiR_{16}R_{17}$, $NR_{18}$, $C(=O)$, $S(=O)_2$, O and S;

$R_{13}$, $R_{14}$, $R_{15}$, $R_{16}$, $R_{17}$ and $R_{18}$ are each independently selected from the group consisting of a single bond, H, D, F, CN, $NO_2$, $CF_3$, alkenyl, alkynyl, amine, acyl, amide, cyano, isocyano, alkoxy, hydroxy, carbonyl, sulfone, an alkyl group containing 1 to 60 carbon atoms, a cycloakyl group containing 3 to 60 carbon atoms, an aromatic group containing 6 to 60 carbon atoms, a heterocyclic aryl group containing 3 to 60 carbon atoms, a fused cyclic aromatic group containing 7 to 60 carbon atoms, and a fused heterocyclic aromatic group containing 4 to 60 carbon atoms.

Further,

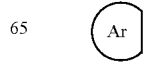

is selected from the group consisting of the following groups and a hydrogen on a ring of the following groups can be further substituted.

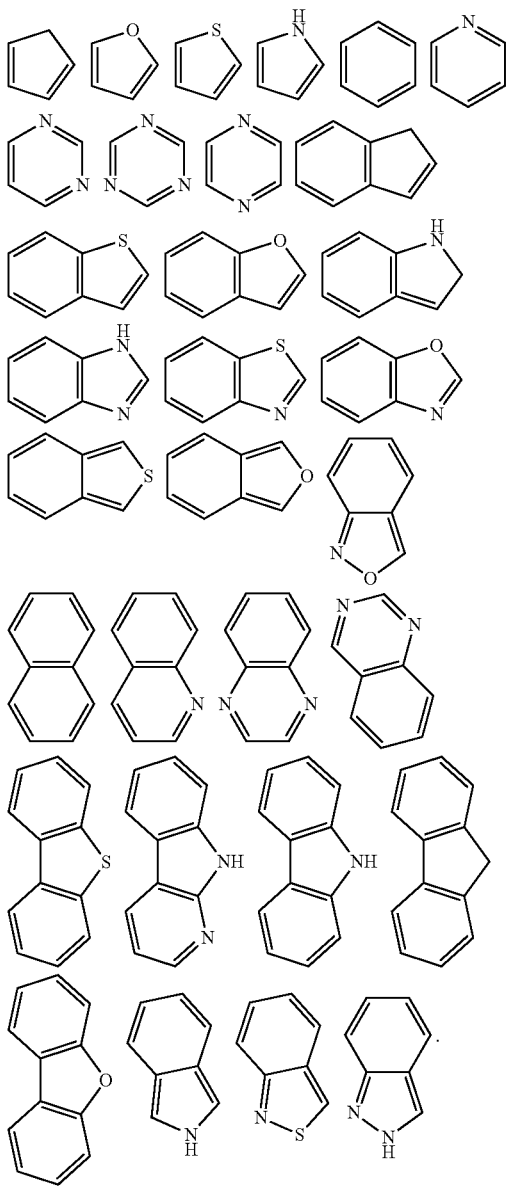

Specifically,

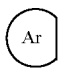

is selected from the group consisting of a phenyl group and a naphthyl group.

$R^1$ and $R^2$ are each independently selected from the group consisting of H, D, F, CN, an alkyl group, an aromatic ring group, an aromatic heterocyclic group, an amino group, a silicon group, a germyl group, an alkoxy group, an aryloxy group, and a siloxy group; the alkyl group is selected from the group consisting of an unsubstituted alkyl group, an unsubstituted fluoroalkyl group, a deuterated alkyl group, and a deuterated fluoroalkyl group; the aromatic ring group is selected from the group consisting of an unsubstituted aromatic ring group and a deuterated aromatic ring group; the aromatic heterocyclic group is selected from the group consisting of an unsubstituted aromatic heterocyclic group and a deuterated aromatic heterocyclic group; the amino group is selected from the group consisting of an unsubstituted amino group and a deuterated amino group; the silicon group is selected from the group consisting of an unsubstituted silicon group and a deuterated silicon group; the germyl group is selected from the group consisting of an unsubstituted germyl group and a deuterated germyl group; the alkoxy group is selected from the group consisting of an unsubstituted alkoxy group, an unsubstituted silylalkoxy group, an unsubstituted fluoroalkoxy group, a deuterated alkoxy group, a deuterated fluoroalkoxy group, and a deuterated silylalkoxy group; the aryloxy group is selected from the group consisting of an unsubstituted aryloxy group and a deuterated aryloxy group; the siloxy group is selected from the group consisting of an unsubstituted siloxy group and a deuterated siloxy group;

p is an integer greater than or equal to 1; further, p is any of integers from 1 to 5; further, p is any of integers from 1 to 3; and the dotted line in the general formula (I) represents a bond to A.

Specifically, in the general formula (I), the organic group having an optoelectronic function is selected from the group consisting of an organic group having a hole (also called electronic hole) injection function, an organic group having a hole transport function, and an organic group having a hole blocking function, an organic group having an electron injection function, an organic group having an electron transport function, an organic group having an electron blocking function, an organic group having an organic host function, an organic group having a singlet light emitting function(fluorescent light emitting function), an organic group having a triplet light emitting function (phosphorescent light emitting function), and an organic group having a thermal activated delayed fluorescence function. Wherein, the group of the above optoelectronic function may refer to a corresponding organic functional material containing the above optoelectronic function, that is, the organic functional material is selected from a hole (also called electronic hole) injection material (HIM), a hole transport material (HTM), a hole blocking material (HBM), an electron injection material (ELM), an electron transport material (ETM), an electron blocking material (EBM), an organic matrix material (Host), a singlet emitter (fluorescent emitter), a triplet emitter (phosphorescent emitter), and the like. And the above organic functional materials may be the organic functional material may be those disclosed in WO2010135519A1, US20090134784A1 and WO2011110277A1.

Further, the organic functional compound is treated at 190° C. for 2 hours under an environment of isolation from water and oxygen to cause a Bergman cycloaromatization reaction, which lowers the solubility of the molecule, thereby curing the film.

Specifically, the reaction formula of the Bergman cycloaromatization reaction is as follows:

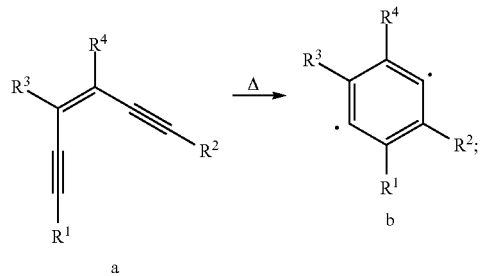

Small molecules with structure a, under heating (180° C. to 200° C.), will undergo a ring-closing reaction to form a new conjugated 6-membered ring radical.

In the presence of a hydrogen donor such as water in the air, other adjacent material molecules and a small amount of solvent molecules will cause the structure b to further react as follows:

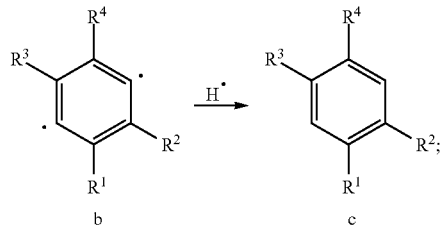

In an inert environment that is isolated from water and oxygen and is very pure (meaning that it contains only small molecules of o-diacetylenic bonds and very few impurities), new covalent bonds are formed between the benzene ring radicals to form a conjugated cross-linked structure, the specific reaction formula is as follows:

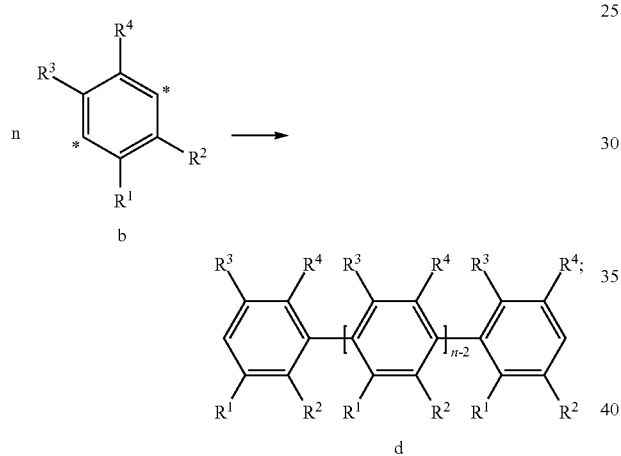

This reaction was first reported by Bergman, R G, and is specifically described in J. Am. Chem. Soc. 1972, 94, 660-661.

Further, the organic functional compound according to the present embodiment can form a solvent-insoluble layer to cure the film, and the principle may be:

The above organic functional compound is capable of undergoing Bergman cycloaromatization reaction to form a compound having the following formula (IV) or (IVa):

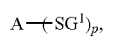
(IV)

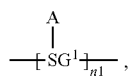
(IVa)

and there is an organic solvent S that is a good solvent for the organic functional compound represented by the general formula (I) and that is a poor solvent for the compound represented by the general formula (IV) or (IVa).

Wherein —$SG^1$ is a group represented by a structural formula

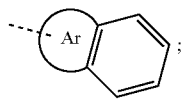

in the compounds of the formula (IVa), the attachment sites between —$SG^1$s are shown by * in the following formula:

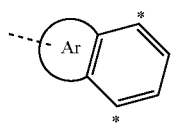

wherein n1 is an integer greater than or equal to 2; further, n1 is any of integers from 2 to 50; further, n1 is any of integers from 2 to 10; further, n1 is any of integers from 2 to 5. Also, A and

in the general formula (IV) or (IVa), and p in the general formula (IV) are defined similarly to A,

and p in the general formula (I).

Further, A has a structural formula (III) as follows:

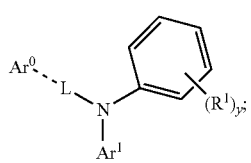
(III)

wherein the structural formula of $Ar^0$ is selected from

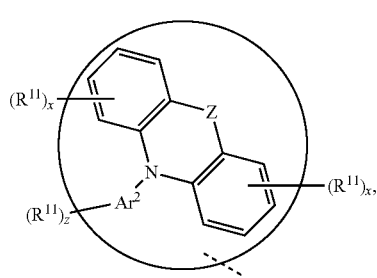
(IIIa)

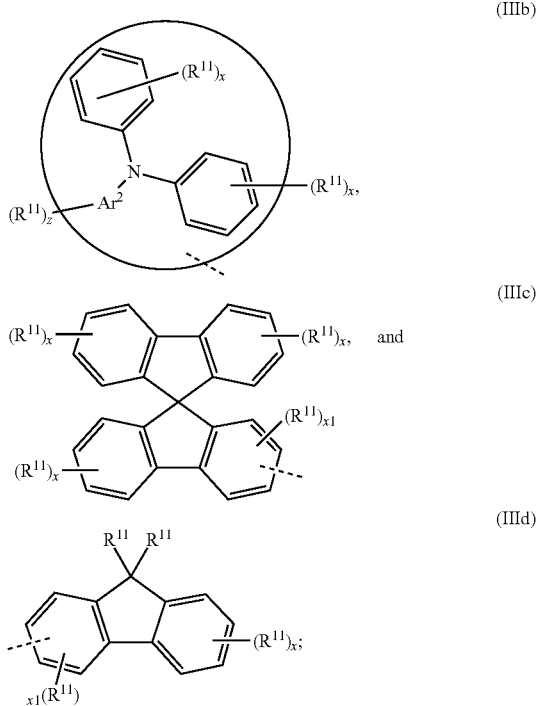

in the structural formula (III) and the structural formula (IIIa)-(IIIb), $Ar^1$ and $Ar^2$ are each independently selected from the group consisting of an unsubstituted aromatic hydrocarbon group, an unsubstituted aromatic heterocyclic hydrocarbon group, an $R^{11}$ substituted aromatic hydrocarbon group, and an $R^{11}$ substituted aromatic heterocyclic hydrocarbon group.

In the structural formula (III), the structural formula (IIIa), the structural formula (IIIb), the structural formula (IIIc) and the structural formula (IIId) and the above $Ar^1$ and $Ar^2$, $R^{11}$ is selected from the group consisting of F, Cl, Br, I, D, CN, $NO_2$, $CF_3$, a linear alkane group, an alkane ether group, an alkane thioether group containing 1 to 10 carbon atoms, a branched alkane group, and a cycloalkane group, or $R^{11}$ is an linear alkane group in which one or more non-adjacent methylene groups are substituted by one of $R^{12}C$═$CR^{12}$, C═C, $Si(R^{12})_2$, $Ge(R^{12})_2$, C═O, C═S, C═Se, C═N($R^{12}$), O, S ester group and $CONR^{12}$, or $R^{11}$ is an alkane ether group in which one or more non-adjacent methylene groups are substituted by one of $R^{12}C$═$CR^{12}$, C═C, $Si(R^{12})_2$, $Ge(R^{12})_2$, $Sn(R^{12})_2$, C═S, C═Se, C═N($R^{12}$), O, S, ester group and $CONR^{12}$, or $R^{11}$ is an alkane thioether group containing 1 to 10 carbon atoms in which one or more non-adjacent methylene groups are substituted by one of $R^{12}C$═$CR^{12}$, C═C, $Si(R^{12})_2$, $Ge(R^{12})_2$, $Sn(R^{12})_2$, C═O, C═S, C═Se, C═N($R^{12}$), O, S, ester group and $CONR^{12}$, or $R^{11}$ is a branched alkane group in which one or more non-adjacent methylene groups are substituted by one of $R^{12}C$═$CR^{12}$, C═C, $Si(R^{12})_2$, $Ge(R^{12})_2$, $Sn(R^{12})_2$, C═O, C═S, C═Se, C═N($R^{12}$), O, S, ester group and $CONR^{12}$, or $R^{11}$ is a cycloalkane group in which one or more non-adjacent methylene groups are substituted by one of $R^{12}C$═$CR^{12}$, C═C, $Si(R^{12})_2$, $Ge(R^{12})_2$, $Sn(R^{12})_2$, C═C═S, C═Se, C═N($R^{12}$), O, S, ester group and $CONR^{12}$;

the linear alkane group is selected from the group consisting of an unsubstituted linear alkane group and a linear alkane group substituted with at least one reactive group $R^{12}$, or is a linear alkane group in which at least one H atom is substituted by one of D, F, Cl, Br, I, CN, an aromatic amine group containing a reactive group $R^{12}$, an aromatic amine group containing an aromatic group, an aromatic amine group containing a heteroaromatic ring, and carbazole; the alkane ether group is selected from the group consisting of an unsubstituted alkane ether group and a alkane ether group substituted with at least one reactive group $R^{12}$, or is a alkane ether group in which at least one H atom is substituted by one of D, F, Cl, Br, I, CN, an aromatic amine group containing a reactive group $R^{12}$, an aromatic amine group containing an aromatic group, an aromatic amine group containing a heteroaromatic ring, and carbazole; the alkane thioether group containing 1 to 10 carbon atoms is selected from the group consisting of an unsubstituted alkane thioether group containing 1 to 10 carbon atoms and an alkane thioether group having containing 1 to 10 carbon atoms substituted with at least one reactive group $R^{12}$, or is an alkane thioether group containing 1 to 10 carbon atoms in which at least one H atom is substituted by one of D, F, Cl, Br, I, CN, an aromatic amine group containing a reactive group $R^{12}$, an aromatic amine group containing an aromatic group, an aromatic amine group containing a heteroaromatic ring, and carbazole; the branched alkane group is selected from the group consisting of an unsubstituted branched alkane group and a branched alkane group substituted with at least one reactive group $R^{12}$, or is a branched alkane group in which at least one H atom is substituted by one of D, F, Cl, Br, I, CN, an aromatic amine group containing a reactive group $R^{12}$, an aromatic amine group containing an aromatic group, an aromatic amine group containing a heteroaromatic ring, and carbazole; the cycloalkane group is selected from the group consisting of an unsubstituted cycloalkane group and a cycloalkane group substituted with at least one reactive group $R^{12}$, or is a cycloalkane group in which at least one H atom is substituted by one of D, F, Cl, Br, I, CN, an aromatic amine group containing a reactive group $R^{12}$, an aromatic amine group containing an aromatic group, an aromatic amine group containing a heteroaromatic ring, and carbazole;

$R^{12}$ is each independently selected from the group consisting of H, D, an aliphatic alkane group containing 1 to 10 carbon atoms, an aromatic hydrocarbon, an aromatic ring group containing 5 to 10 ring-forming atoms, and a heteroaromatic group containing 5 to 10 ring atoms;

—Z— is a single bond, or Z is a doubly-bridging group.

When Z is a doubly-bridging group, Z is selected from the structural formulas in Table 1:

TABLE 1

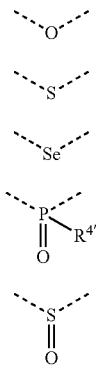

TABLE 1-continued
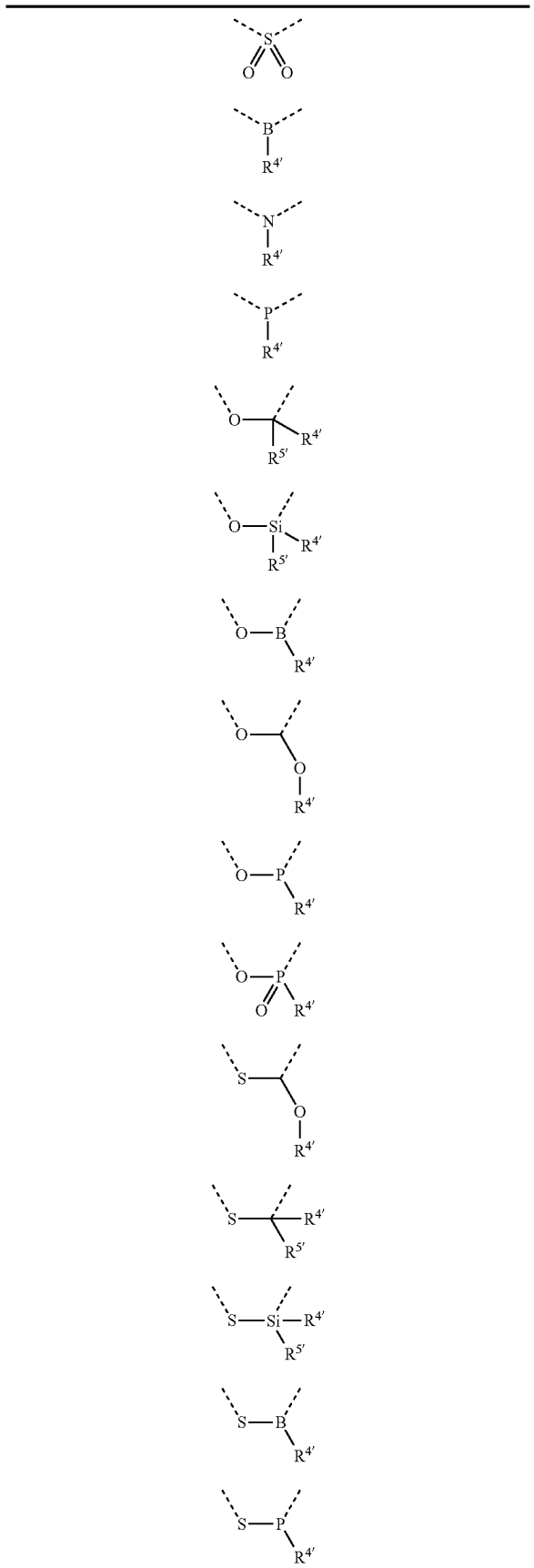
TABLE 1-continued
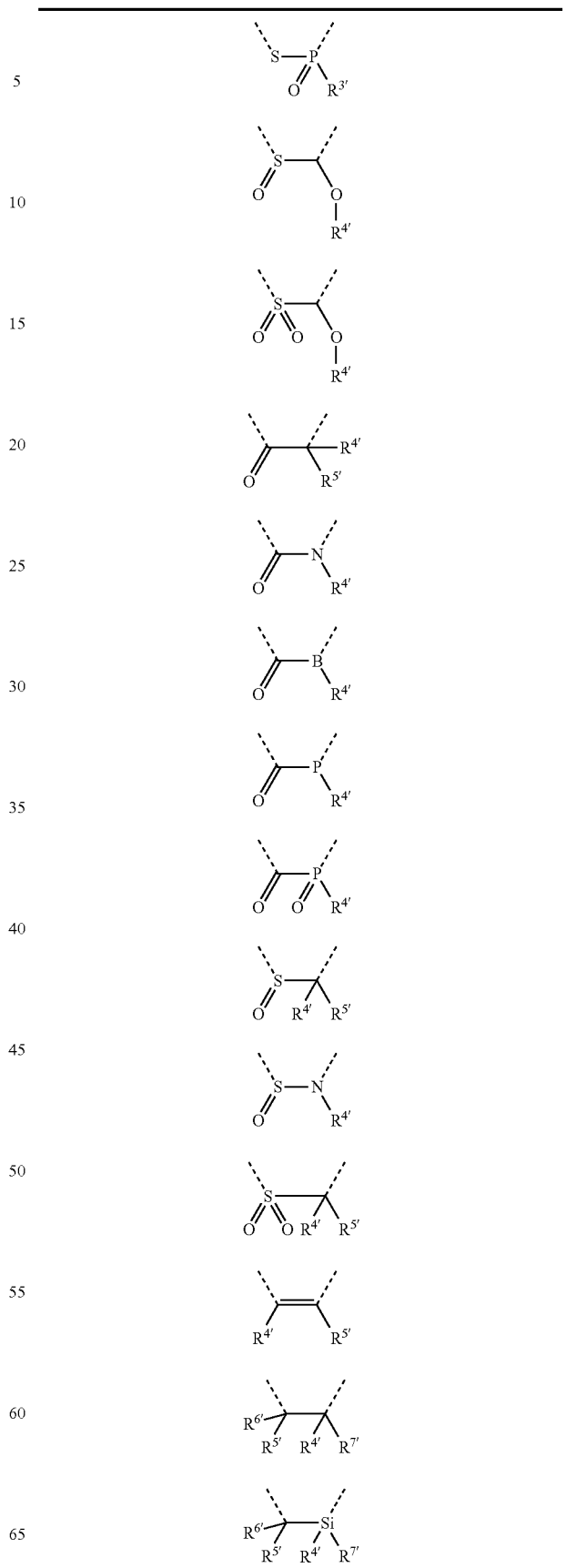

TABLE 1-continued

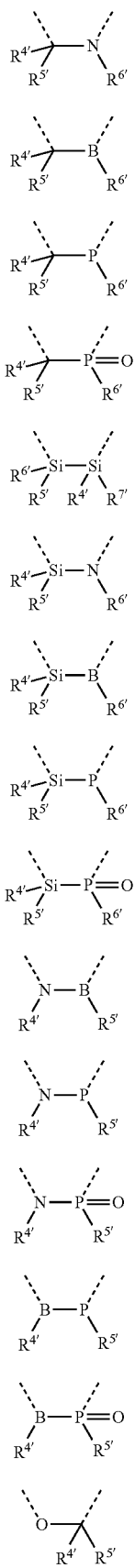

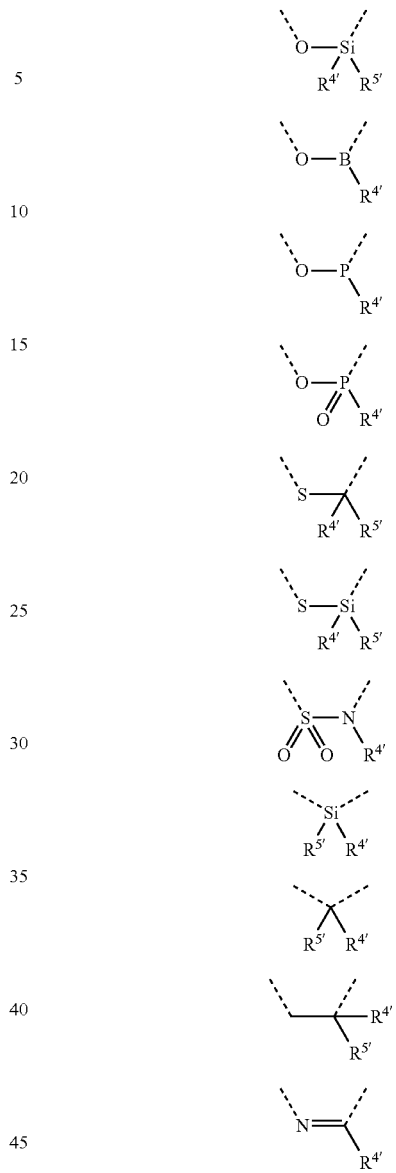

In Table 1, the symbols $R^{4'}$, $R^{5'}$, $R^{6'}$ and $R^{7'}$ are each independently selected from the group consisting of H, D, F, CN, an alkyl group, an aromatic ring group, an aromatic heterocyclic group, an amino group, a silicon group, a germyl group, an alkoxy group, an aryloxy group, and a siloxy group; the alkyl group is selected from the group consisting of an unsubstituted alkyl group, a fluoroalkyl group, a deuterated alkyl group, and a deuterated fluoroalkyl group; the aromatic ring group is selected from the group consisting of an unsubstituted aromatic ring group and a deuterated aromatic ring group; the aromatic heterocyclic group is selected from the group consisting of an unsubstituted aromatic heterocyclic group and a deuterated aromatic heterocyclic group; the amino group is selected from the group consisting of an unsubstituted amino group and a deuterated amino group; the silicon group is selected from the group consisting of an unsubstituted silicon group and a deuterated silicon group; the germyl group is selected from the group consisting of an unsubstituted germyl group and a deuterated germyl group; the alkoxy group is selected from the group consisting of an unsubstituted alkoxy group, a silyalkoxy group, a fluoroalkoxy group, a deuterated alkoxy group, a deuterated fluoroalkoxy group, and a deuterated silylalkoxy group; the aryloxy group is selected from the group consisting of an unsubstituted aryloxy group and a deuterated aryloxy group; the siloxy group is selected from the group consisting of an unsubstituted siloxy group and a deuterated siloxy group; the dashed bonds represent a bond bonded to two benzene rings in the general formula (III).

In structural formula (III), structural formula (IIIa), structural formula (IIIb), structural formula (IIIc), and structural formula (IIId), x is any of integers from 0 to 4, x1 is any of integers from 0 to 3, and y is any of integers from 0 to 5, and z is any of integers from 0 to 5;

-L- is a single bond, or, L is selected from the group consisting of a $R^1$-substituted conjugated aromatic group containing 5 to 40 carbon atoms and an unsubstituted conjugated aromatic group containing 5 to 40 carbon atoms.

Further, L is selected from groups having the following structural formulas B1 and B2:

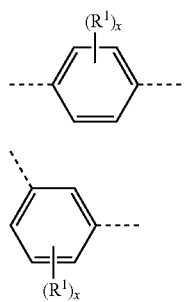

wherein, in the structural formulas B1 and B2, the dashed lines represent a bond to an adjacent group;

The dashed lines in structural formulas (III) and (IIIa) represent the linkage of L to the group within the circle. The position at which L is bonded to the group in the circle may be on two benzene rings in the circle, or may be any possible position on the aromatic ring or heteroaromatic ring contained in $Ar^2$.

Further, L, $Ar^1$ and $Ar^2$ are each independently selected from an aryl group containing 5 to 40 ring atoms and a heteroaryl group containing 5 to 40 ring atoms; further, L, $Ar^1$ and $Ar^2$ are each independently selected from an aryl group containing 5 to 30 ring atoms and a heteroaryl group containing 5 to 30 ring atoms. Further, L, $Ar^1$ and $Ar^2$ are each independently selected from an aryl group containing 5 to 20 ring atoms and a heteroaryl group containing 5 to 20 ring atoms; further, L, $Ar^1$ and $Ar^2$ are each independently selected from an aryl group containing 5 to 15 ring atoms and a heteroaryl group containing 5 to 15 ring atoms Further, L, $Ar^1$ and $Ar^2$ are each independently selected from an aryl group containing 6 to 15 carbon atoms and a heteroaryl group containing 2 to 15 carbon atoms and hetero atom; further, L, $Ar^1$ and $Ar^2$ are each independently selected from an aryl group containing 6 to 10 carbon atoms and a heteroaryl group containing 2 to 10 carbon atoms and hetero atom. When L, $Ar^1$ and $Ar^2$ each are a heteroaryl group containing 2 to 15 carbon atoms and hetero atom, the sum of the number of carbon atoms and hetero atoms in L, Ar1 and Ar2 is at least 4. And the hetero atom is at least one selected from the group consisting of Si, N, P, O, S, and Ge; further, the hetero atom is at least one selected from the group consisting of Si, N, P, O, and S; and still further, the hetero atom is at least one selected from the group consisting of N, O, and S.

It should be noted that, herein, the aromatic group means a hydrocarbon group containing at least one aromatic ring, including a monocyclic group and a polycyclic group. The heterocyclic aromatic group means an aromatic hydrocarbon group containing at least one heteroaromatic hydrocarbon (contains a hetero atom), including a monocyclic group and a polycyclic group. The polycyclic group may have two or more rings in which two carbon atoms are shared by two adjacent rings, that is a fused ring. At least one of the polycyclic groups is an aromatic ring or a heteroaromatic ring. Herein, both the aromatic group and the heterocyclic aromatic group are not limited to a system including an aromatic ring or a heteroaromatic ring, and also include a non-aromatic ring system. Wherein, a plurality of aromatic groups or heteroaromatic groups may be spaced by short non-aromatic units (<10% of non-H atoms, furthermore less than 5% of non-H atoms, such as C, N or O atoms). Therefore, systems such as 9,9'-spirobifluorene, 9,9-diarylfluorene, triarylamine, diaryl ether and the like are also considered to be aromatic groups.

Specifically, examples of the aromatic group include: benzene, naphthalene, anthracene, phenanthrene, perylene, tetracene, pyrene, benzopyrene, triphenylene, acenaphthene, fluorene, spirofluorene and derivatives thereof.

Specifically, examples of the heteroaromatic group include: furan, benzofuran, dibenzofuran, thiophene, benzothiophene, dibenzothiophene, pyrrole, pyrazole, triazole, imidazole, oxazole, oxadiazole, thiazole, tetrazole, indole, carbazole, pyrroloimidazole, pyrrolopyrrole, thienopyrrole, thienothiophene, furopyrrole, furofuran, thienofuran, benzisoxazole, benzisothiazole, benzimidazole, pyridine, pyrazine, pyridazine, pyrimidine, triazine, quinoline, isoquinoline, cinnoline, quinoxaline, phenanthridine, perimidine, quinazoline, quinazolinone, and derivatives thereof.

Alternatively, both $Ar^1$ and $Ar^2$ are an aryl group containing 6 to 40 ring atoms further, both $Ar^1$ and $Ar^2$ are aryl groups containing 6 to 30 ring atoms; further, both $Ar^1$ and $Ar^2$ are aryl groups containing 6 to 25 ring atoms.

Specifically, in the general formulae (III) and (IIIa), L, $Ar^1$ and $Ar^2$ are each independently selected from the group consisting of following groups:

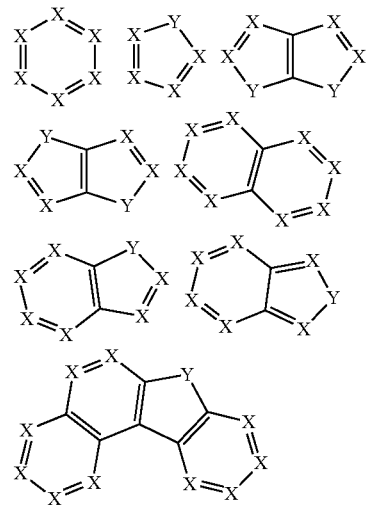

-continued

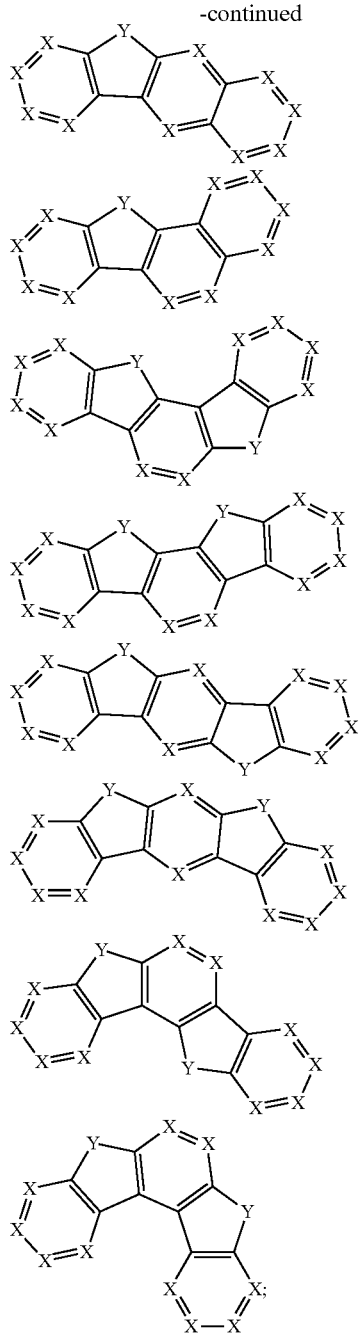

wherein X is selected from the group consisting of $CR_{13}$ and N; further, all X in the structural formula are $CR_{13}$;

Y is selected from the group consisting of $CR_{14}R_{15}$, $SiR_{16}R_{17}$, $NR_{18}$, C(=O), S(=O)$_2$, O and S;

$R_{13}$, $R_{14}$, $R_{15}$, $R_{16}$, $R_{17}$ and $R_{18}$ are each independently selected from the group consisting of a single bond, H, D, F, CN, $NO_2$, $CF_3$, alkenyl, alkynyl amine, acyl, amide, cyano, isocyano, alkoxy, hydroxy, carbonyl, sulfone, an alkyl group containing 1 to 60 carbon atoms, a cycloalkyl group containing 3 to 60 carbon atoms, an aromatic group containing 6 to 60 carbon atoms, a heterocyclic aryl group containing 3 to 60 carbon atoms, a fused cyclic aromatic group containing 7 to 60 carbon atoms, and a fused heterocyclic aromatic group containing 4 to 60 carbon atoms.

Further, $Ar^1$ and $Ar^2$ are each independently selected from the group consisting of the general formulas C1 to C36 as follows:

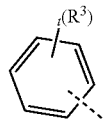

C1

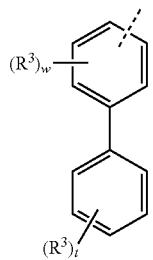

C2

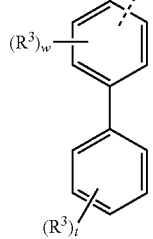

C3

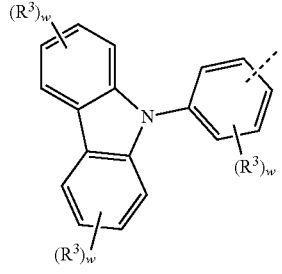

C4

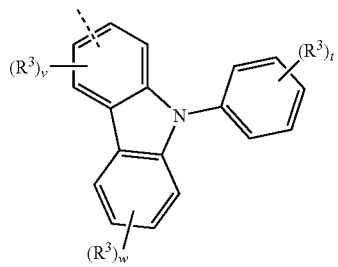

C5

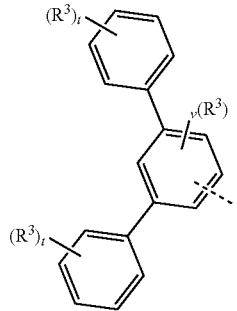

C6 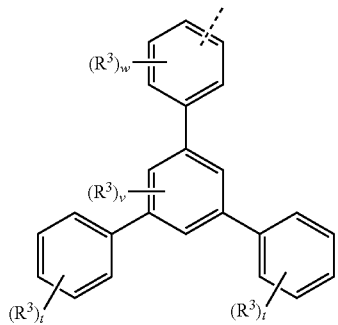
C7 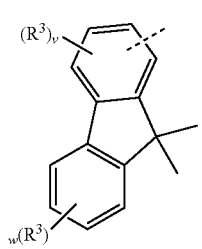
C8 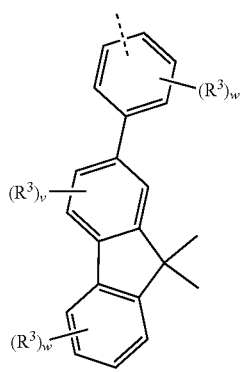
C9 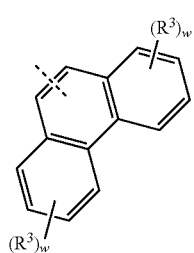
C10 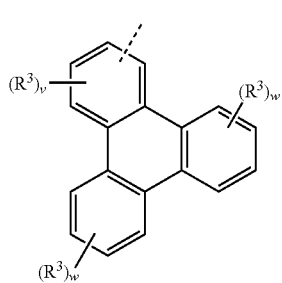
C11 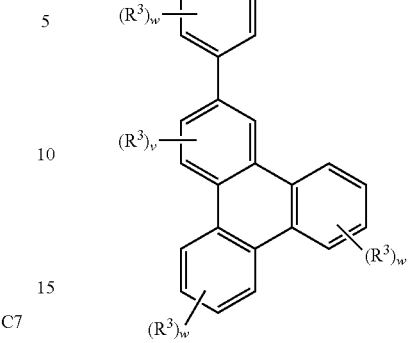
C12 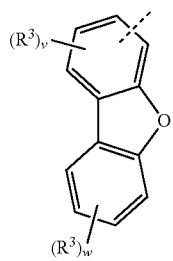
C13 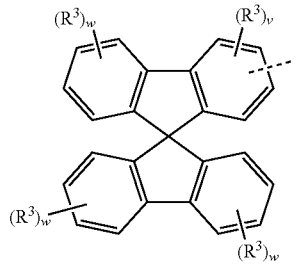
C14 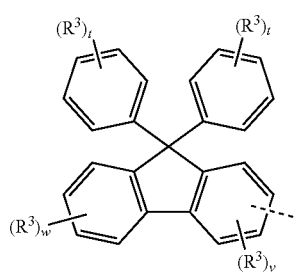
C15 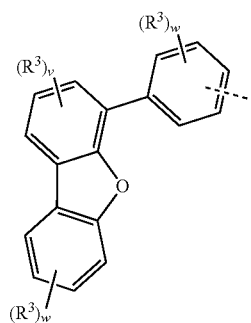

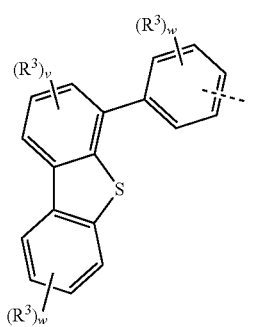
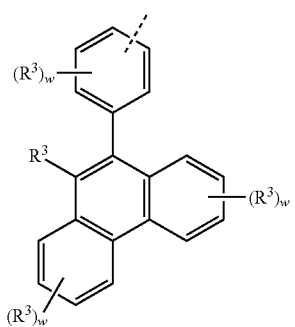
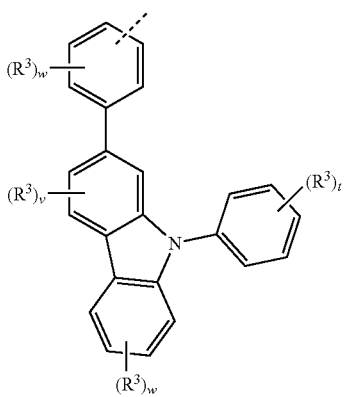
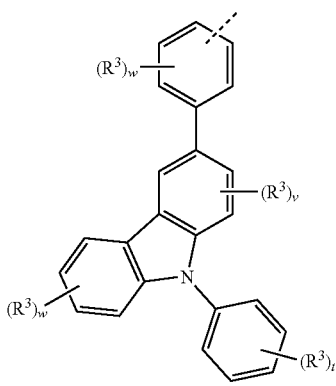
C16
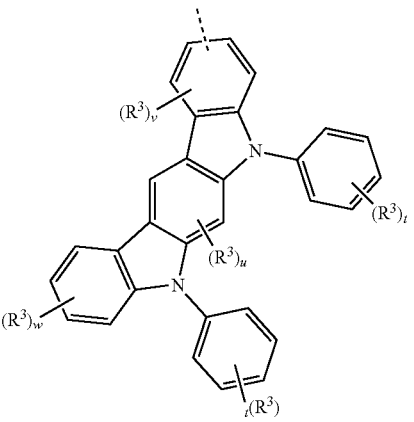
C17
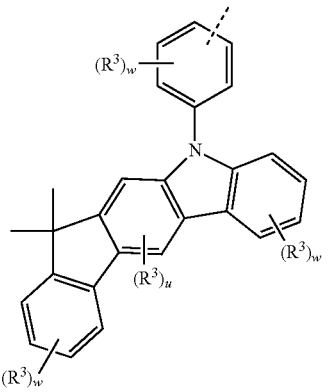
C18
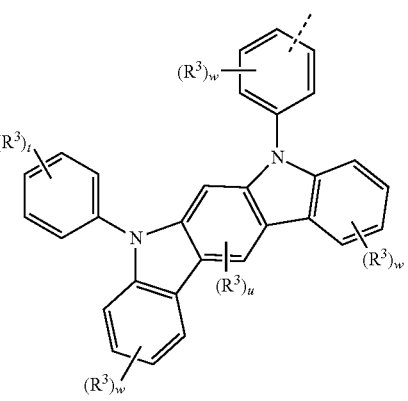
C19
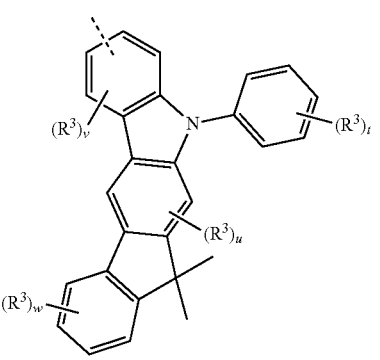
C20
C21
C22
C23

C24
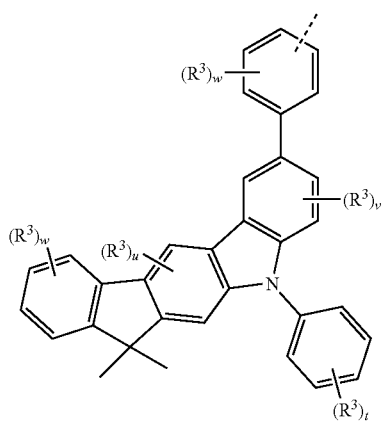
C25
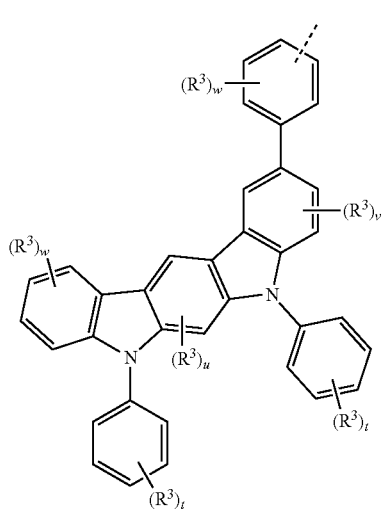
C26
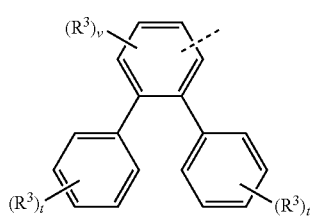
C27
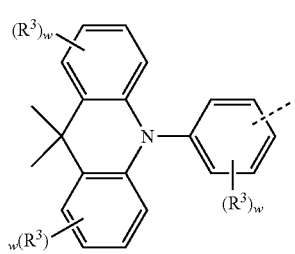
C28
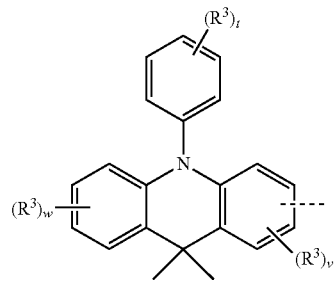
C29
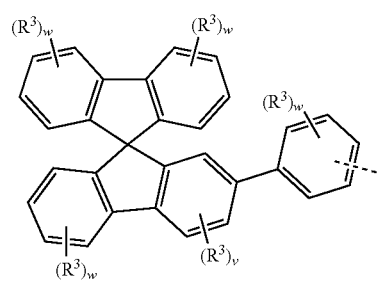
C30
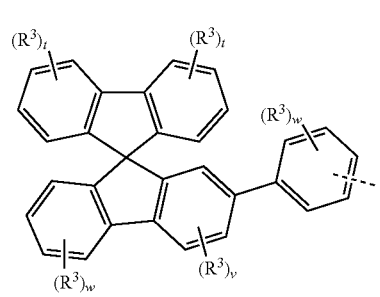
C31
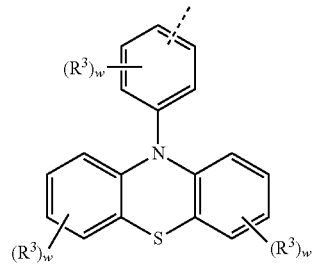
C32
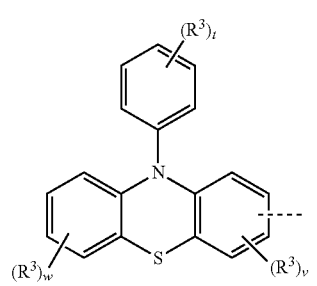

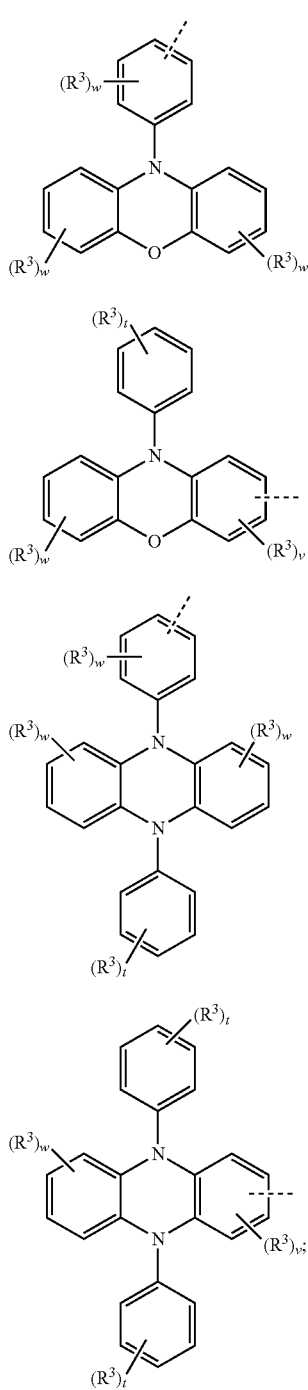

Wherein, in the general formulae C1 to C36, $R^3$ is selected from the group consisting of H, F, Cl, Br, I, D, CN, $NO_2$, $CF_3$, $B(OR^2)_2$, $Si(R^7)_3$, a linear alkane group, an alkane ether group, an alkane thioether group containing 1 to 10 carbon atoms, a cycloalkane group, an alkane ether group containing 3 to 10 carbon atoms, an alkane thioether group containing 3 to 10 carbon atoms, and an aryl group containing 6 to 10 carbon atoms; u is any of integers from 0 to 2, v is any of integers from 0 to 3, w is any of integers from 0 to 4, and t is any of integers from 0 to 5.

When the organic functional compound of the general formula (I) or the compound of the general formula (IV) according to the present embodiment has a hole transporting function, it can be used in an organic electronic device, particularly a hole transport layer in an organic light emitting diode (OLED).

When the organic functional compound of the general formula (I) or the compound of the general formula (IV) according to the present embodiment has a higher LUMO, that is, an electron blocking function, it can be used in an organic electronic device, particularly an electron blocking layer in an organic light emitting diode. It should be noted that the higher LUMO here means that the electron blocking layer has a higher LUMO than the adjacent functional layer (such as the light emitting layer in the organic light emitting diode).

When the organic functional compound of the general formula (I) or the compound of the general formula (IV) according to the present embodiment has a higher triplet excited state energy level T1, that is, a triplet exciton blocking function, it can be used in an organic electronic device, particularly an exciton blocking layer in the organic light emitting diode. It should be noted that the higher T1 here means that the exciton blocking layer has a higher T1 than the adjacent functional layer (such as the light emitting layer in the phosphorescent OLED).

When the organic functional compound of the general formula (I) or the compound of the general formula (IV) according to the present embodiment has a higher singlet excited state energy level S1, that is, a singlet exciton blocking function, it can be used in an organic electronic device, particularly an exciton blocking layer in the organic light emitting diode. It should be noted that the higher T1 here means that the exciton blocking layer has a higher S1 than the adjacent functional layer (such as the light emitting layer in the fluorescent OLED).

Further, when A is a group having a hole transporting function, the A includes at least one of the following groups: a phthalocyanine group, a porphyrin group, an amine group, an aromatic amine group, a biphenyl triarylamine group, a thiophene group, a fused-thiophenyl group (such as a dithienothiophenyl group and a bi-thiophenyl group, etc.), a pyrrolyl group, an phenylamino group, a carbazolyl group, a indolocarbazole group, and derivatives thereof Further, the aromatic amine group having a hole transporting function is selected from one of, but not limited to the following structural formula:

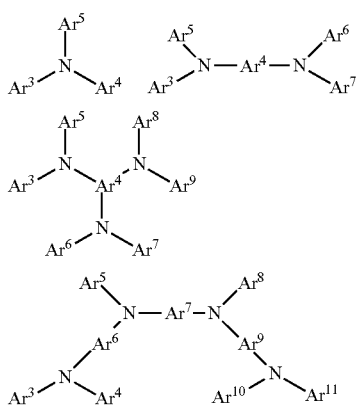

-continued

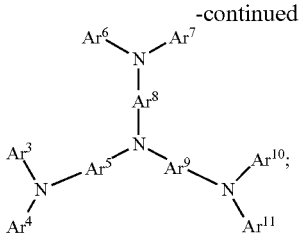

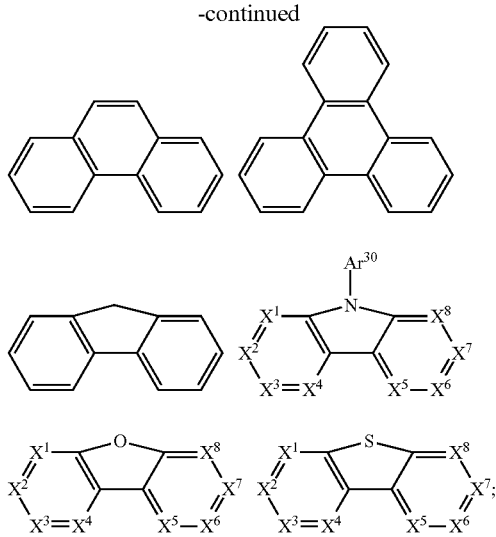

Wherein, $Ar^3$, $Ar^4$, $Ar^5$, $Ar^6$, $Ar^6$, $Ar^7$, $Ar^8$, $Ar^9$, $Ar^{10}$ and $Ar^{11}$ are each independently selected from the group consisting of a cyclic aromatic hydrocarbon group, an aromatic heterocyclic group, and a group having 2 to 10 rings; the cyclic aromatic hydrocarbon group is selected from the group consisting of phenyl, biphenyl, triphenyl, benzo, naphthyl, anthryl, phenalenyl, phenanthryl, fluorenyl, pyrenyl, chrysenyl, perylenyl, and azulenyl; the aromatic heterocyclic group is selected from the group consisting of dibenzothiophenyl, dibenzofuryl, furyl, thienyl, benzofuryl, benzothiophenyl, carbazolyl, pyrazolyl, imidazolyl, triazolyl, isoxazolyl, thiazolyl, oxadiazolyl, oxatriazole, dioxazolyl, thiadiazolyl, pyridyl, pyndazinyl, pyrimidinyl, pyrazinyl, triazinyl, oxazinyl, oxathiazinyl, oxadiazinyl, indolyl, benzimidazolyl, indazolyl, indolizinyl, benzoxazolyl, benzoisoxazolyl, benzothiazolyl, quinolyl, isoquinolyl, o-diaza (hetero)naphthyl, quinazolinyl, quinoxalinyl, naphthyl, phthalidyl, pteridinyl, xanthenyl, acridinyl, phenazinyl, phenothiazinyl, phenoxazinyl, dibenzoselenophenyl, benzoselenophenyl, benzofuran pyridyl, indole carbazolyl, pyridine indolyl, pyrrole dipyridyl, furan dipyridyl, benzothiophene pyridinyl, thiophene pyridinyl, benzoselene pyridinyl and selenophene dipyridyl; each ring in the groups having 2 to 10 rings may be the cyclic aromatic hydrocarbon group or the aromatic heterocyclic group, and may be each other linked together directly or by at least one of the following: an oxygen atom, a nitrogen atom, a sulfur atom, a silicon atom, a phosphorus atom, a boron atom, a chain aliphatic group, and an aliphatic ring group. Wherein, $Ar^3$, $Ar^4$, $Ar^5$, $Ar^6$, $Ar^6$, $Ar^7$, $Ar^8$, $Ar^9$, $Ar^{10}$ and $Ar^{11}$ may be further substituted with substituent that is selected from the group consisting of hydrogen, an alkyl group, an alkoxy group, an amino group, an alkene, an alkyne, an aralkyl group, a heteroalkyl group, an aryl group, and a heteroaryl group.

Further, $Ar^3$, $Ar^4$, $Ar^5$, $Ar^6$, $Ar^6$, $Ar^7$, $Ar^9$, $Ar^{10}$ and $Ar^{11}$ are each independently selected from the group consisting of the following groups:

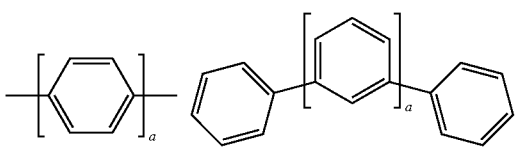

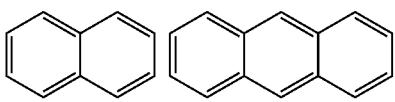

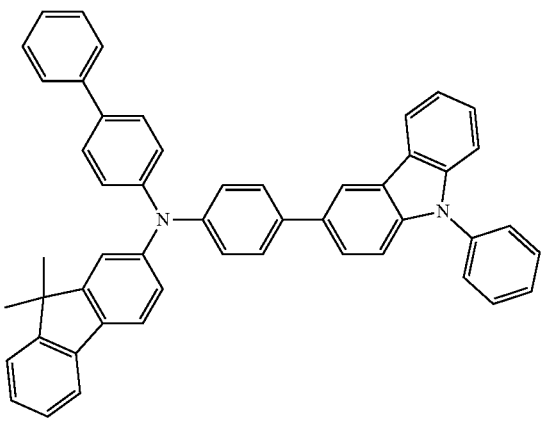

a is any of integers from 1 to 20; $X^1$ to $X^8$ are each independently selected from the group consisting of CH and N; and $Ar^{30}$ is defined the same as $Ar^3$.

Specifically, a corresponding aromatic amine compound having a hole transport function may also be disclosed in U.S. Pat. Nos. 3,567,450, 4,720,432, 5,061,569, 3,615,404 and 5,061,569.

Specifically, the group A having a hole transporting function in the organic functional compound of the general formula (I) or the compound of the general formula (IV) is selected from one of, but not limited to, the following groups:

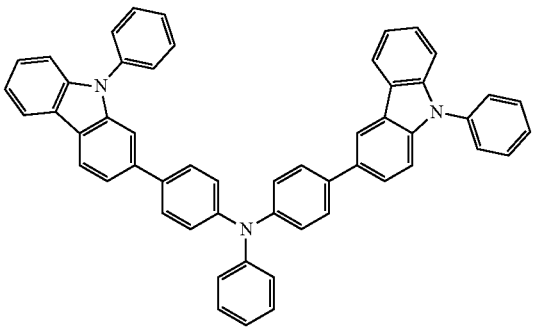

31
-continued
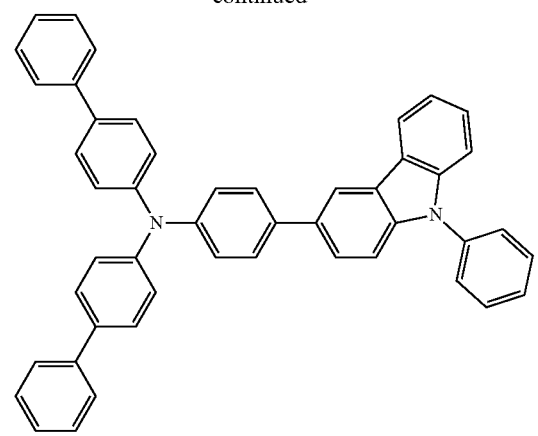
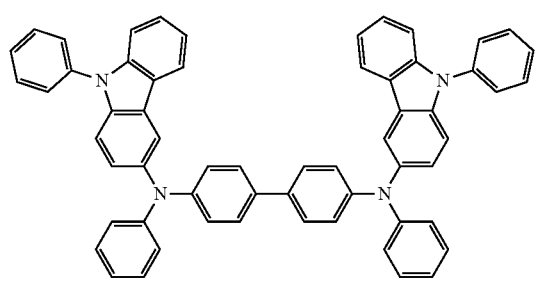
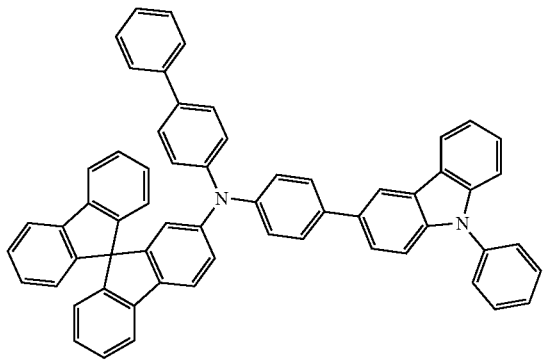
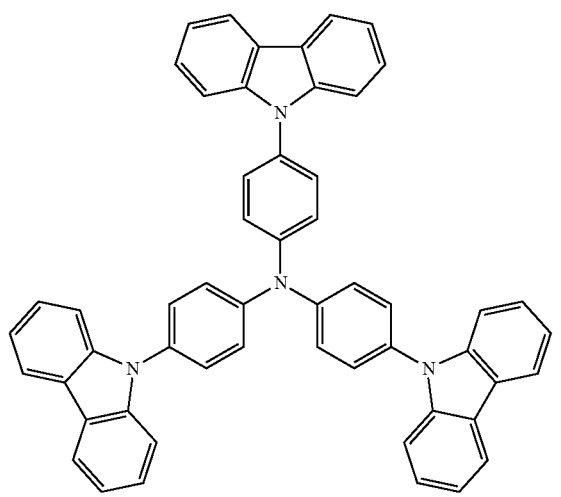
32
-continued
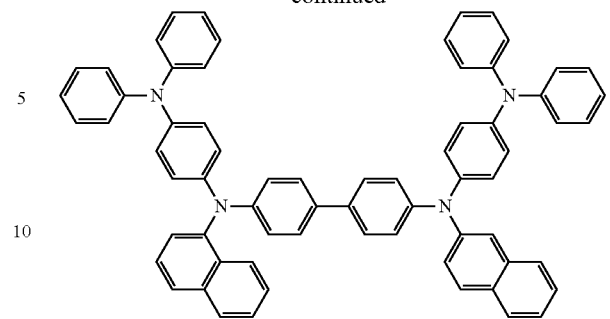
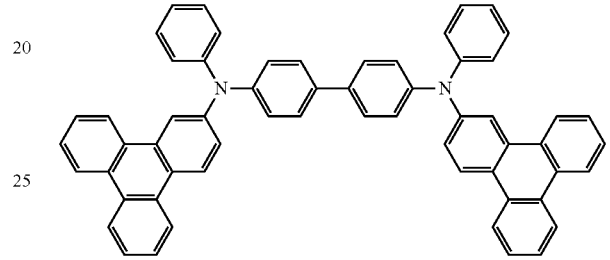
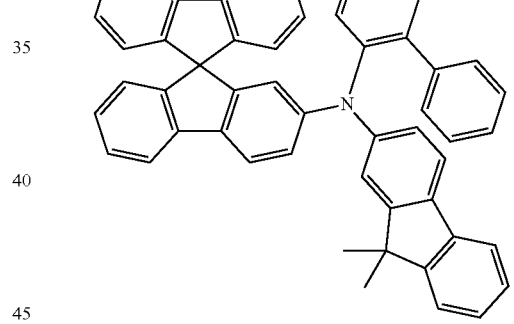
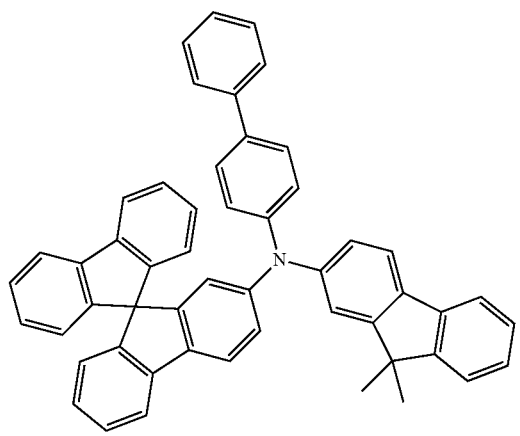

-continued

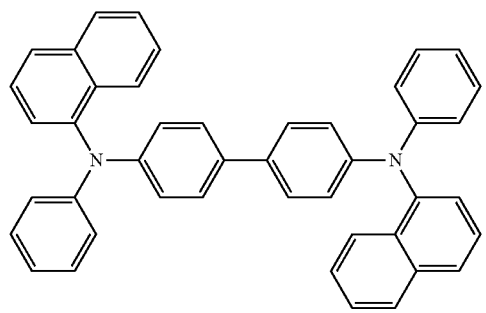

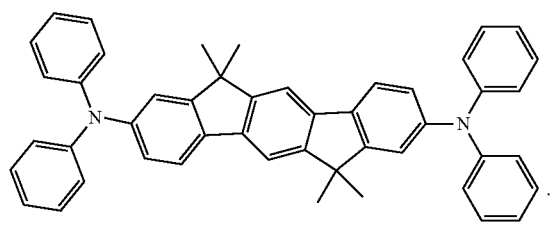

When A in the general formula (I) is a group having an organic host function (a fluorescent host and a phosphorescent host), A comprises one of structural formula (1)

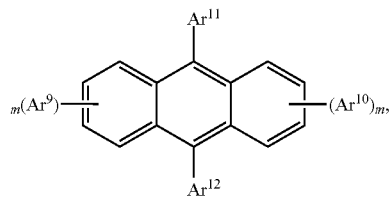

structural formula (2)

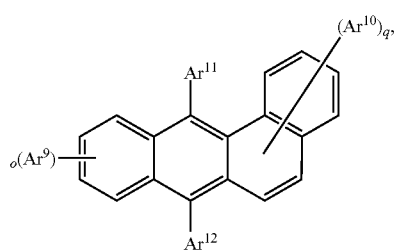

structural formula (3)

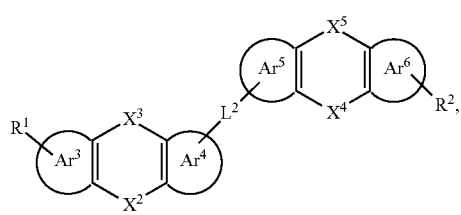

structural formula (4)

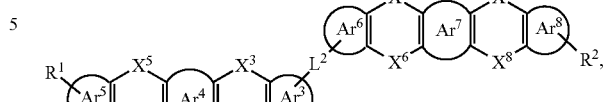

structural formula (5)

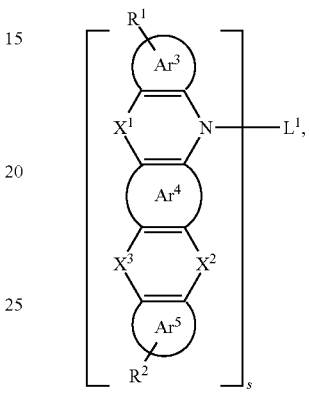

and structural formula (6)

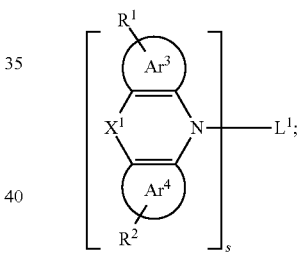

In the structural formulas (1) and (2), $Ar^{11}$ and $Ar^{12}$ are each independently selected from an aromatic group containing 6 to 60 carbon atoms, an heteroaryl group containing 3 to 60 carbon atoms, a fused cyclic aromatic group containing 6 to 60 carbon atoms, and a fused heteroaryl group containing 3 to 60 carbon atoms;

In the structural formulas (3) to (6),

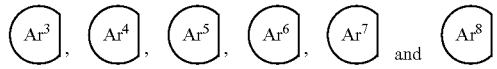

are each independently selected from an aromatic group containing 5 to 30 ring atoms, and an heteroaryl group containing 5 to 30 ring atoms; further,

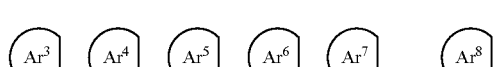

are each independently selected from an aromatic group containing 5 to 25 ring atoms, and an heteroaryl group containing 5 to 25 ring atoms;

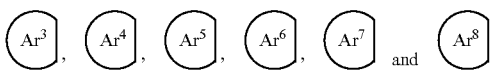

are each independently selected from an aromatic group containing 5 to 20 ring atoms, and an heteroaryl group containing 5 to 20 ring atoms;

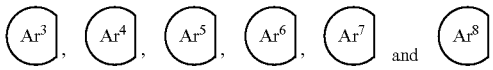

are each independently selected from an aromatic group containing 5 to 15 ring atoms, and an heteroaryl group containing 5 to 15 ring atoms;

In the structural formulas (1) and (2), $Ar^9$ and $Ar^{10}$ are each independently selected from the group consisting of H, D, F, CN, $NO_2$, $CF_3$, alkenyl, alkynyl, amine, acyl, amide, cyano, isocyano, alkoxy, hydroxy, carbonyl, sulfone, an alkyl group containing 1 to 60 carbon atoms, a cycloalkyl group containing 3 to 60 carbon atoms, and an aromatic group containing 6 to 60 carbon atoms; a heterocyclic aryl group containing 3 to 60 carbon atoms, a fused cyclic aromatic group containing 7 to 60 carbon atoms, and a fused heterocyclic aromatic group containing 4 to 60 carbon atoms;

In the structural formulas (1) and (2), $L^1$ is selected from an aromatic group containing 5 to 60 ring atoms and an heteroaryl group containing 5 to 60 ring atoms; further, $L^1$ is selected from an aromatic group containing 5 to 50 ring atoms and an heteroaryl group containing 5 to 50 ring atoms; further, $L^1$ is selected from an aromatic group containing 5 to 40 ring atoms and an heteroaryl group containing 5 to 40 ring atoms; further, $L^1$ is selected from an aromatic group containing 6 to 30 ring atoms and an heteroaryl group containing 6 to 30 ring atoms.

In the structural formulas (3) and (4), $-L^2-$ is a single bond, or $L^2$ is selected from an aromatic group containing 5 to 30 ring atoms and an heteroaryl group containing 5 to 30 ring atoms, and $L^2$ can be attached to any carbon atom on the ring; further, $-L^2-$ is a single bond, or $L^2$ is selected from an aromatic group containing 5 to 25 ring atoms and an heteroaryl group containing 5 to 25 ring atoms, and $L^2$ can be attached to any carbon atom on the ring; or $-L^2-$ is a single bond, or $L^2$ is selected from an aromatic group containing 5 to 15 ring atoms and an heteroaryl group containing 5 to 15 ring atoms, and $L^2$ can be attached to any carbon atom on the ring.

In the structural formulas (5) and (6), $-X^1-$ is a single bond, or $X^1$ is selected from $N(R)$, $C(R)_2$, $Si(R)_2$, O, $C=N(R)$, $C=C(R)_2$, $P(R)$, $P(=O)R$, S, $S=O$ and $SO_2$; further, $-X^1-$ is a single bond, or $X^1$ is selected from $N(R)$, $C(R)_2$, O and S.

In the formulas (3) and (4), $-X^2-$, $-X^3-$, $-X^4-$, $-X^5-$, $-X^6-$, $-X^7-$, $-X^8-$ and $-X^9-$ are each independently selected from a single bond, $-N(R)-$, $-C(R)_2-$, $-O-$, $-(C=N(R))-$, $-(C=C(R)_2)$, $-P(R)-$, $-(P(=O)R)-$, $-S-$, $-(S=O)-$ and $-(SO_2)-$, and at most one of $-X^2-$ and $-X^3-$ is a single bond, at most one of $-X^4-$ and $-X^5-$ is a single bond, at most one of $-X^6-$ and $-X^7-$ is a single bond, and at most one of $-X^8-$ and $-X^9-$ is a single bond; further, $-X^2-$, $-X^3-$, $-X^4-$, $-X^5-$, $-X^6-$, $-X^7-$, $-X^8-$ and $-X^9-$ are each independently selected from a single bond, $-N(R)-$, $-C(R)_2-$, $-O-$, and $-S-$.

Wherein, R is selected from the group consisting of H, D, F, CN, alkenyl, alkenyl, nitrile, amine, nitro, acyl, alkoxy, carbonyl, sulfone, an alkyl having 1 to 30 carbon atoms, a cycloalkyl group containing 3 to 30 carbon atoms, an aromatic hydrocarbon group containing 5 to 60 ring-forming atoms, and an aromatic heterocyclic group containing 5 to 60 ring-forming atoms.

In the structural formulas (3) to (5), $R^1$ and $R^2$ are defined the same as those in the general formula (II). Further, in the structural formulas (3) to (5), at least one carbon atom is replaced by $R^1$ and $R^2$.

In the structural formula (1), m is any of integers from 0 to 4.

In the structural formula (2), o is any of integers from 0 to 4, and q is any of integers from 0 to 6.

In the structural formulas (5) and (6), s is any of integers from 1 to 4. Further, s is any of integers from 1 to 3; further, s is any of integers from 1 to 2.

Further, $Ar^{11}$, $A^{12}$, $Ar^9$ and $Ar^{10}$ in the formulas (1) to (2) and

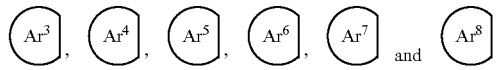

in the formulas (3) to (6) are each independently selected from the group consisting of the following groups and those obtained by substituting a hydrogen on a ring of the following groups:

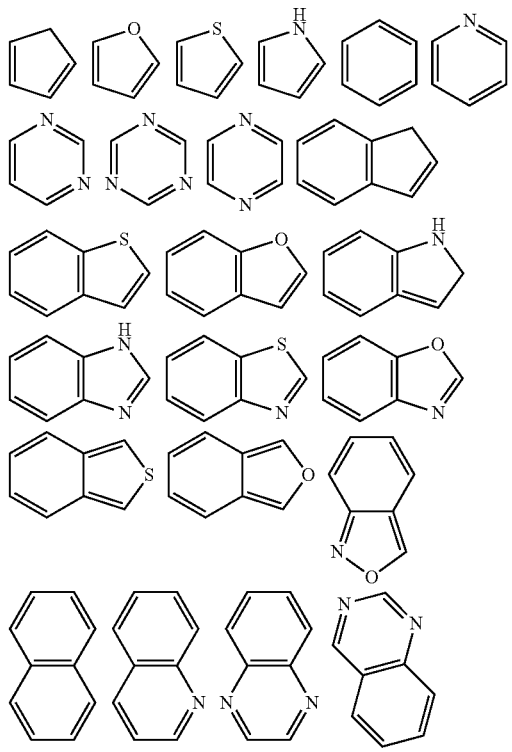

-continued

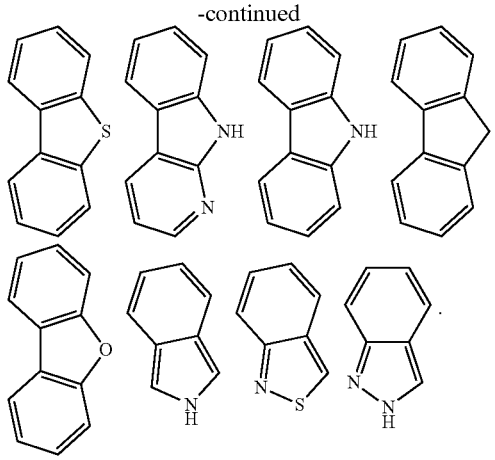

Specifically, according to the structural formula (1), A is selected from one of the following structural formulas:

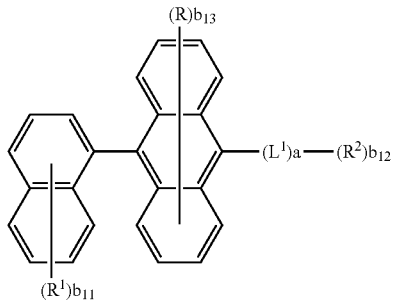

(1-1)

(1-2)

In the structural formulas (1-1) and (1-2), $L^1$, $R^1$, $R^2$ and R are defined the same as those in the structural formulas (1) to (6); a is any integer of 1 to 3; $b_{11}$ to $b_{13}$ are each independently selected from any integer of 0 to 6.

Further, according to the structural formula (1), A is selected from the group consisting of the following structural formulas:

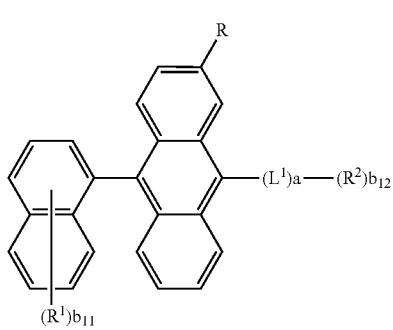

(1-1a)

-continued

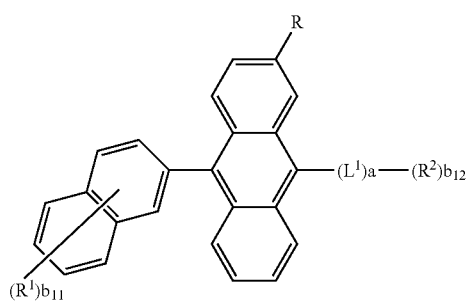

(1-2a)

In the structural formulas (1-1a) and (1-2a), $L^1$, $R^1$, $R^2$, a, R, $b_{11}$ and $b_{12}$ are defined the same as those in the structural formula (1-1) and (1-2).

Specifically, according to the structural formulas (1) and (2), the group A having an organic host function in the general formula (I) and (IV) is selected from one of, but not limited to, the following groups:

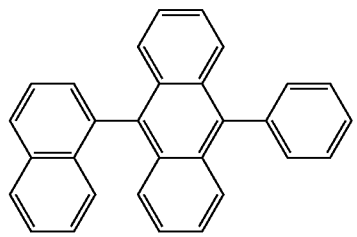

FH-1

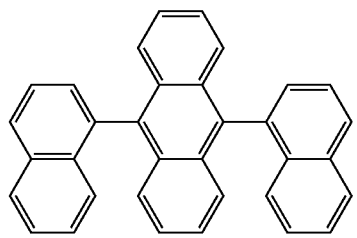

FH-2

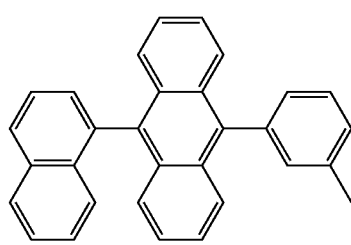

FH-3

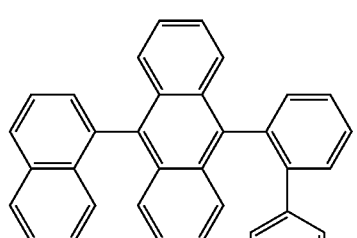

FH-4

FH-5
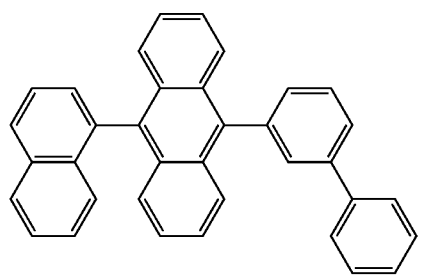
FH-6
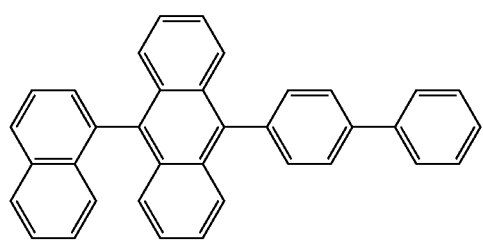
FH-7
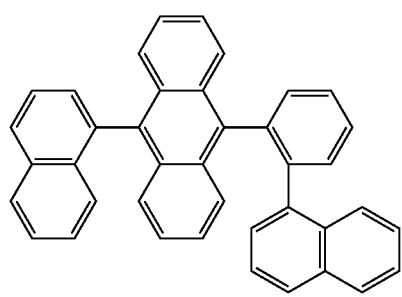
FH-8
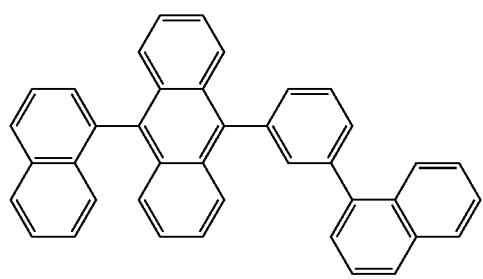
FH-9
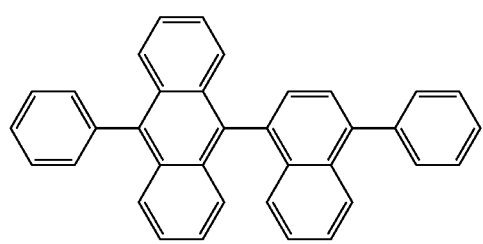
FH-10
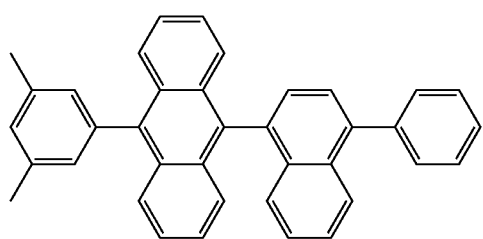
FH-11
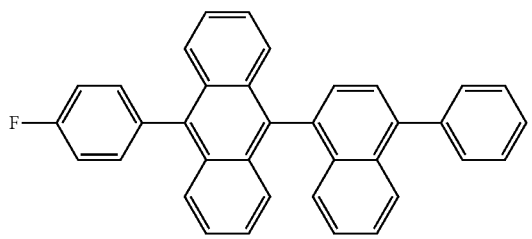
FH-12
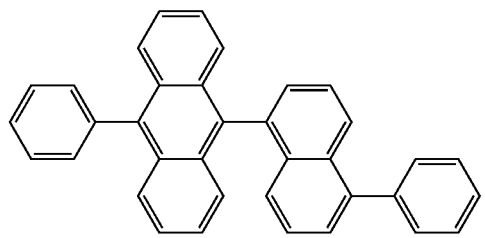
FH-13
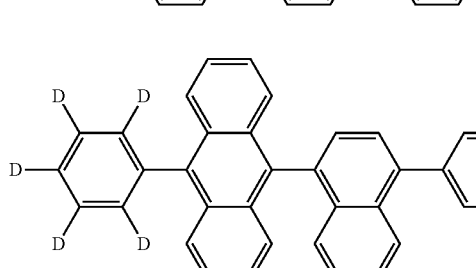
FH-14
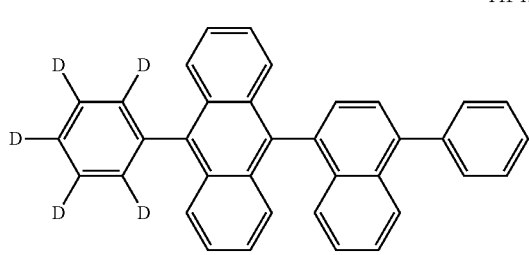
FH-15
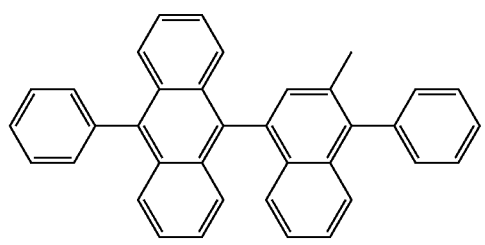
FH-16
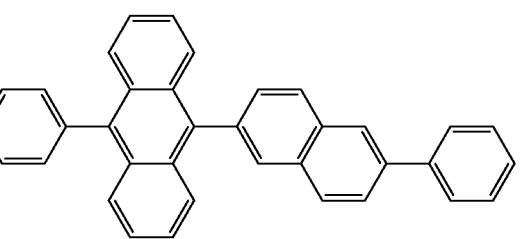

-continued
FH-17
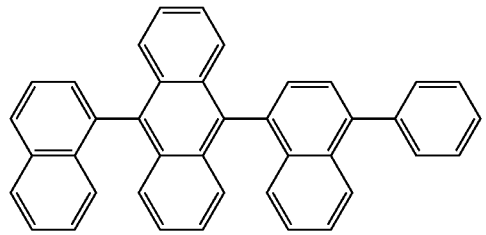
FH-18
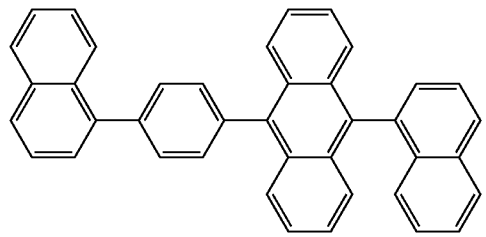
FH-19
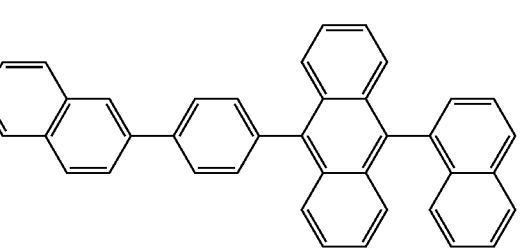
FH-20
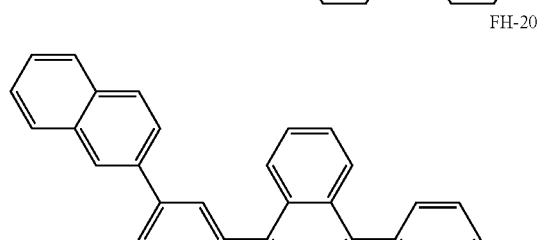
FH-21
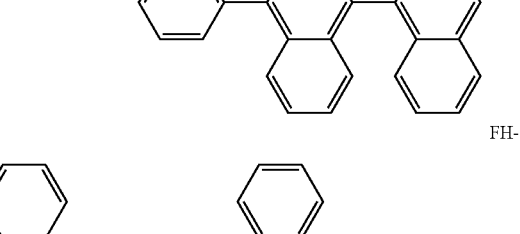
FH-22
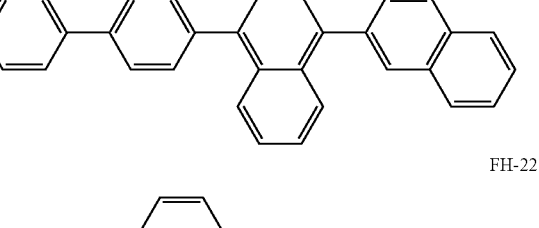
-continued
FH-23
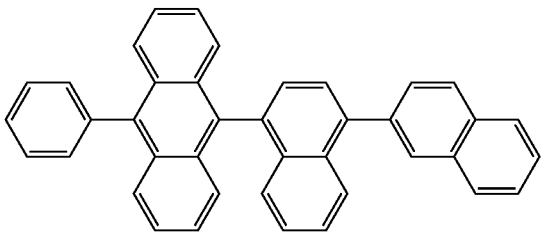
FH-24
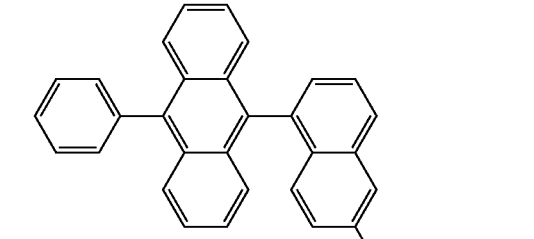
FH-25
FH-26
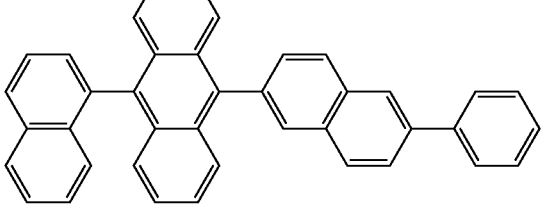
FH-27
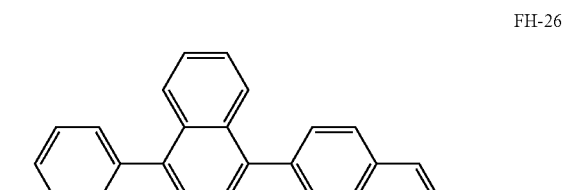

FH-28
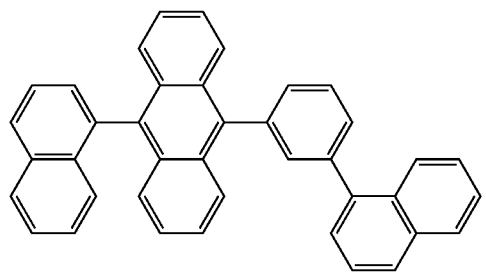
FH-29
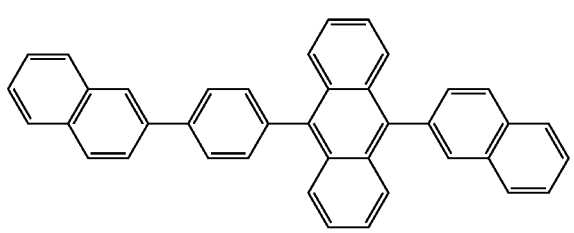
FH-30
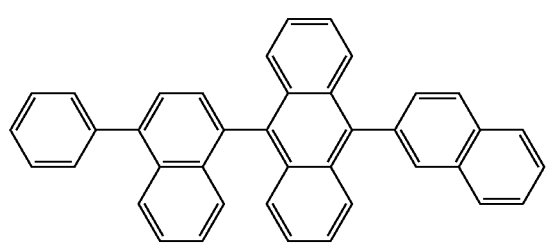
FH-31
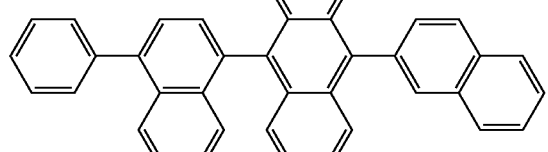
FH-32
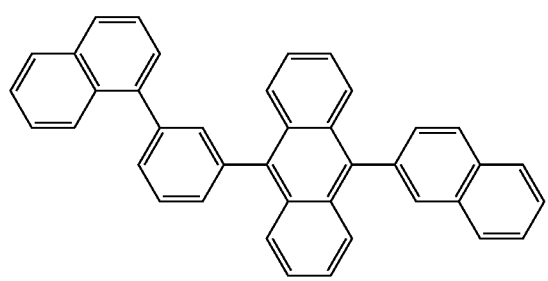
FH-33
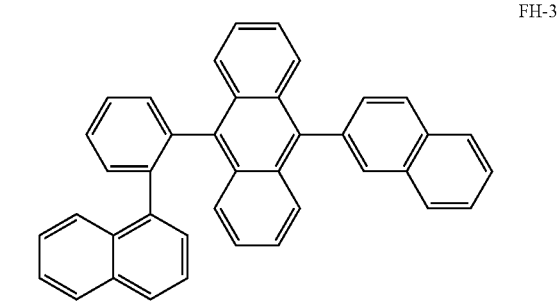
FH-34
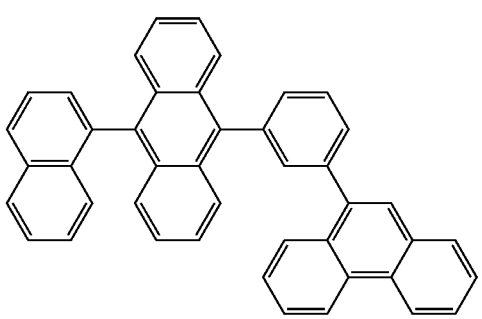
FH-35
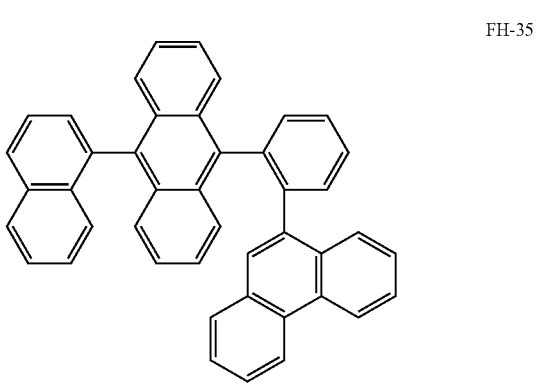
FH-36
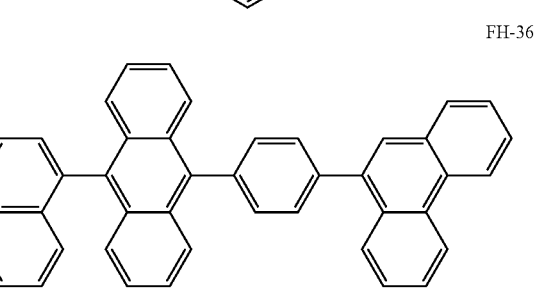
FH-37
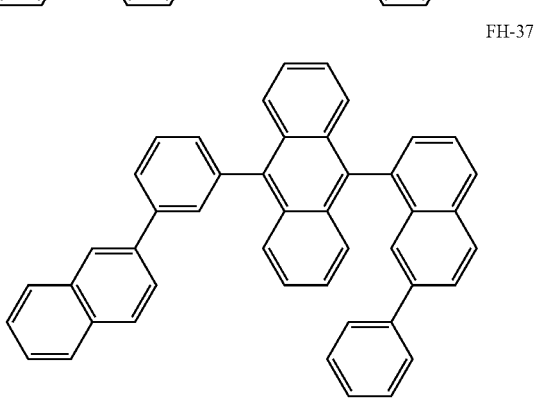
FH-38
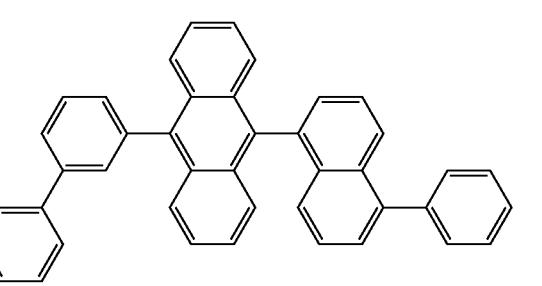

FH-39
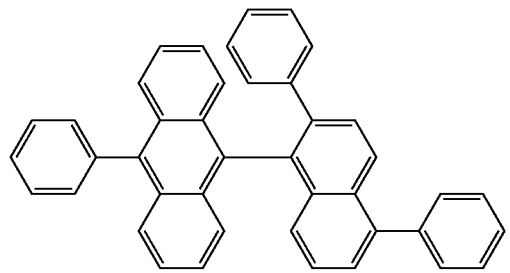
FH-45
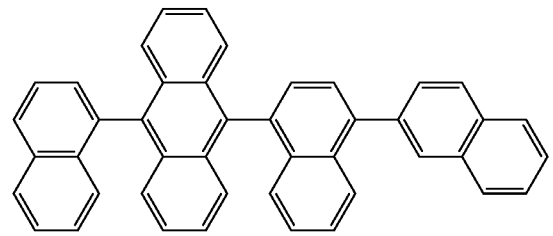
FH-40
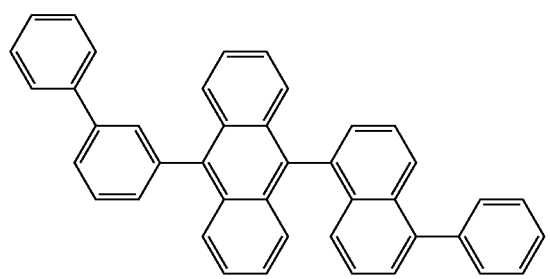
FH-46
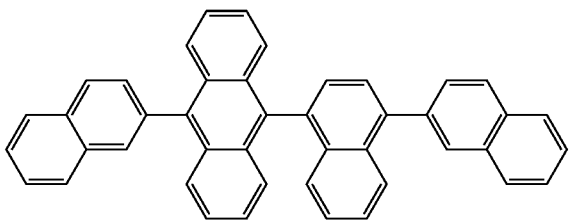
FH-41
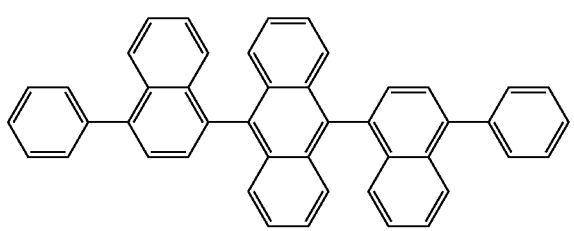
FH-47
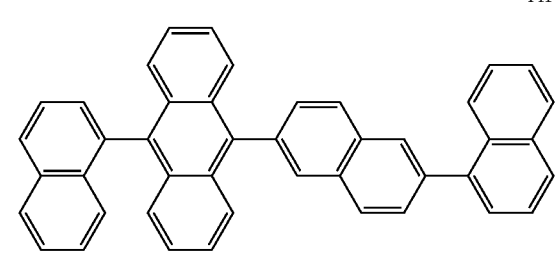
FH-42
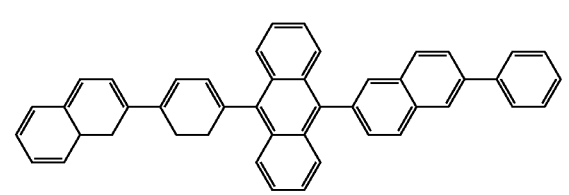
FH-48
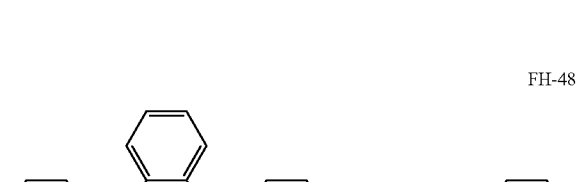
FH-43
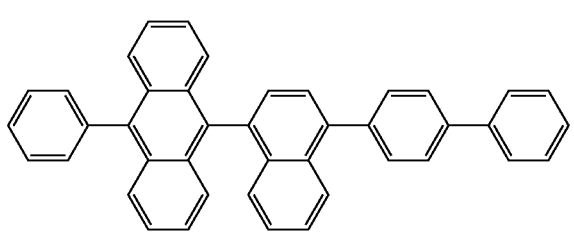
FH-49
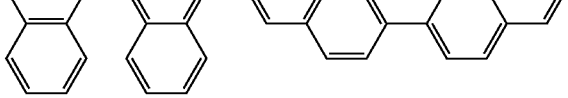
FH-44
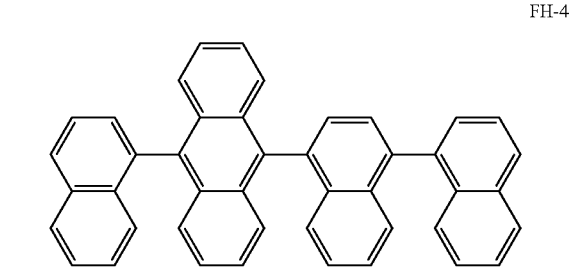
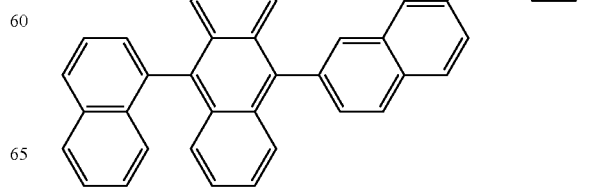

FH-50
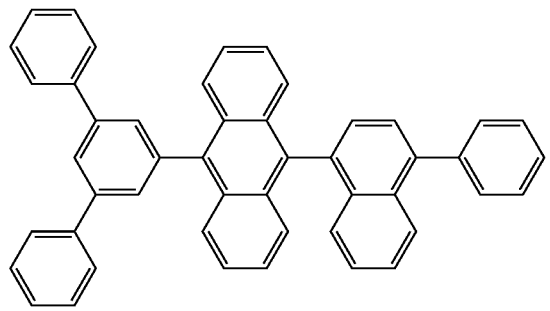
FH-51
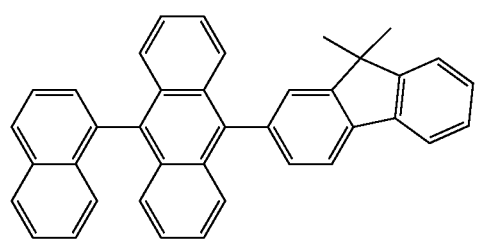
FH-52
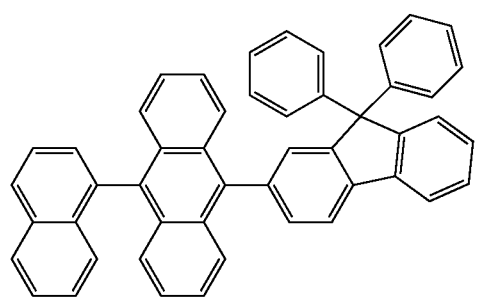
FH-53
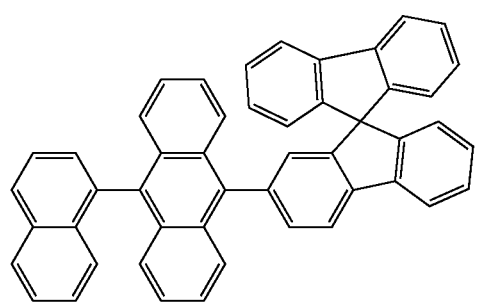
FH-54
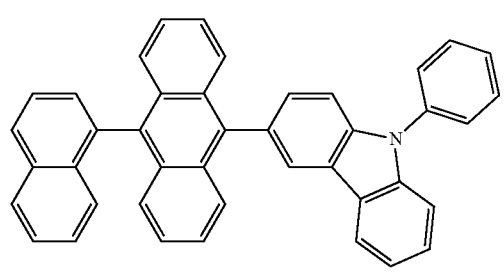
FH-55
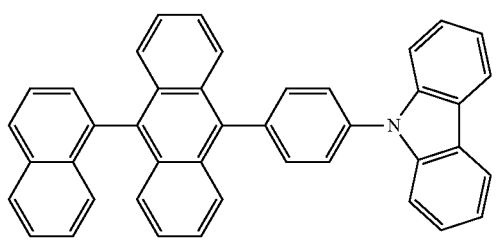
FH-56
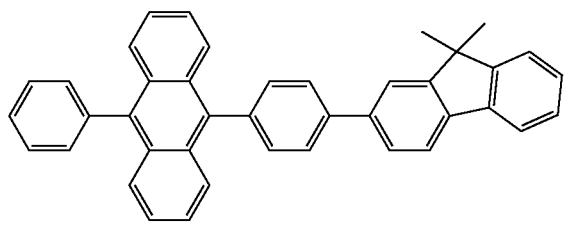
FH-57
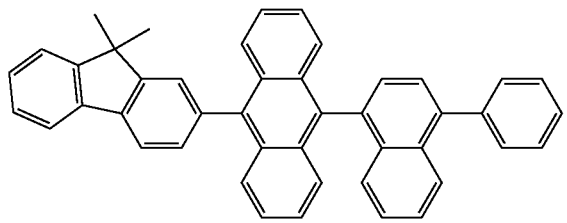
FH-58
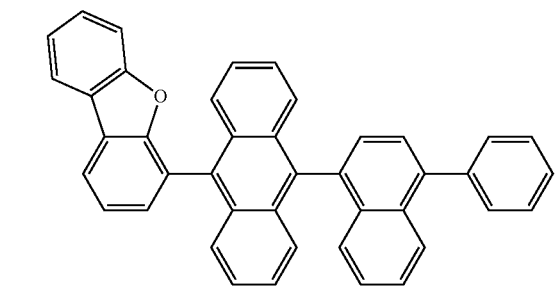
FH-59
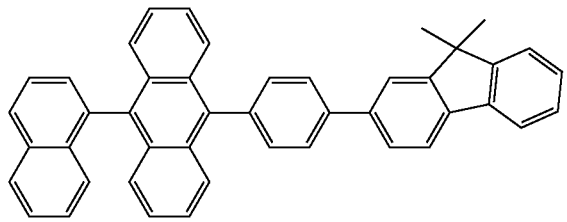
FH-60
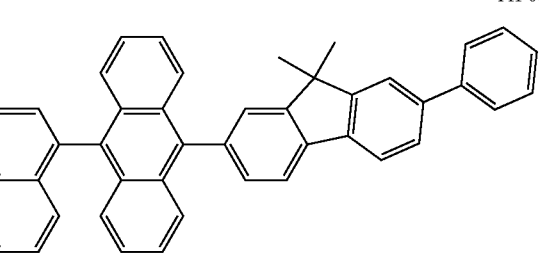

FH-61
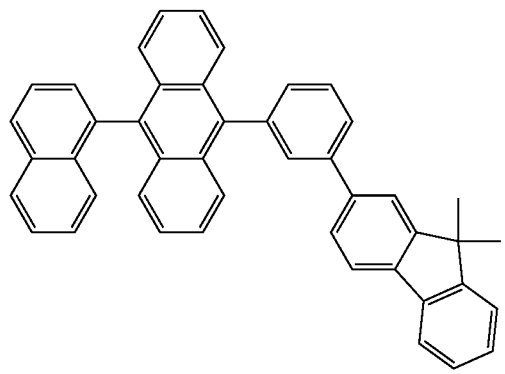
FH-62
FH-63
FH-64
FH-65
FH-66
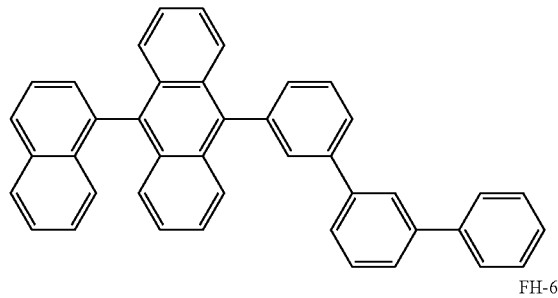
FH-67
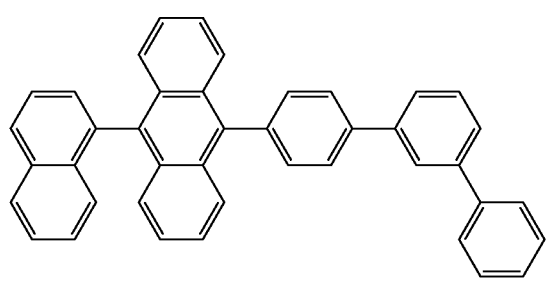
FH-68
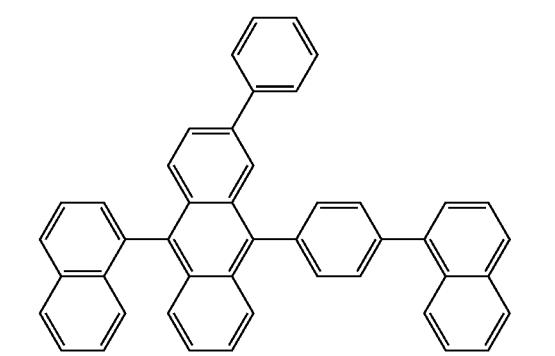
FH-69
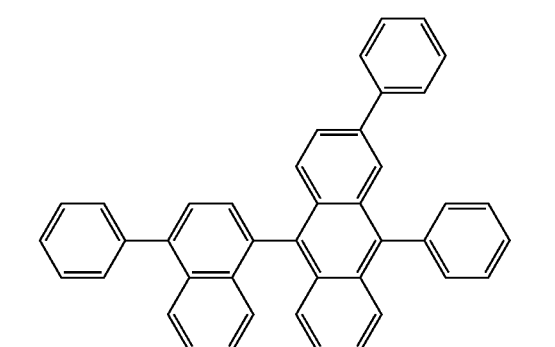
FH-70
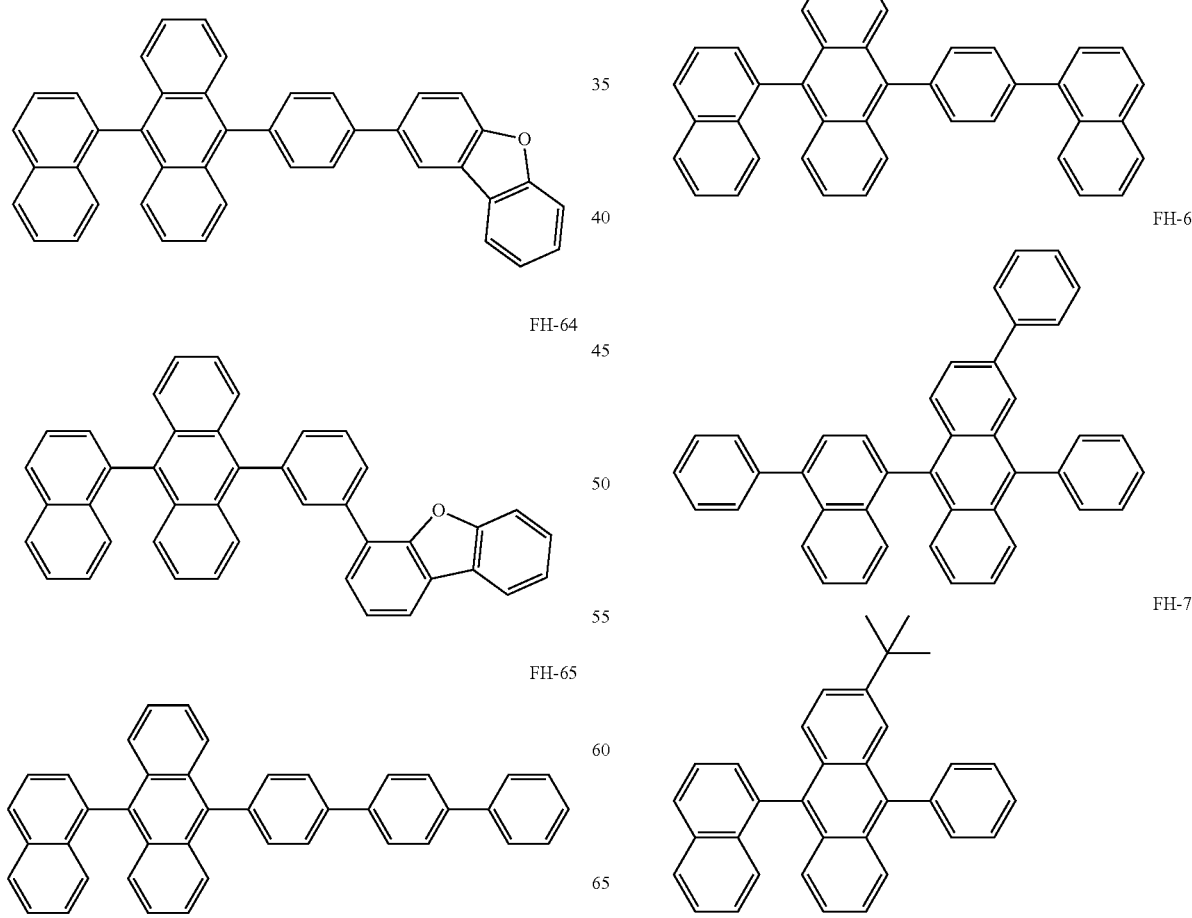

FH-71
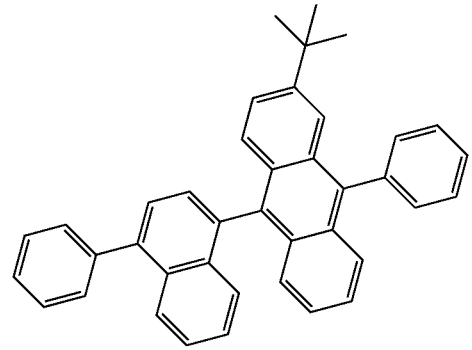

FH-72
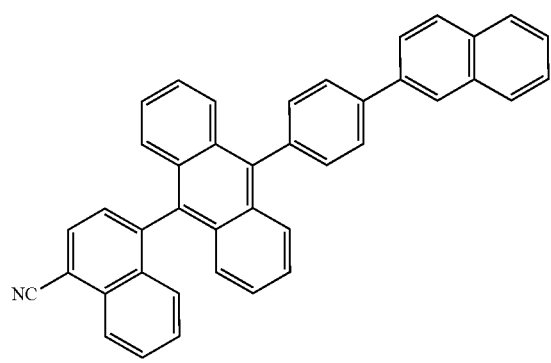

FH-73
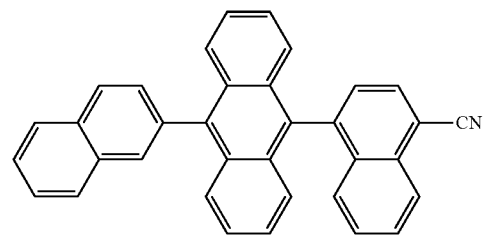

FH-74
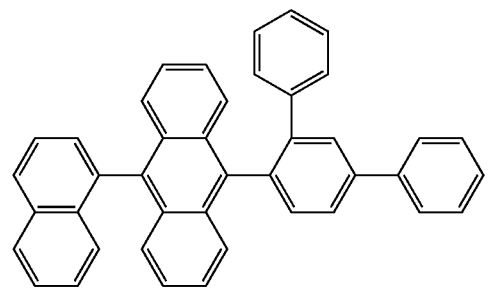

FH-75
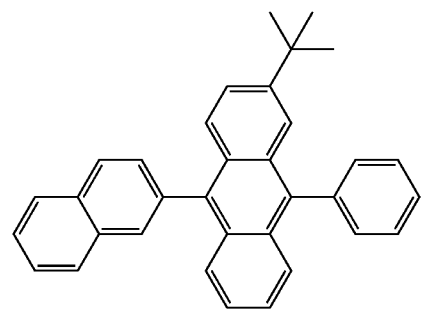

FH-76
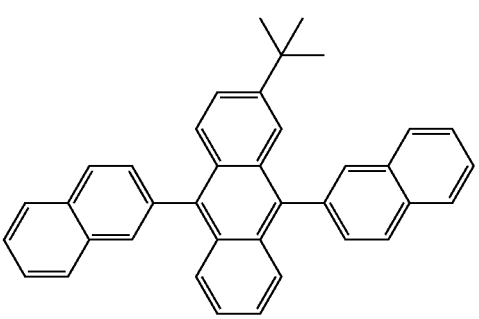

FH-77

FH-78

Further, A is a group having a singlet host function (fluorescent host function), in this case, A core group is selected from a group containing a cyclic aromatic hydrocarbon, a group containing an aromatic heterocyclic ring, and a group having 2 to 10 rings; the group containing a cyclic aromatic hydrocarbon is selected from the group consisting of biphenyl, triphenyl, benzo, naphthalene, anthracene, phenalene, phenanthrene, fluorene, pyrene, chrysene, petylene, and azulene; the group containing an aromatic heterocyclic ring is selected from the group consisting of dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, isoxazole, thiazole, oxadiazole, oxytriazole, dioxazole, thiadiazole, pyridine, pyridazine, pyrimidine, pyrazine, triazine, oxazine, oxathiazine, oxadiazine, indole, benzimidazole, indazole, indolizine, benzoxazole, benzoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furan dipyridine, benzothiophene pyridine, thiophene dipyridine, benzoselenophene pyridine and selenophene dipyridine; each ring in the groups having 2 to 10 rings may be the cyclic aromatic hydrocarbon group or the aromatic heterocyclic group, may be each other linked together directly or by at least one of the following: an oxygen atom, a nitrogen atom, a sulfur atom, a silicon atom, a phosphorus atom, a boron atom, a chain aliphatic group, and an aliphatic ring group.

Further, when A is a group having a singlet host function, the core group of A is selected from the group consisting of the following groups:

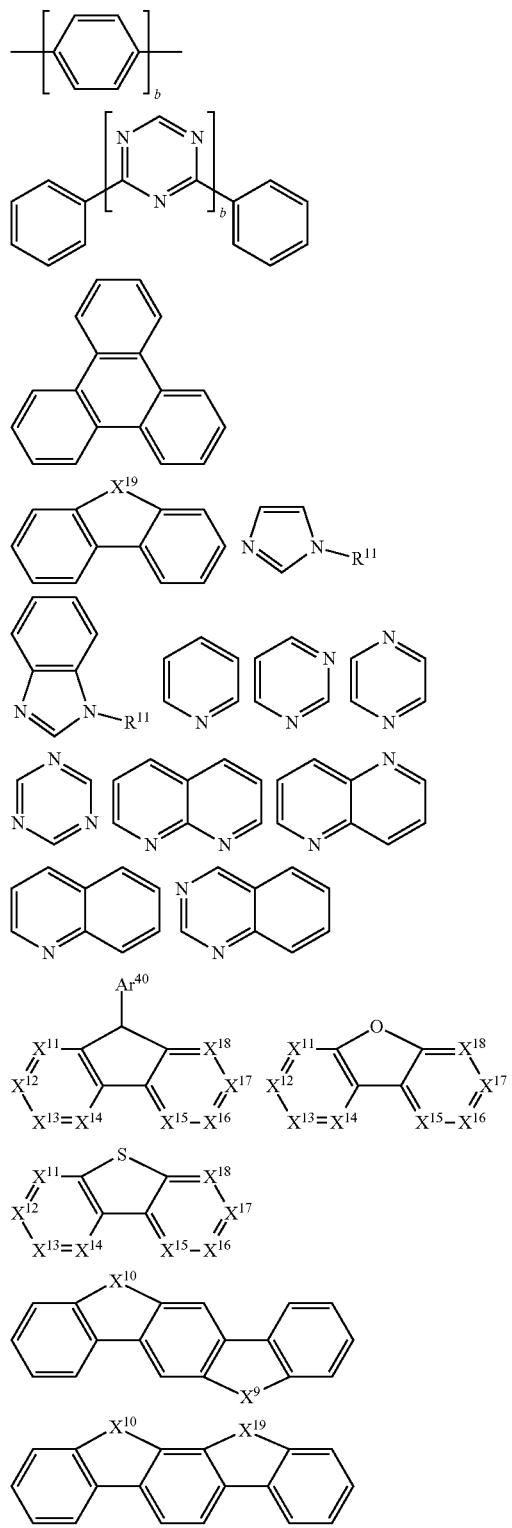

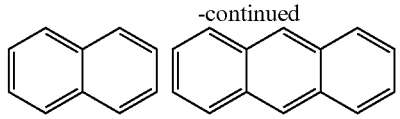

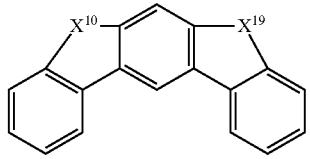

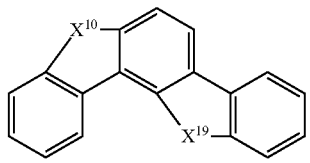

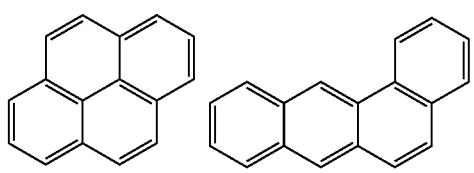

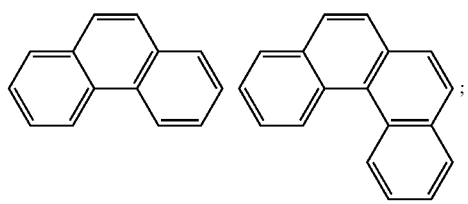

Wherein $R^{11}$ is selected from the group consisting of hydrogen, an alkyl group, an alkoxy group, an amino group, an alkenyl group, an alkynyl group, an aralkyl group, a heteroalkyl group, an aryl group and a heteroaryl group; $Ar^{40}$ is selected from the group consisting of an aromatic group containing 6 to 60 carbon atoms, an heteroaryl group containing 3 to 60 carbon atoms, a fused aromatic group containing 6 to 60 carbon atoms, and an fused heteroaryl group containing 3 to 60 carbon atoms; b is any of integers from 0 to 20; $X^{11}$ to $X^{18}$ are each independently selected from the group consisting of CH and N; $X^{19}$ and $X^{10}$ are each independently selected from $CR^1R^2$ and $NR^1$, respectively. $R^1$ and $R^2$ are defined as those in the structural formulas (1) to (6).

Further, A in the formula (I) is a group having a phosphorescent host function, and in this case, A having a phosphorescent host function is selected from the above structural formulas (3) to (6).

Further, when A is in the structural formula (3), the structural formula of A having a phosphorescent host function is selected from the groups

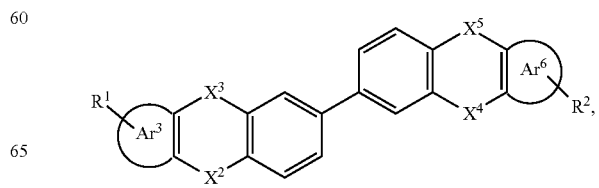

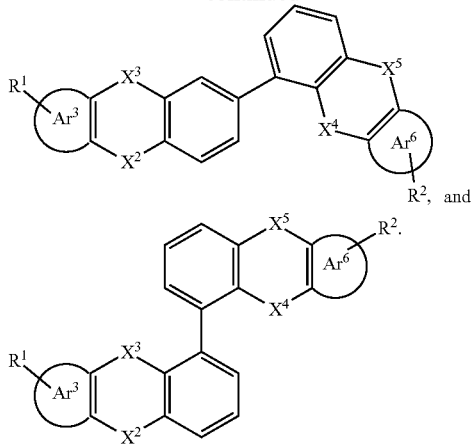

Wherein, Ar³, Ar⁶, X², X³, X⁴, X⁵, R¹ and R² have the same meanings as in the structural formula (3).

Further, according to the structural formula (3), the structural formula of A having a phosphorescent host function is as follows:

Wherein, $R^1$, $R^2$, $L^1$ and $L^2$ have the same meanings as in the structural formulas (3) to (6); $L^3$ is selected from an aromatic group containing 5 to 60 ring atoms and an heteroaryl group containing 5 to 60 ring atoms; further, $L^3$ is selected from an aromatic group containing 5 to 50 ring atoms and an heteroaryl group containing 5 to 50 ring atoms; further, $L^3$ is selected from an aromatic group containing 5 to 40 ring atoms and an heteroaryl group containing 5 to 40 ring atoms; further, $L^3$ is selected from an aromatic group containing 6 to 30 ring atoms and an heteroaryl group containing 6 to 30 ring atoms;

Specifically, according to the structural formula (3), the group A having a phosphorescent host function in the general formula (I) and (IV) is selected from one of, but not limited to, the following groups:

(3-1)
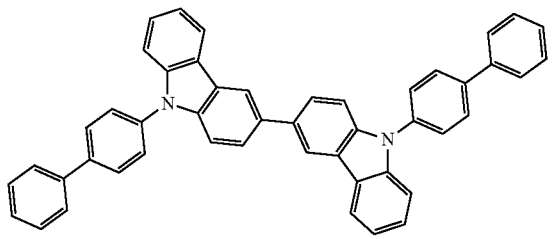

(3-2)
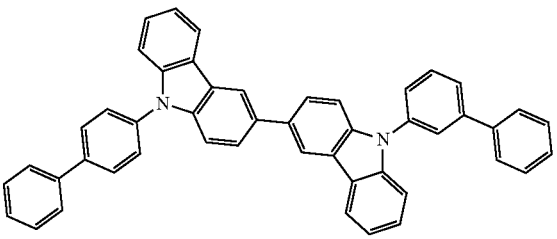

(3-3)
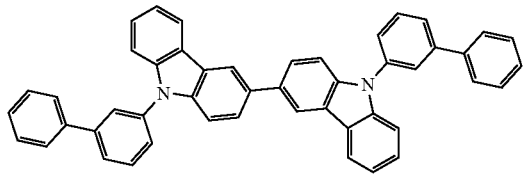

(3-4)
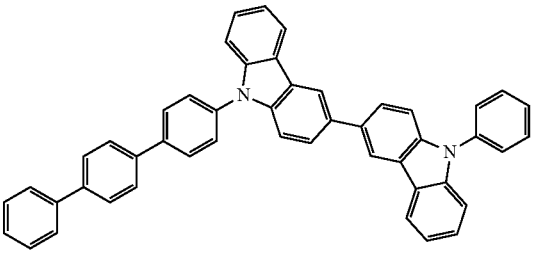

(3-5)
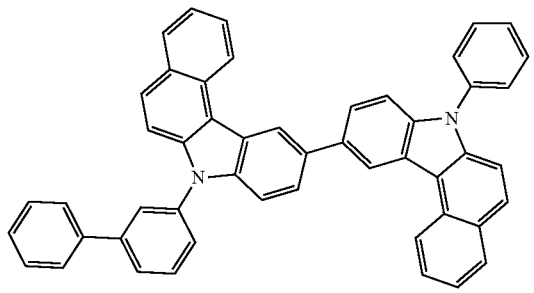

(3-6)
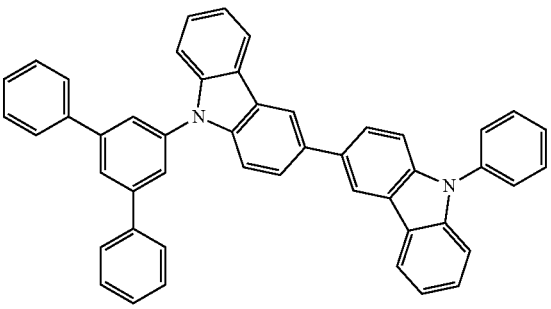

(3-7)
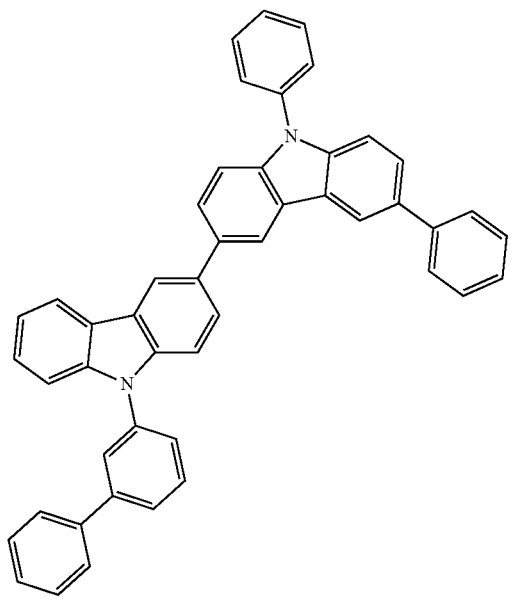
(3-8)
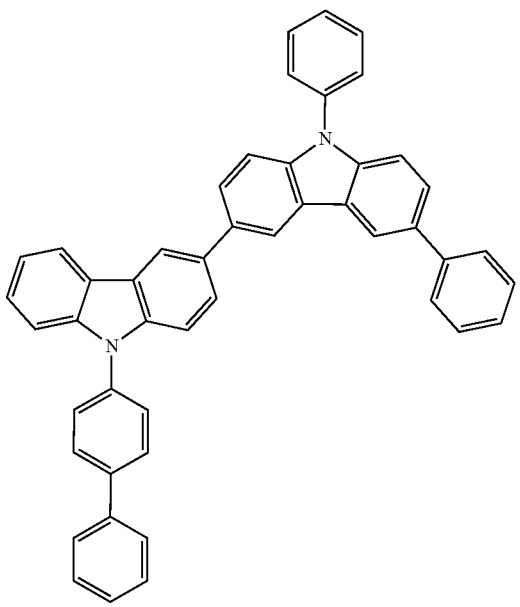
(3-9)
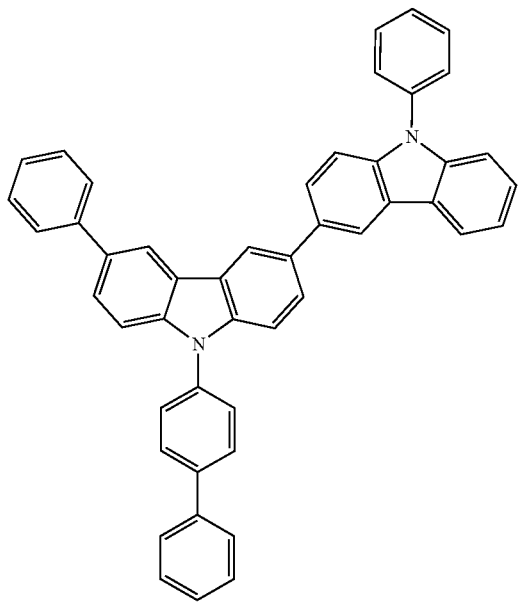
(3-10)
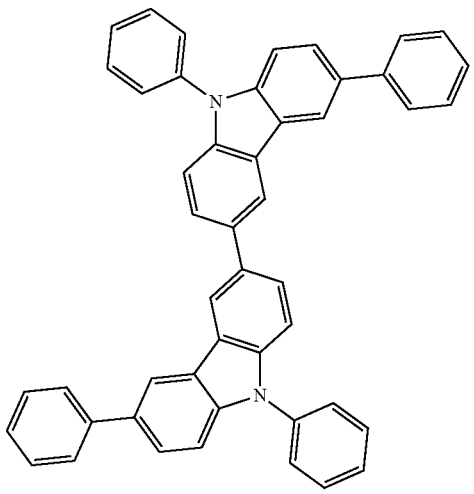
(3-11)
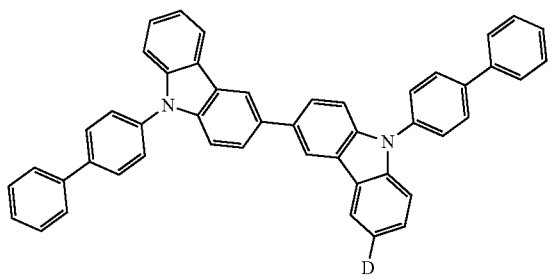
(3-12)
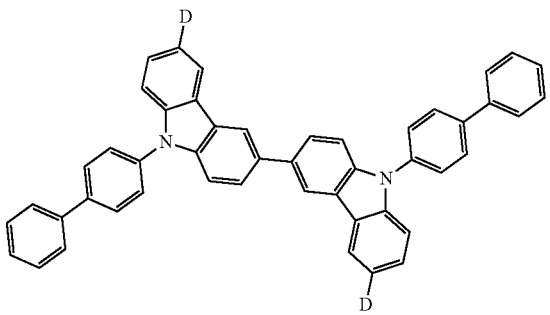

-continued
(3-13)
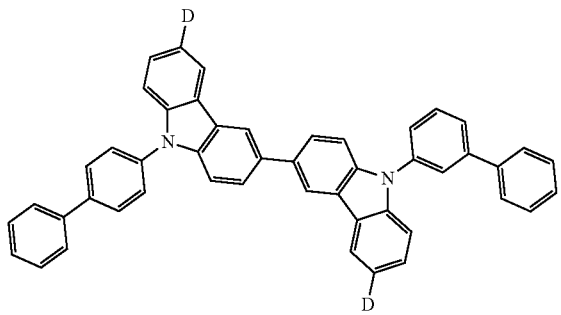
(3-14)
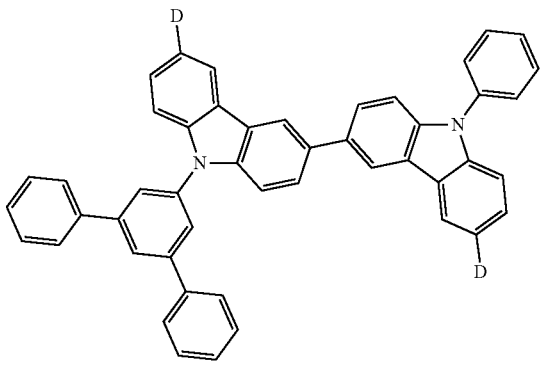
(3-15)
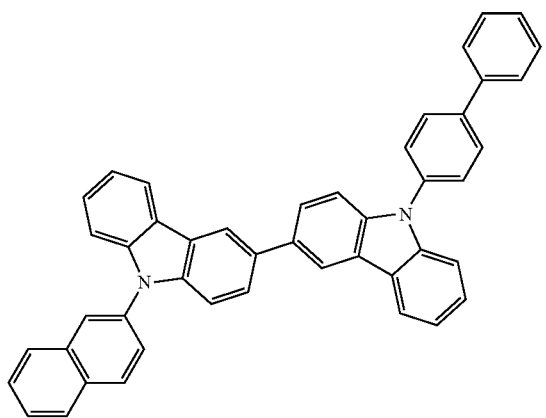
(3-16)
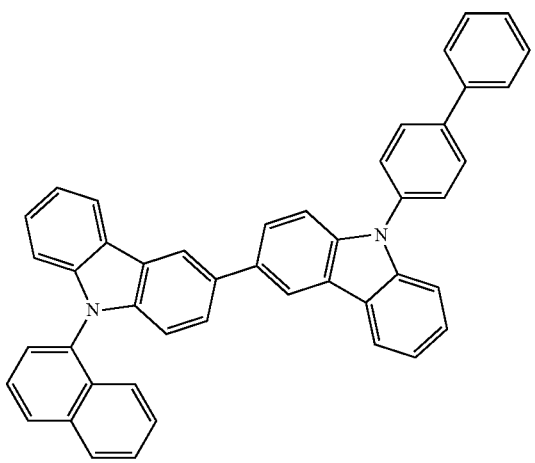
(3-17)
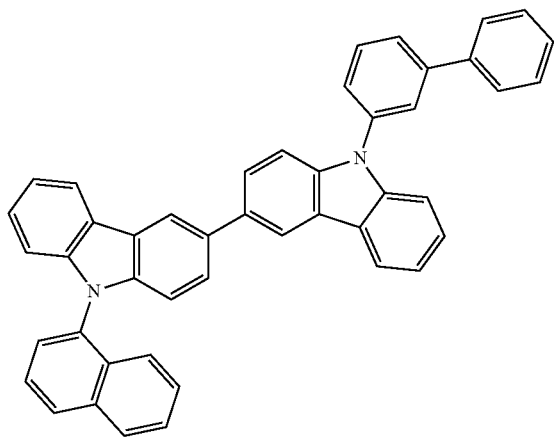
(3-18)
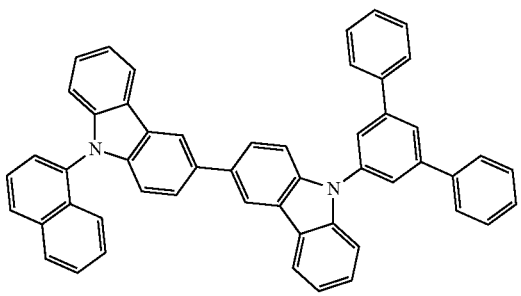
(3-19)
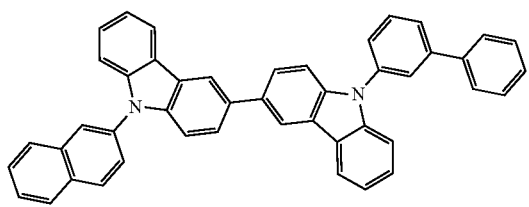
(3-20)
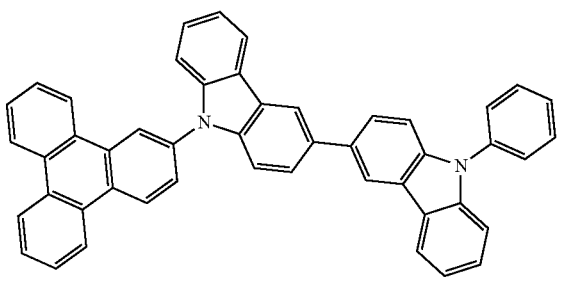

-continued
(3-21)
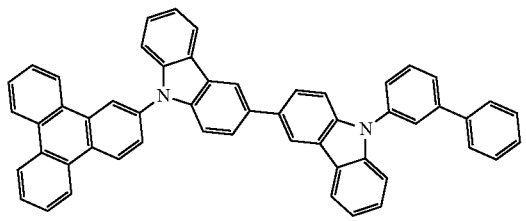
(3-22)
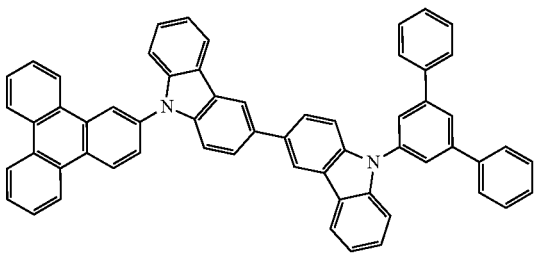
(3-23)
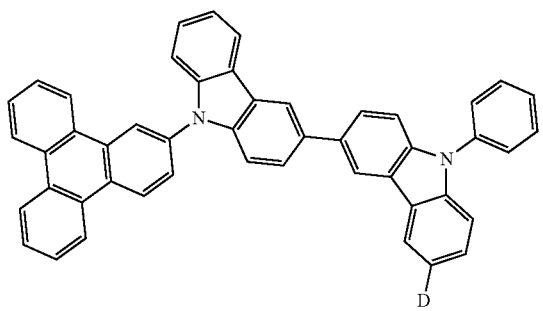
(3-24)
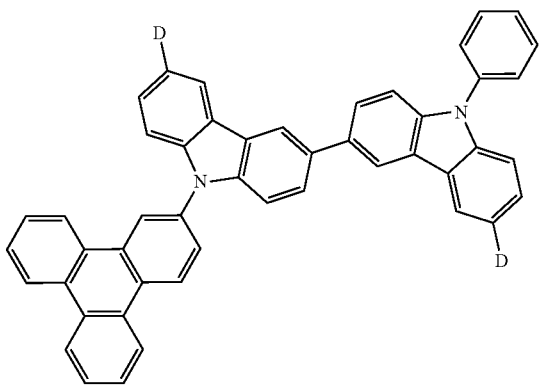
(3-25)
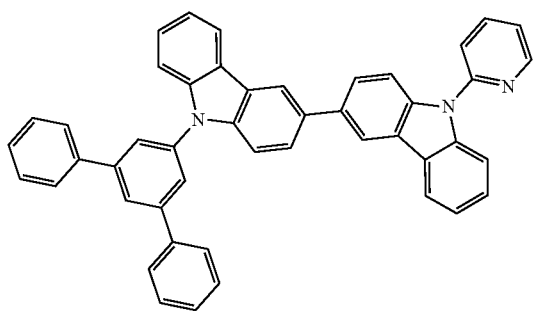
(3-26)
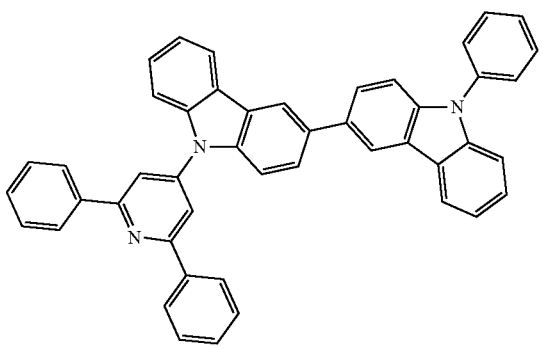
(3-27)
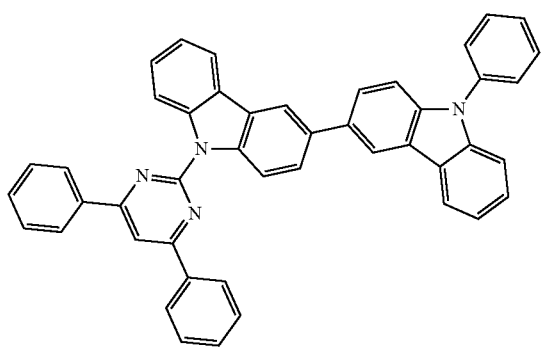
(3-28)
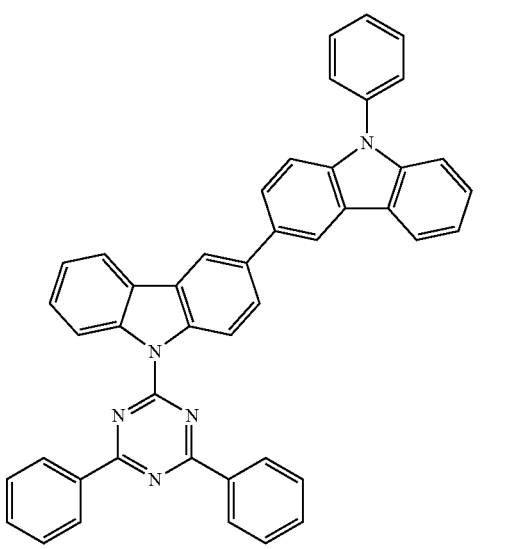

-continued
(3-29)
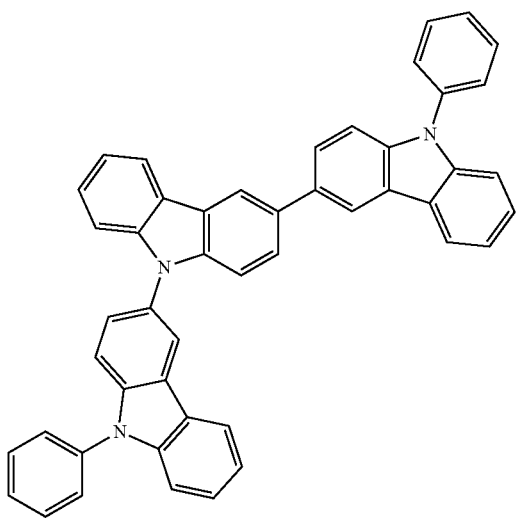
(3-30)
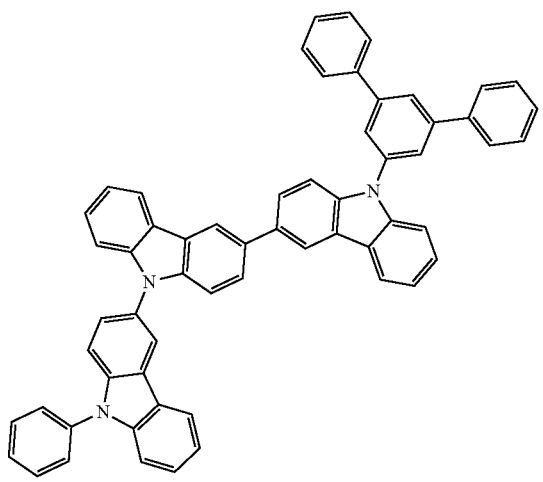
(3-31)
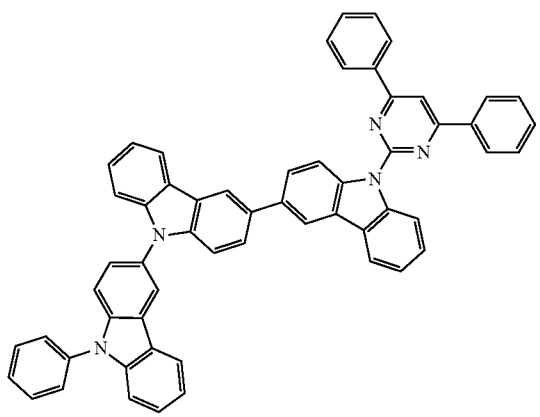
(3-32)
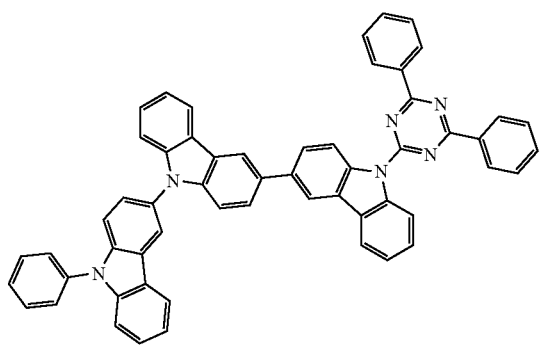
(3-33)
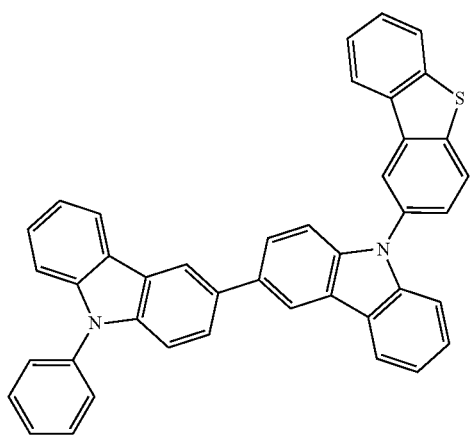
(3-34)
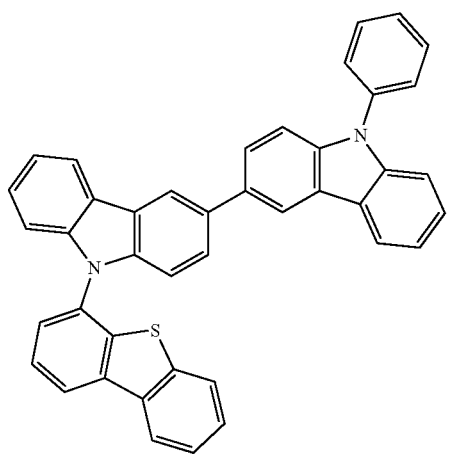

-continued
(3-35)
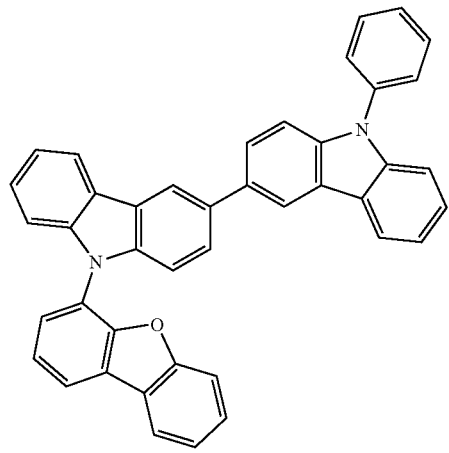
(3-36)
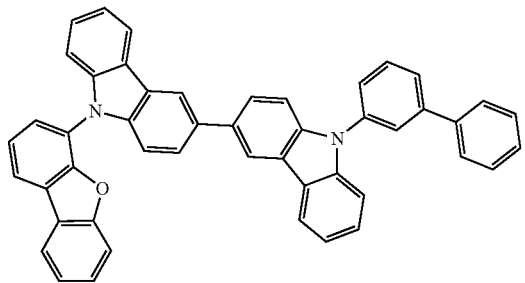
(3-37)
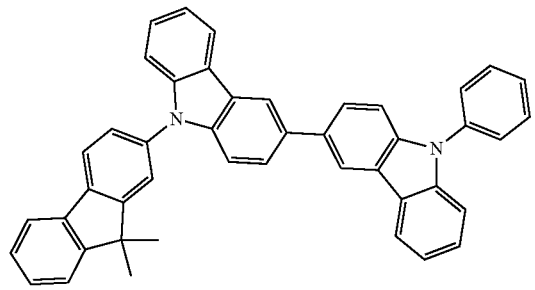
(3-38)
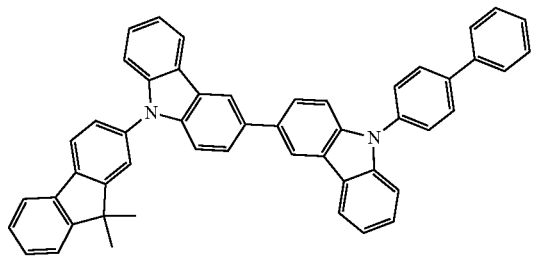
(3-39)
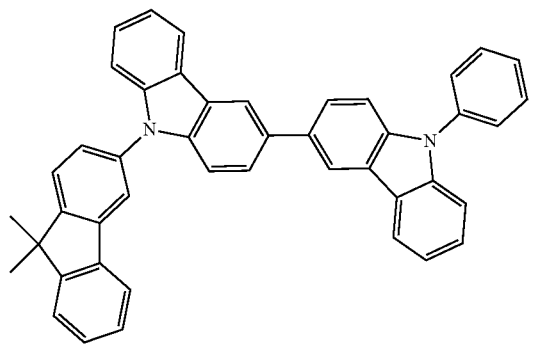
(3-40)
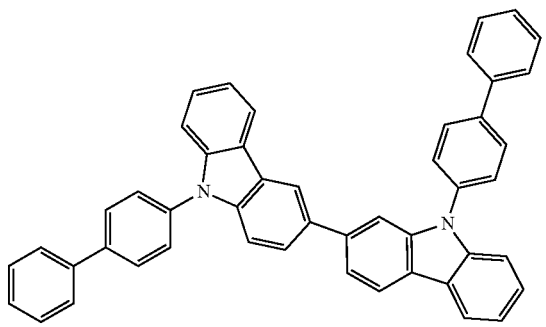
(3-41)
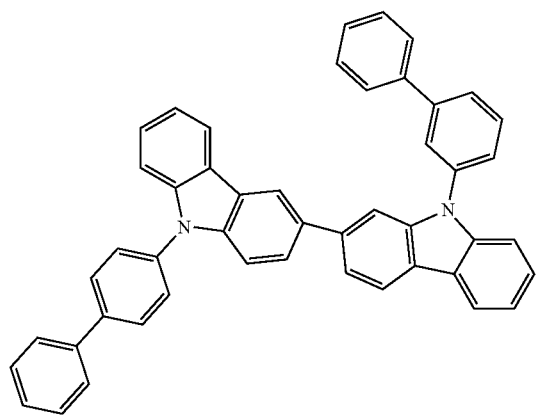
(3-42)
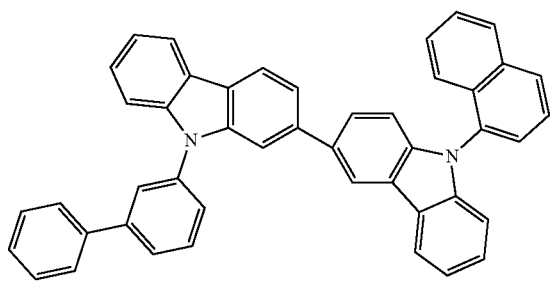

(3-43)
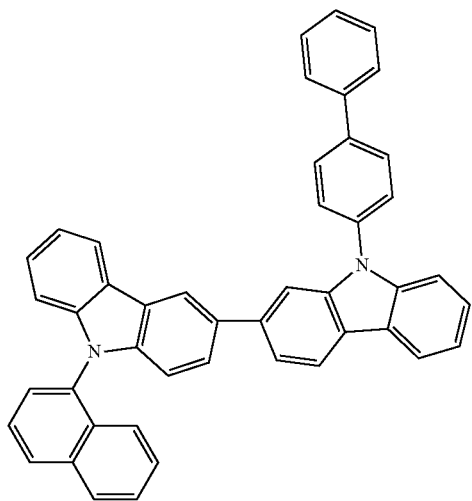
(3-44)
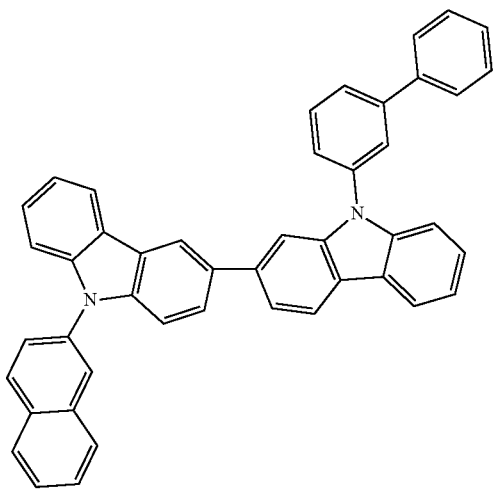
(3-45)
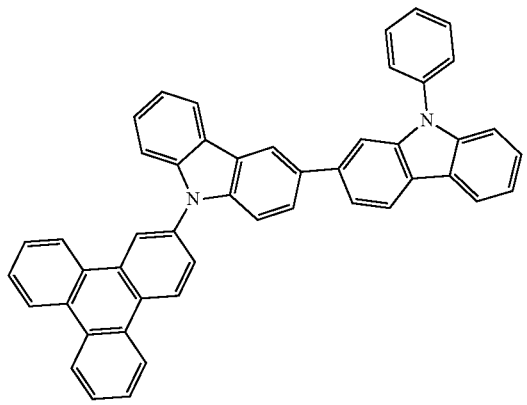
(3-46)
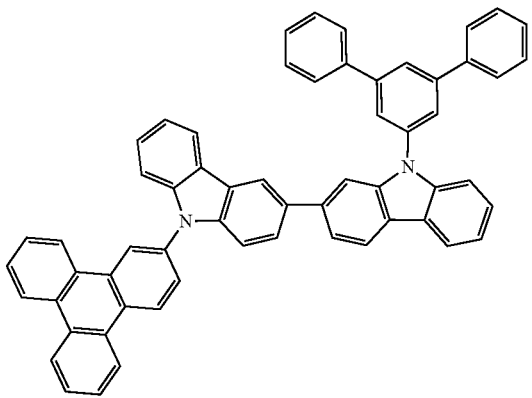
(3-47)
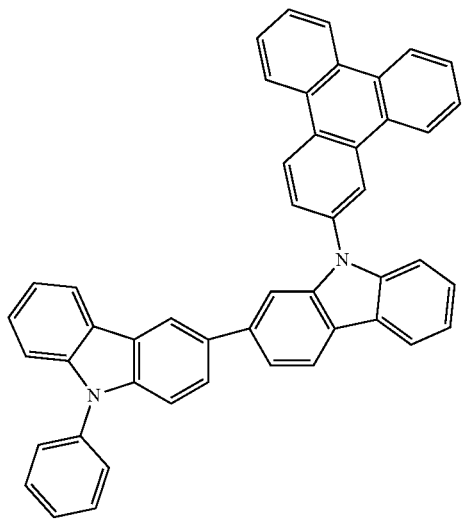
(3-48)
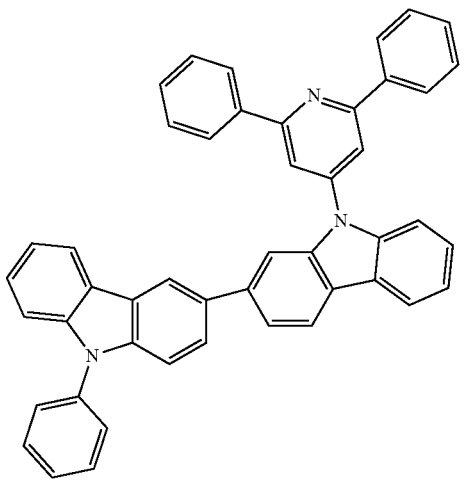

-continued
(3-49)
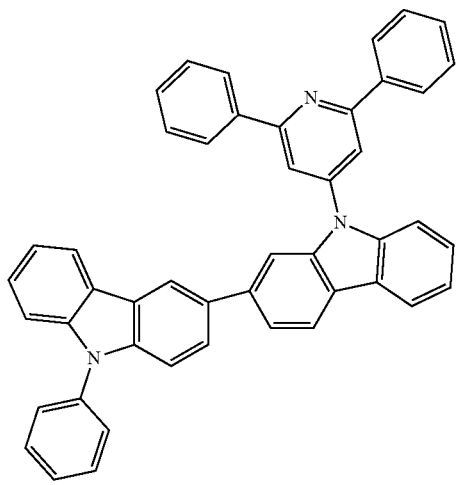
(3-50)
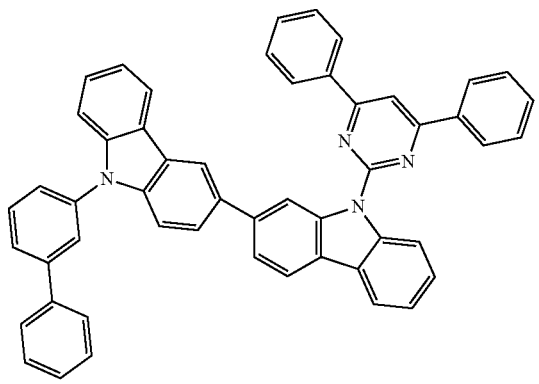
(3-51)
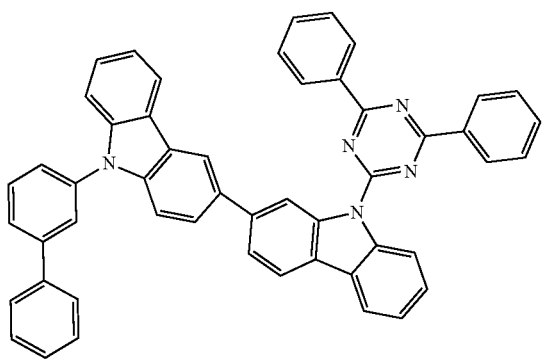
(3-52)
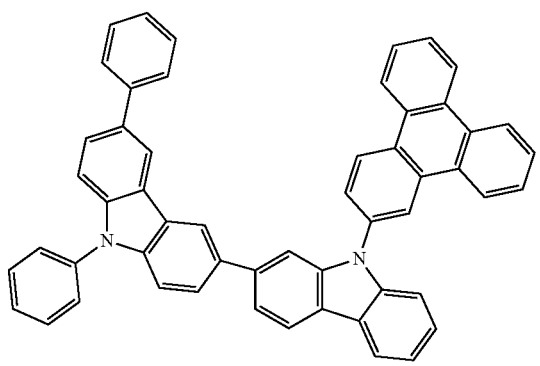
(3-53)
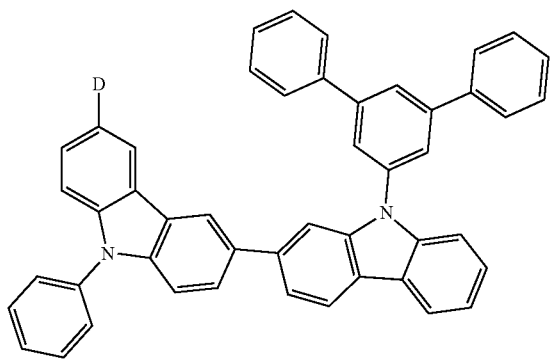
(3-54)
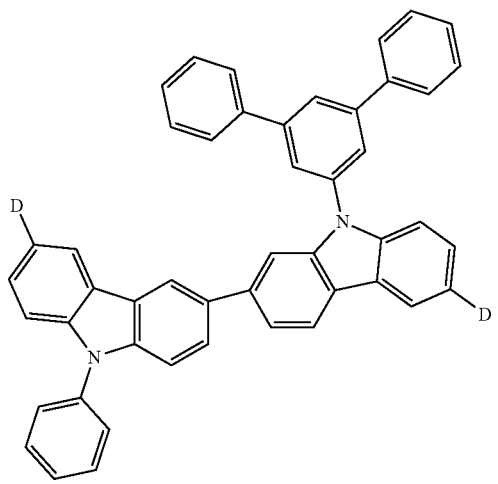

-continued
(3-55)
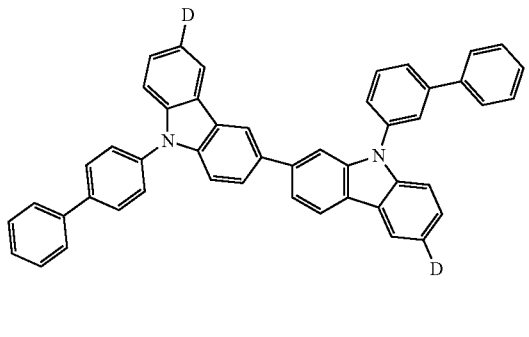
(3-56)
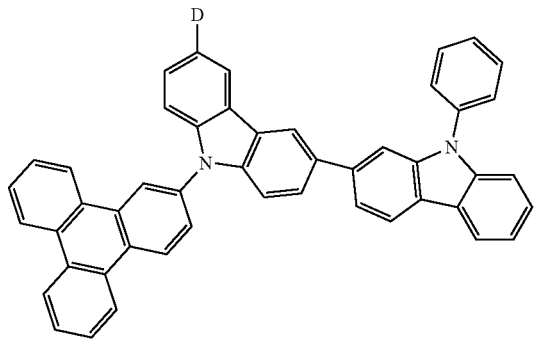
(3-57)
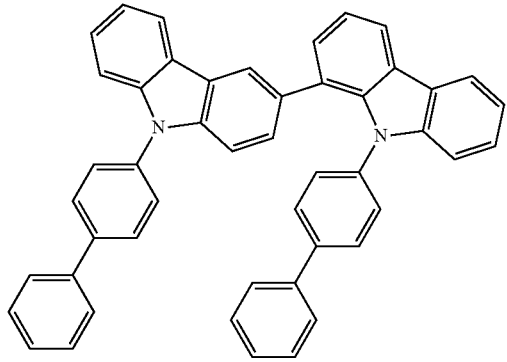
(3-58)
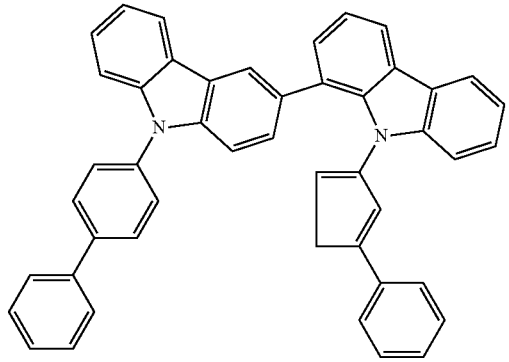
(3-59)
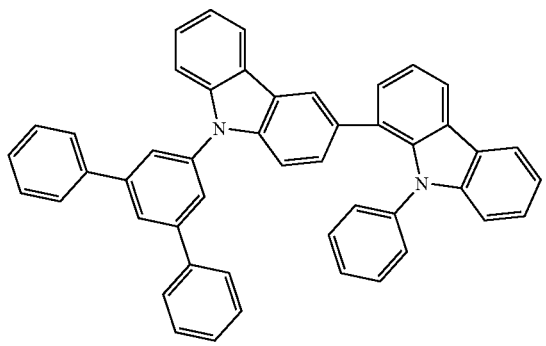
(3-60)
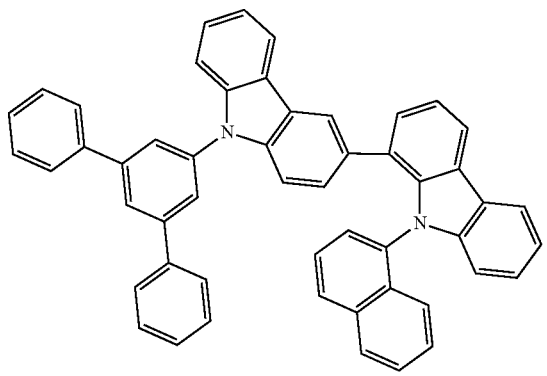
(3-61)
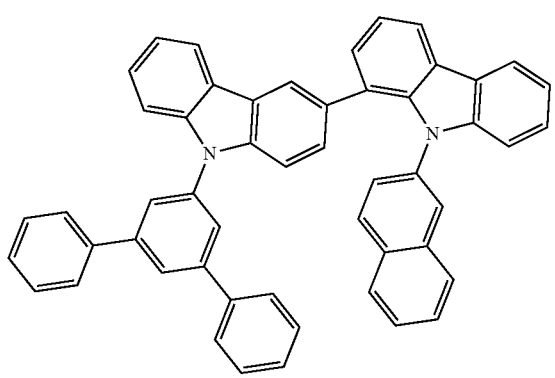
(3-62)
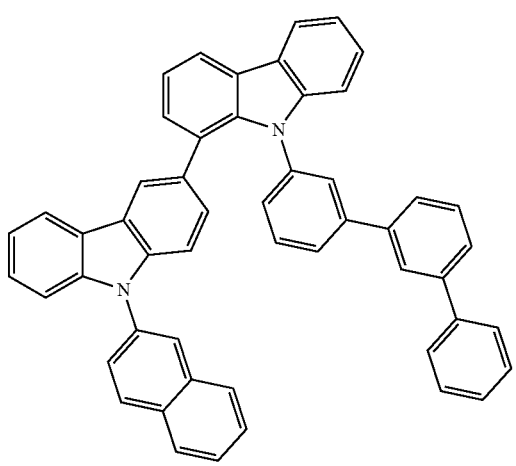

(3-63)
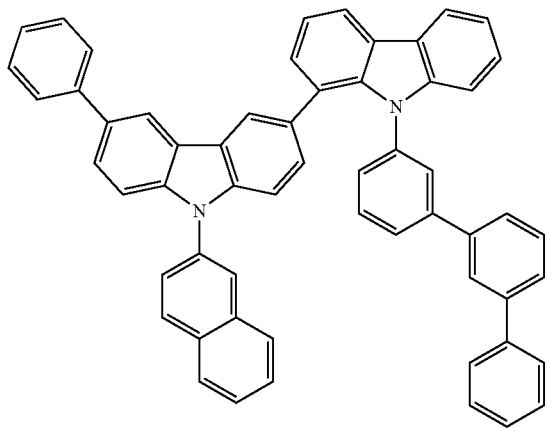
(3-64)
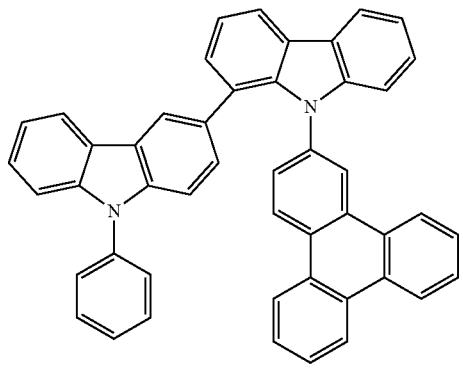
(3-65)
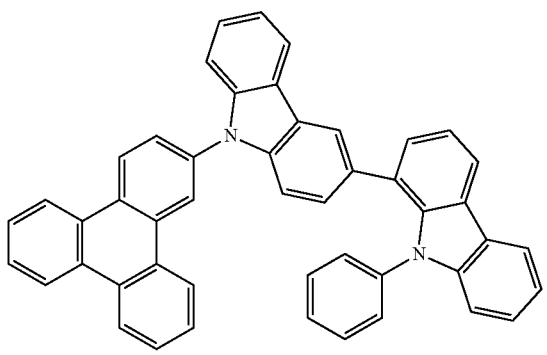
(3-66)
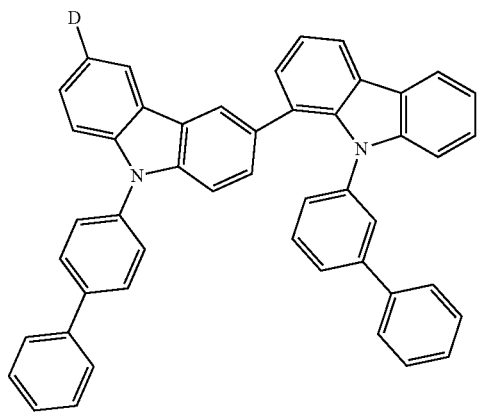
(3-67)
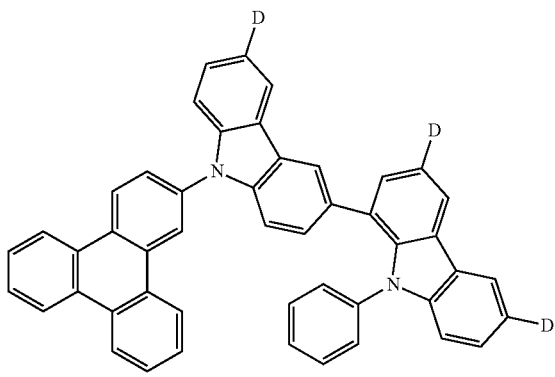
(3-68)
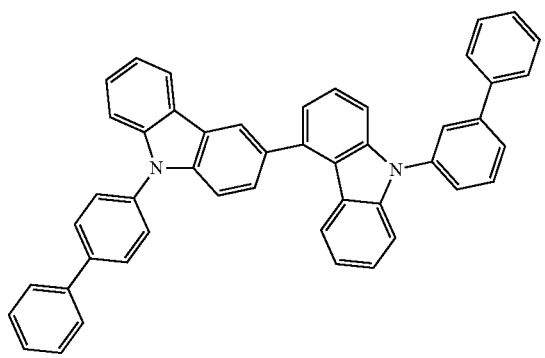

(3-69)
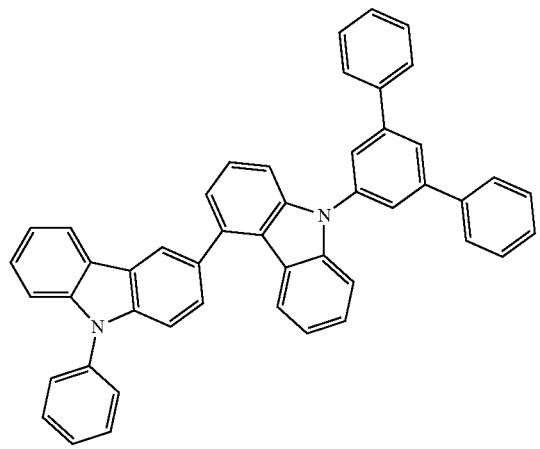
(3-70)
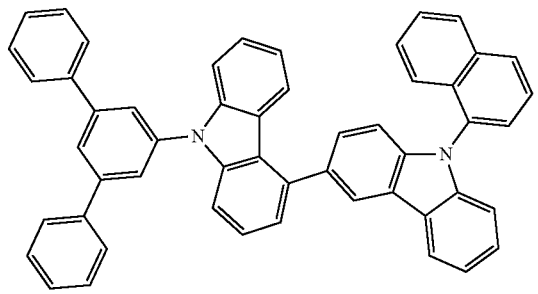
(3-71)
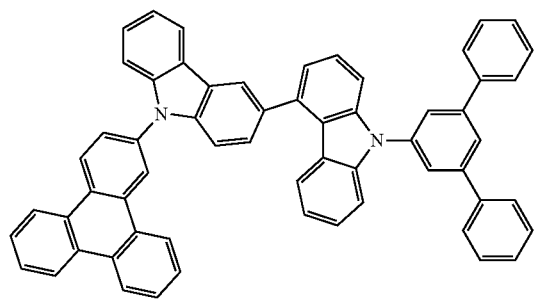
(3-72)
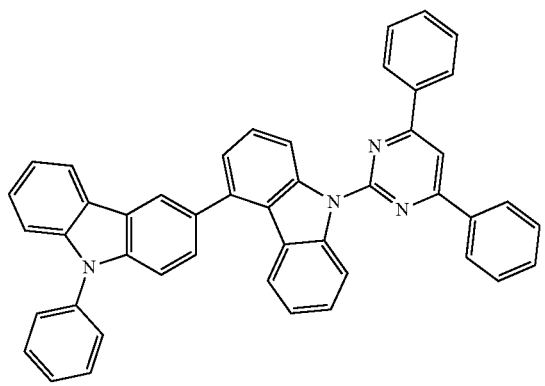
(3-73)
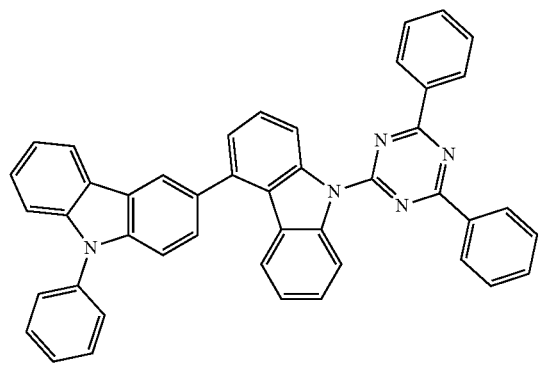
(3-74)
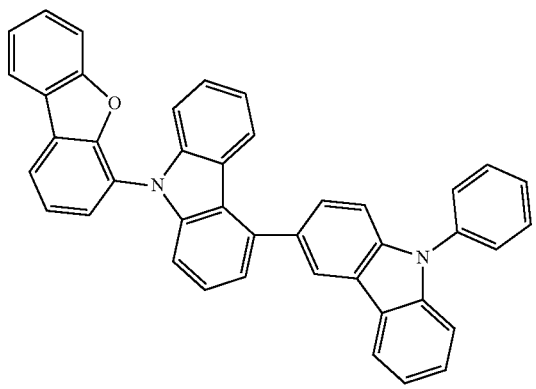

-continued
(3-75)
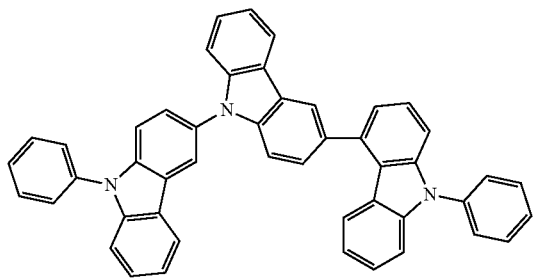
(3-76)
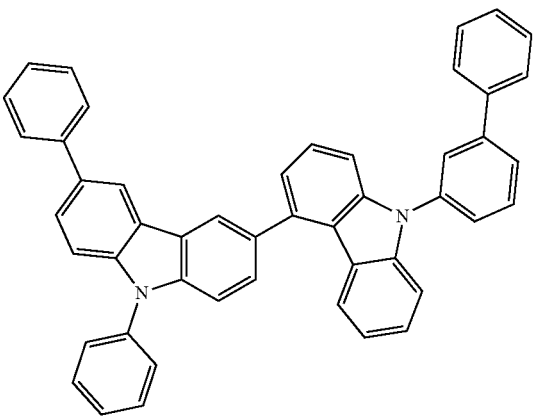
(3-77)
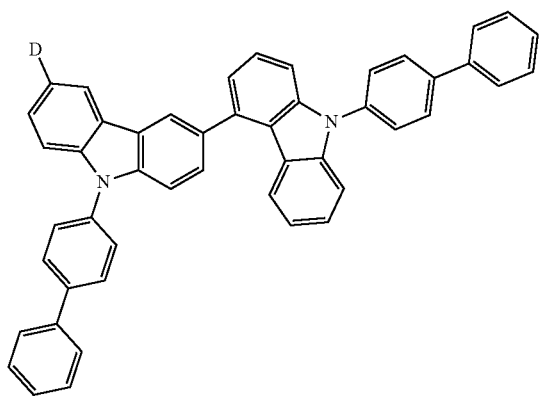
(3-78)
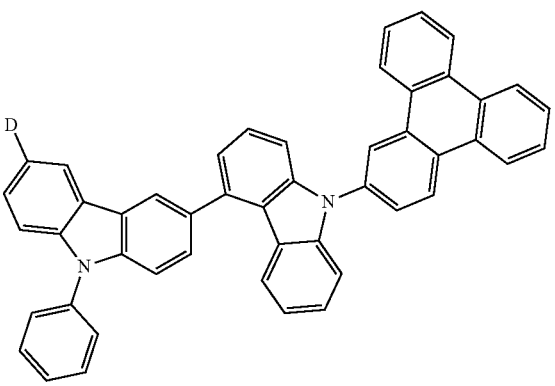
(3-79)
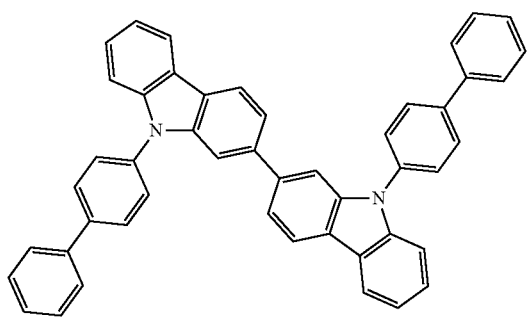
(3-80)
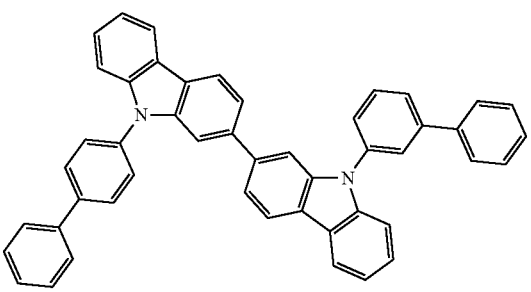
(3-81)
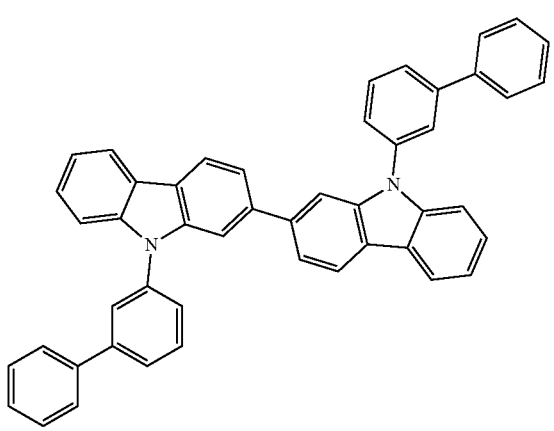
(3-82)
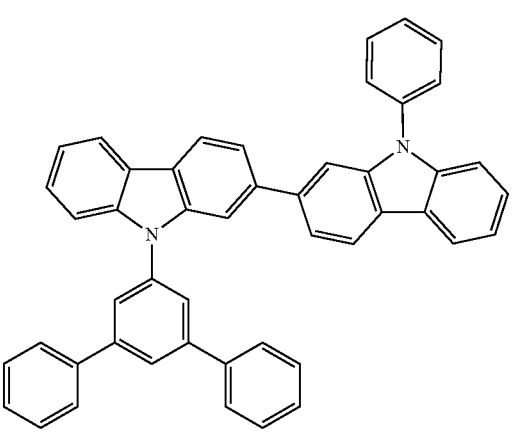

-continued
(3-83)
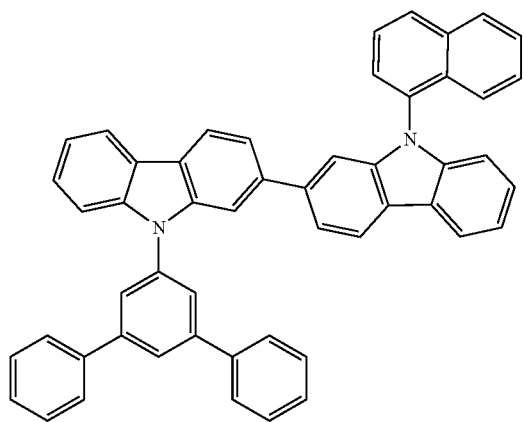
(3-84)
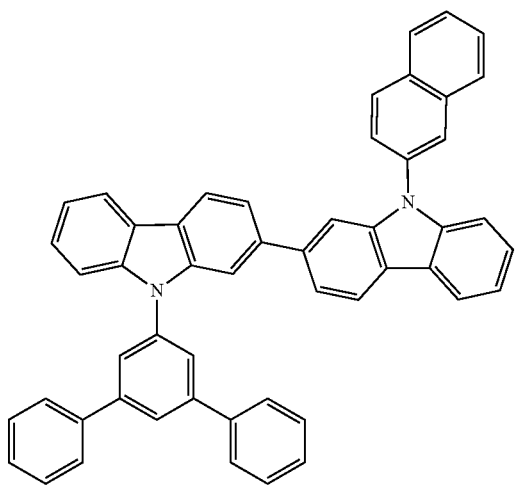
(3-85)
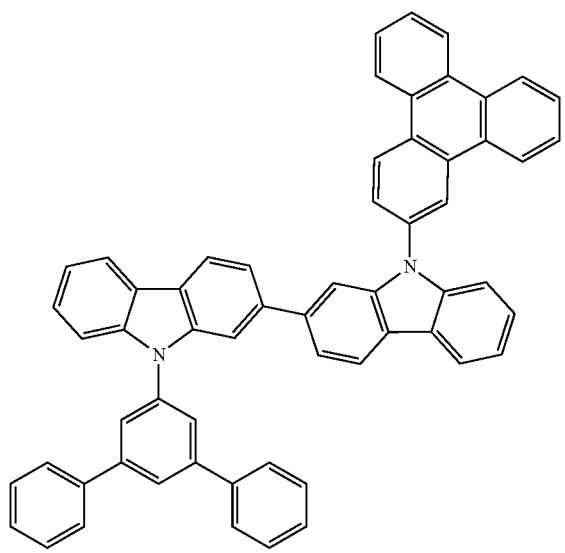
(3-86)
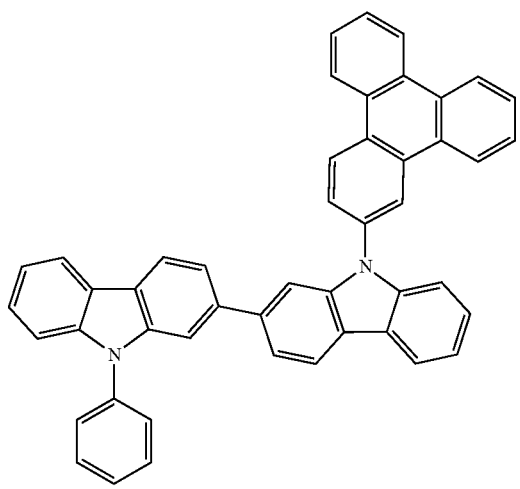
(3-87)
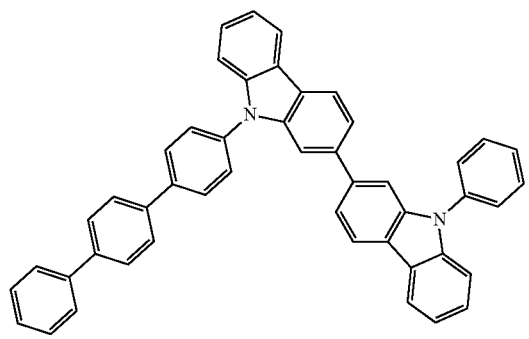
(3-88)
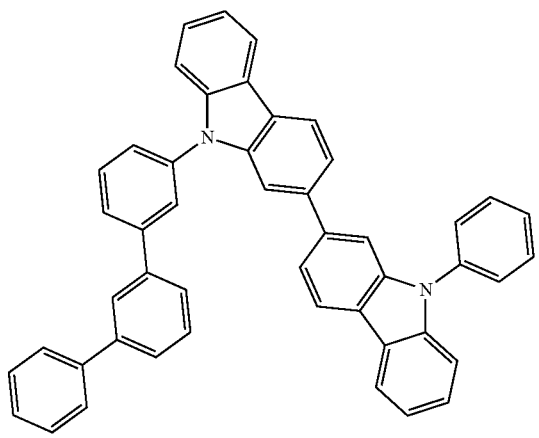

(3-89)
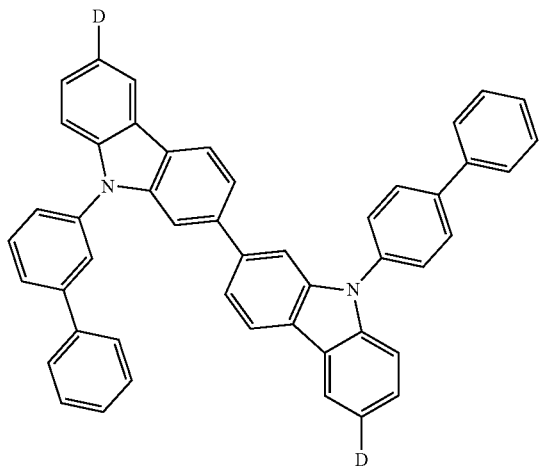
(3-90)
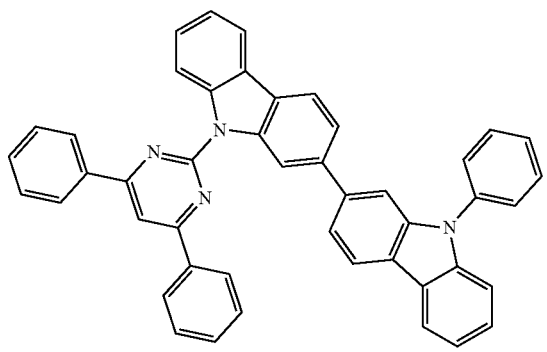
(3-91)
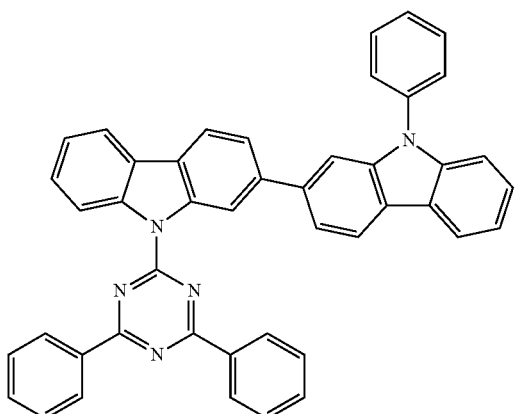
(3-92)
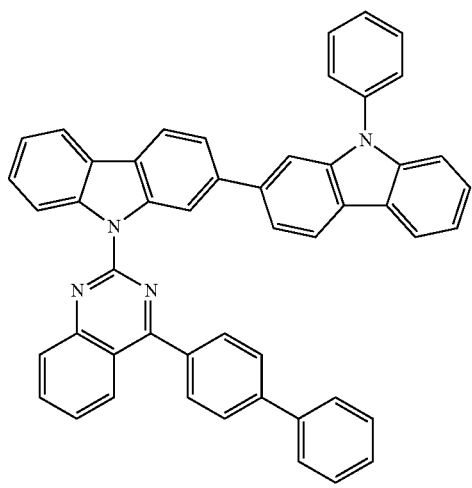
(3-93)
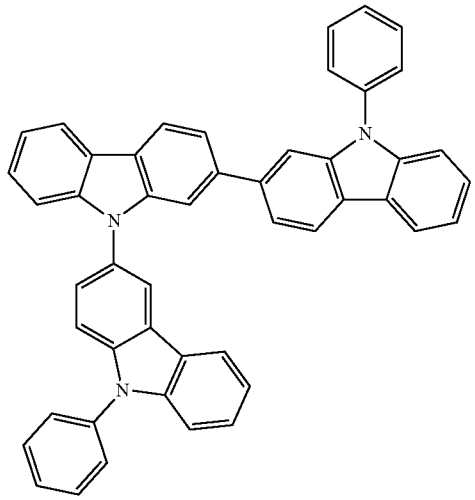
(3-94)
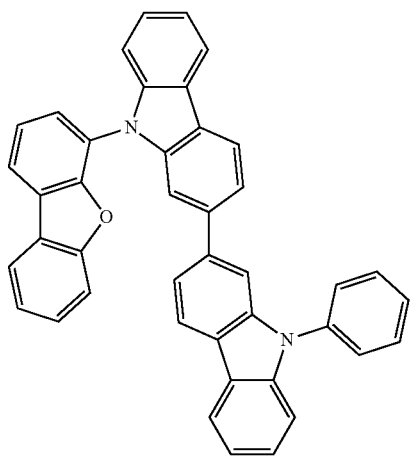

-continued
(3-95)
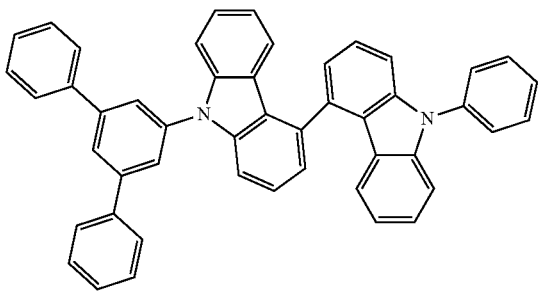
(3-96)
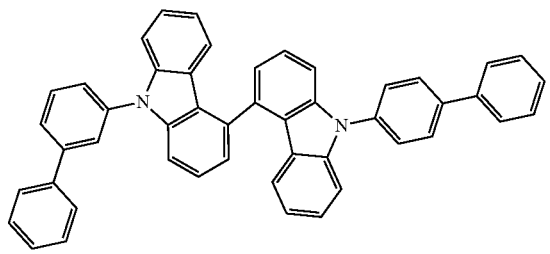
(3-97)
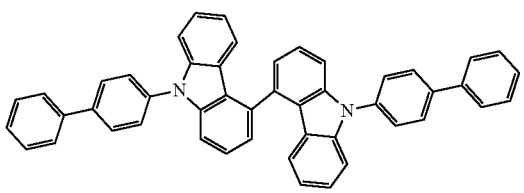
(3-98)
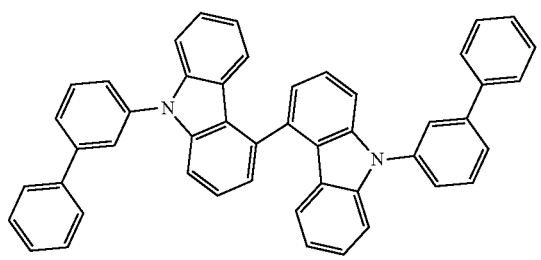
(3-99)
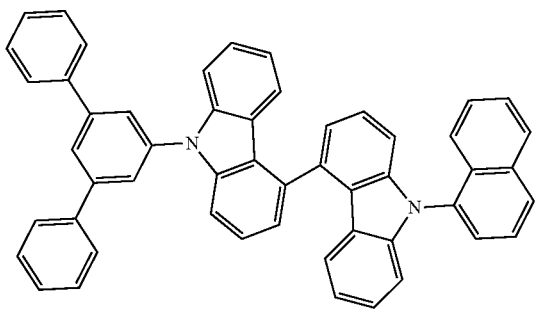
(3-100)
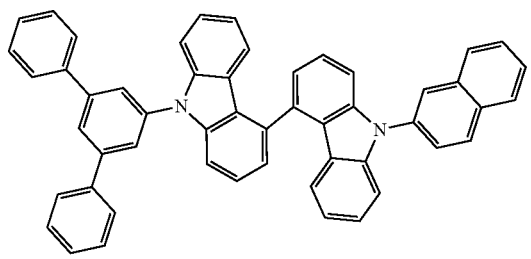
(3-101)
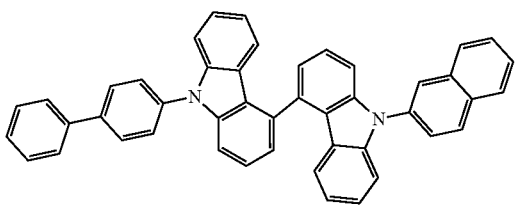
(3-102)
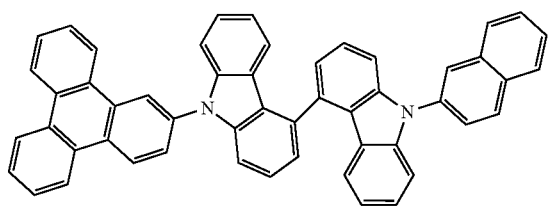
(3-103)
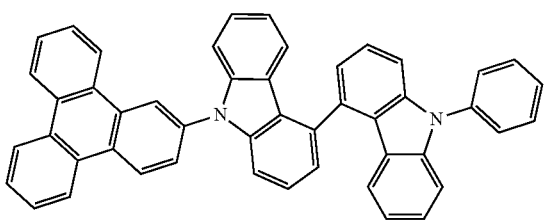
(3-104)
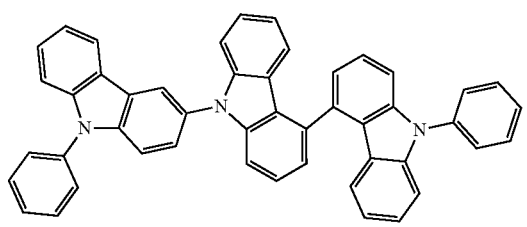

-continued
(3-105)
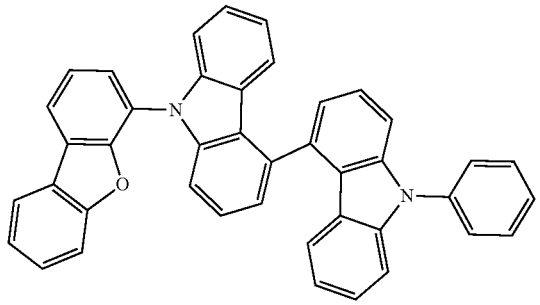
(3-106)
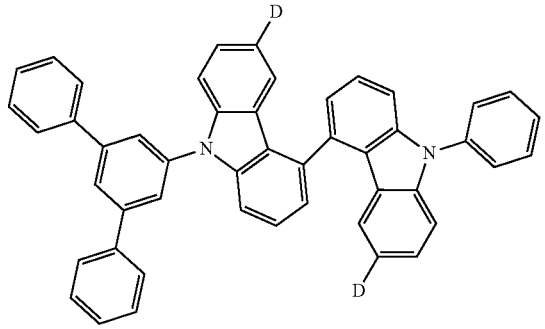
(3-107)
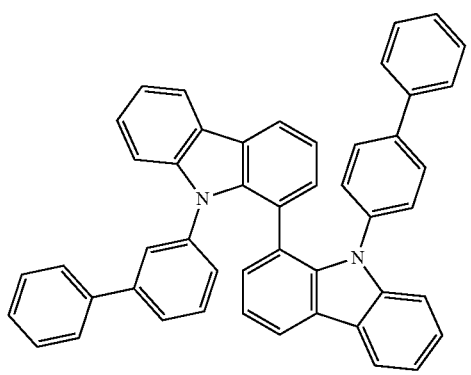
(3-108)
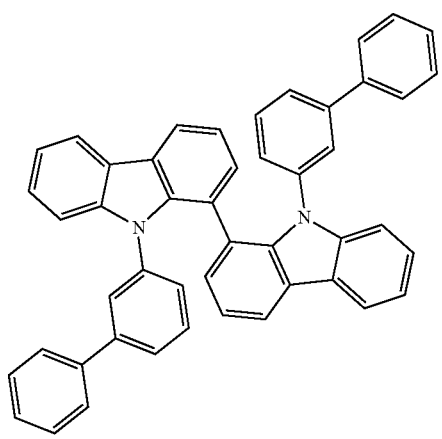
(3-109)
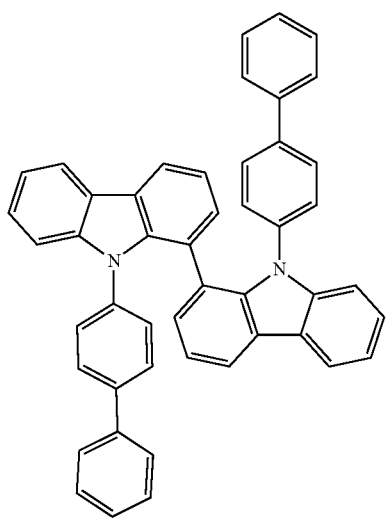
(3-110)
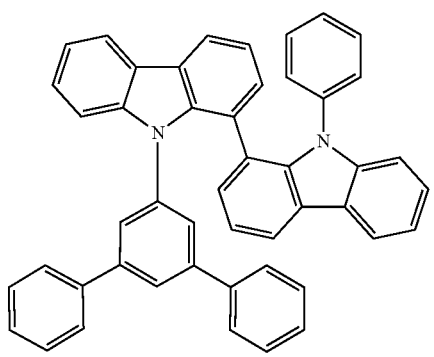

-continued
(3-111)
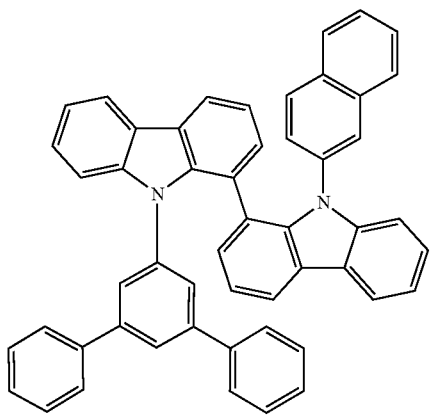
(3-112)
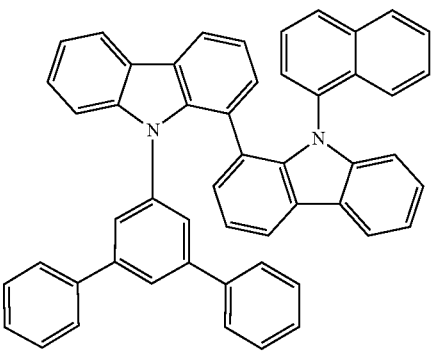
(3-113)
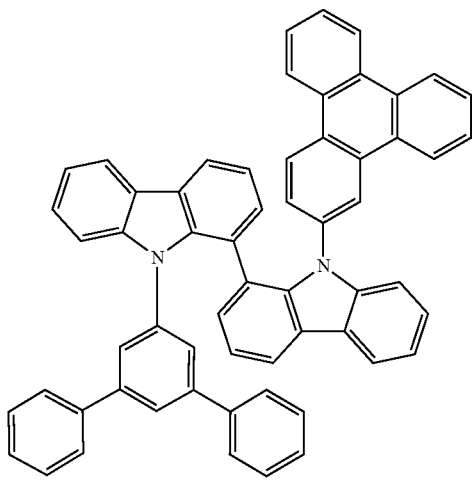
(3-114)
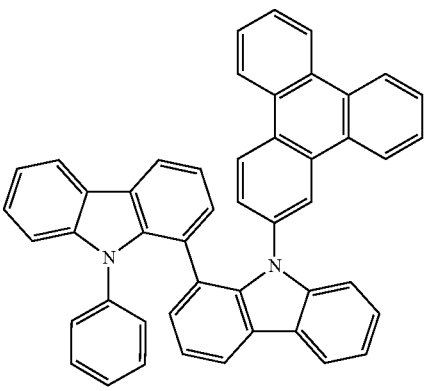
(3-115)
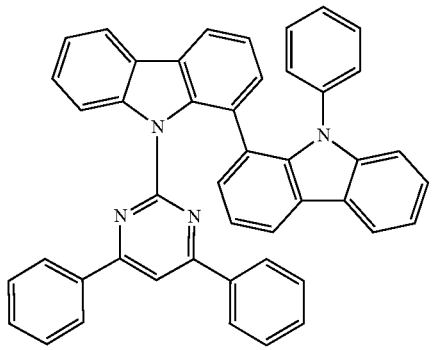
(3-116)
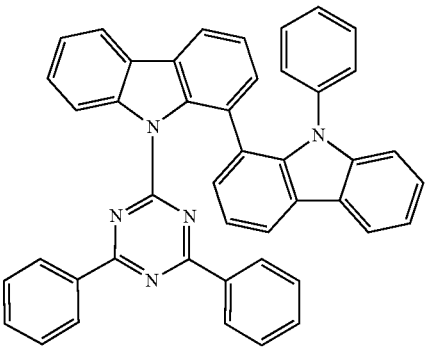
(3-117)
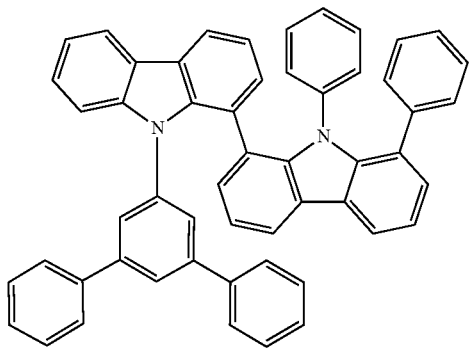
(3-118)
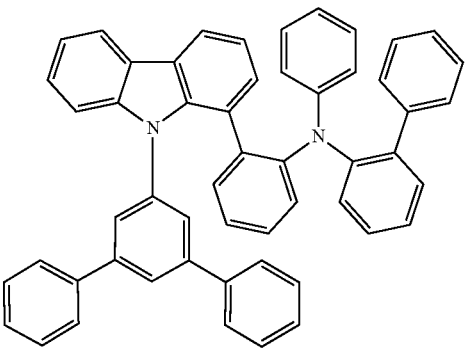

-continued
(3-119)
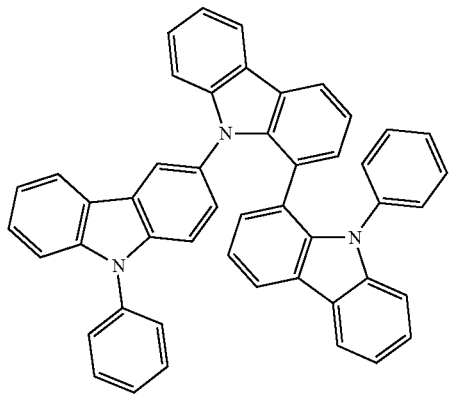
(3-120)
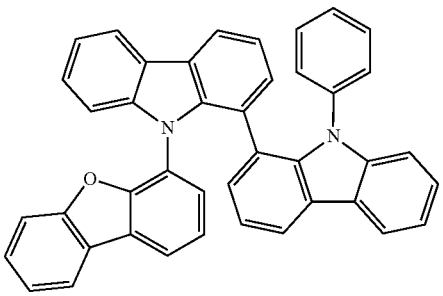
(3-121)
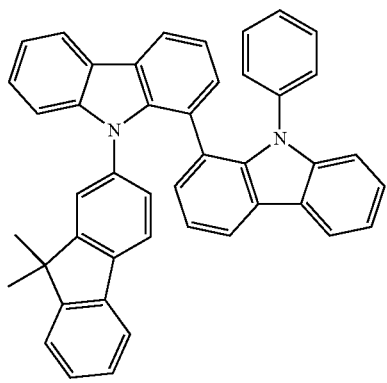
(3-122)
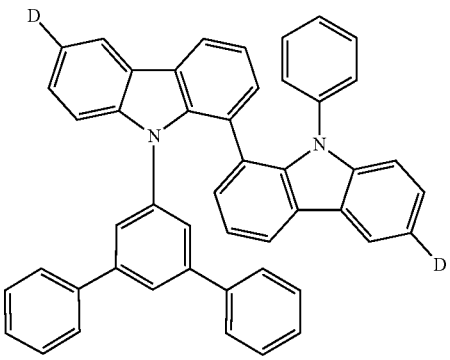
(3-123)
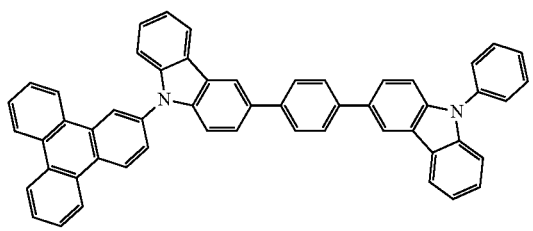
(3-124)
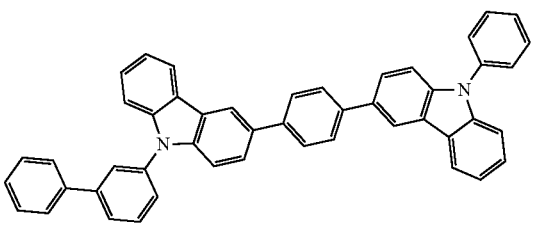
(3-125)
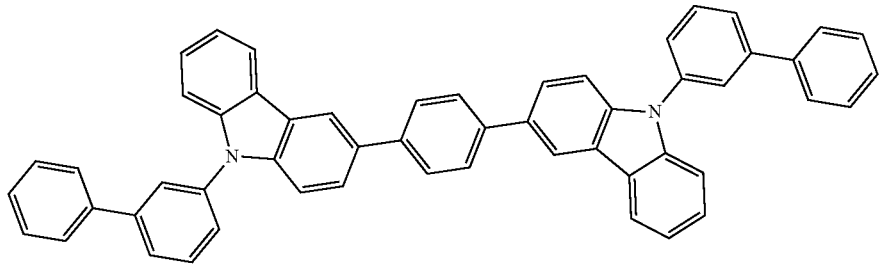
(3-126)
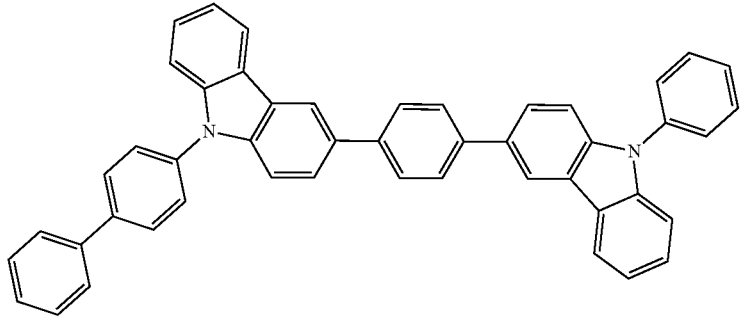

-continued
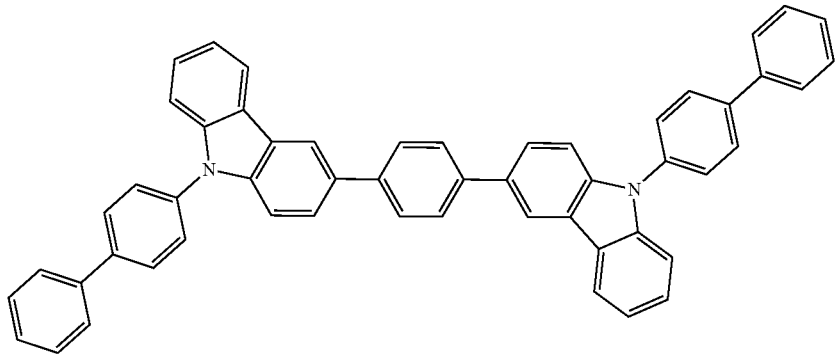
(3-127)
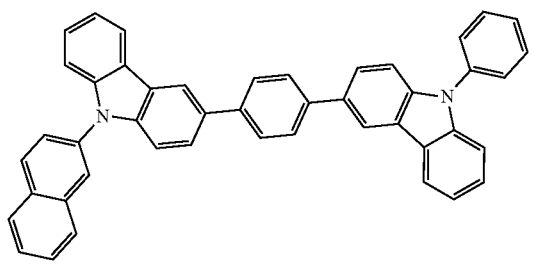
(3-128)
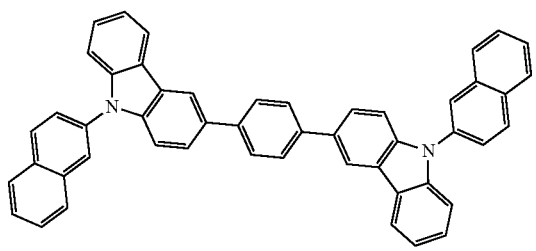
(3-129)
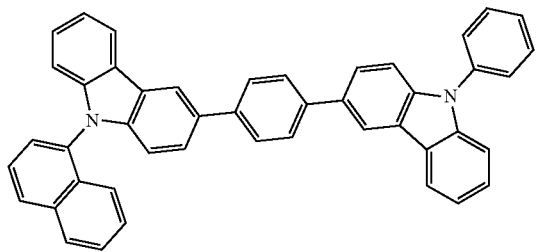
(3-130)
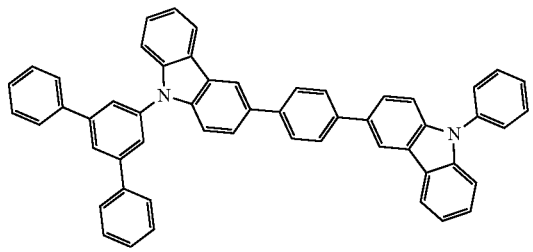
(3-131)
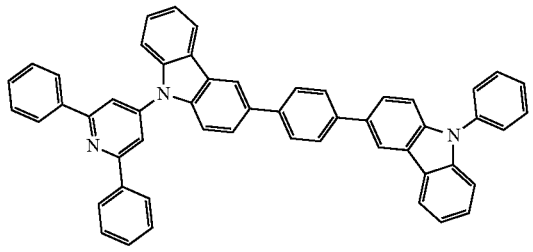
(3-132)
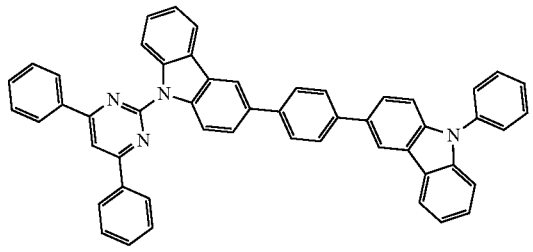
(3-133)
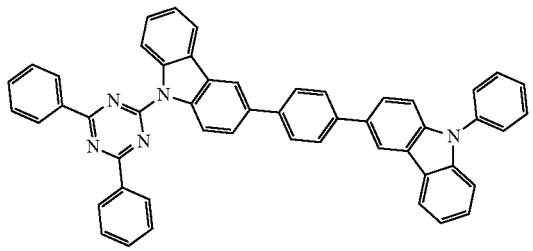
(3-134)
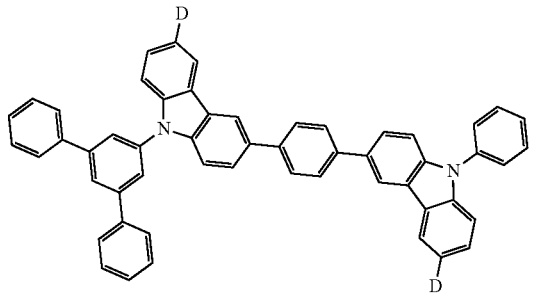
(3-135)

(3-136)
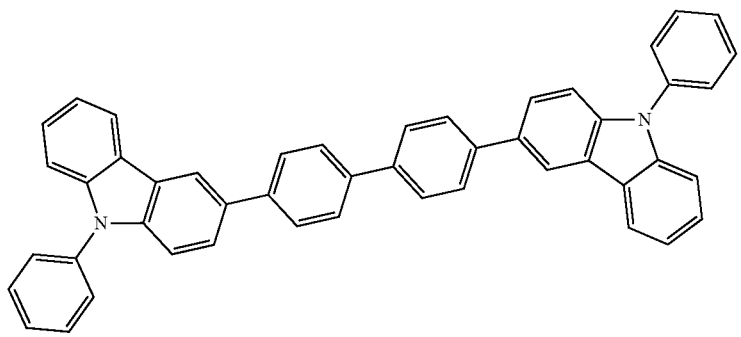
(3-137)
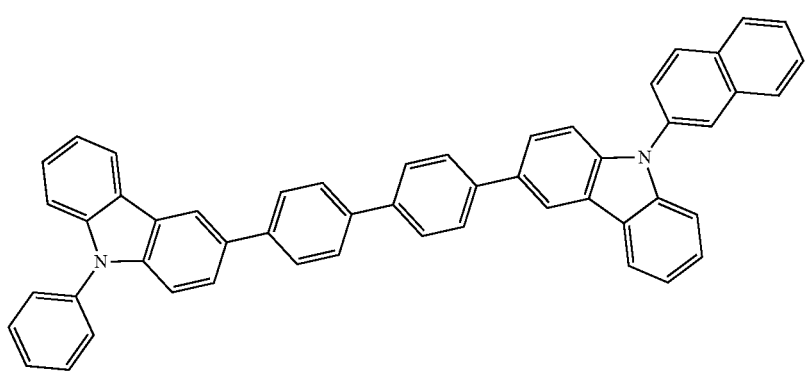
(3-138)
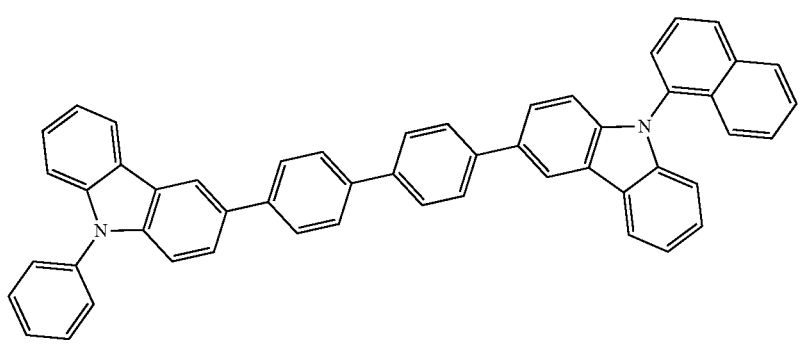
(3-139)
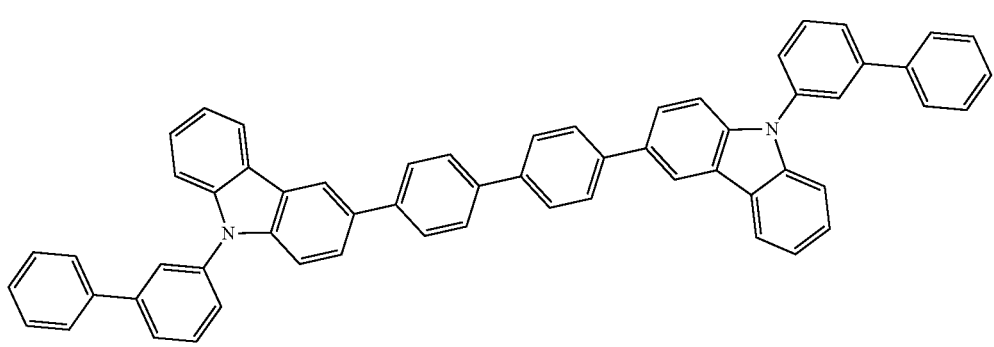

(3-140)
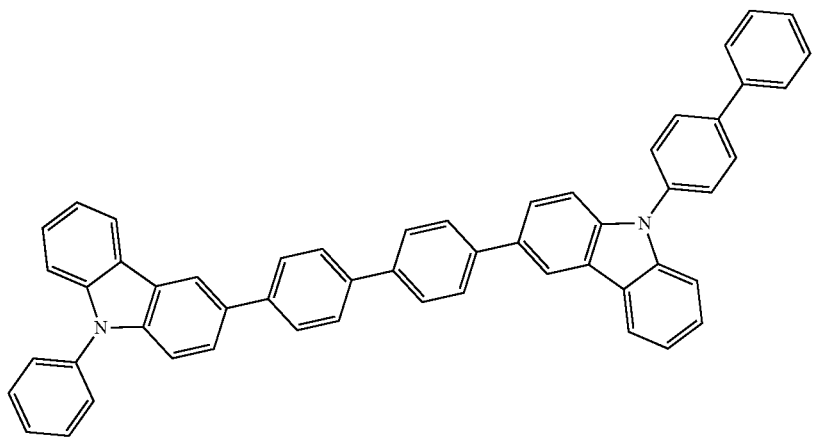
(3-141)
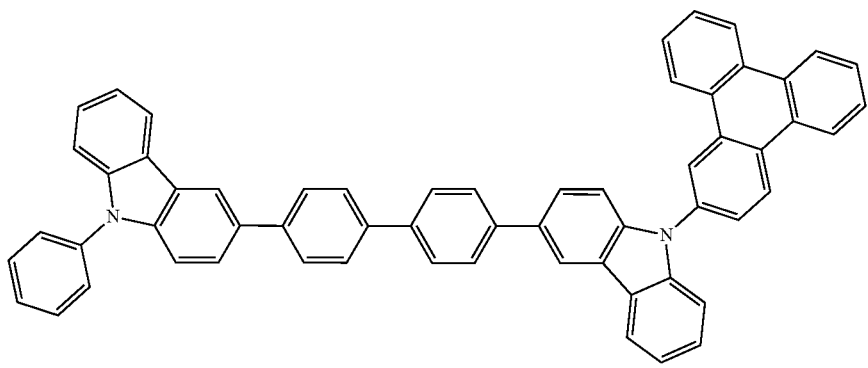
(3-142)
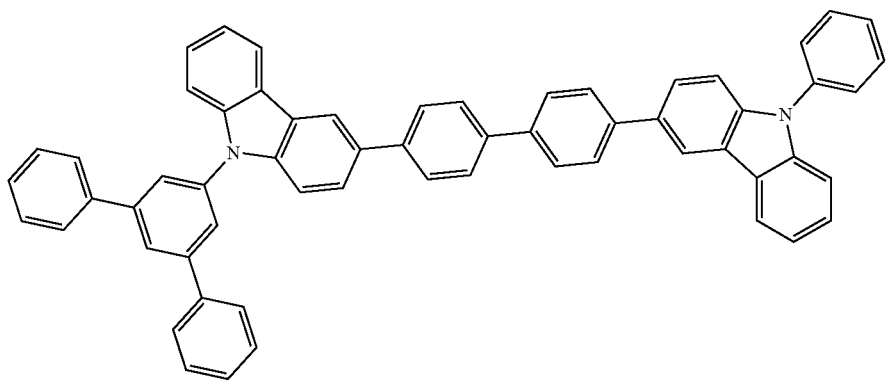
(3-143)
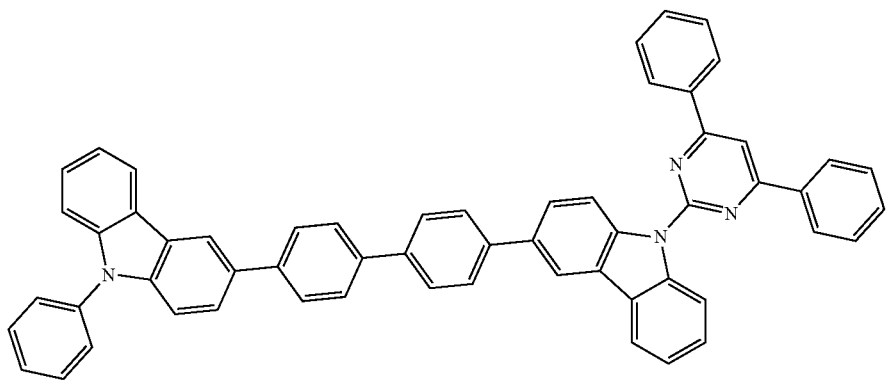

(3-144)
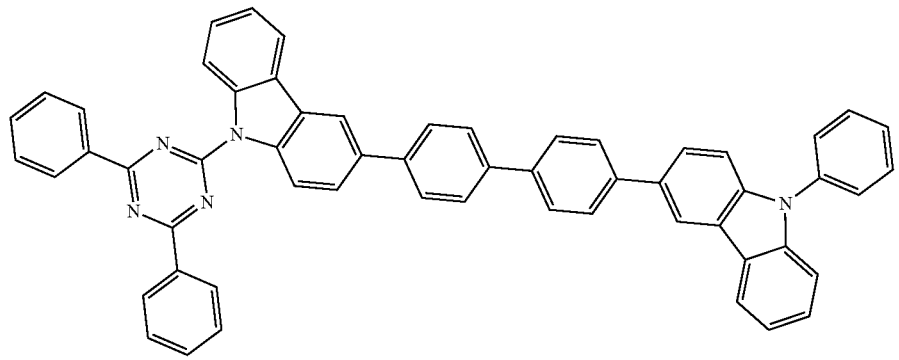
(3-145)
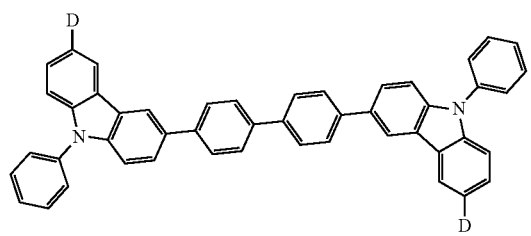
(3-146)
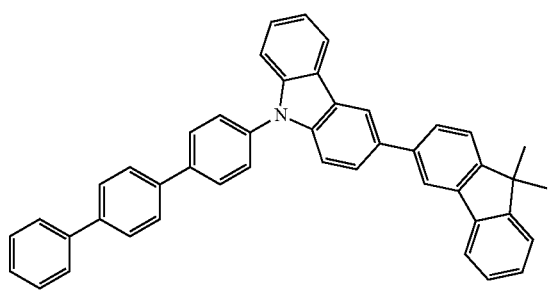
(3-147)
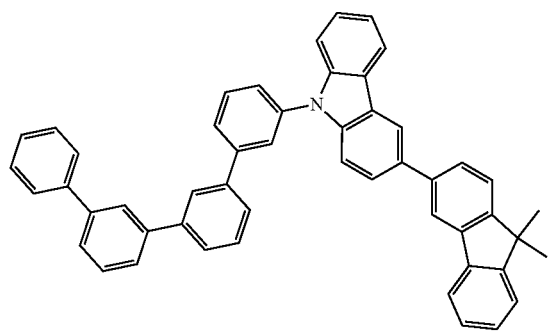
(3-148)
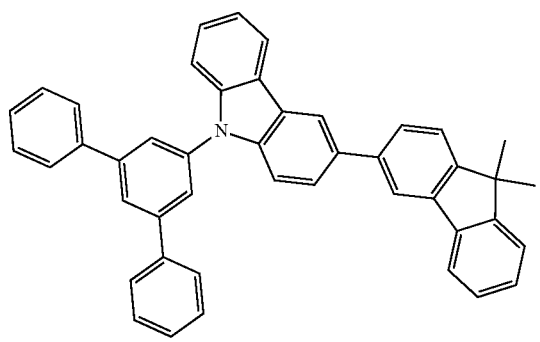
(3-149)
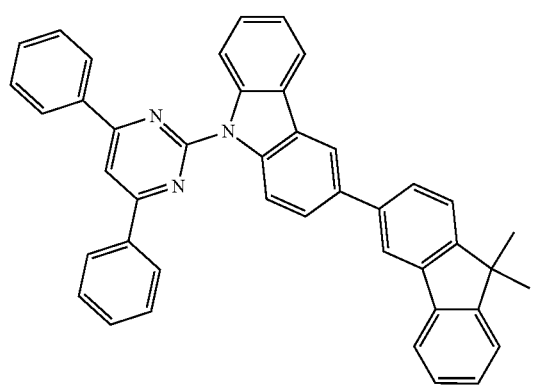
(3-150)
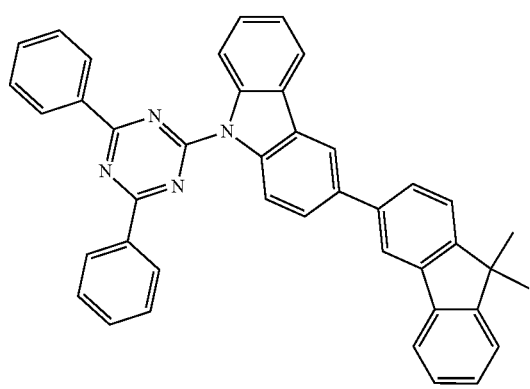

-continued
(3-151)
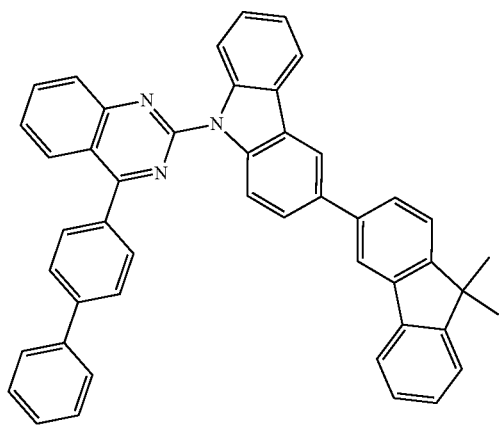
(3-152)
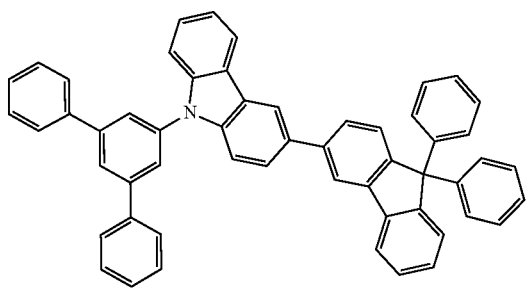
(3-153)
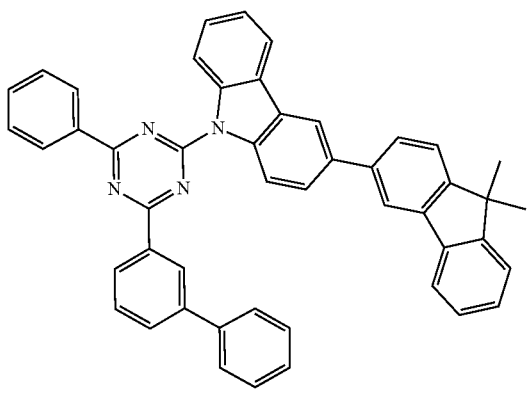
(3-154)
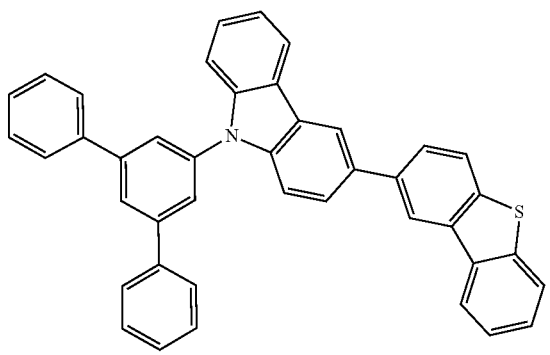
(3-155)
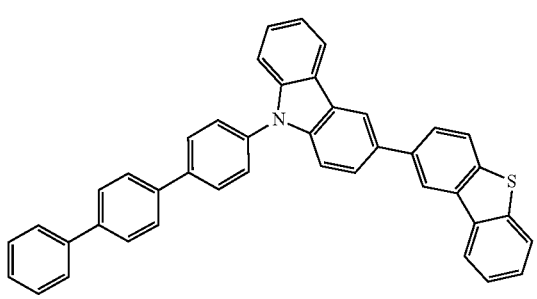
(3-156)
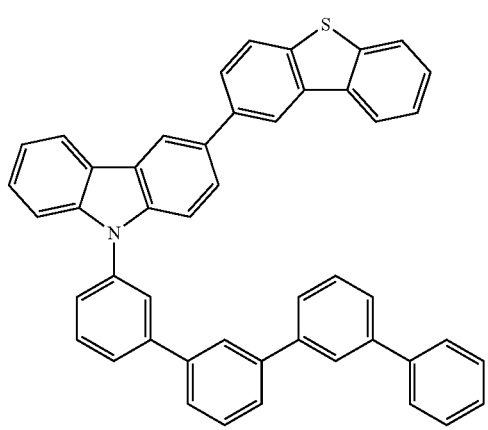

-continued
(3-157)
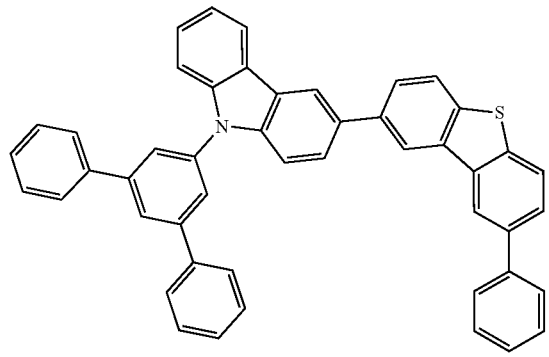
(3-158)
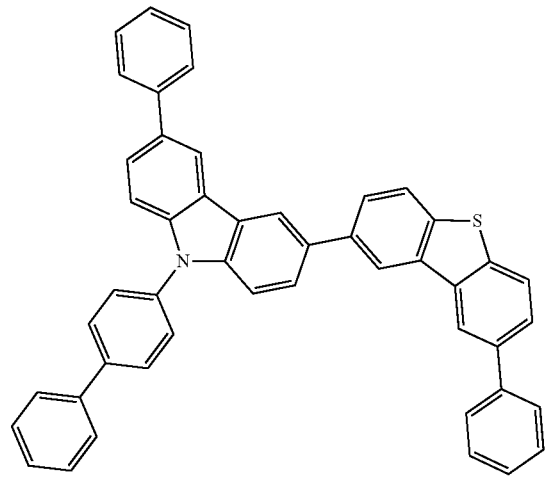
(3-159)
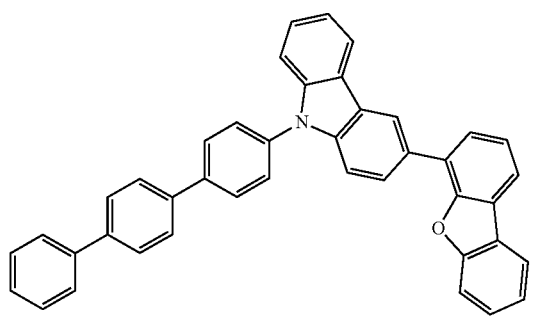
(3-160)
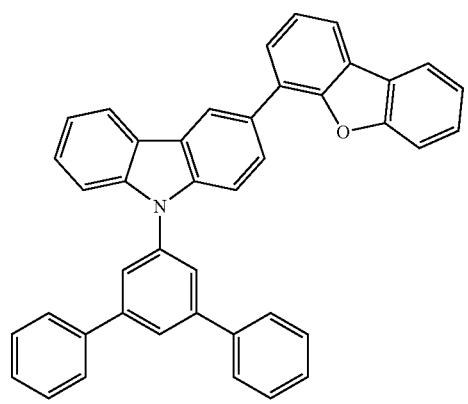
(3-161)
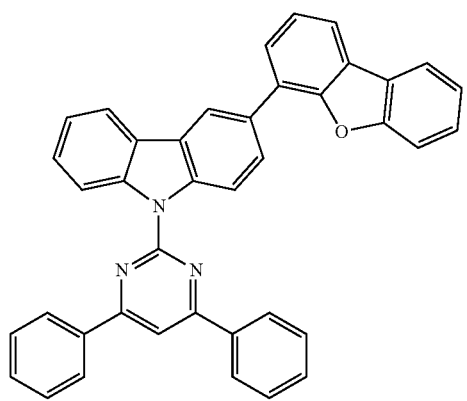
(3-162)
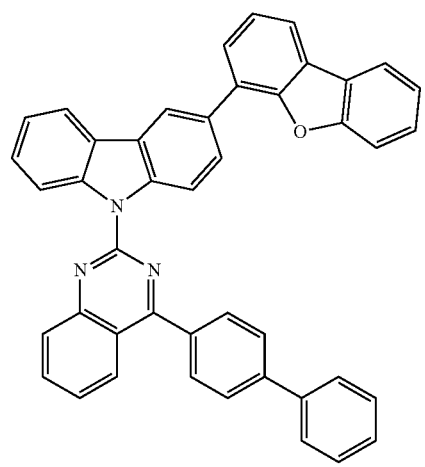

-continued
(3-163)
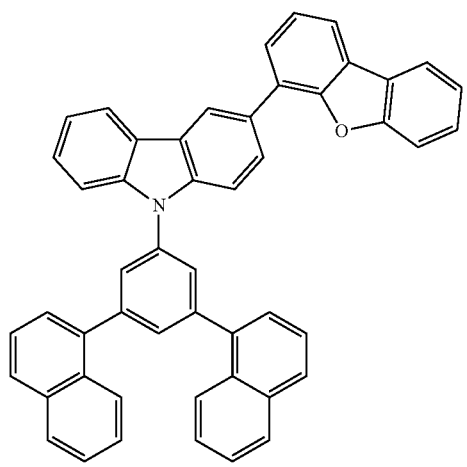
(3-164)
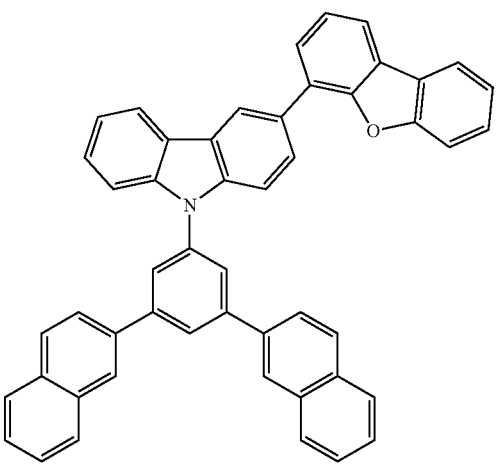
(3-165)
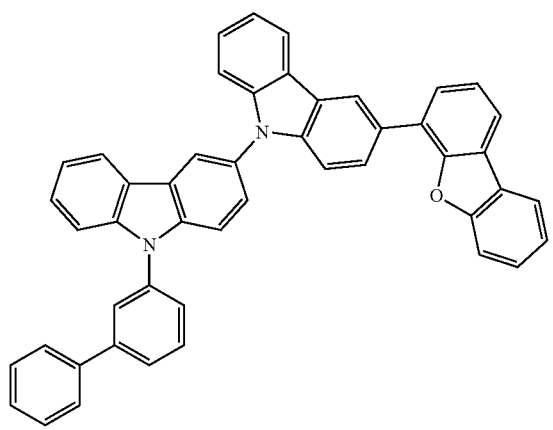
(3-166)
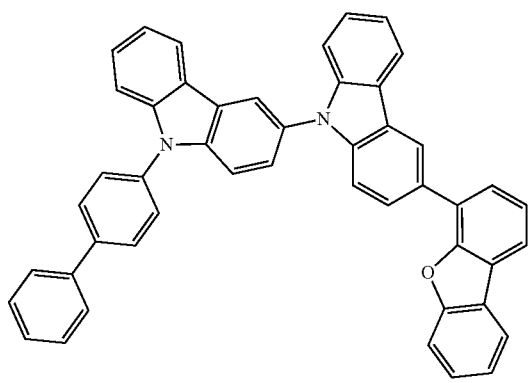
(3-167)
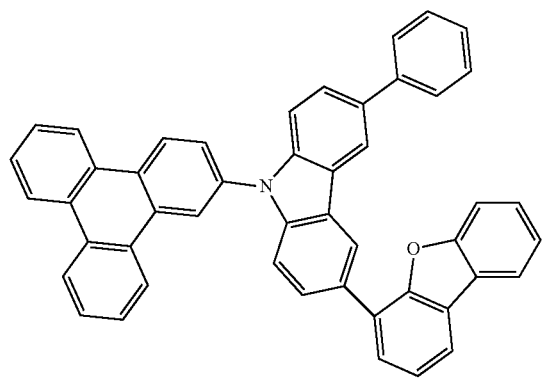
(3-168)
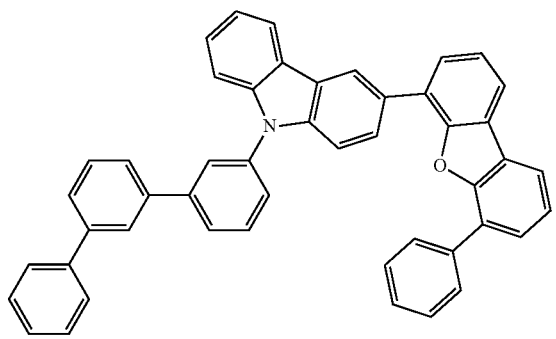

-continued
(3-169)
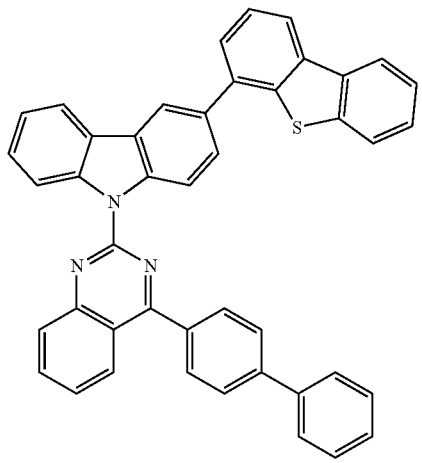
(3-170)
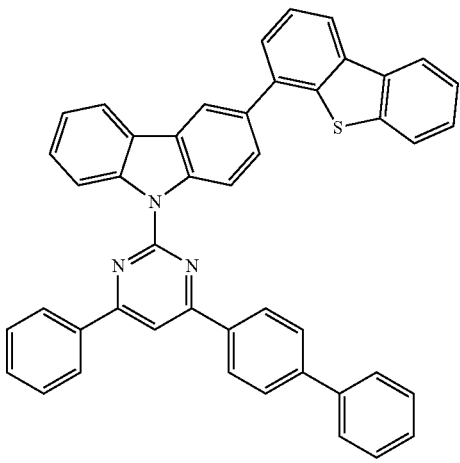
(3-171)
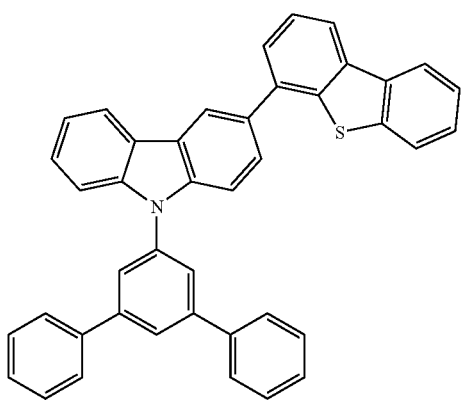
(3-172)
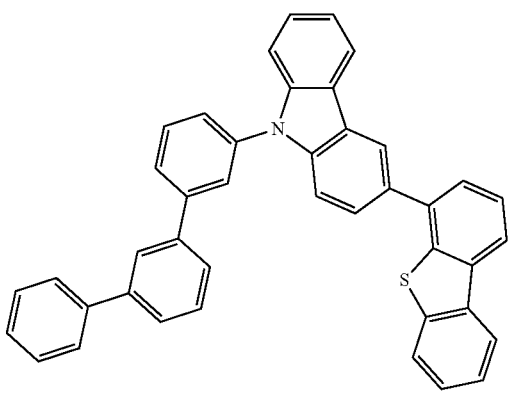
(3-173)
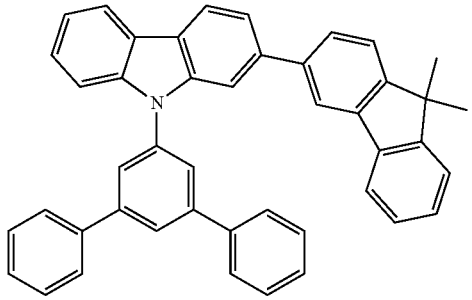
(3-174)
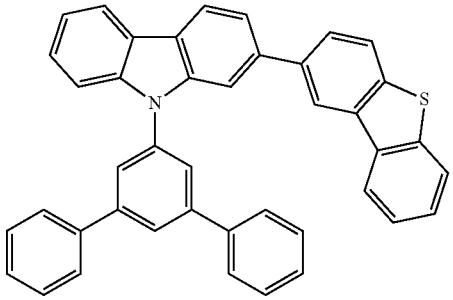

-continued
(3-175)
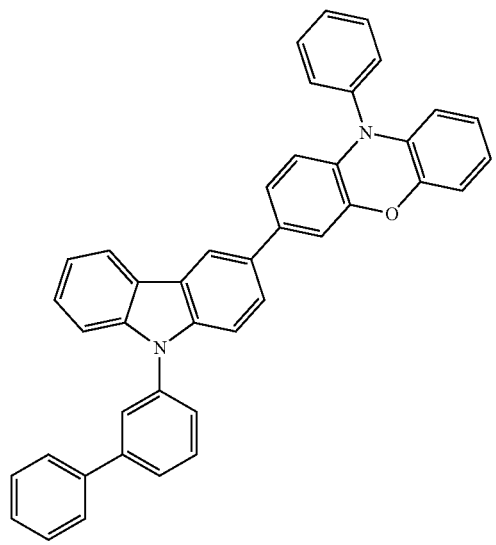
(3-176)
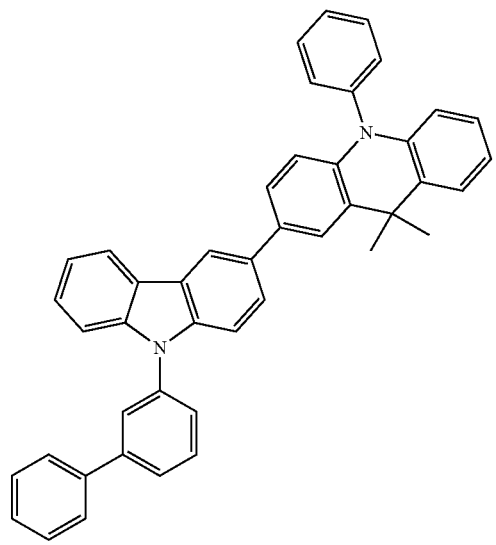
(3-177)
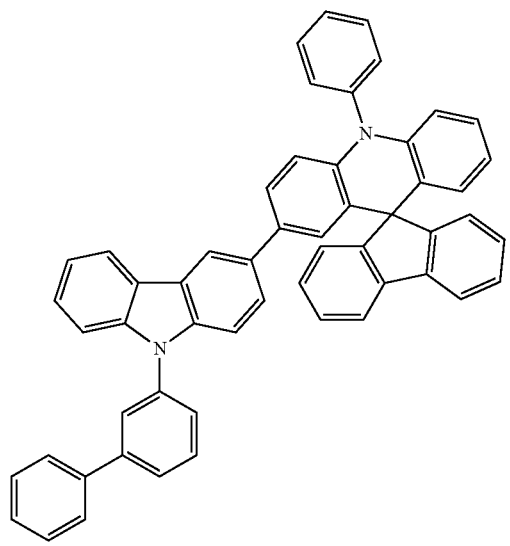
(3-178)
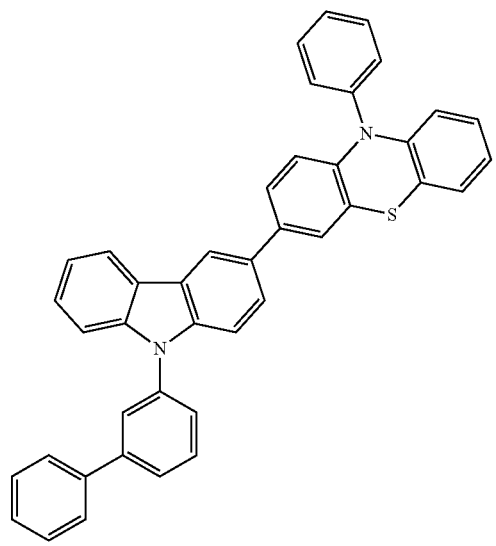

-continued
(3-179)
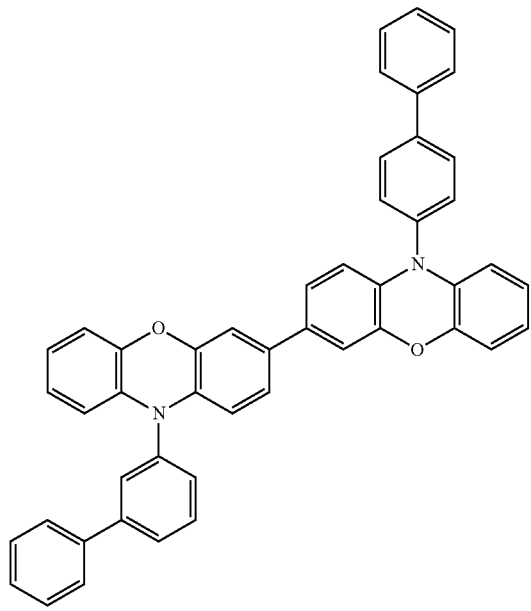
(3-180)
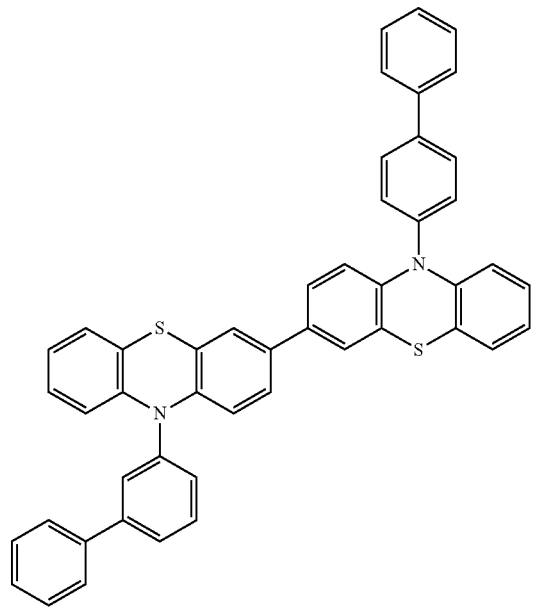
(3-181)
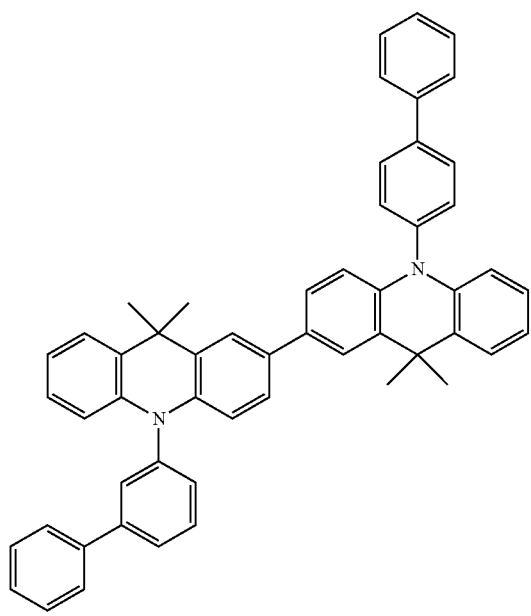
(3-182)
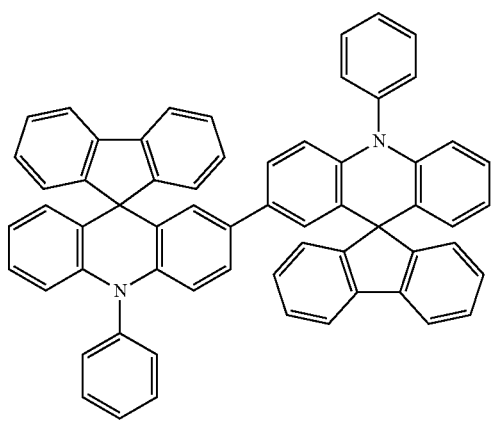

-continued
(3-183)
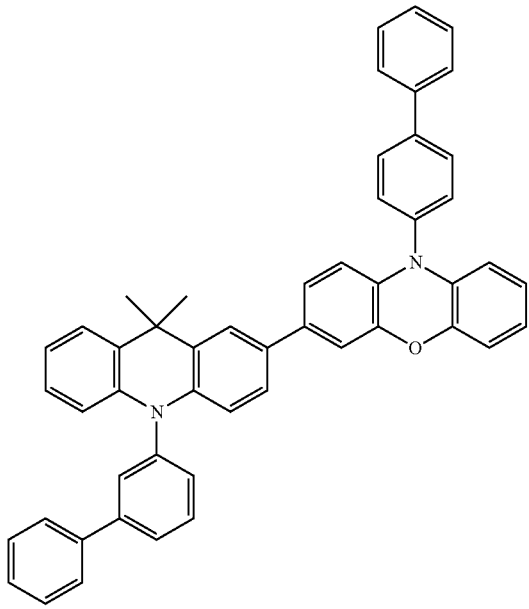
(3-184)
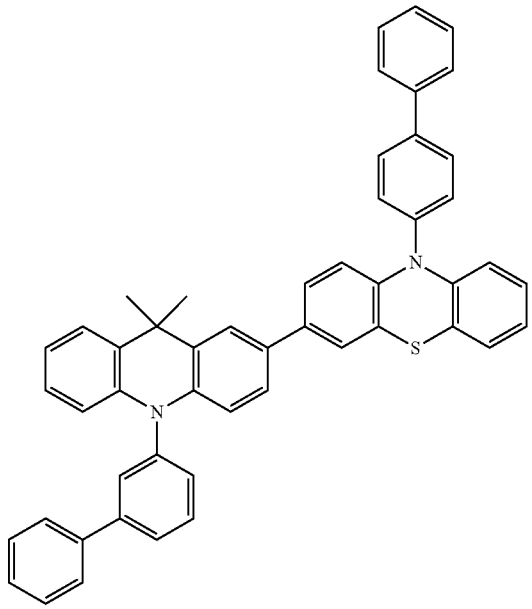
(3-185)
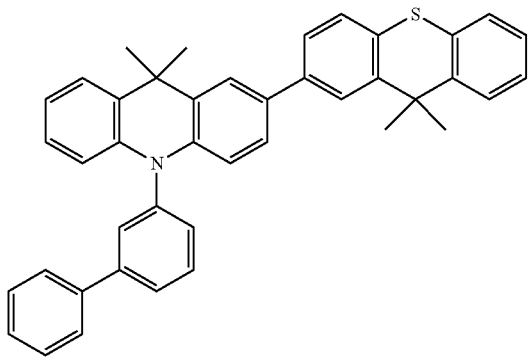
In particular, according to the structural formula (4) of the group A, the structural formula of the group A is selected from
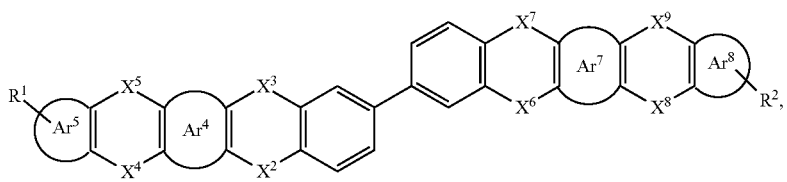
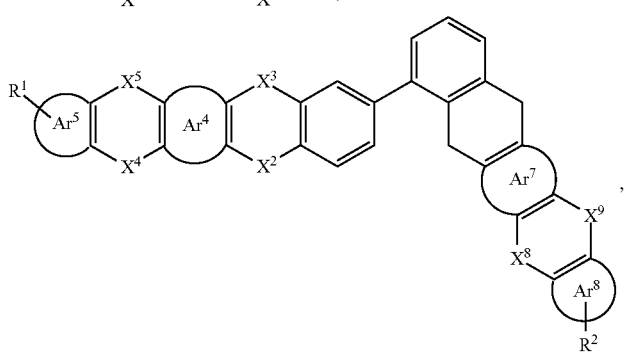

-continued

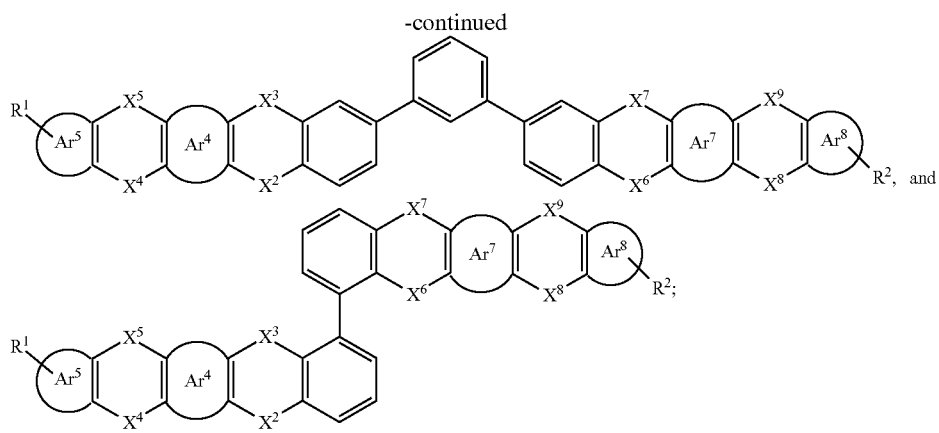

wherein Ar$^4$, Ar$^5$, Ar$^7$, Ar$^8$, X$^2$, X$^3$, X$^4$, X$^5$, X$^6$, X$^7$, X$^8$, X$^9$, R$^1$, R$^2$ have the same meanings as the structural formulas (1) to (6).

Further, according to the structural formula (4) of the group A, the structural formula of the group A is as follows:

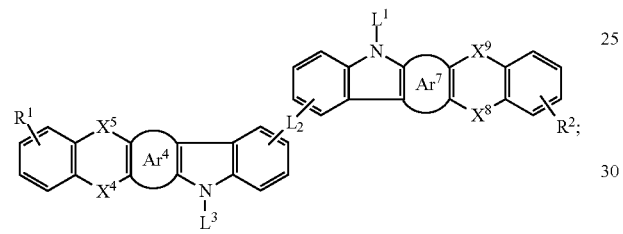

Wherein, Ar$^4$, Ar$^7$, X$^4$, X$^5$, X$^8$, X$^9$, R$^1$, R$^2$ have the same meanings as the structural formulas (1) to (6).

Specifically, according to the structural formula (4), the group A having a phosphorescent host function in the general formula (I) and (IV) is selected from one of, but not limited to, the following groups:

(4-1)

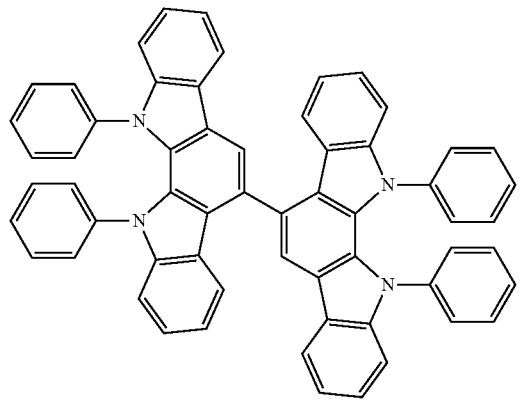

(4-2)

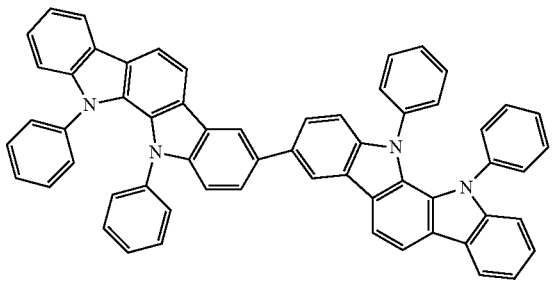

(4-3)

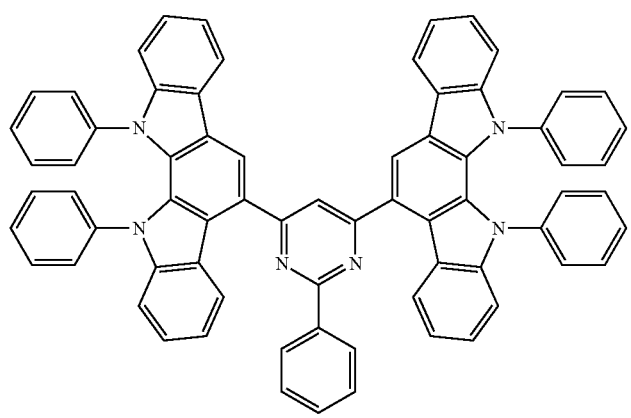

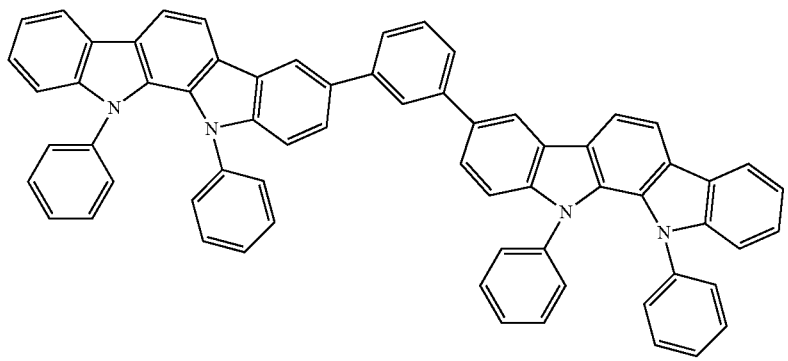
(4-4)
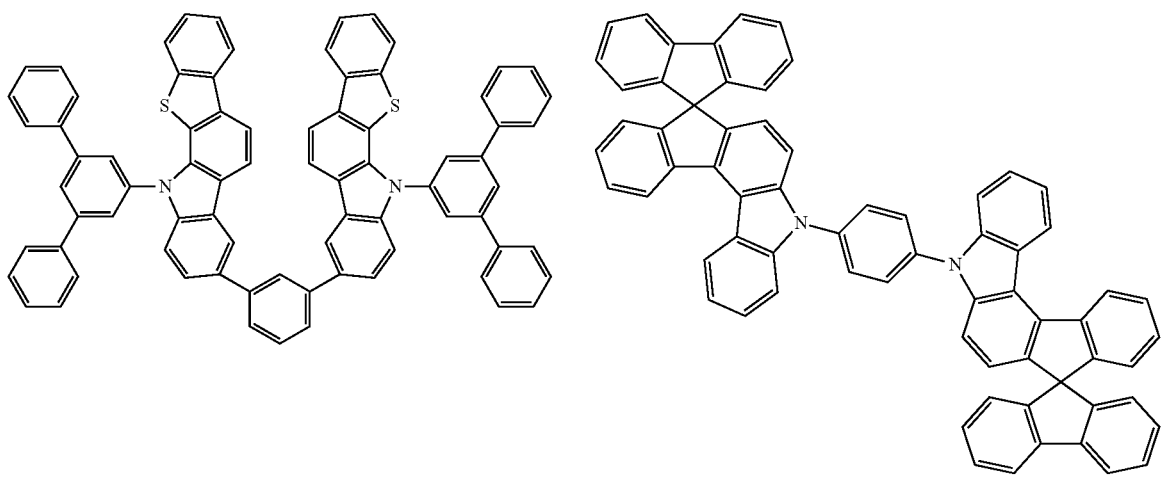
(4-5) (4-6)
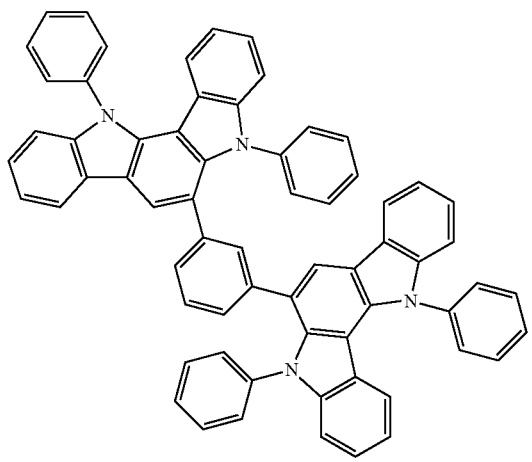
(4-7)
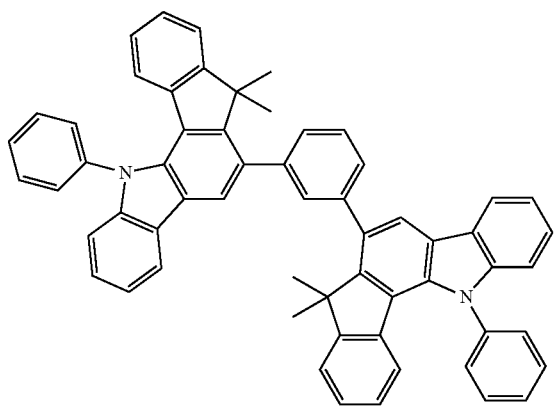
(4-8)

(4-9)
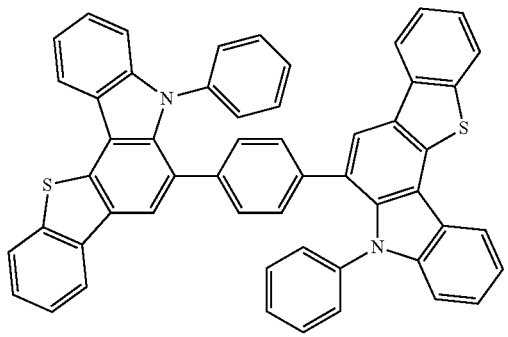
(4-10)
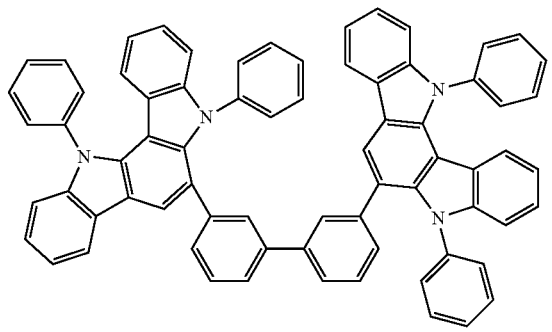
(4-11)
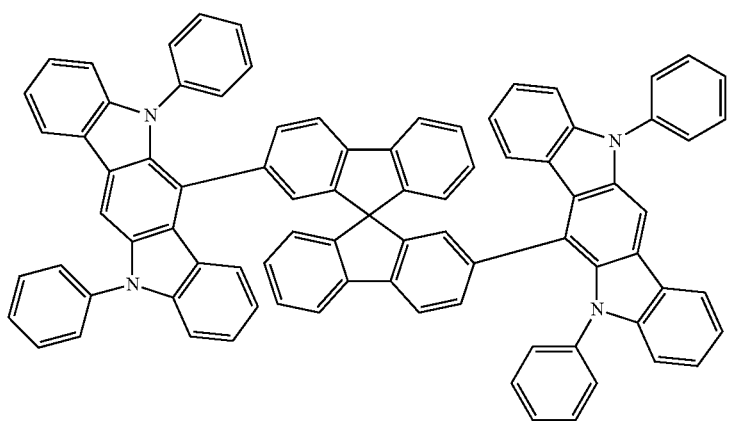
(4-12)
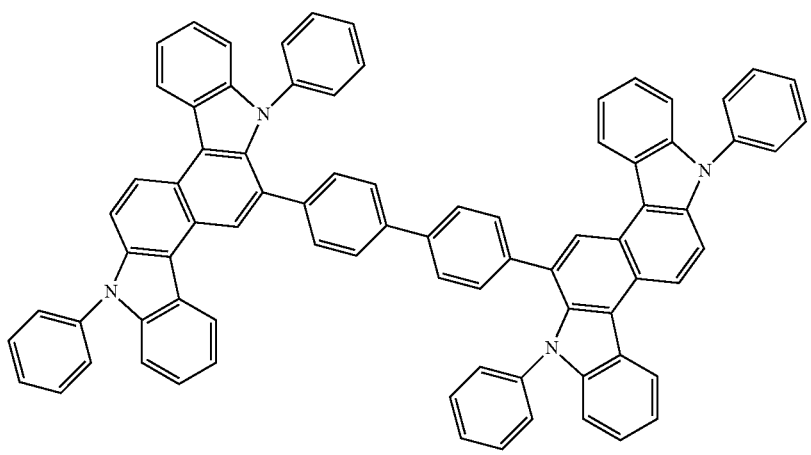

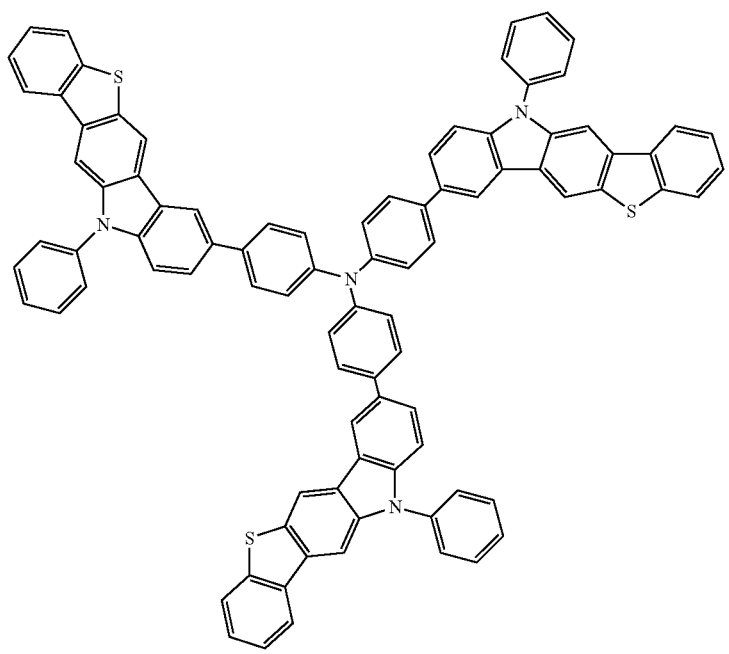
(4-13)
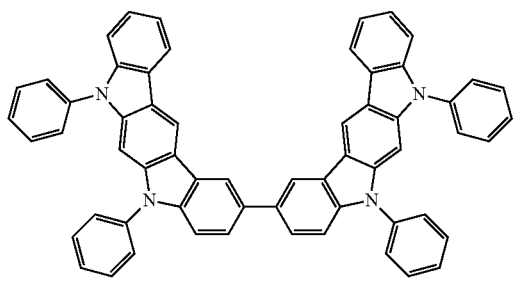
(4-14)
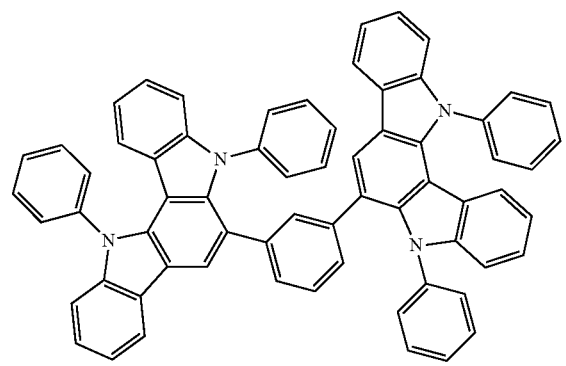
(4-15)
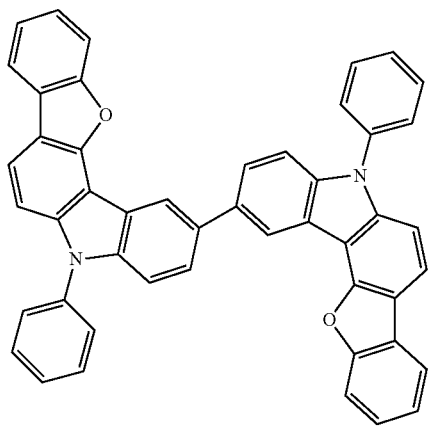
(4-16)
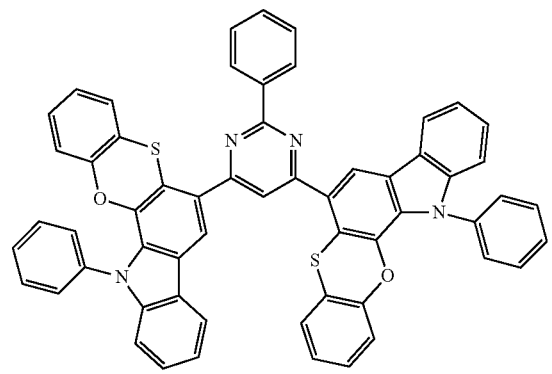
(4-17)

(4-18)
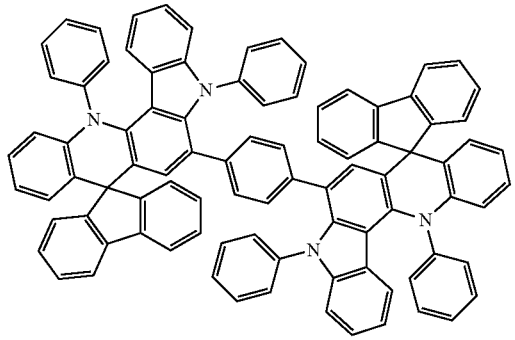
(4-19)
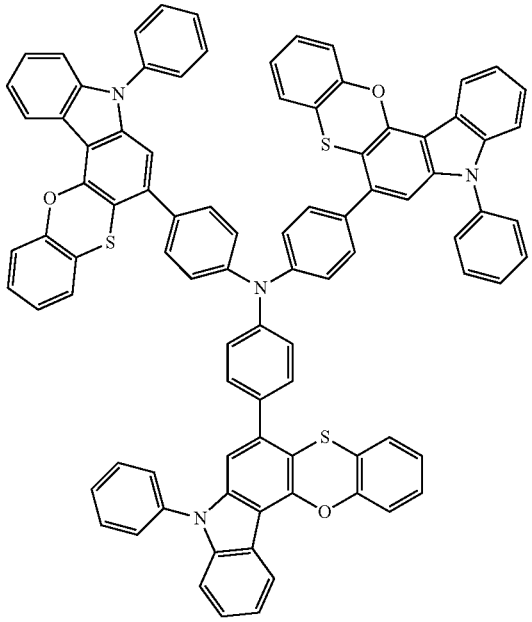
(4-20)
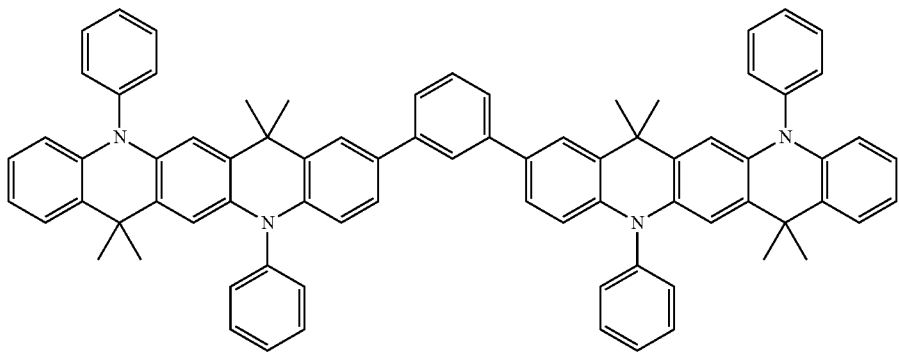
In particular, according to the structural formula (5) of the group A, the structural formula of the group A is selected from
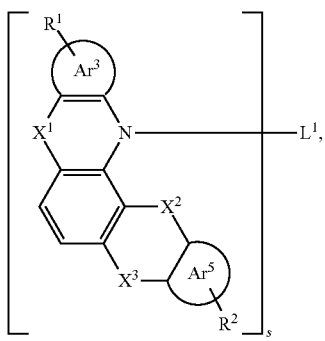
-continued
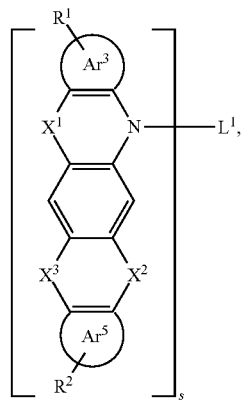

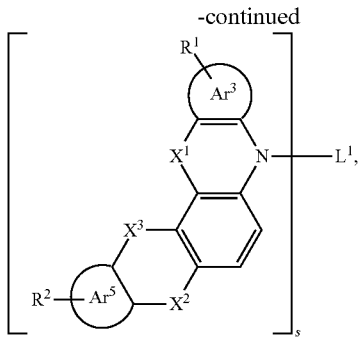

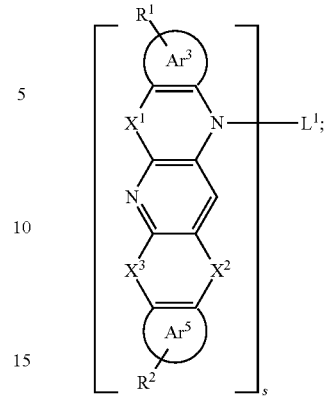

wherein Ar$^3$, Ar$^5$, X$^1$, X$^2$, X$^3$, R$^1$, R$^2$, L$^1$, s have the same meanings as the structural formulas (1) to (6).

Further, according to the structural formula (5) of the group A, the structural formula of the group A is as follows:

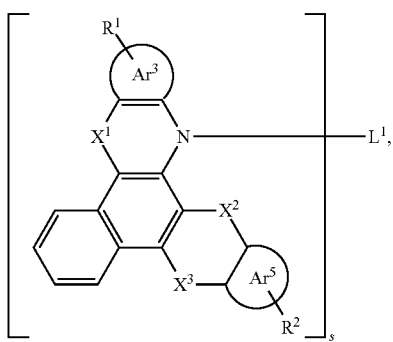

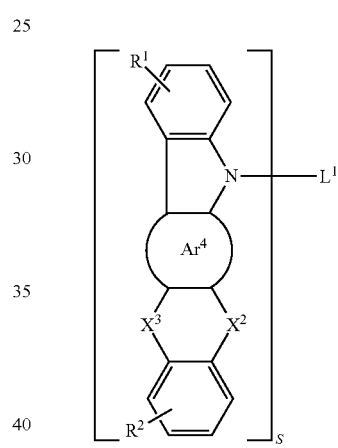

Wherein, X$^2$, X$^3$, R$^1$, R$^2$, L$^1$, and s have the same meanings as the structural formulas (1) to (6).

Specifically, according to the structural formula (5), the group A having a phosphorescent host function in the general formula (I) and (IV) is selected from one of, but not limited to, the following groups:

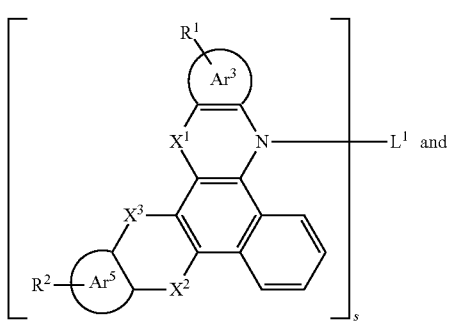

(5-1)

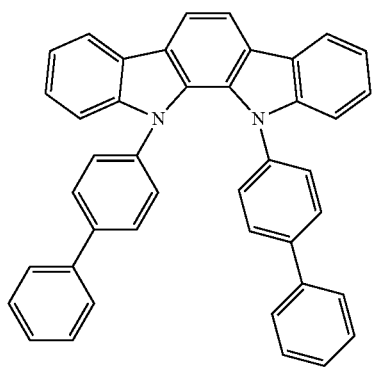

(5-2)

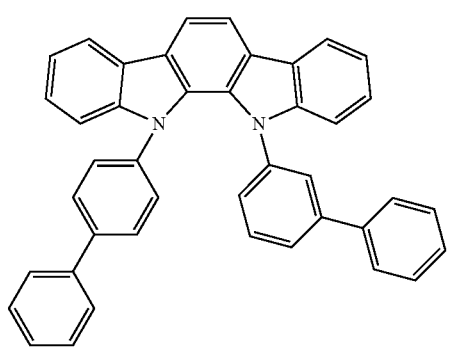

-continued
(5-3)
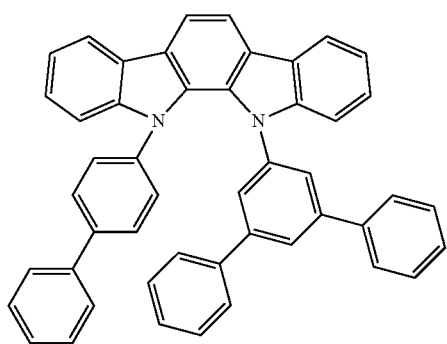
(5-4)
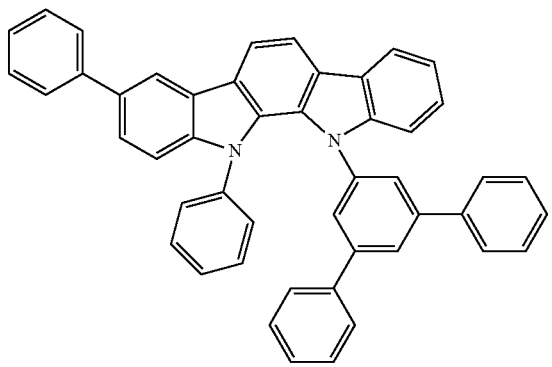
(5-5)
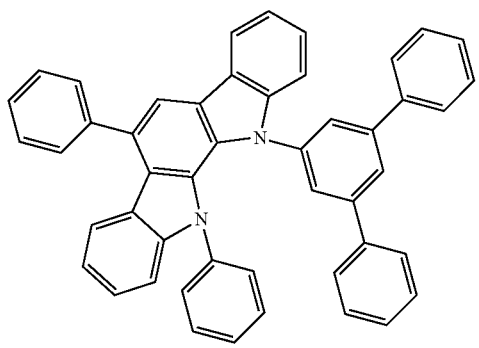
(5-6)
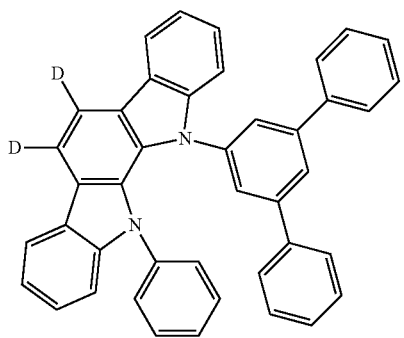
(5-7)
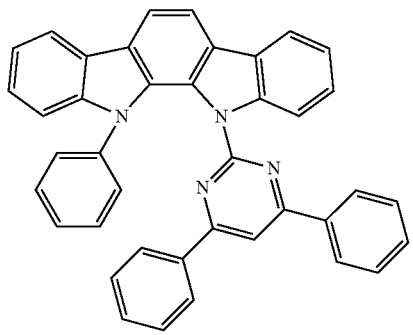
(5-8)
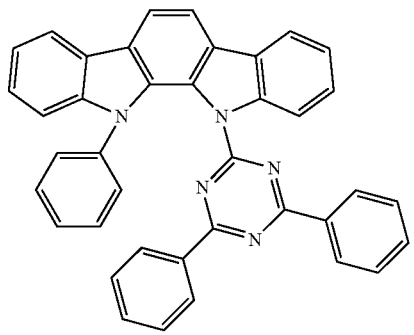
(5-9)
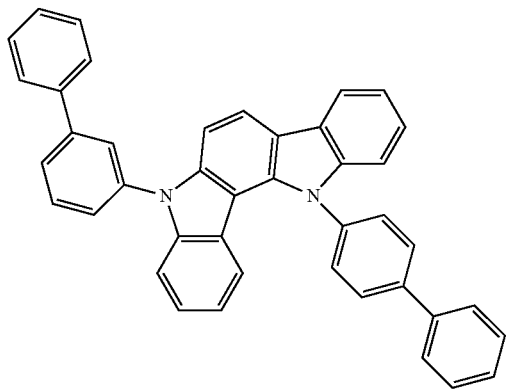
(5-10)
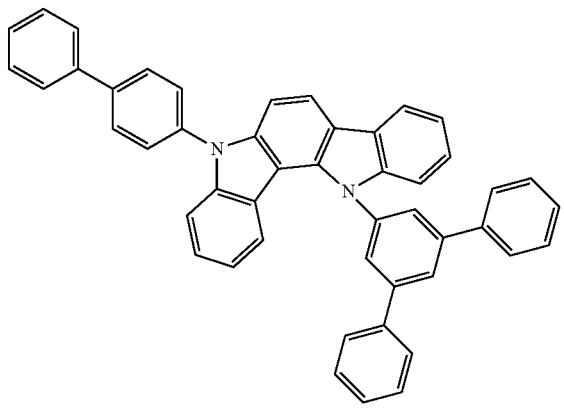

-continued
(5-11)
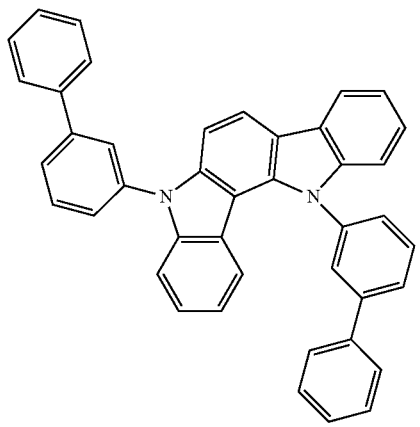
(5-12)
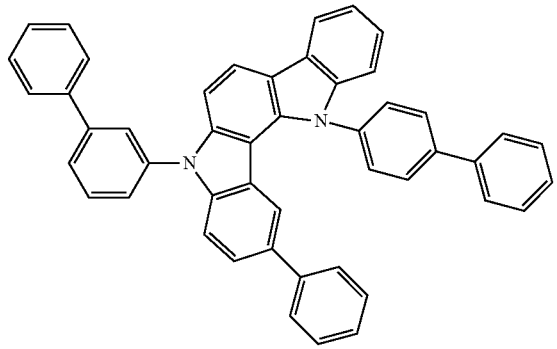
(5-13)
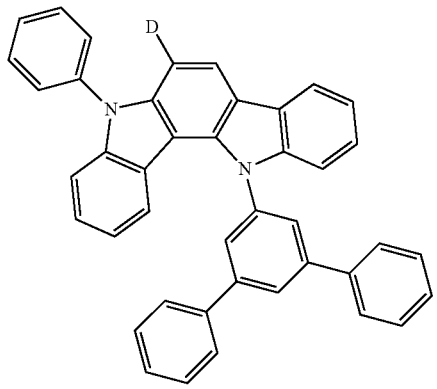
(5-14)
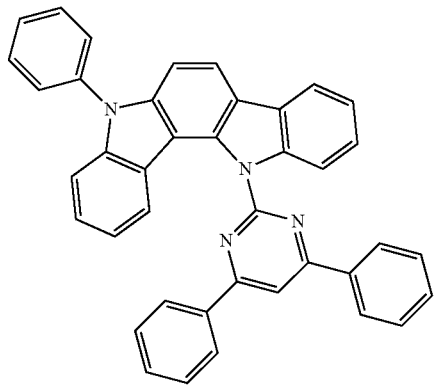
(5-15)
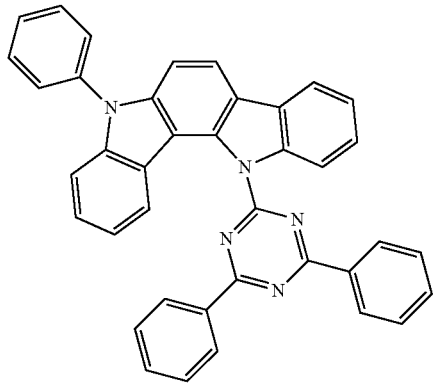
(5-16)
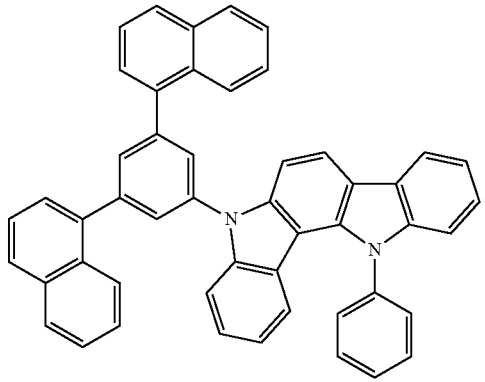

-continued
(5-17)
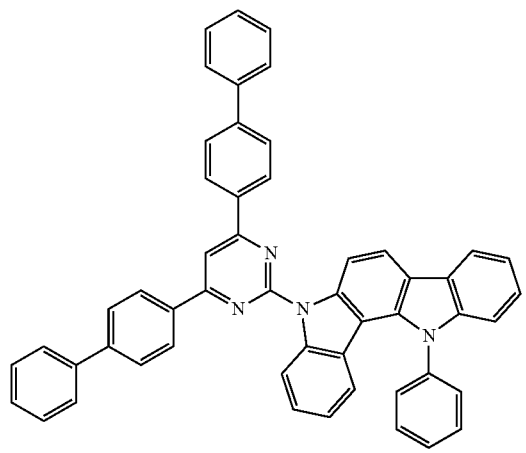
(5-18)
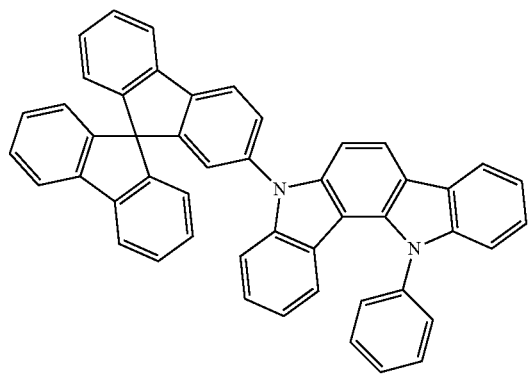
(5-19)
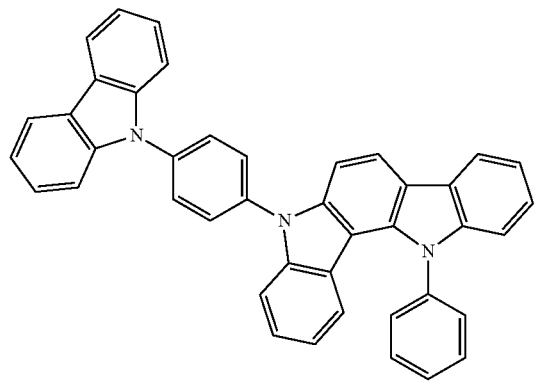
(5-20)
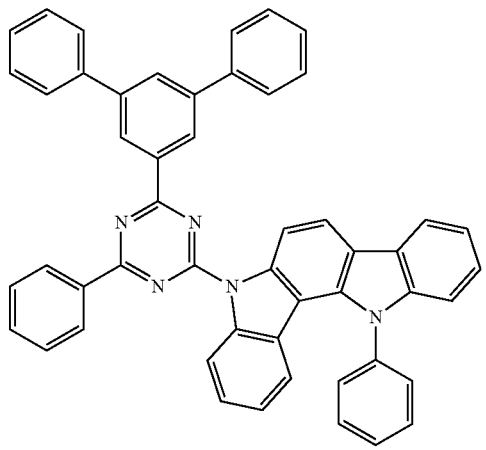
(5-21)
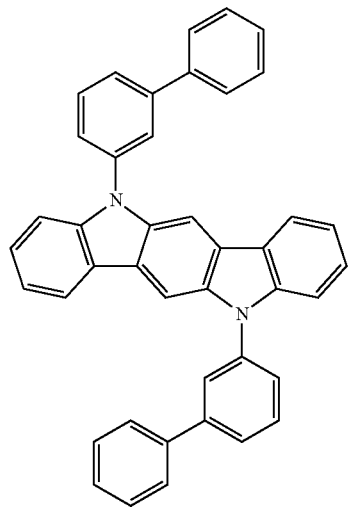
(5-22)
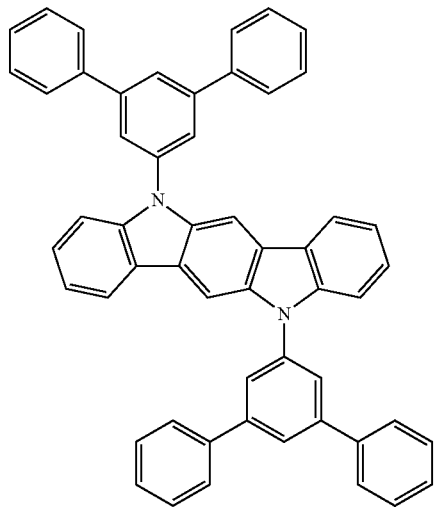

(5-23) 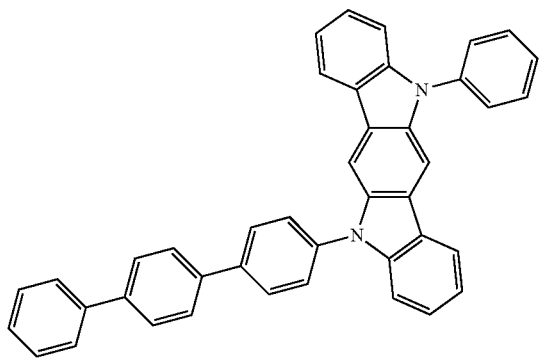
(5-24) 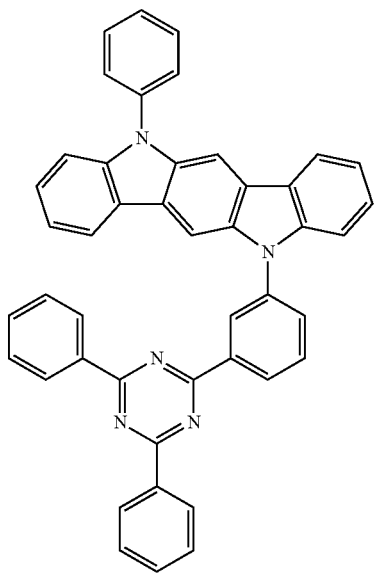
(5-25) 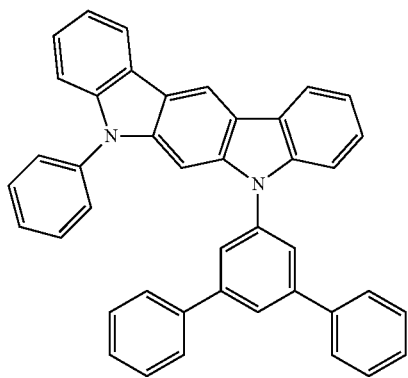
(5-26) 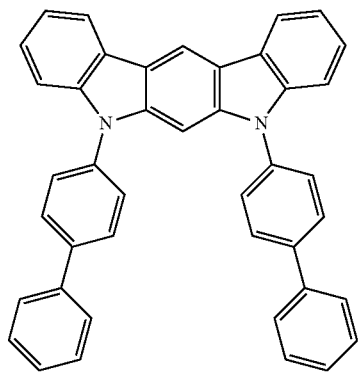
(5-27) 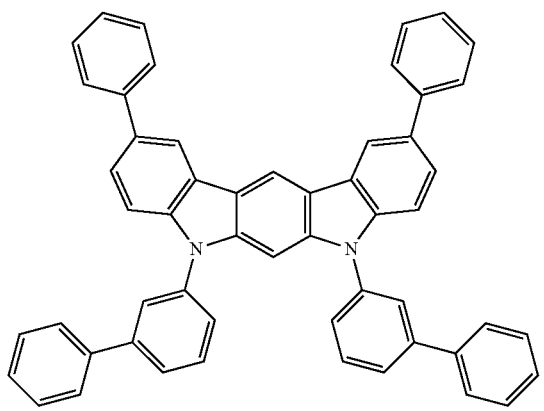
(5-28) 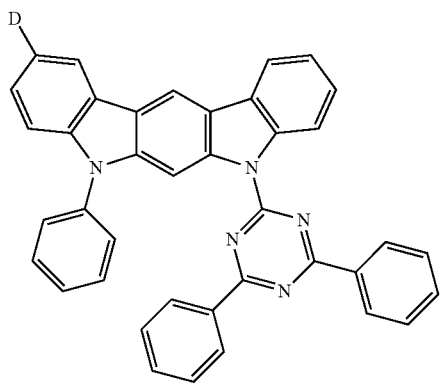

(5-29)
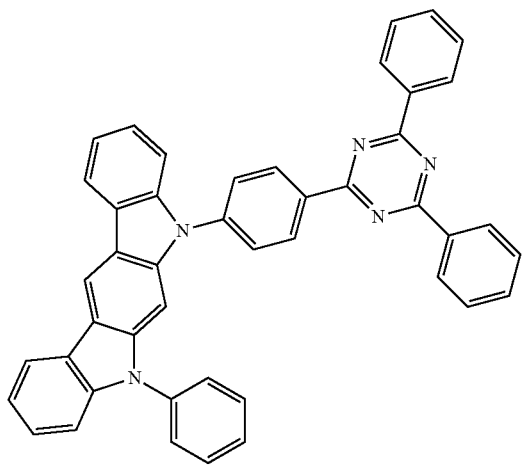
(5-30)
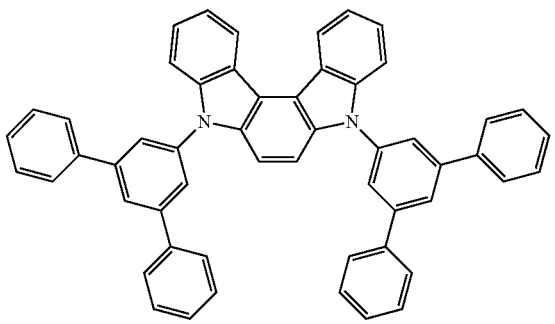
(5-31)
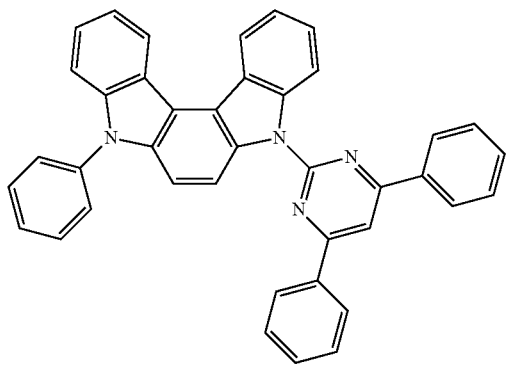
(5-32)
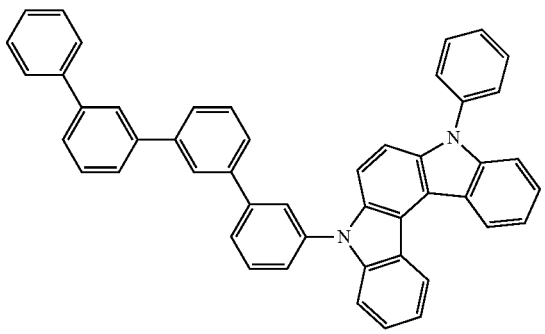
(5-33)
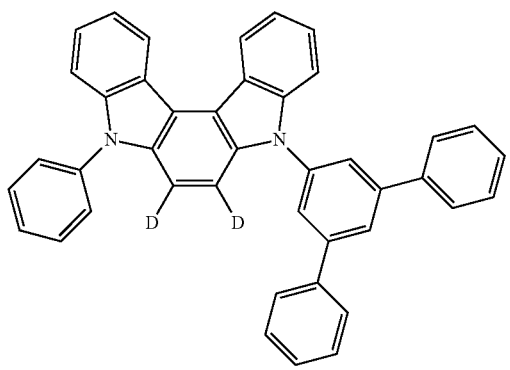
(5-34)
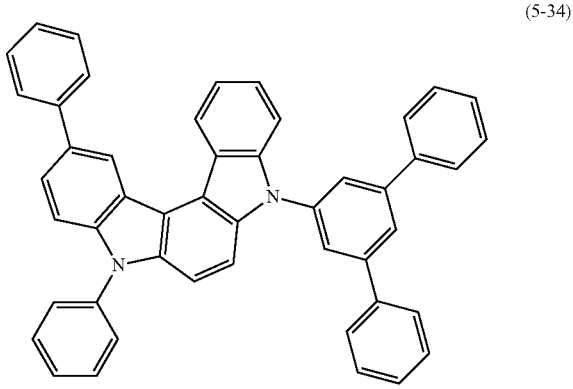
(5-35)
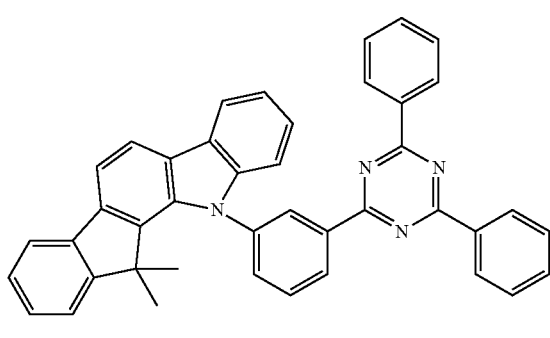
(5-36)
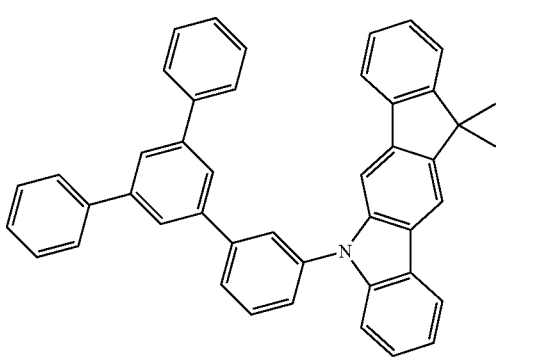

-continued
(5-37)
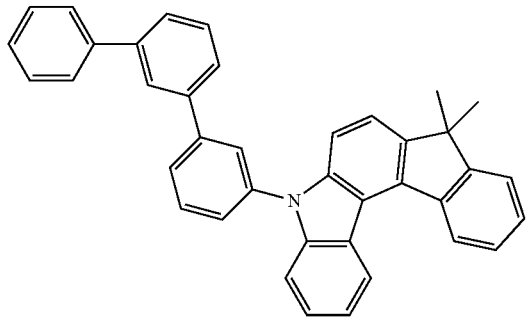
(5-38)
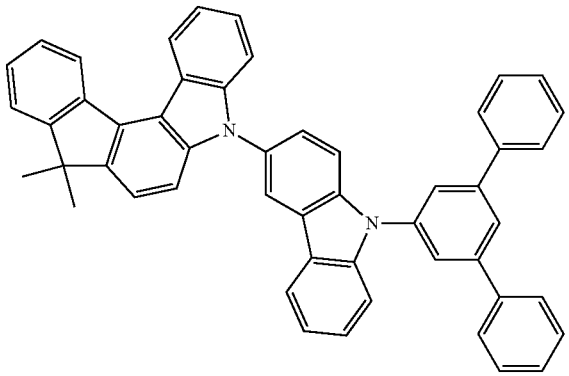
(5-39)
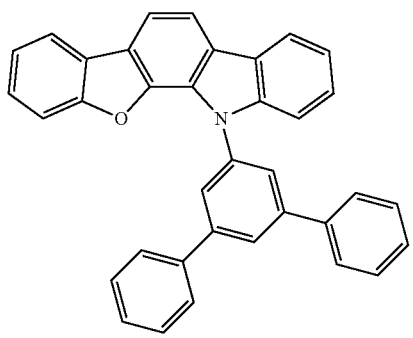
(5-40)
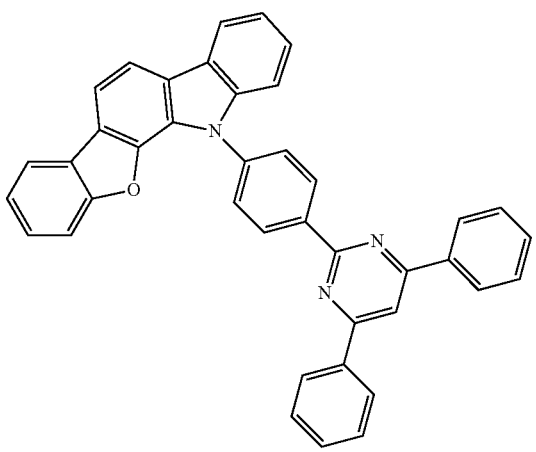
(5-41)
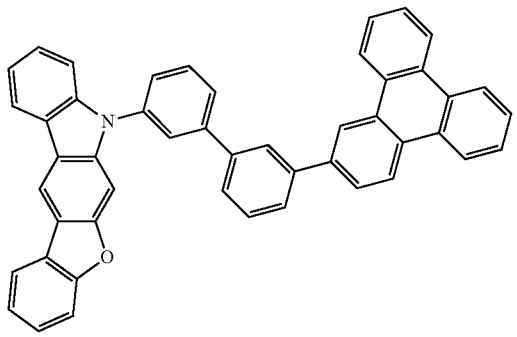
(5-42)
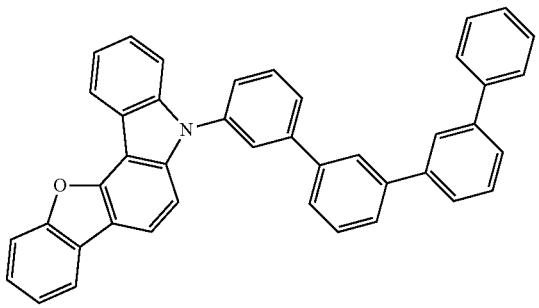
(5-43)
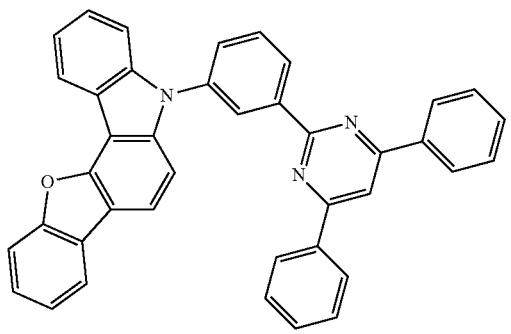
(5-44)
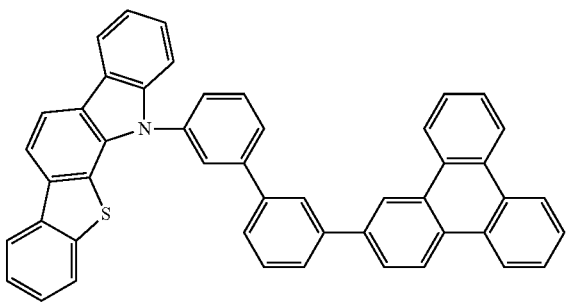

-continued
(5-45)
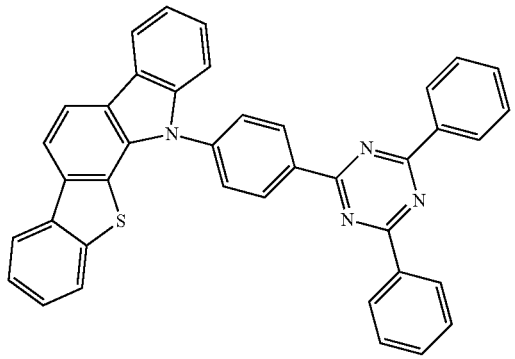
(5-46)
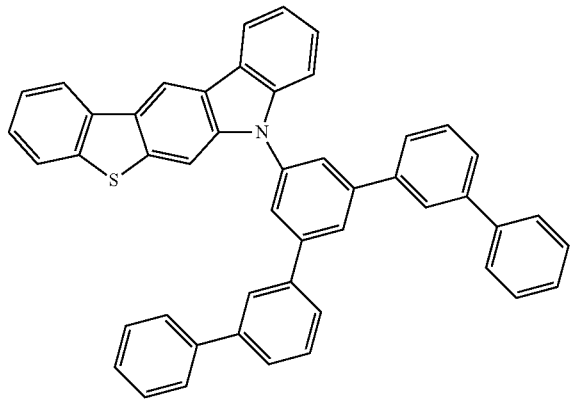
(5-47)
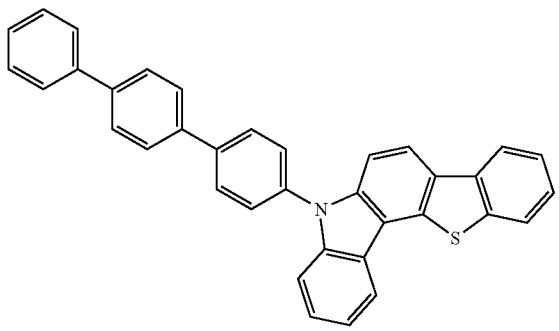
(5-48)
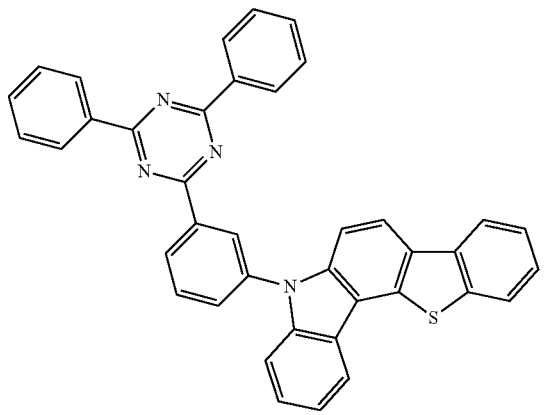
(5-49)
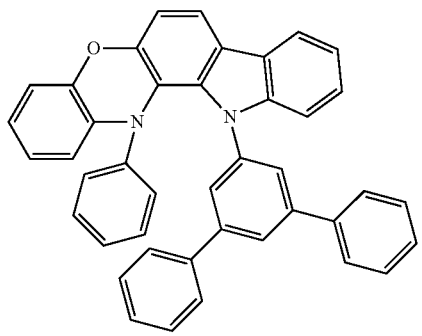
(5-50)
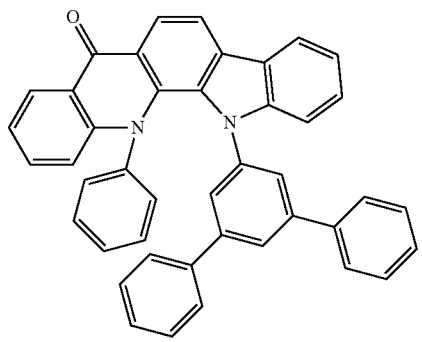
(5-51)
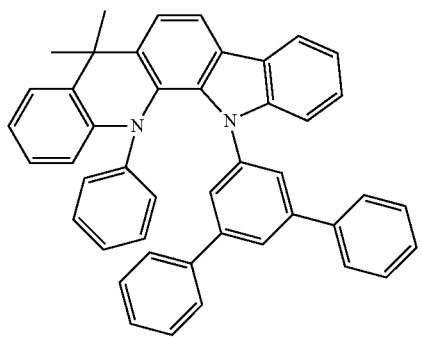
(5-52)
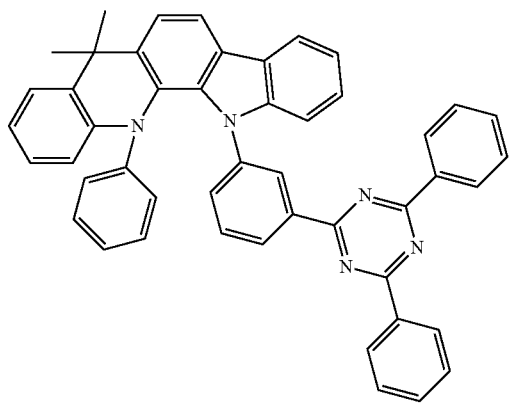

-continued
(5-53)
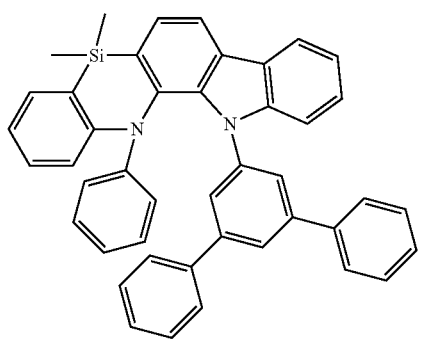
(5-54)
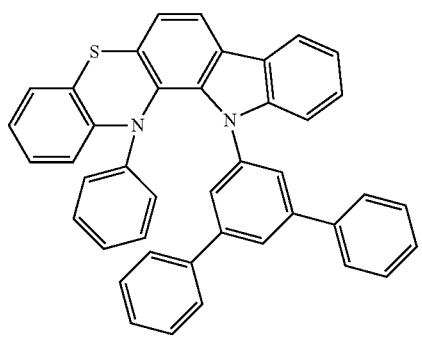
(5-55)
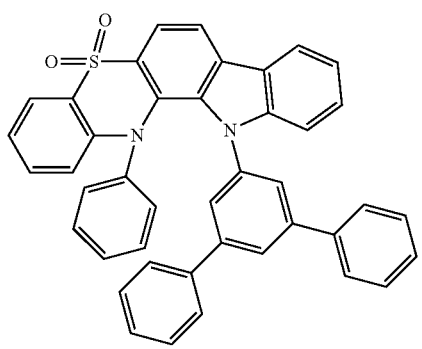
(5-56)
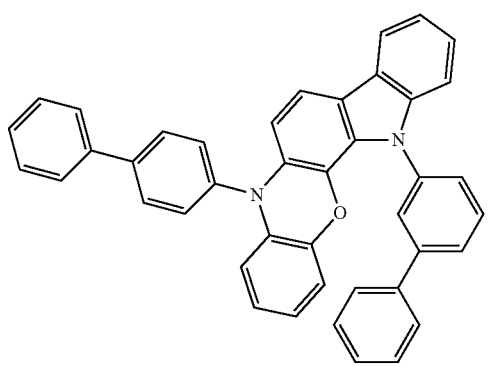
(5-57)
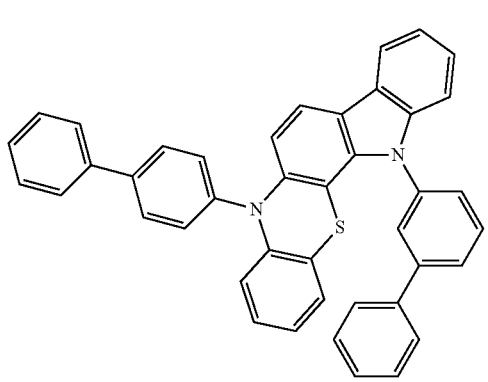
(5-58)
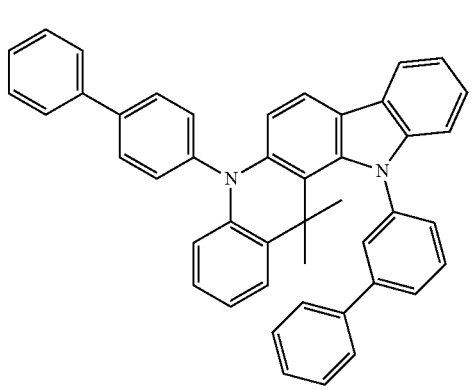
(5-59)
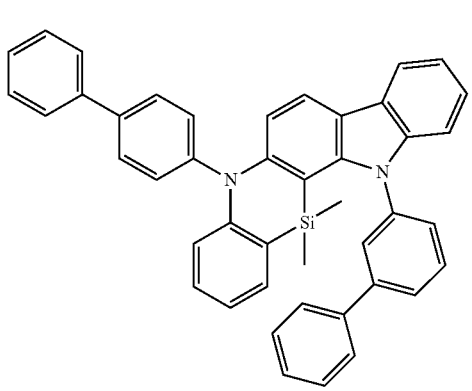
(5-60)
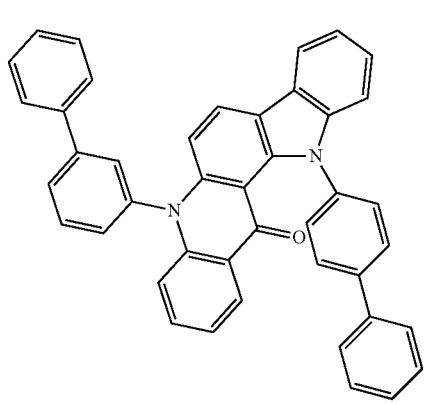

-continued
(5-61)
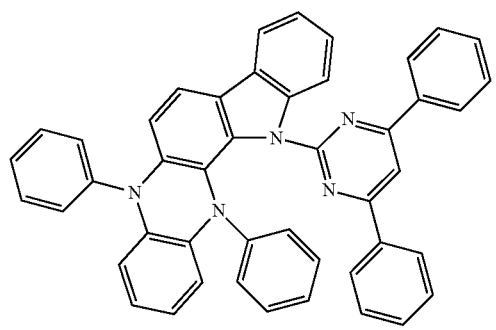
(5-62)
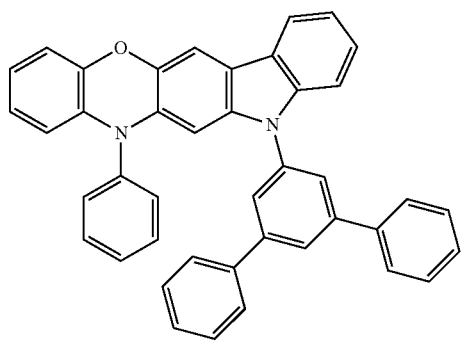
(5-63)
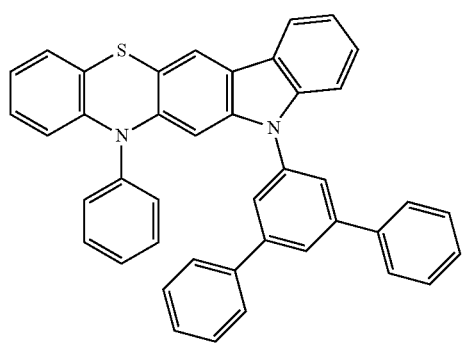
(5-64)
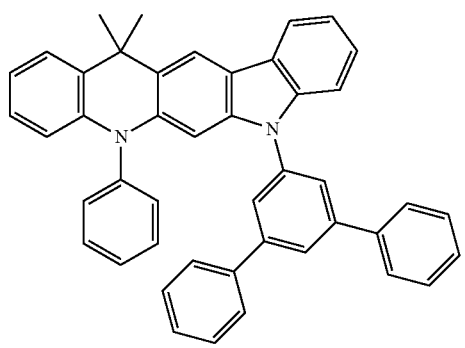
(5-65)
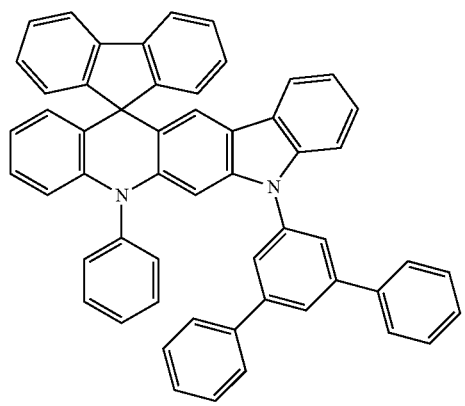
(5-66)
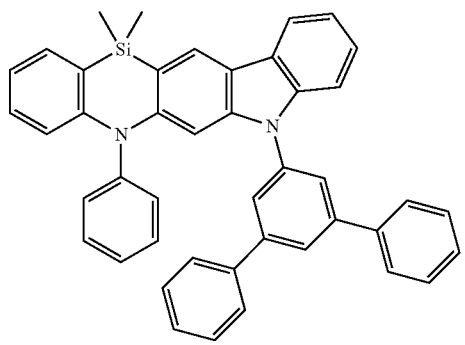
(5-67)
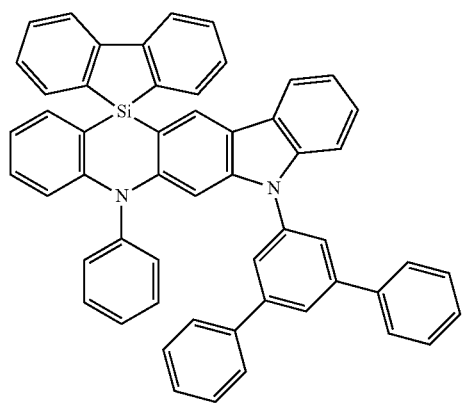
(5-68)
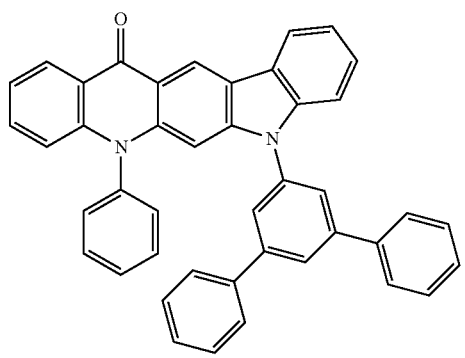

-continued
(5-69)
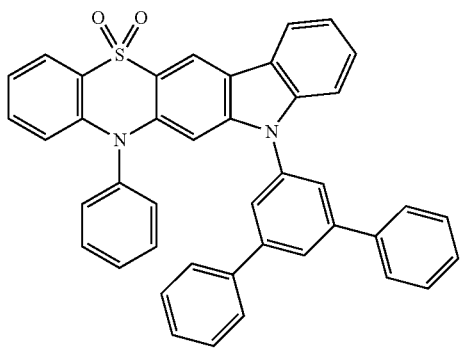
(5-70)
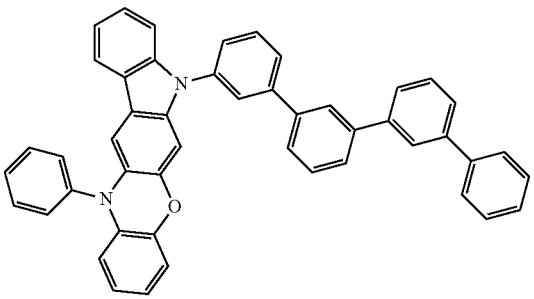
(5-71)
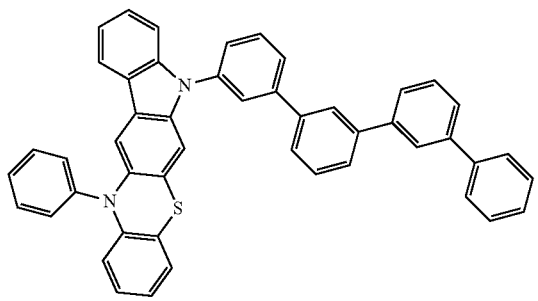
(5-72)
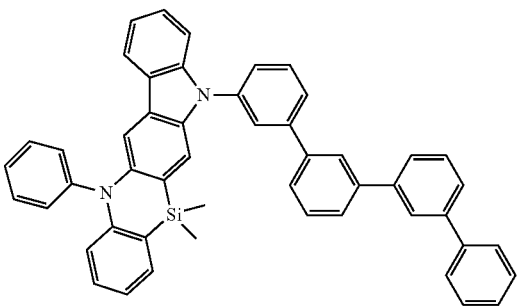
(5-73)
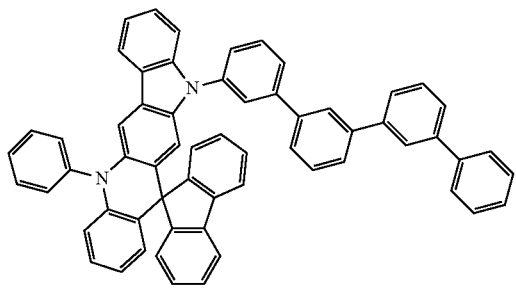
(5-74)
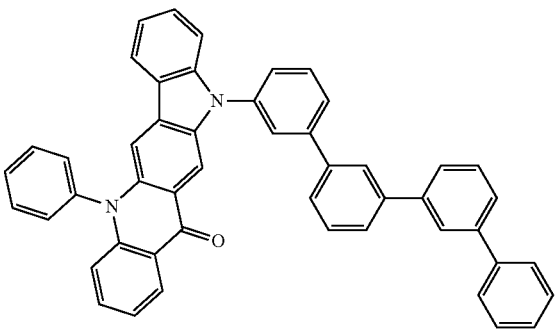
(5-75)
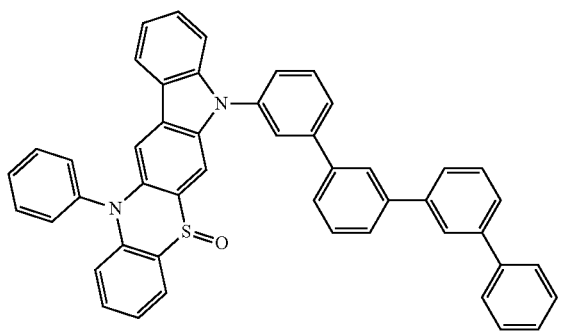
(5-76)
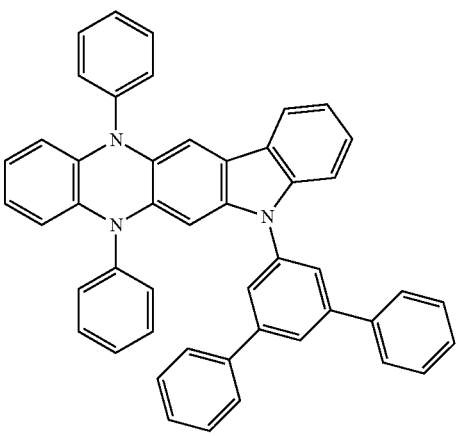

-continued
(5-77)
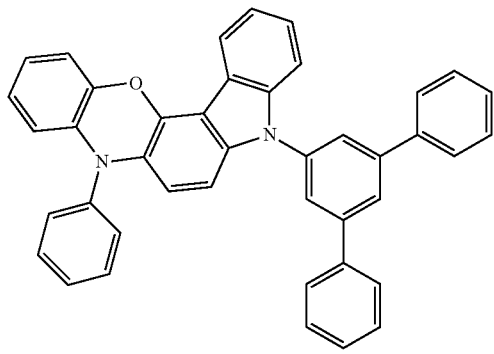
(5-78)
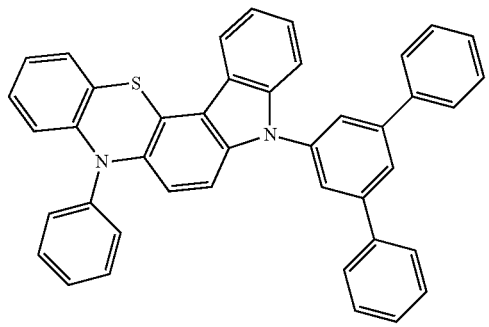
(5-79)
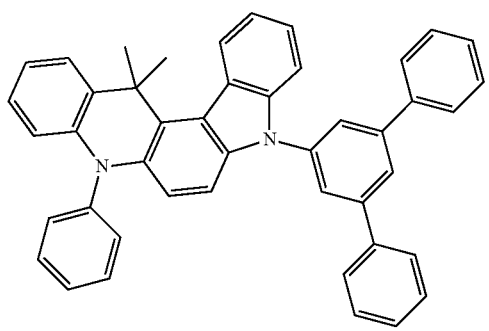
(5-80)
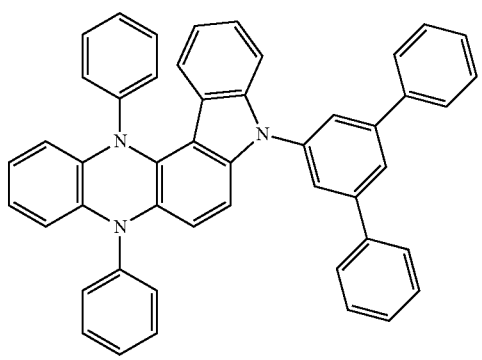
(5-81)
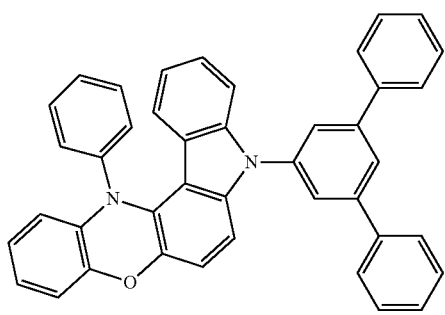
(5-82)
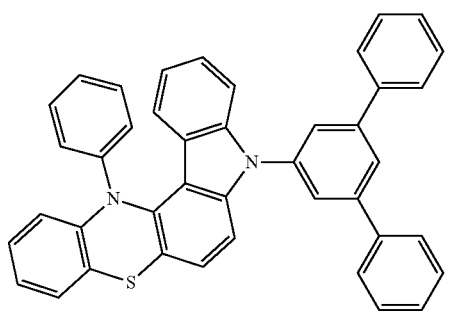
(5-83)
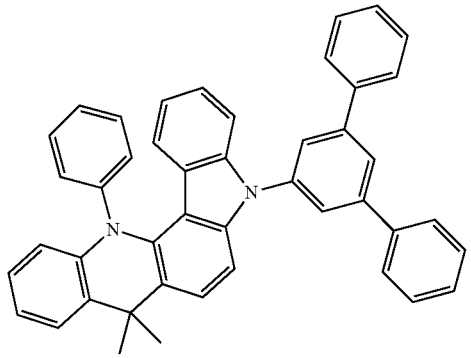
(5-84)
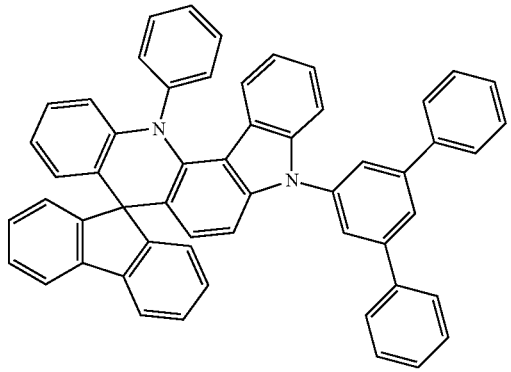

-continued
(5-85)
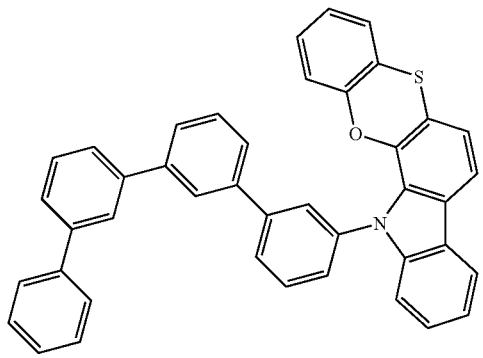
(5-86)
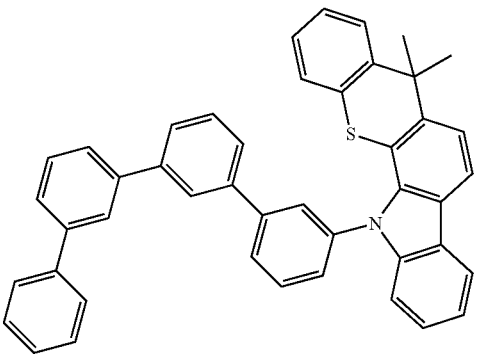
(5-87)
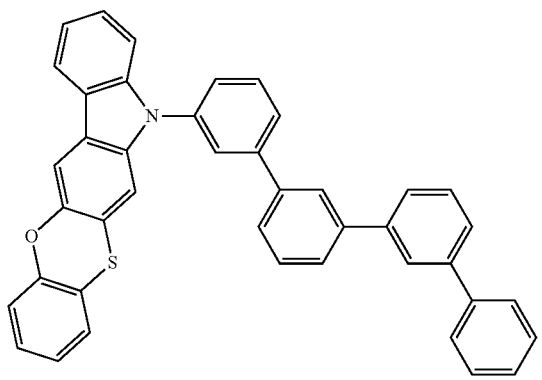
(5-88)
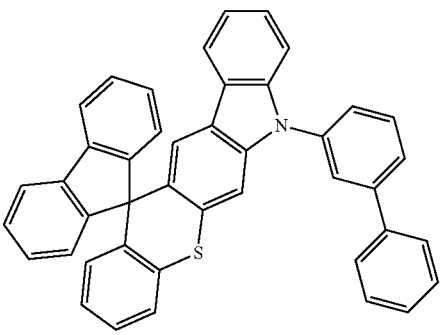
(5-89)
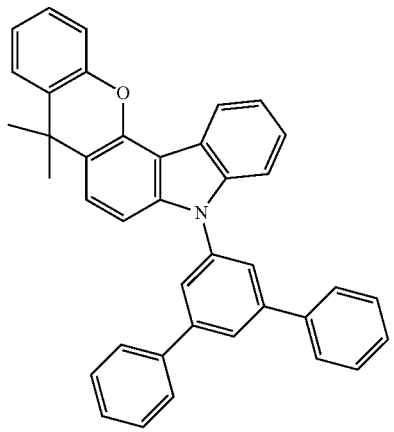
(5-90)
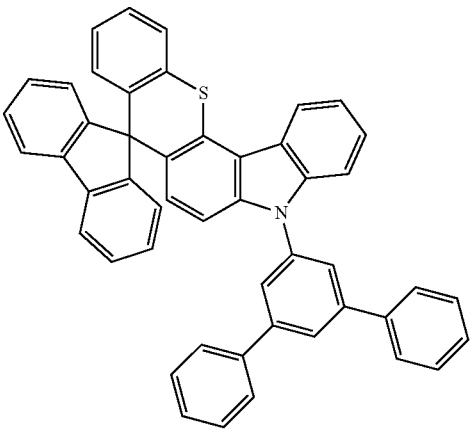
(5-91)
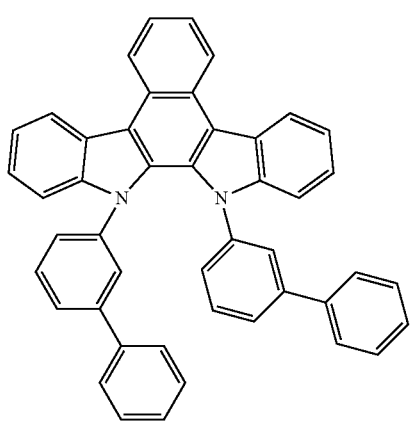
(5-92)
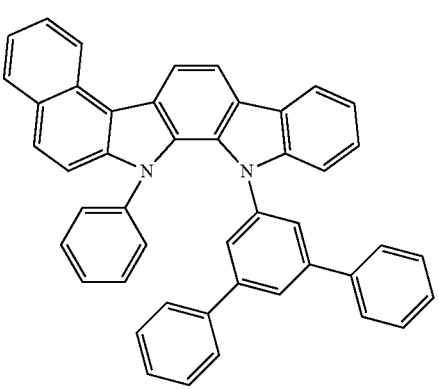

-continued
(5-93)
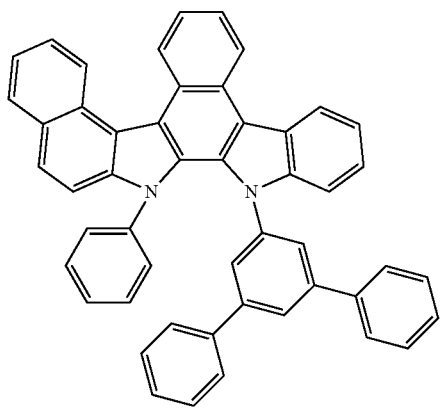
(5-94)
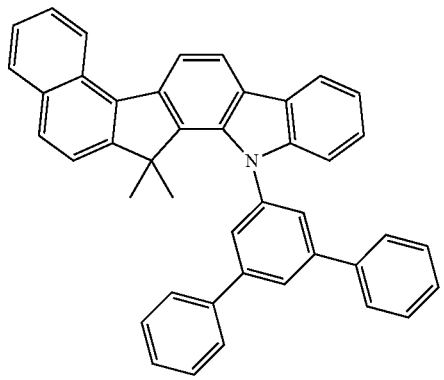
(5-95)
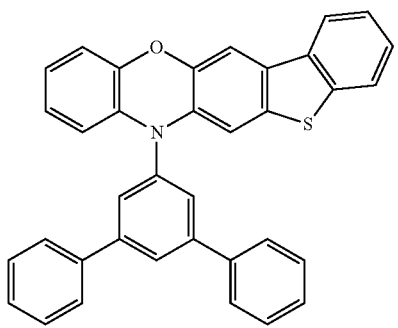
(5-96)
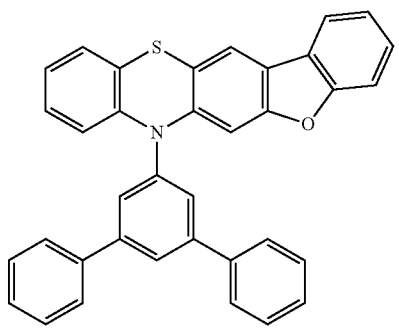
(5-97)
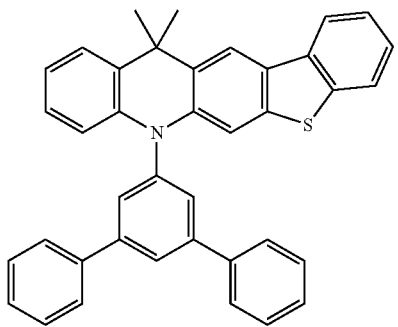
(5-98)
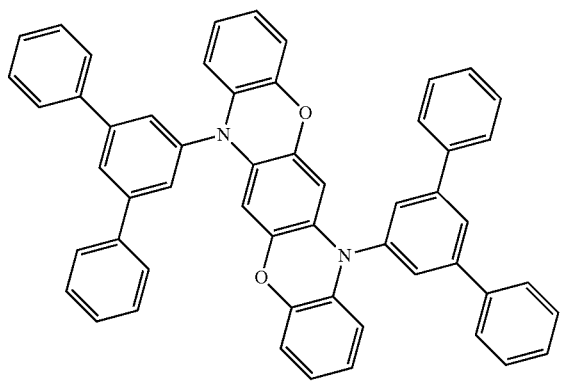
(5-99)
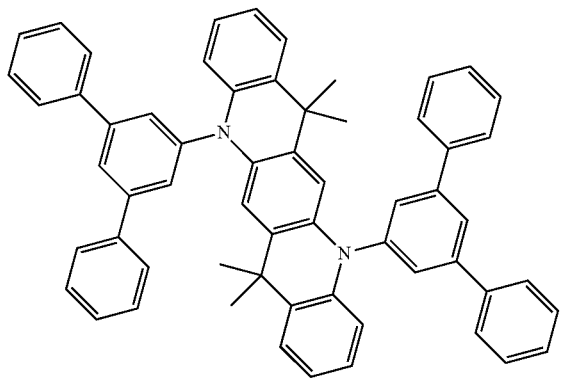
(5-100)
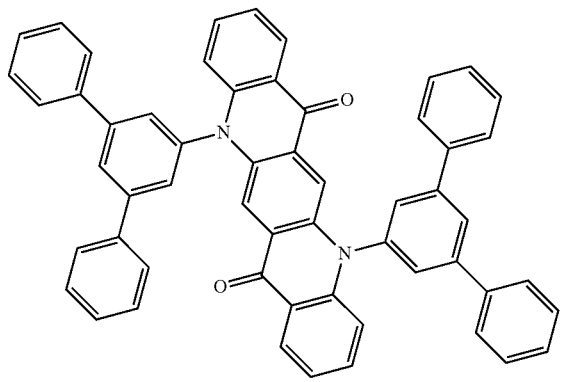

-continued
(5-101)
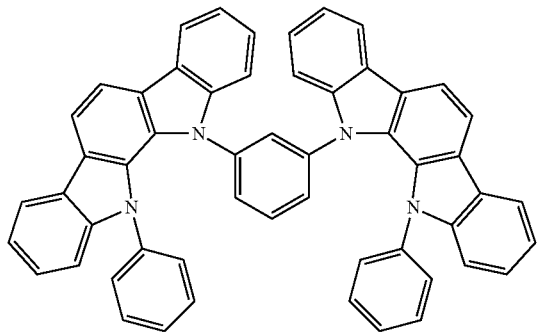
(5-102)
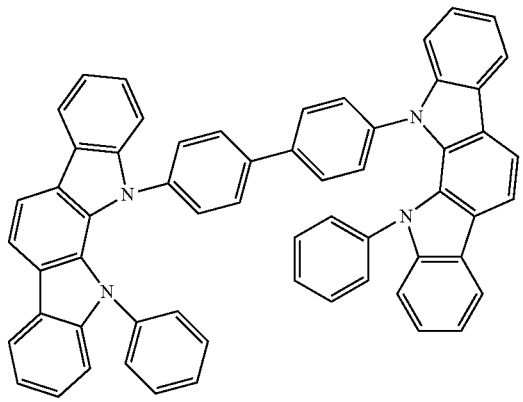
(5-103)
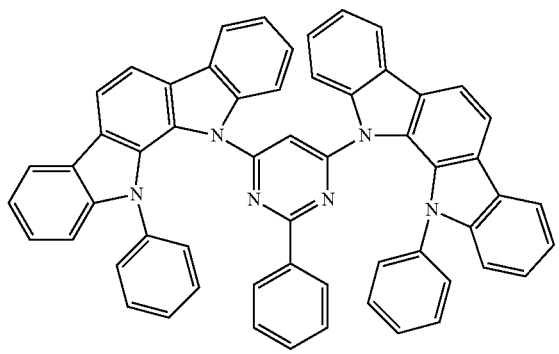
(5-104)
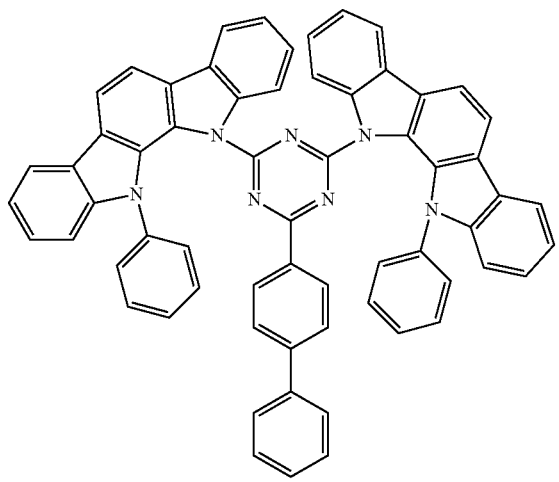
(5-105)
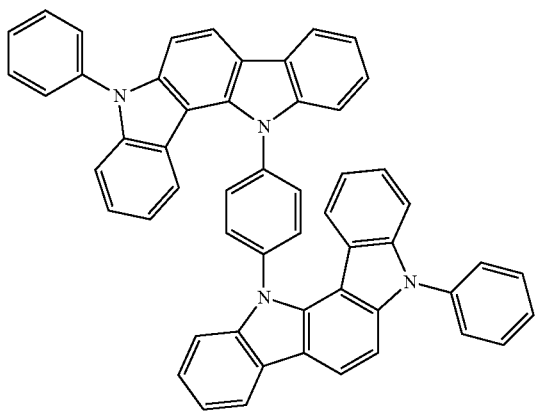
(5-107)
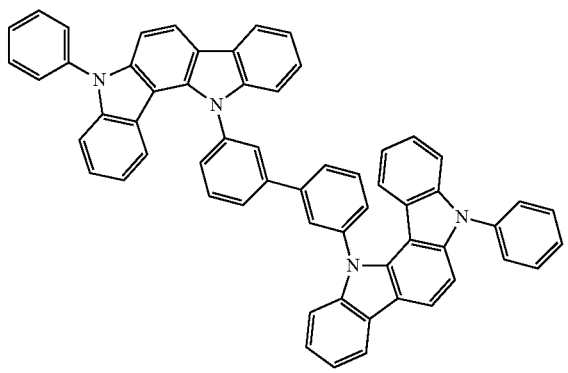

-continued
(5-108)
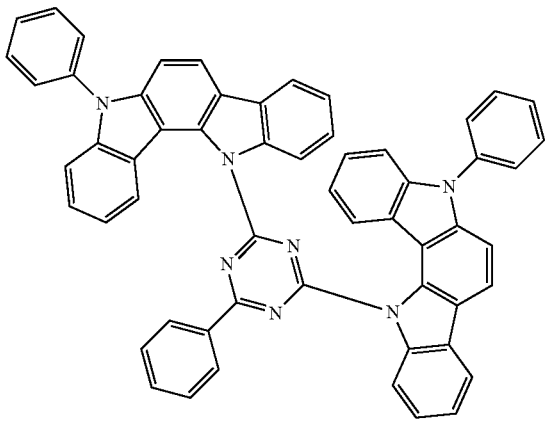
(5-109)
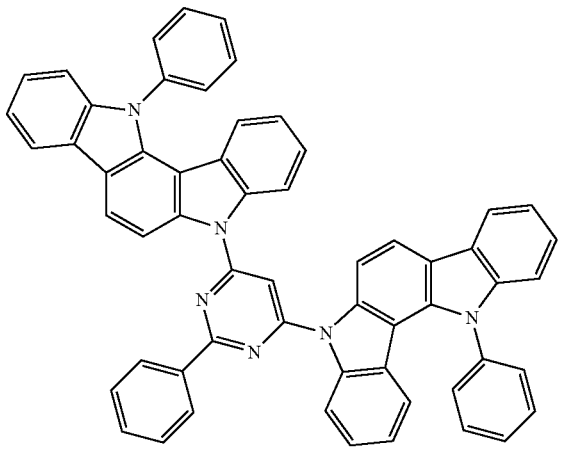
(5-110)
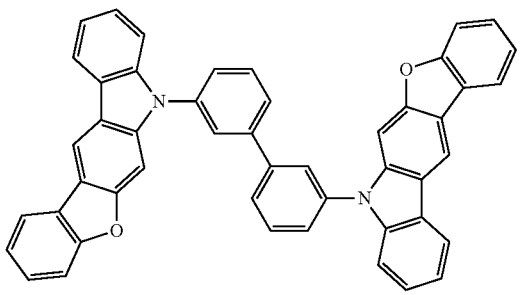
(5-111)
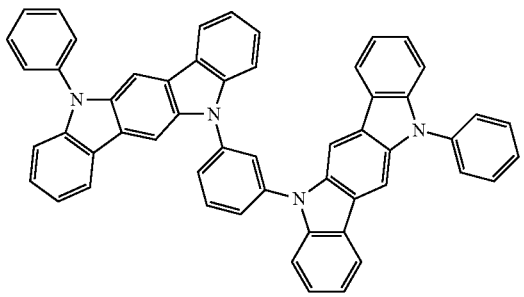
(5-112)
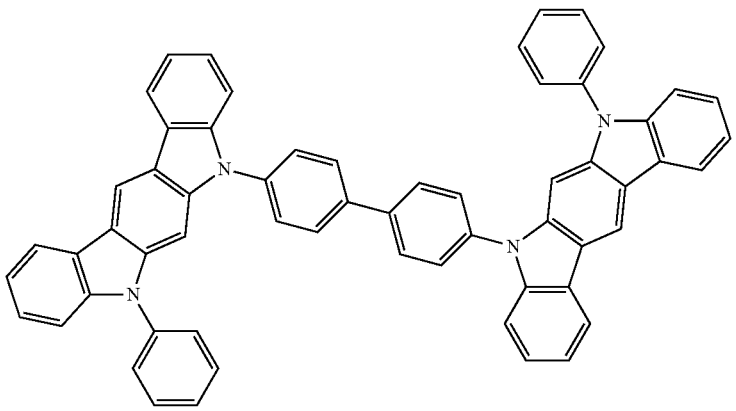
(5-113)
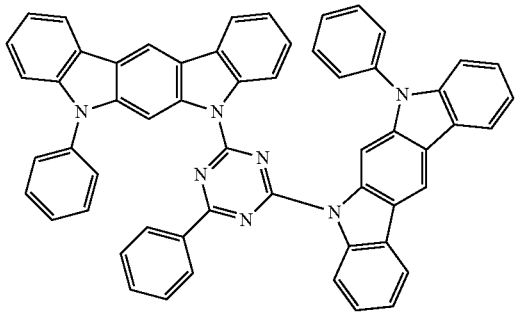
(5-114)
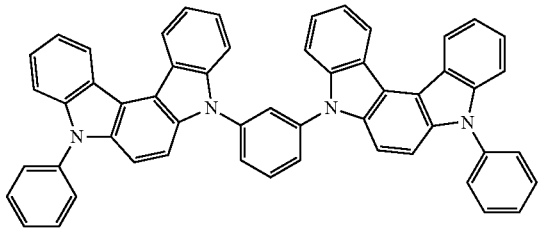

(5-115)
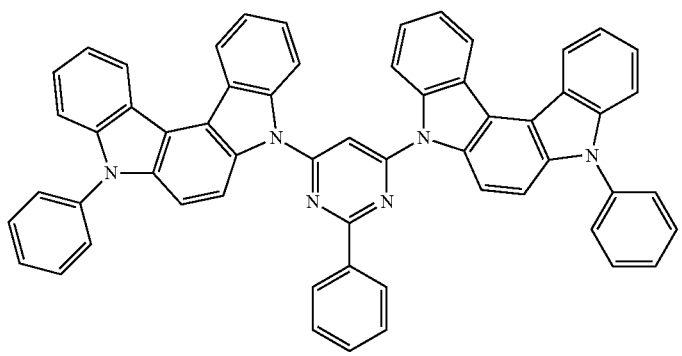
(5-116)
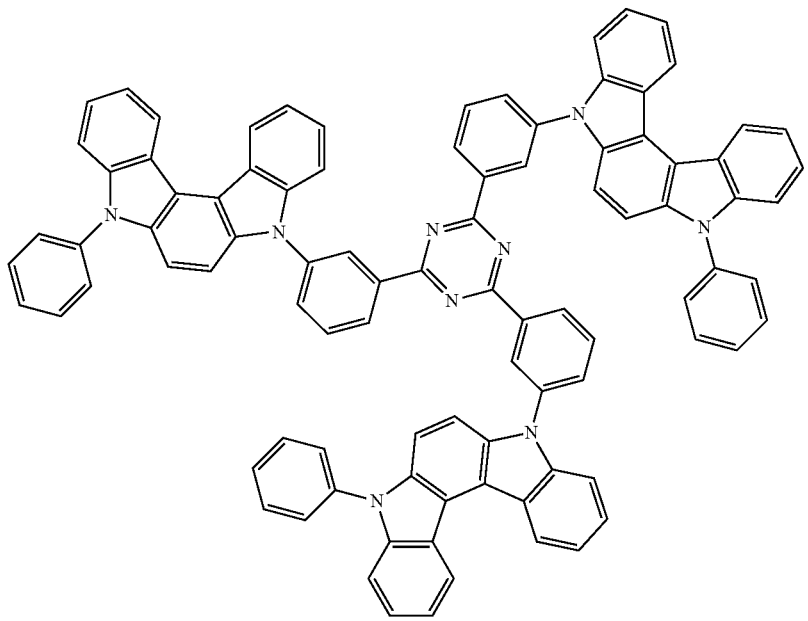
(5-117)
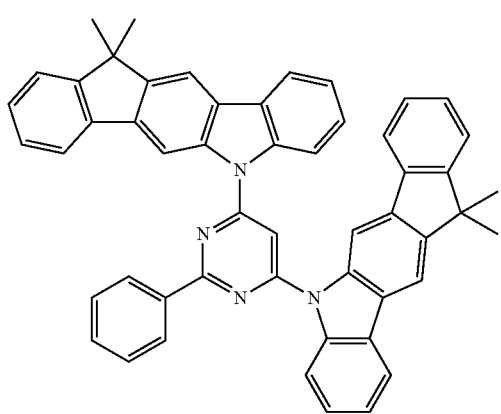

-continued

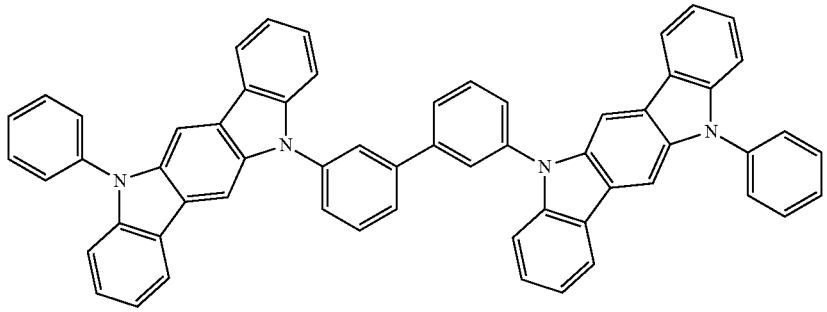
(5-118)

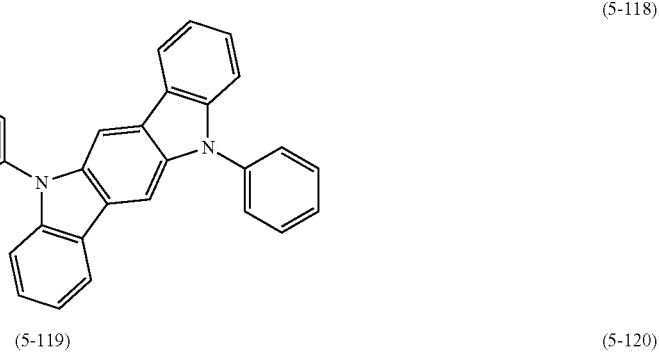
(5-119) (5-120)

In particular, according to the structural formula (6) of the group A, the structural formula of the group A is selected from

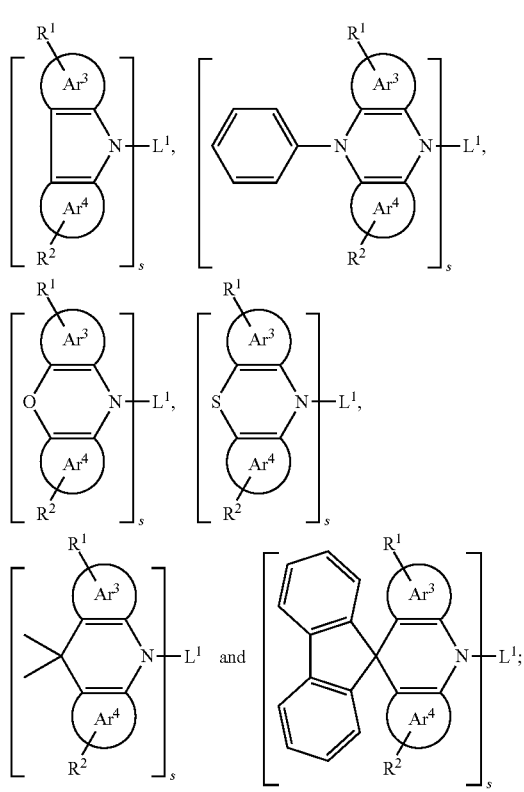

wherein Ar³, Ar⁴, R¹, R², L¹, s have the same meanings as the structural formulas (1) to (6).

Further, according to the structural formula (6) of the group A, the structural formula of the group A is as follows:

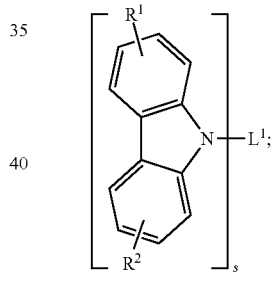

Wherein, the meanings of $R^1$, $R^2$, $L^1$, and s are the same as those in the structural formulae (1) to (6).

A in the formula (I) is a functional group having a triplet host function, and the core group of A is selected from the group consisting of a group having a cyclic aromatic hydrocarbon group, a group having an aromatic heterocyclic group, and a group having 2 to 10 ring structures, Wherein the group having a cyclic aromatic hydrocarbon group is selected from a biphenyl group, a triphenyl group, a benzo group and a fluorenyl group; the group having an aromatic heterocyclic group is selected from dibenzothiophenyl, dibenzofuryl, dibenzoselenophenyl, furyl, thienyl, benzofuryl, benzothiophenyl, benzoselenophenyl, carbazolyl, indole carbazolyl, pyridine indolyl, pyrrole dipyridyl, pyrazolyl, imidazolyl, triazolyl, oxazolyl, thiazolyl, oxadiazolyl, oxatriazole, dioxazolyl, thiadiazolyl, pyridyl, pyridazinyl, pyrimidinyl, pyrazinyl, triazinyl, oxazinyl, oxathiazinyl, oxadiazinyl, indolyl, benzimidazolyl, indazolyl, oxazolyl, dibenzoxazolyl, benzoisoxazolyl, benzothiazolyl, quinolyl, isoquinolyl, o-diaza(hetero)naphthyl, quinazolinyl, quinoxalinyl, naphthyl, phthalidyl, pteridinyl, xanthenyl, acridinyl, phenazinyl, phenothiazinyl, phenoxazinyl, benzofuran pyridyl, furopyridinyl, benzothiophene pyridinyl, thiophene pyridinyl, benzoselene pyridinyl and selenophene benzodipyridyl; each ring in the groups having 2 to 10 rings may be same or different kind of cyclic aromatic hydrocarbon group or aromatic heterocyclic group, and may be each other linked together directly or by at least one of the following: an oxygen atom, a nitrogen atom, a sulfur atom, a silicon atom, a phosphorus atom, a boron atom, a chain aliphatic group, and an aliphatic ring group.

Further, A in the formula (I) is a core group having a triplet host function, which is selected from the following groups:

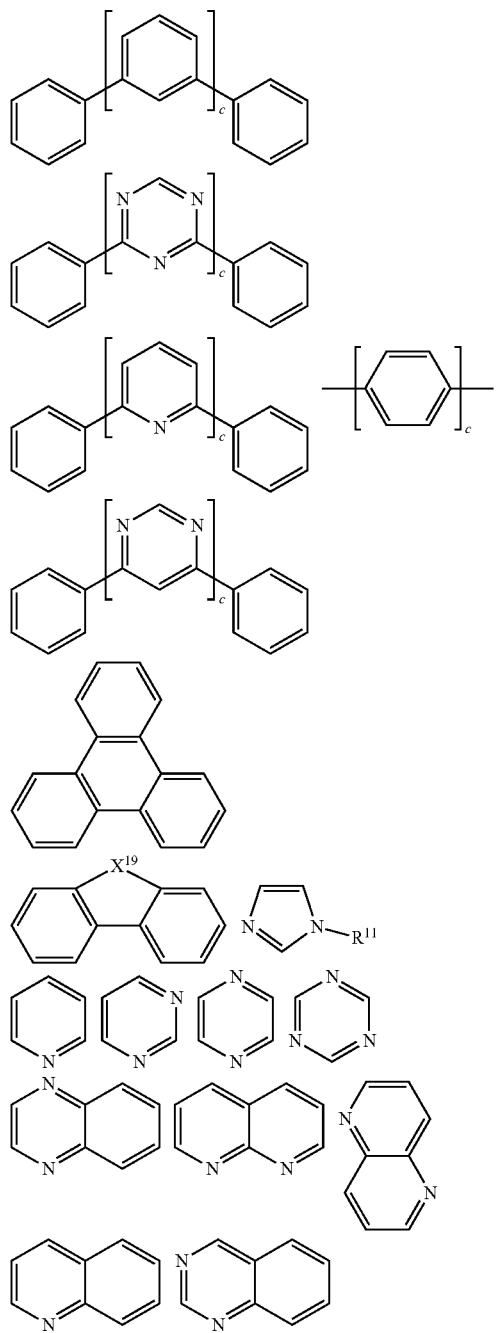

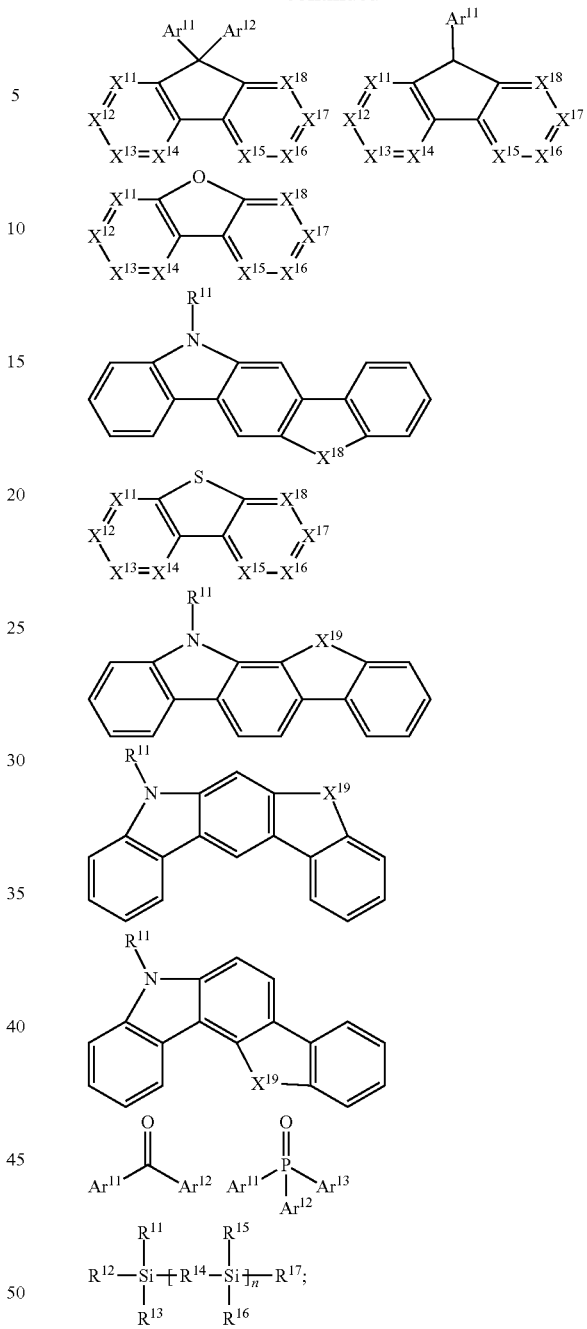

Wherein $R^{11}$ to $R^{17}$ are each independently selected from the group consisting of hydrogen, an alkyl group, an alkoxy group, an amino group, an alkenyl group, an alkynyl group, an aralkyl group, a heteroalkyl group, an aryl group and a heteroaryl group. $Ar^{11}$ is selected from an aryl group containing 6 to 60 carbon atoms, a heteroaryl group containing 3 to 60 carbon atoms, an fused aryl group containing 6 to 60 carbon atoms, and a fused heteroaryl group containing 3 to 60 carbon atoms; c is any integers from 0 to 20; $X^{11}$ to $X^{18}$ are each independently selected from the group consisting of CH and N; and $X^{19}$ is selected from $CR^1R^2$ and $NR^1$. $R^1$ and $R^2$ are each independently selected from the group consisting of H, D, F, CN, alkenyl, alkynyl, nitrile, amine, nitro, acyl, alkoxy, carbonyl, sulfone, and an alkyl group containing 1 to 30 carbon atoms, a cycloalkyl group containing 3 to 30 carbon atoms, an aromatic hydrocarbon group containing 5 to 60 ring atoms, and an aromatic heterocyclic group containing 5 to 60 ring atoms.

Alternatively, Ar in the general formula (II) may be none. In this case, —SG is a group having the following structural formula:

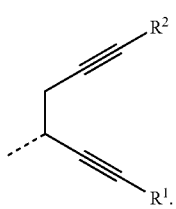

(II-1)

Further, according to the general formula (II), the solubilizing structural unit-SG is selected from structural formulas as follows:

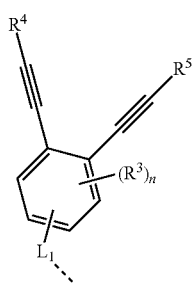

SG-01

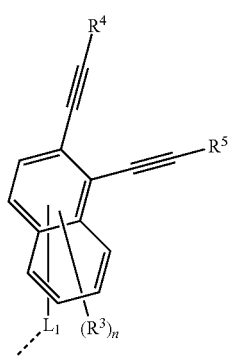

SG-02

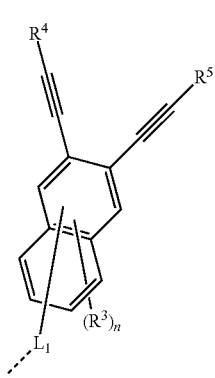

SG-03

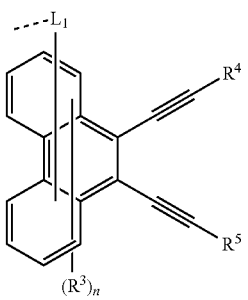

SG-04

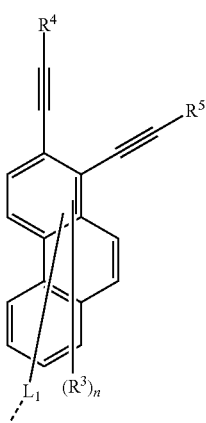

SG-05

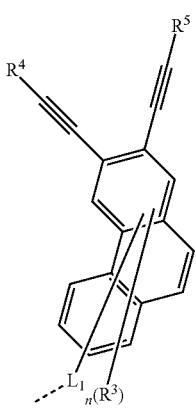

SG-06

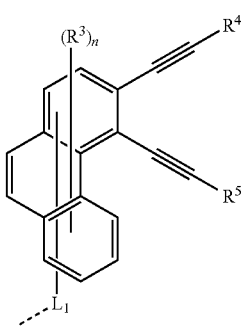

SG-07

-continued
SG-08
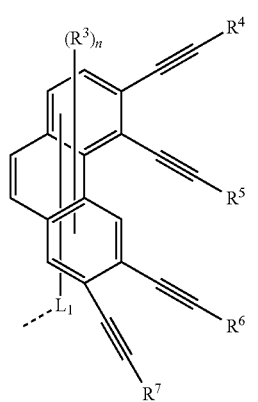
SG-09
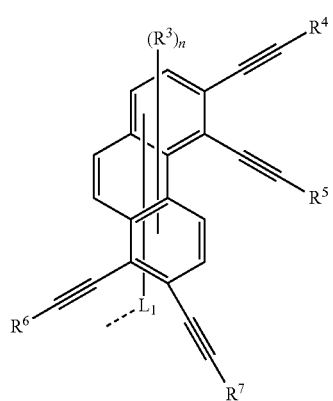
SG-10
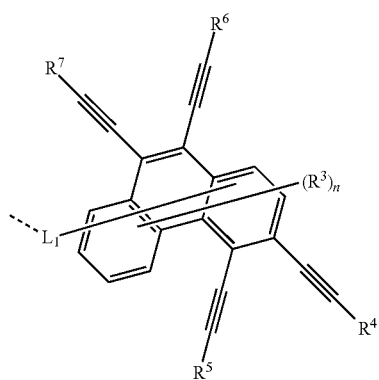
SG-11
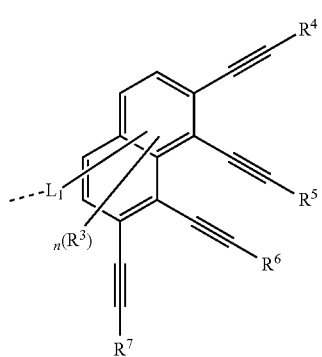
-continued
SG-12
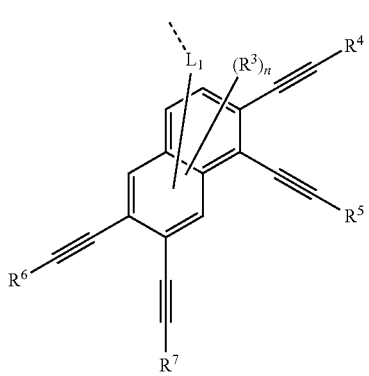
SG-13
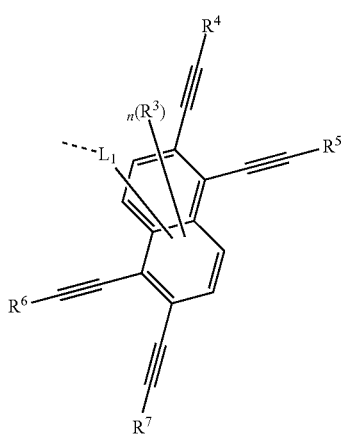
SG-14
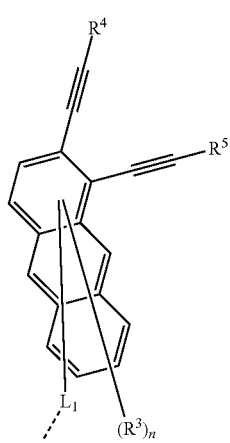
SG-15
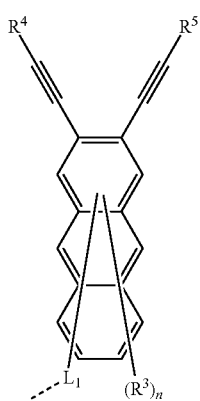

SG-16
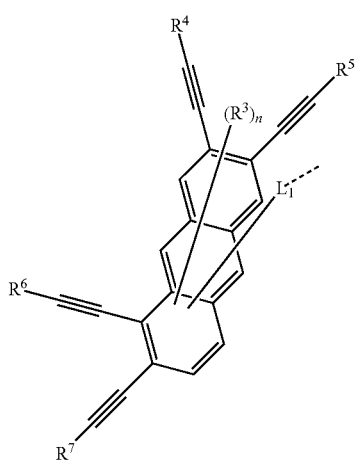
SG-17
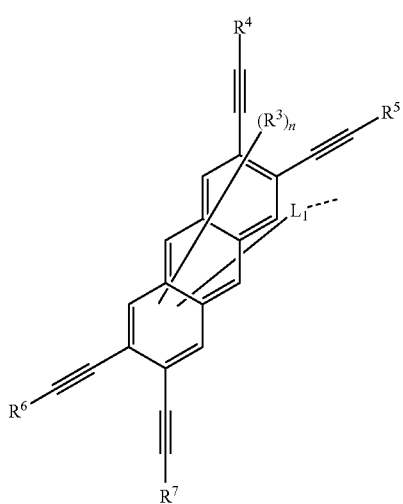
SG-18
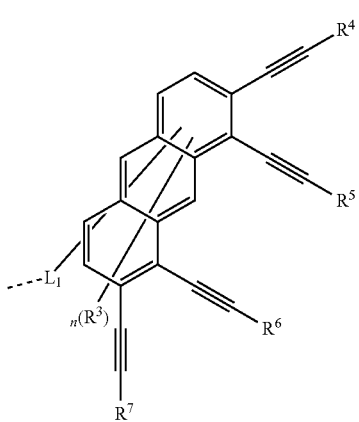
SG-19
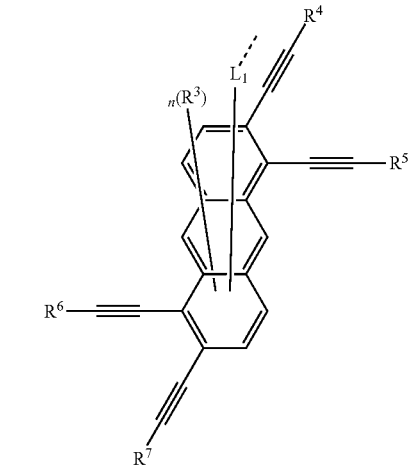
SG-20
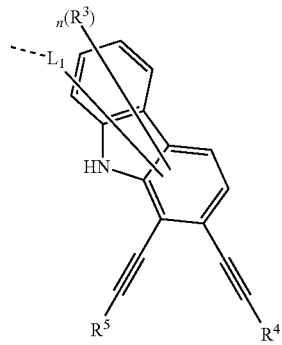
SG-21
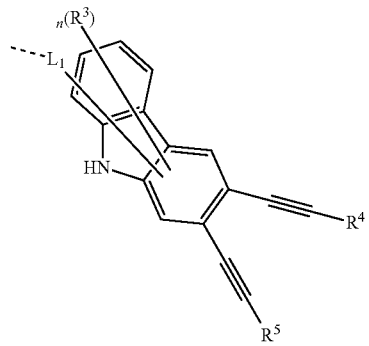
SG-22
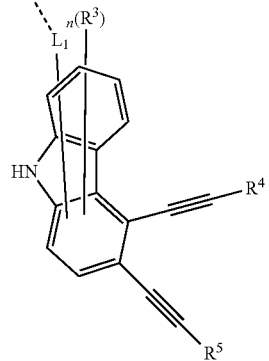

SG-23

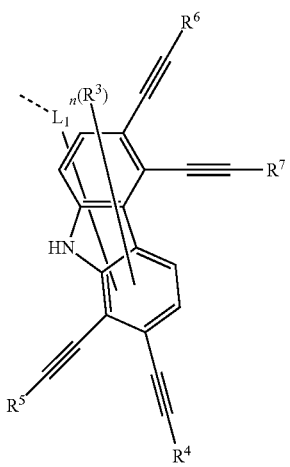

SG-24

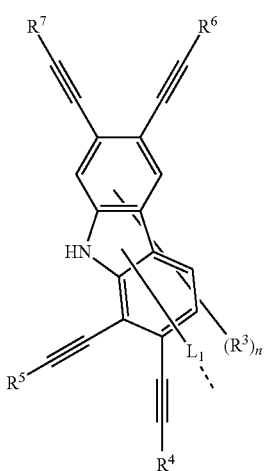

SG-25

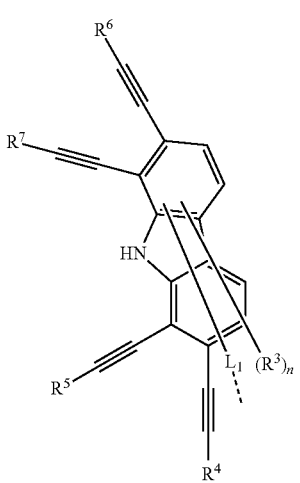

SG-26

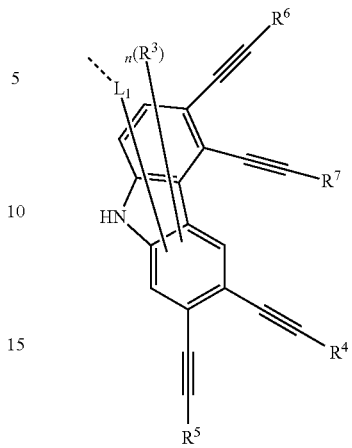

SG-27

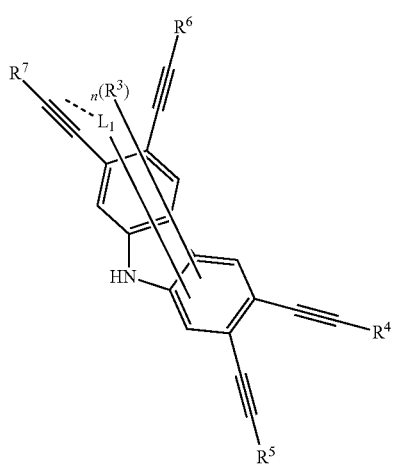

In one of embodiments, in the structural formulas SG-01 to SG-27 of the solubilizing structural unit SG, $R^3$, $R^4$, $R^5$, $R^6$ and $R^7$ are each independently one selected from the group consisting of H, D, F, CN, an alkyl chain, an aromatic ring group, an aromatic heterocyclic group, an amino group, a silicon group, a formyl group, an alkoxy group, an aryloxy group and a siloxy group, the alkyl chain is selected from the group consisting of an unsubstituted alkyl chain, a fluoroalkyl chain, a deuterated alkyl chain, and a deuterated partially fluoroalkyl chain; the aromatic ring group is selected from the group consisting of an unsubstituted aromatic ring group and a deuterated aromatic ring group; the aromatic heterocyclic group is selected from the group consisting of an unsubstituted aromatic heterocyclic group and a deuterated aromatic heterocyclic group; the amino group is selected from the group consisting of an unsubstituted amino group and a deuterated amino group; the silicon group is selected from the group consisting of an unsubstituted silicon group and a deuterated silicon group; the germyl group is selected from the group consisting of an unsubstituted germyl group and a deuterated germyl group; the alkoxy group is selected from the group consisting of an unsubstituted alkoxy group, a silyalkoxy group, a fluoroalkoxy group, a deuterated alkoxy group, a deuterated fluoroalkoxy group, and a deuterated silylalkoxy group; the aryloxy group is selected from the group consisting of an unsubstituted aryloxy group and a deuterated aryloxy group; the siloxy group is selected from the group consisting of an unsubstituted siloxy group and a deuterated siloxy group.

Further, $R^3$, $R^4$, $R^5$, $R^6$ and $R^7$ are each independently selected from the group consisting of hydrogen, a linear alkyl group containing 1 to 20 carbon atoms, an alkoxy group containing 1 to 20 carbon atoms, a branched alkyl group containing 3 to 20 carbon atoms, and a branched alkoxy group containing 3 to 20 carbon atoms.

In the structural formula of the solubilizing structural unit SG, n is an integer greater than 0; -$L_1$- is a single bond, or $L_1$ is selected from an aryl group and a heteroaryl group; a dashed line represents a bond that is bonded to the functional structural unit Ar.

Further, $L_1$ is selected from the group consisting of following single bond and structural formulas:

| single bond | $L_1$-1 |
|---|---|

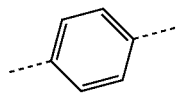

$L_1$-2

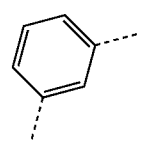

$L_1$-3

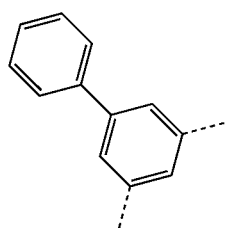

$L_1$-4

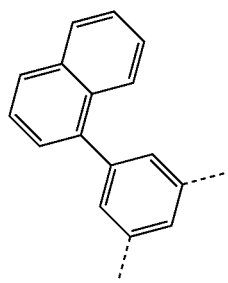

$L_1$-5

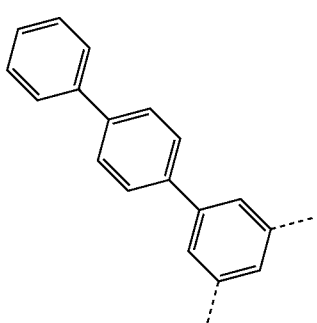

$L_1$-6

-continued

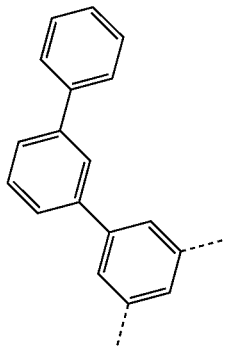

$L_1$-7

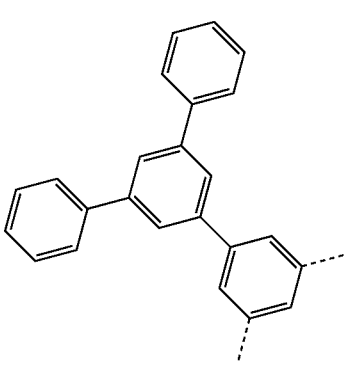

$L_1$-8

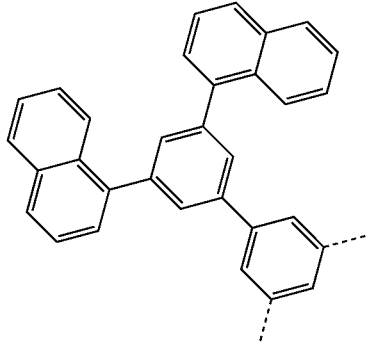

$L_1$-9

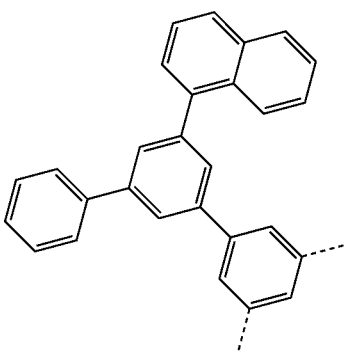

$L_1$-10

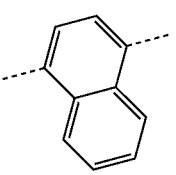

$L_1$-11

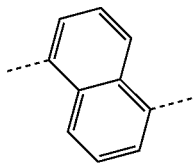
L₁-12

Alternatively in another embodiment, in the above structural formulas SG-01 to SG-27, $R^1$, $R^2$, $R^3$ and $R^4$ are one each independently selected from the group consisting of F, Cl, Br, I, N(Ar)$_2$, CN, NO$_2$, Si(R')$_3$, B(OR')$_2$, C(=O)Ar, C(=O)R', P(=O)(Ar)$_2$, P(=O)(R')$_2$, S(=O)Ar, S(=O)R', S(=O)$_2$Ar, S(=O)$_2$R', —CR'=CR'Ar, OSO$_2$R', a linear alkyl containing 1 to 40 carbon atoms (further, a linear alkyl containing 1 to 20 carbon atoms), an alkoxy group (further, an alkoxy group containing 3 to 20 carbon atoms), a thioalkoxy group (further, an thioalkoxy group containing 3 to 20 carbon atoms), a branched alkyl group containing 3 to 40 carbon atoms (further, a branched alkyl group containing 3 to 20 carbon atoms), and a cycloalkyl group containing 3 to 40 carbon atoms (further, a cycloalkyl group containing 3 to 20 carbon atoms); $R^1$, $R^2$, $R^3$ and $R^4$ may be substituted with one or more R' groups, wherein one or more non-adjacent CH$_2$ groups may be substituted with R'C=CR', C=C, Si(R')$_2$, Ge(R')$_2$, Sn(R')$_2$, C=O, C=S, C=Se, C=NR', P(=O)(R'), SO, SO$_2$, NR', O, S or CONR', and wherein one or more atoms may be substituted with F, Cl, Br, I, CN or NO$_2$.

It is to be noted herein that, a single H atom or a CH$_2$ group in this disclosure may be substituted by the above-mentioned group or group R, an alkyl group containing 1 to 40 C atoms is selected from the group consisting of the following groups: methyl, ethyl, n-propyl, isopropyl; cyclopropyl, n-butyl, isobutyl, sec-butyl, tert-butyl, cyclobutyl, 2-methylbutyl, n-pentyl, sec-pentyl, cyclopentyl, n-hexyl, cyclohexyl, n-heptyl, cycloheptyl, n-octyl, cyclooctyl, 2-ethylhexyl, trifluoromethyl, pentafluoroethyl, trifluoroethyl, vinyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentenyl, hexynyl and octynyl. Wherein, the alkoxy group having 1 to 40 carbon atoms is selected from the group consisting of methoxy, trifluoromethoxy, ethoxy, n-propoxy, isopropoxy, n-butoxy, isobutoxy, sec-butoxy, tert-butoxy and methylbutoxy.

Specifically, the glass transition temperature of the organic functional compound according to the present embodiment is ≥100° C.; further, the glass transition temperature is ≥120° C.; further, the glass transition temperature is ≥140° C.; further, the glass transition temperature is ≥160° C.; further, the glass transition temperature is ≥180° C.

Further, the compound generated after Bergman ring-forming reaction, which is represented by the general formula (IV), is HTM with a higher LUMO, generally, the LUMO is equal to or more than −2.7 eV; further, the LUMO is equal to or more than −2.6 eV; furthermore, the LUMO is equal to or more than −2.5 eV; further, the LUMO is equal to or more than −2.4 eV.

Further, for the compound generated after Bergman ring-forming reaction, which is represented by the general formula (IV), generally, (HOMO-1)-HOMO≥0.3 eV, further, (HOMO-1)-HOMO≥0.35 eV; further, (HOMO-1)-HOMO≥0.4 eV; further, (HOMO-1)-HOMO≥0.45 eV; further, (HOMO-1)-HOMO≥0.5 eV. Wherein, the HOMO is the energy level of the highest occupied molecular orbital, and (HOMO-1) is the energy level of the second highest occupied molecular orbital.

Alternatively, the compound generated after Bergman ring-forming reaction, which is represented by the general formula (IV), is HTM with a HOMO equal to or less than −5.0 eV; further, the HOMO is equal to or less than −5.1 eV; further, the HOMO is equal to or less than −5.2 eV.

Alternatively, the compound generated after Bergman ring-forming reaction, which is represented by the general formula (IV), is a phosphorescent host material having a triplet excited state energy level $E_T$ equal to or more than 2.5 eV; further, the triplet excited state energy level $E_r$ is equal to or more than 2.6 eV; further, the triplet excited state energy level $E_T$ is equal to or more than 2.7 eV.

In the energy level structure of organic material, the triplet excited state energy level $E_T$, HOMO, and LUMO play a key role. The determination of these energy levels are described below.

The HOMO and LUMO energy levels can be measured by photoelectric effect, such as XPS (X-ray Photoelectron Spectroscopy) and UPS (Ultraviolet Photoelectron Spectroscopy), or by Cyclic Voltammetry (hereinafter referred to as CV). Recently, quantum chemistry method such as density functional theory (hereinafter referred to as DFT), has also become a feasible method for calculating molecular orbital energy levels.

The triplet excited state energy level $E_T$ of organic materials can be measured by low temperature time-resolved luminescence spectroscopy, or obtained by quantum simulation calculation (e.g., by Time-dependent DFT), such as by the commercial software Gaussian 09W (Gaussian Inc.), and the specific simulation method may refer to WO2011141110 or may be as described in the embodiments below.

It should be noted that, the absolute values of HOMO, LUMO and $E_T$ depend on the measurement or calculation methods used, even for the same method, different HOMO/LUMO value may be obtained by different evaluation methods, such as starting point and peak point on the CV curve may get different values of HOMO/LUMO. Therefore, reasonable and meaningful comparisons should be made by using same measurement method and same evaluation method. The values of HOMO, LUMO and $E_T$ in the present embodiment are obtained based on the simulation of Time-dependent DFT. It should be noted that the acquisition of HOMO, LUMO and $E_T$ is not limited to the method, and they may be obtained by other measurement methods or calculation methods. However, the energy level values determined by different methods should be calibrated to each other.

In this application, HOMO, LUMO is not an absolute value, it is a value relative to the standard material NPB (see the following chemical formula). It should be understood as follows: according to the method herein (see the specific examples), NPB has a HOMO of −5.22 eV and a LUMO of −2.34 eV. Therefore, it is more accurate that the corresponding calibration of HOMO and LUMO is required herein when different methods are involved.

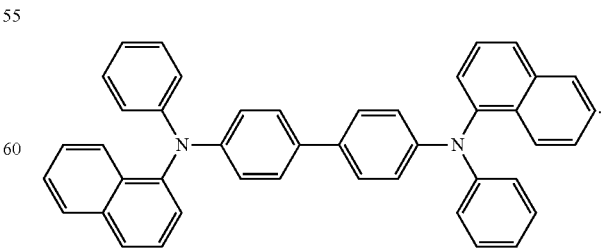

Specifically, the organic functional compound according to the general formula (I) is selected from one of, but not limited to, the following compounds:

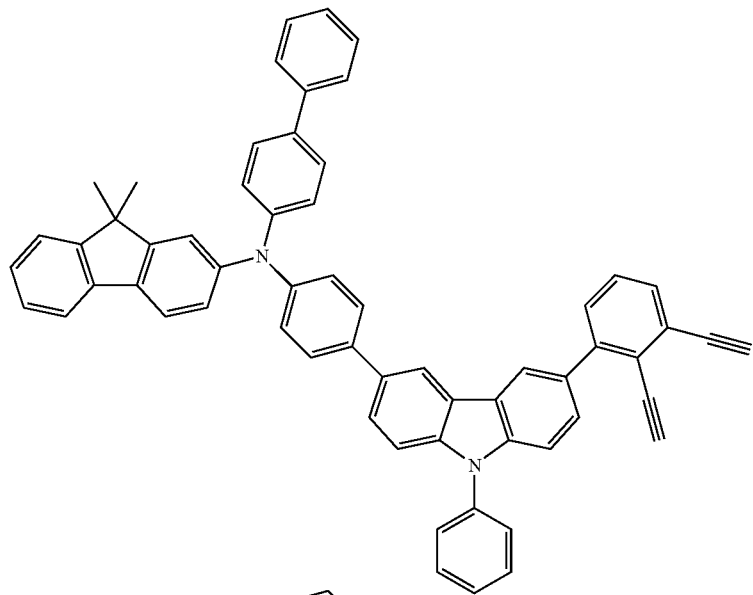
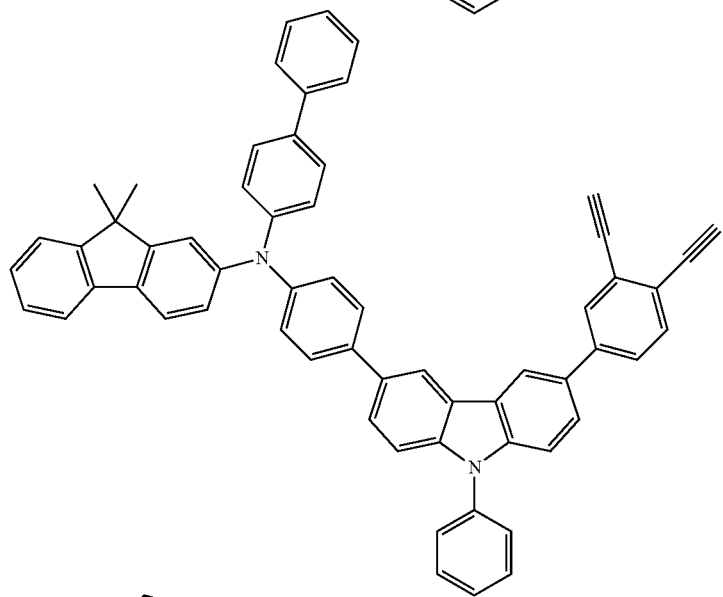
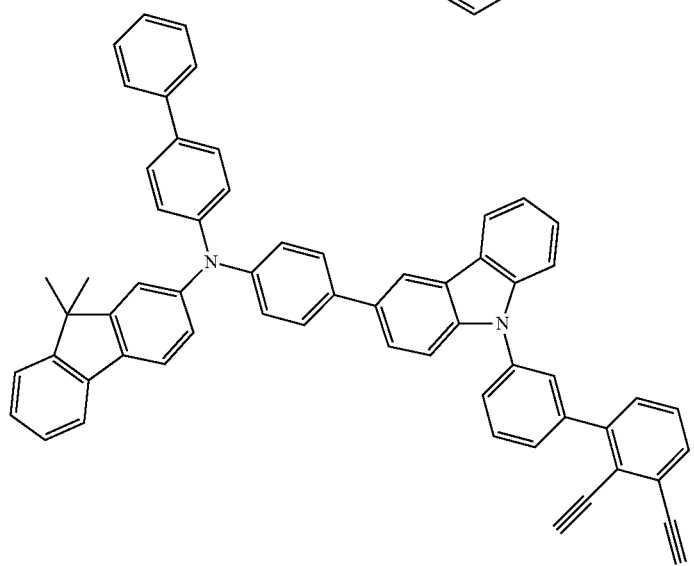

-continued
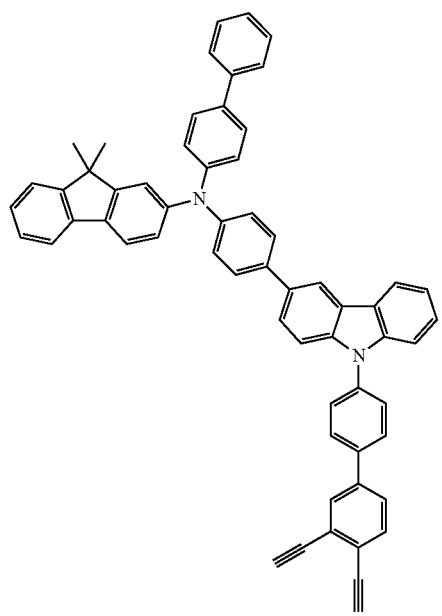
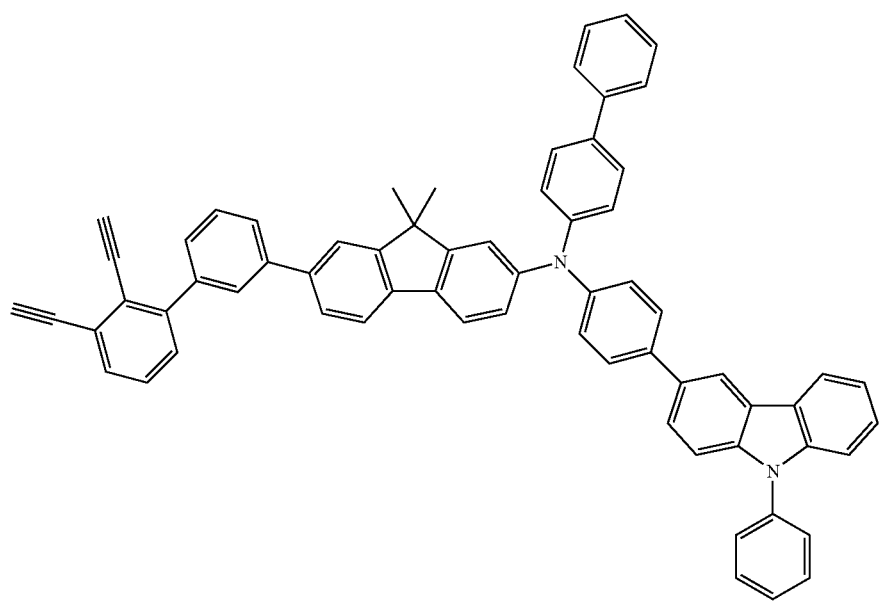

-continued
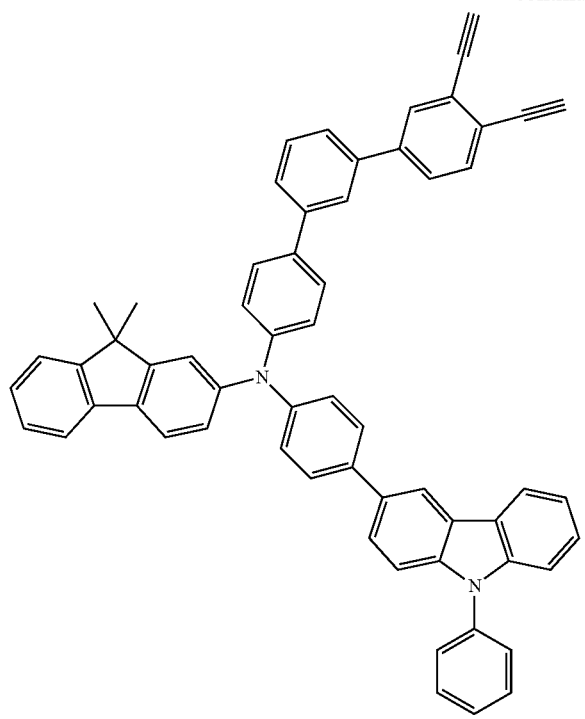
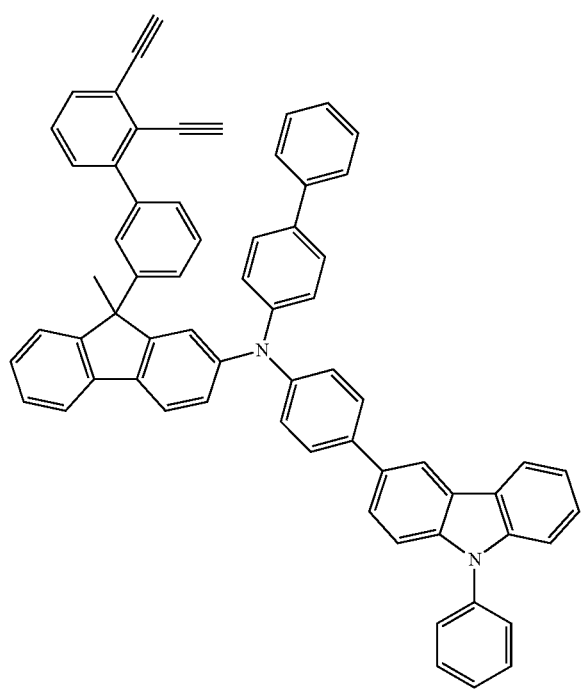

-continued
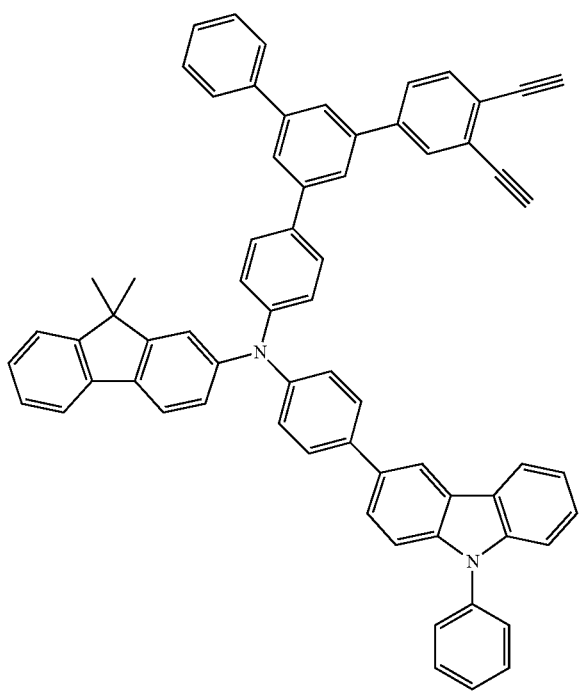
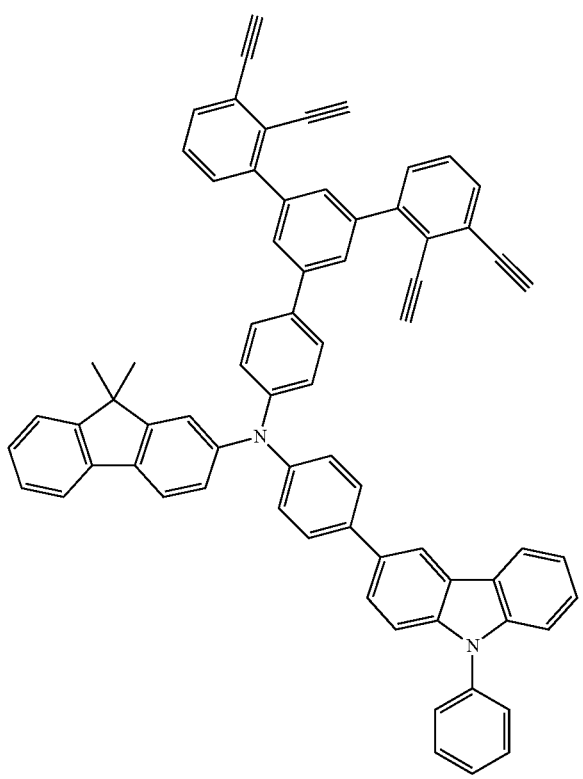

-continued
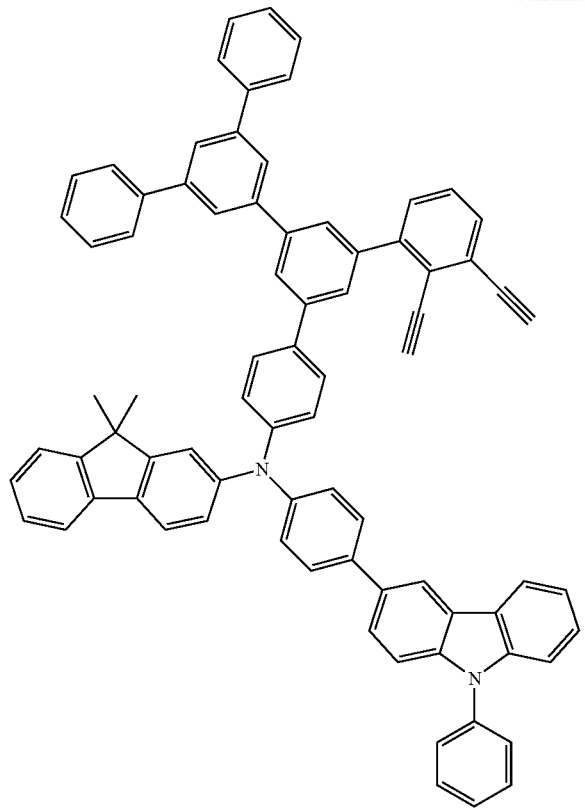
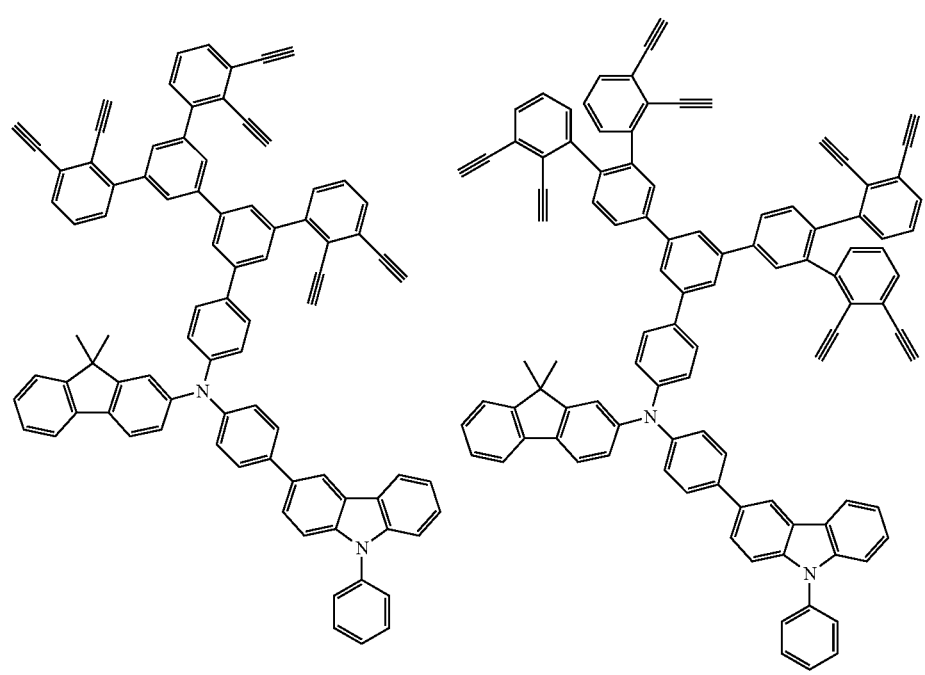 [SMILES: C#Cc1cccc(-c2cc(-c3ccc(N(c4ccc(-c5ccc6c(c5)c5ccccc5n6-c5ccccc5)cc4)c4ccc5c(c4)C(C)(C)c4ccccc4-5)cc3)cc(-c3cc(-c4cccc(C#C)c4C#C)cc(-c4cccc(C#C)c4C#C)c3)c2)c1C#C ; C#Cc1cccc(-c2ccc(-c3cc(-c4ccc(N(c5ccc(-c6ccc7c(c6)c6ccccc6n7-c6ccccc6)cc5)c5ccc6c(c5)C(C)(C)c5ccccc5-6)cc4)cc(-c4ccc(-c5cccc(C#C)c5C#C)c(-c5cccc(C#C)c5C#C)c4)c3)cc2-c2cccc(C#C)c2C#C)c1C#C]

-continued
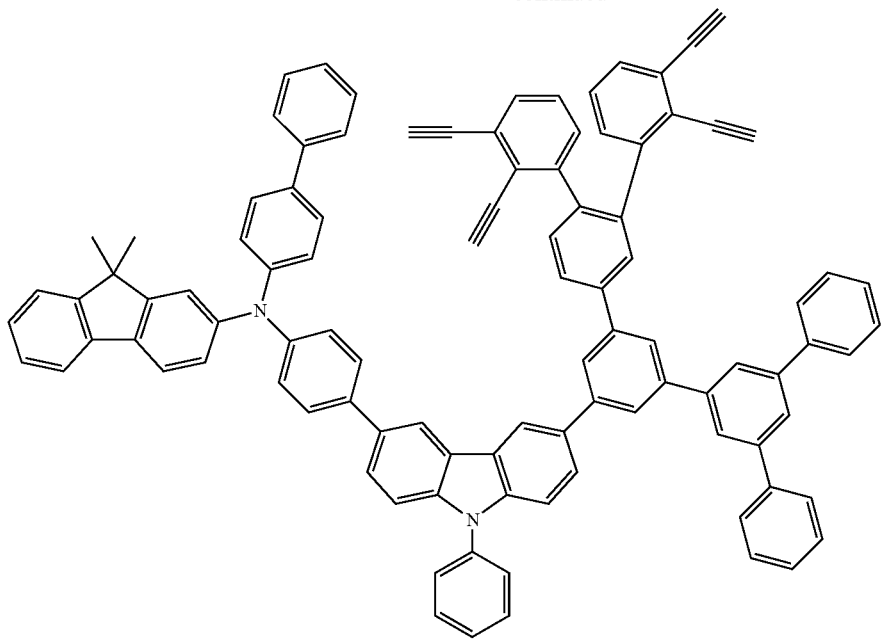
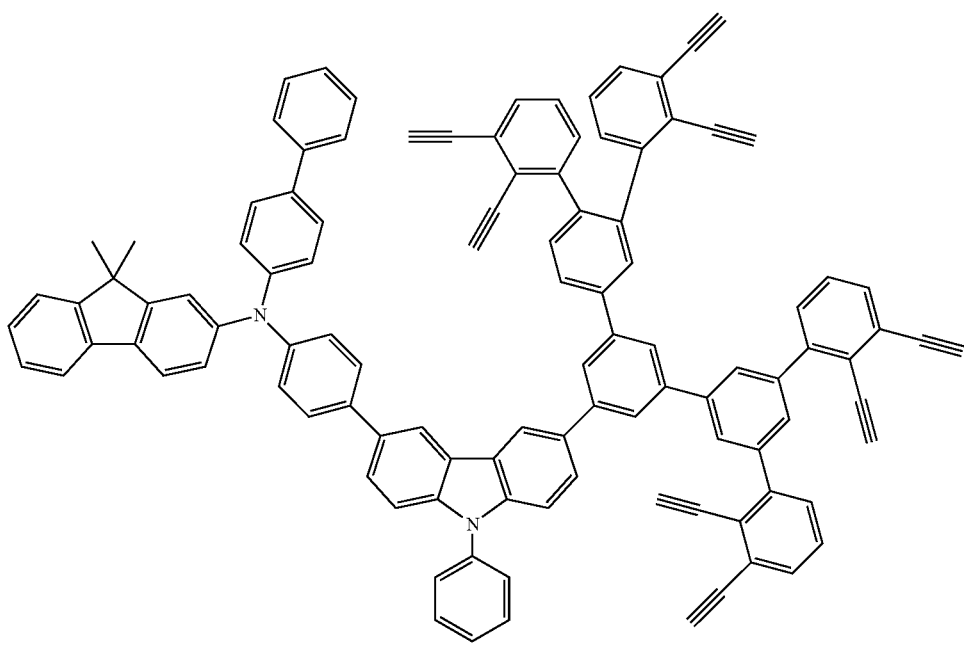

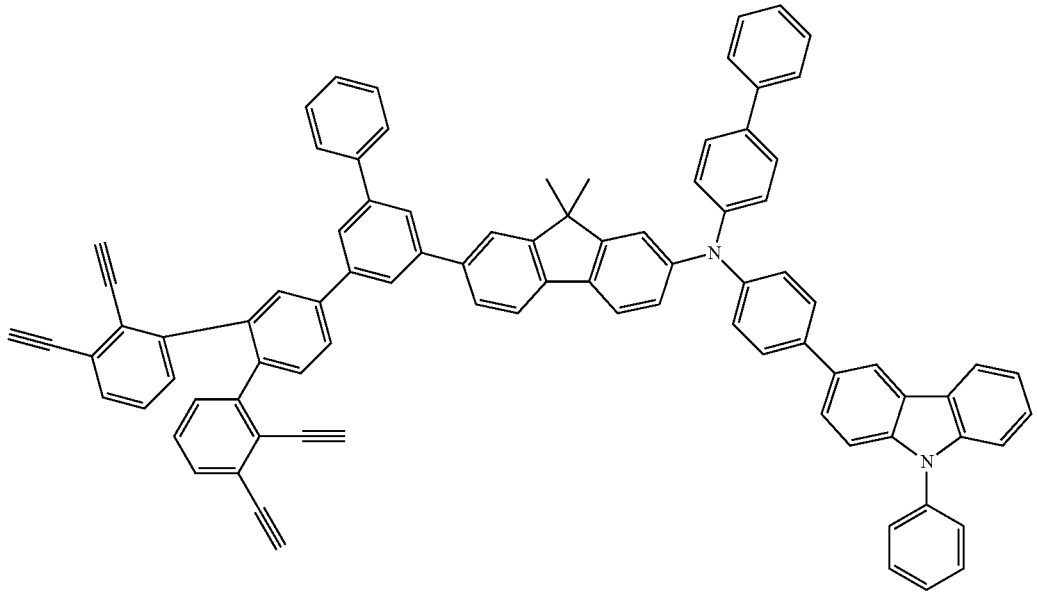
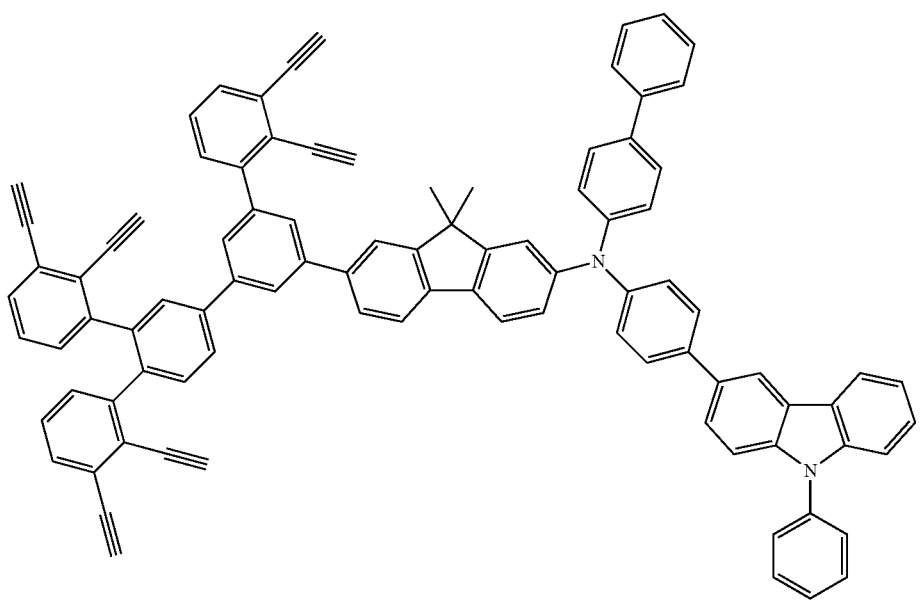

-continued
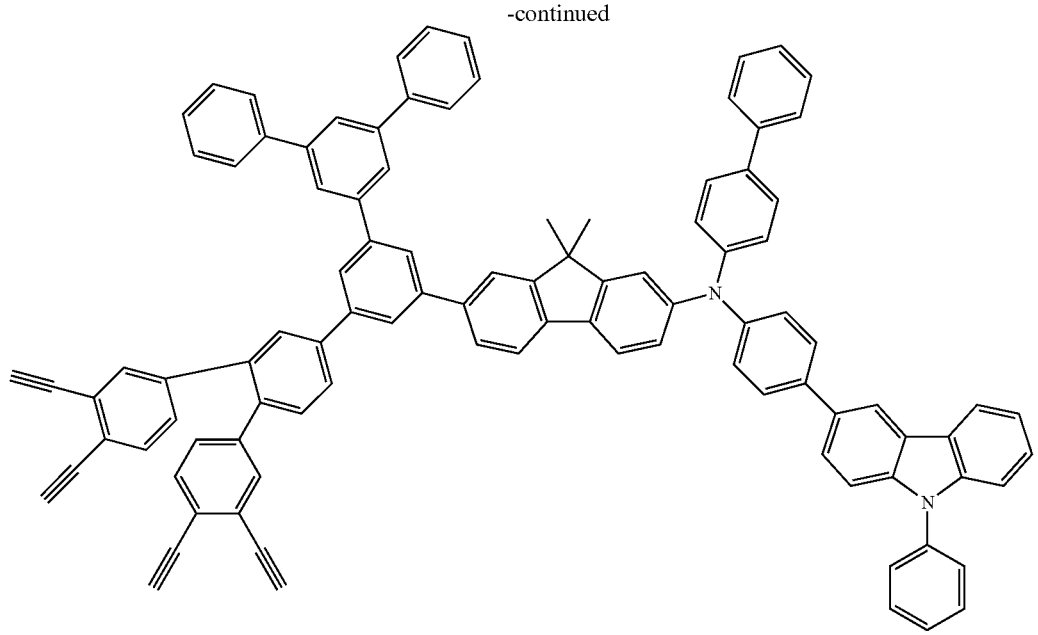
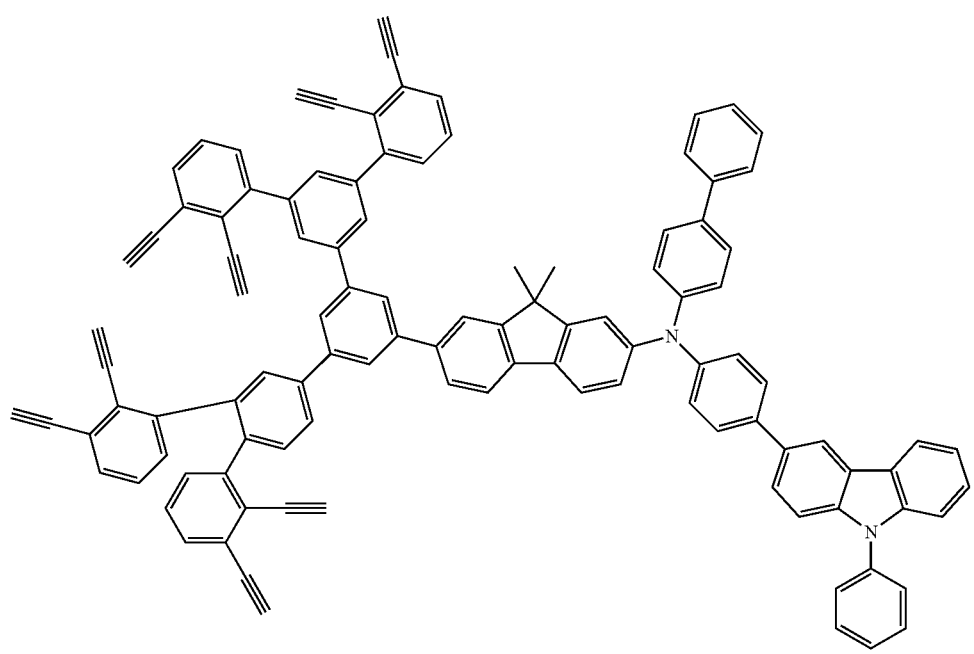

189 190
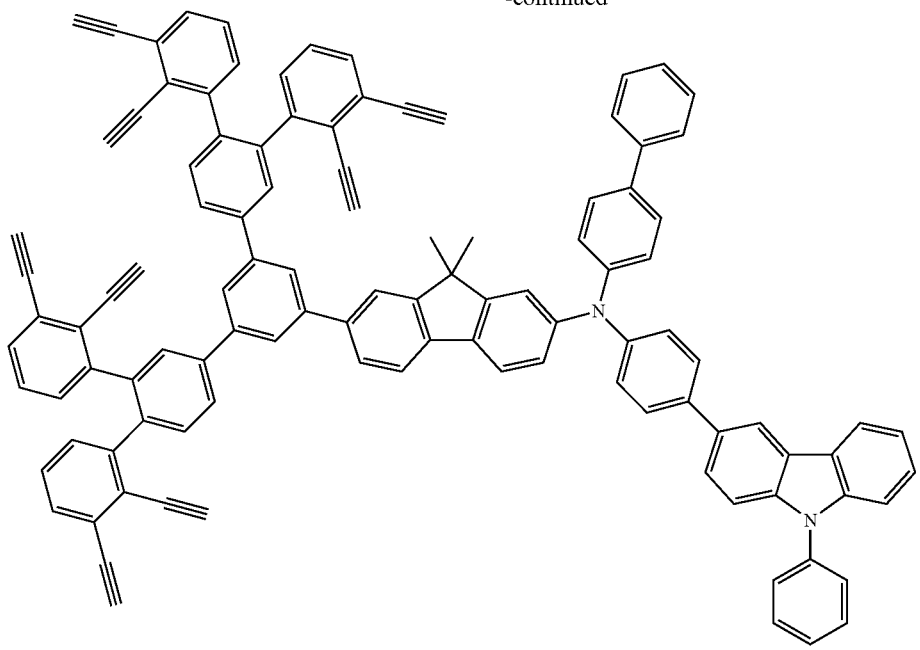
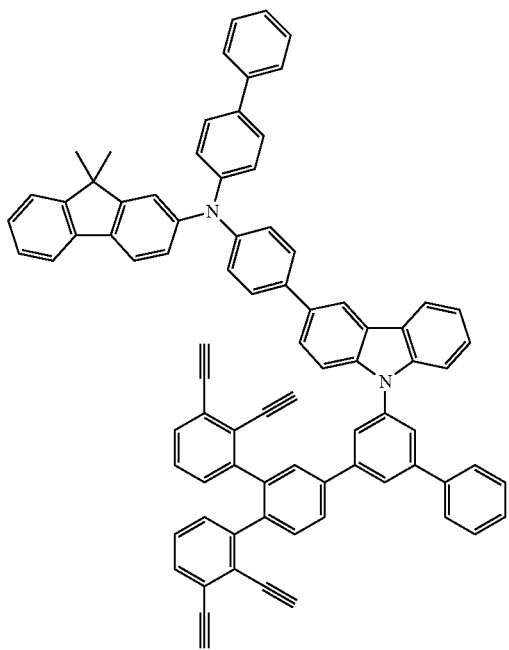 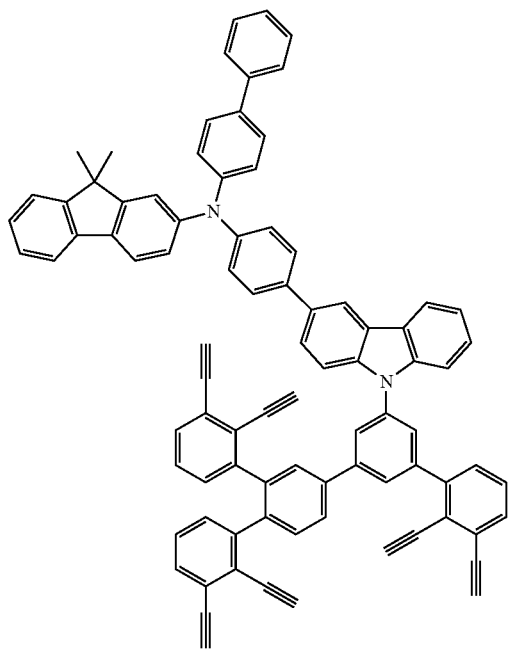

-continued
191
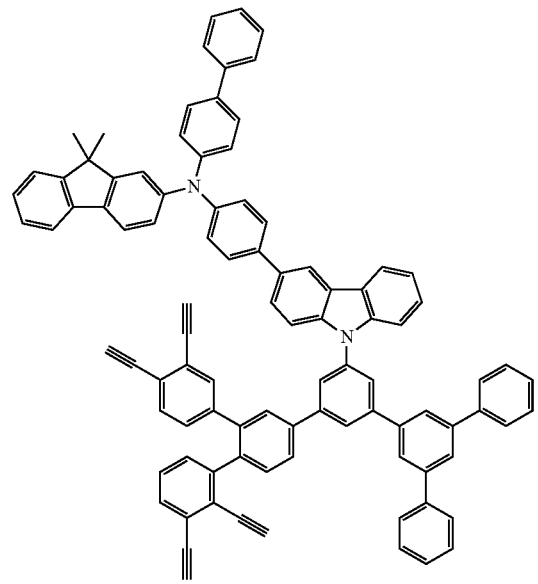
192
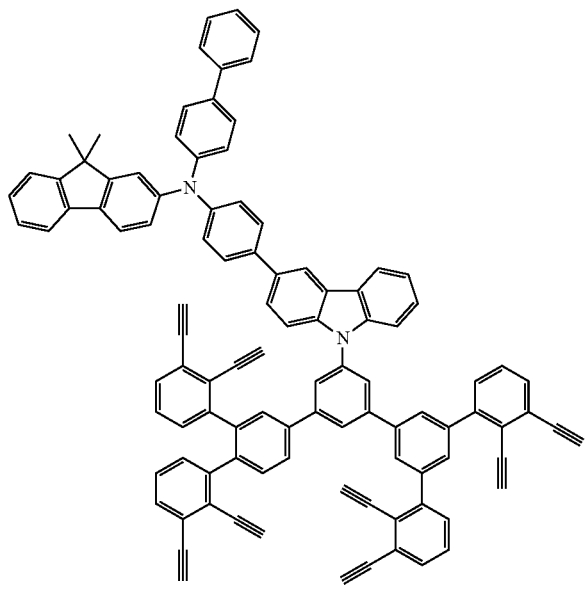
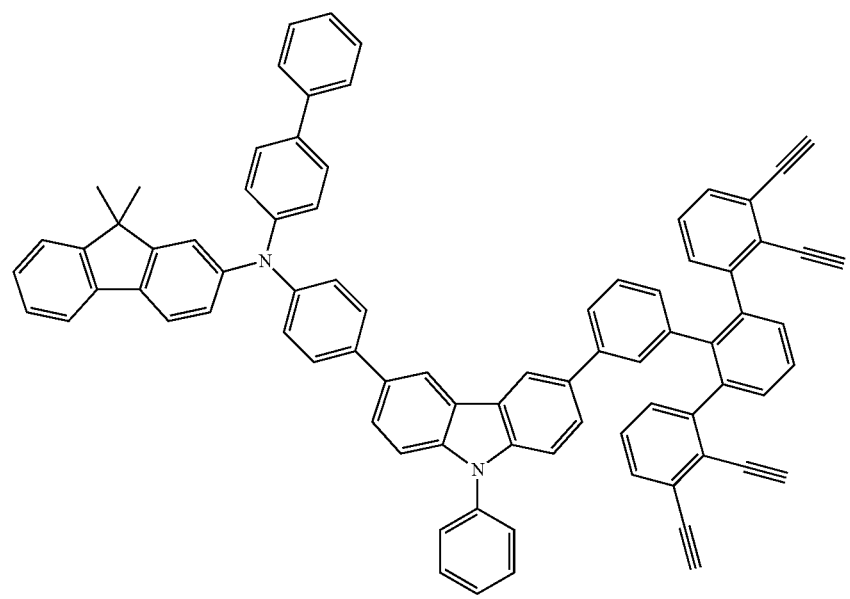

193 194
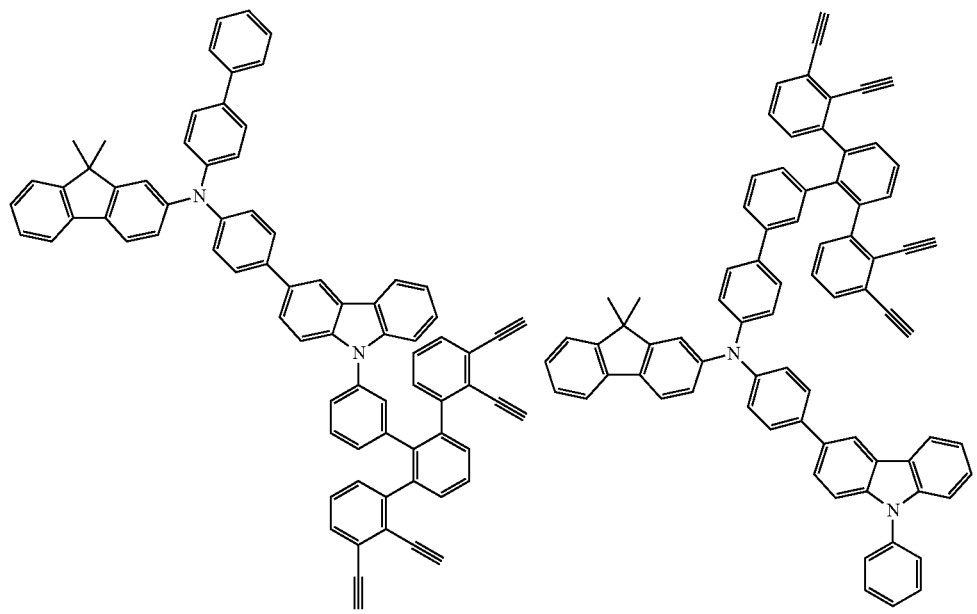
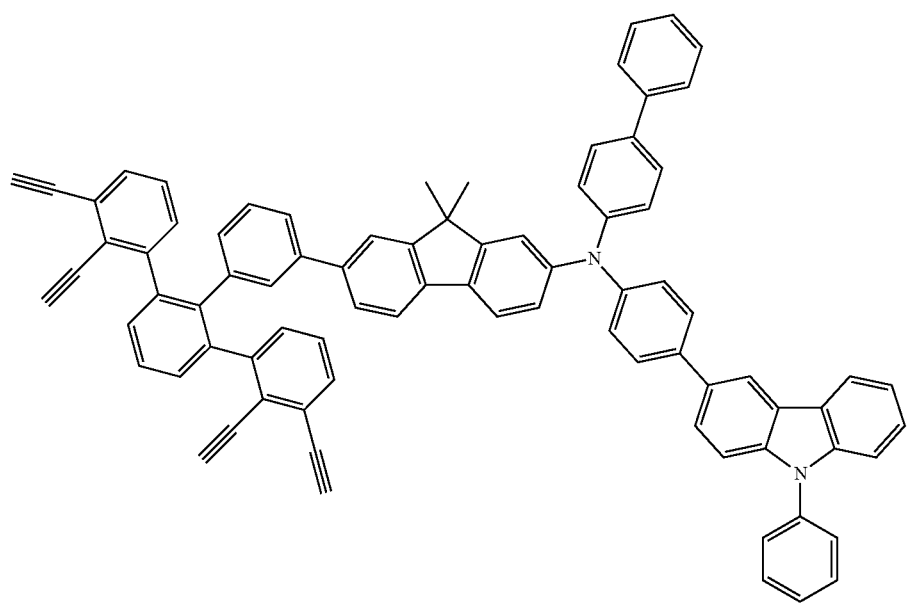

-continued
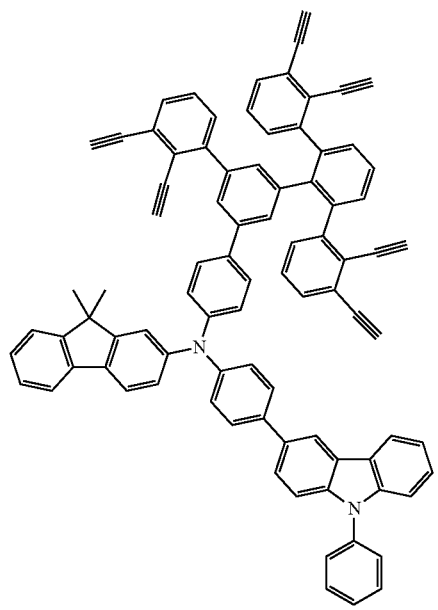
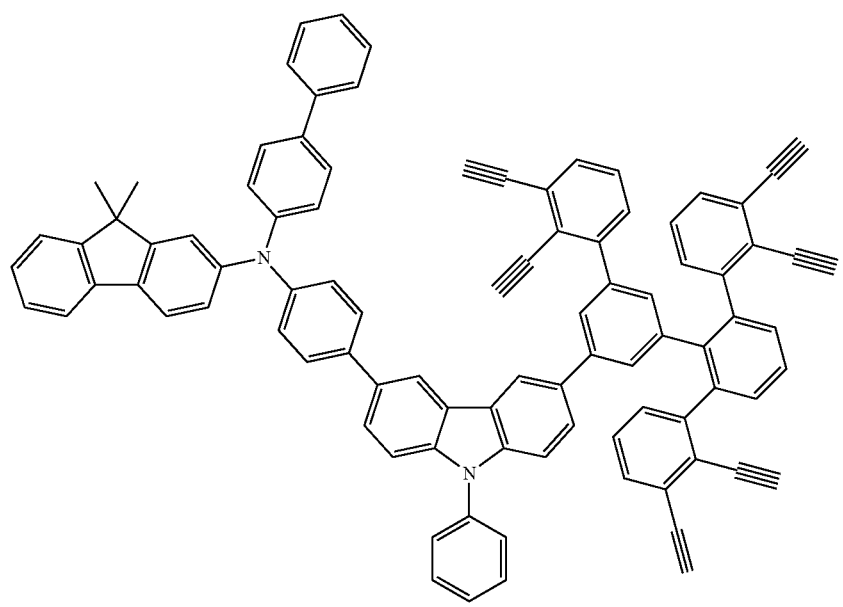

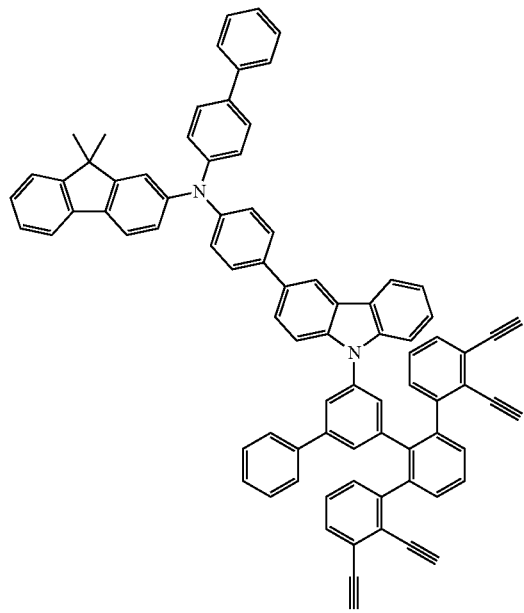

-continued
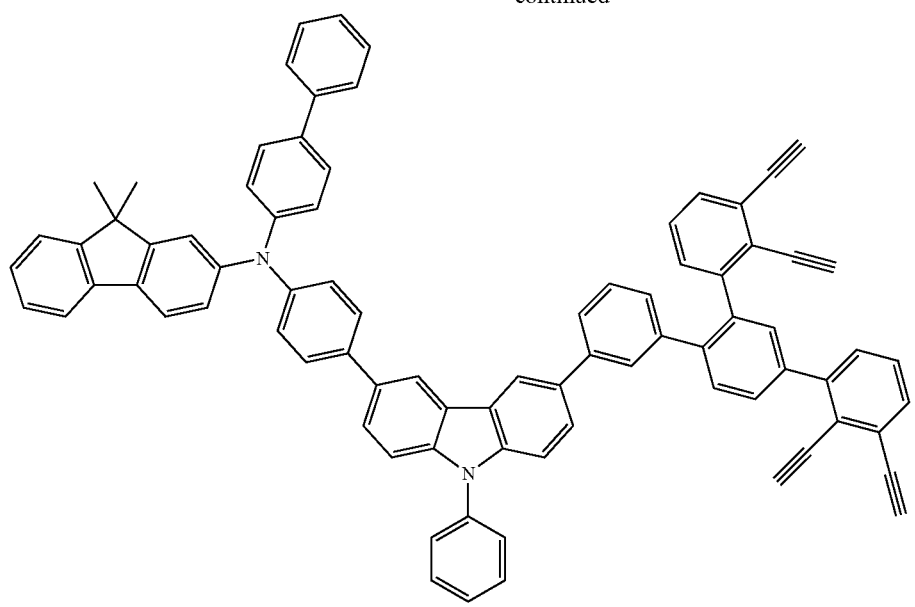
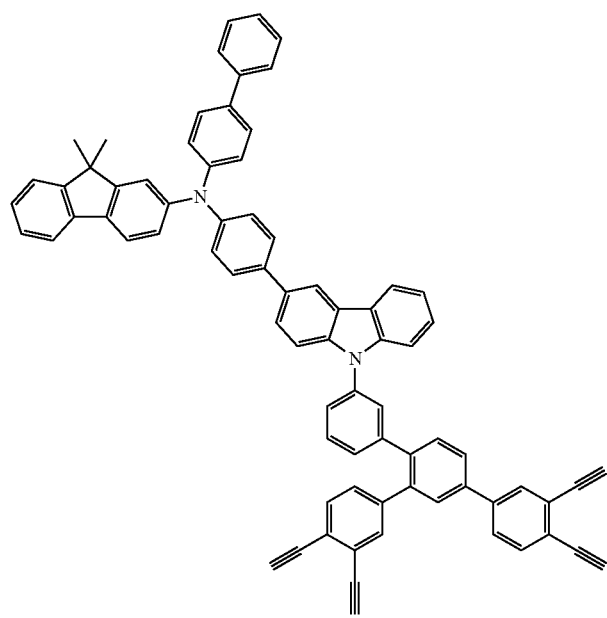

-continued
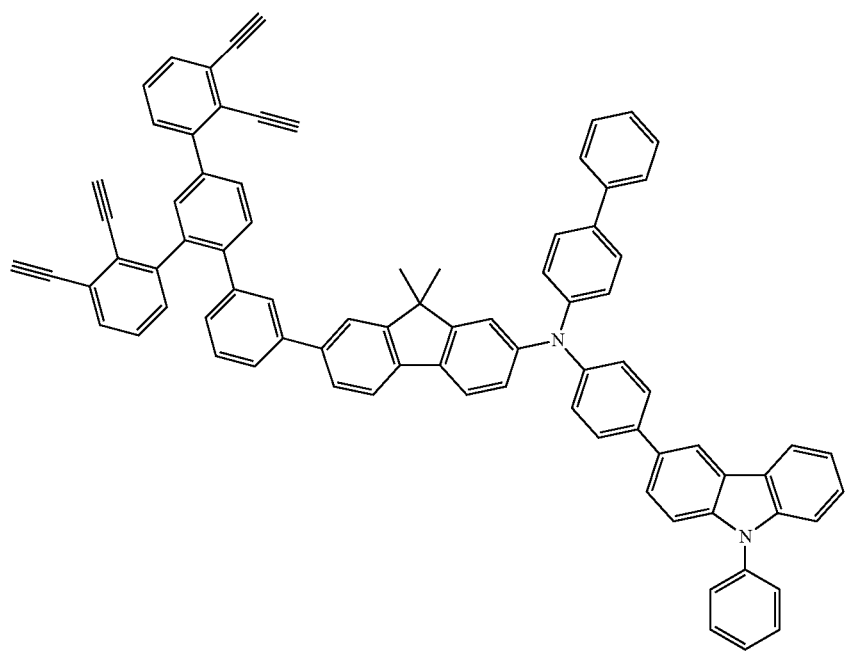
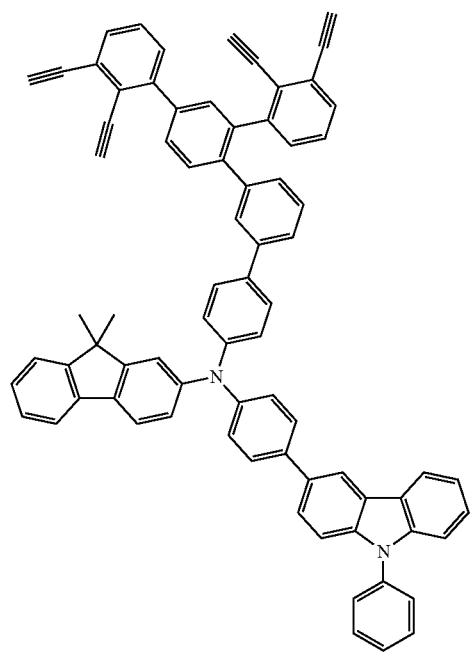

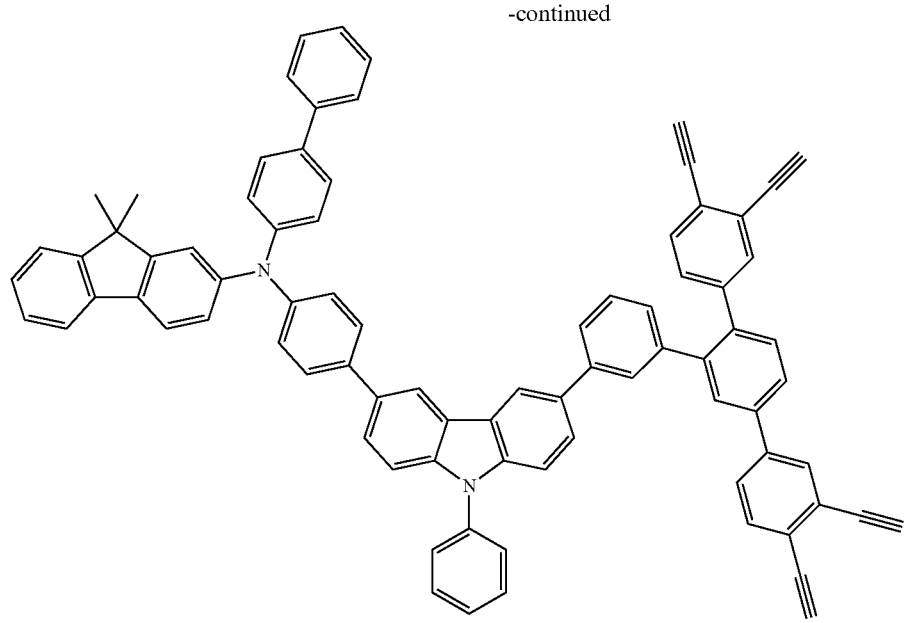
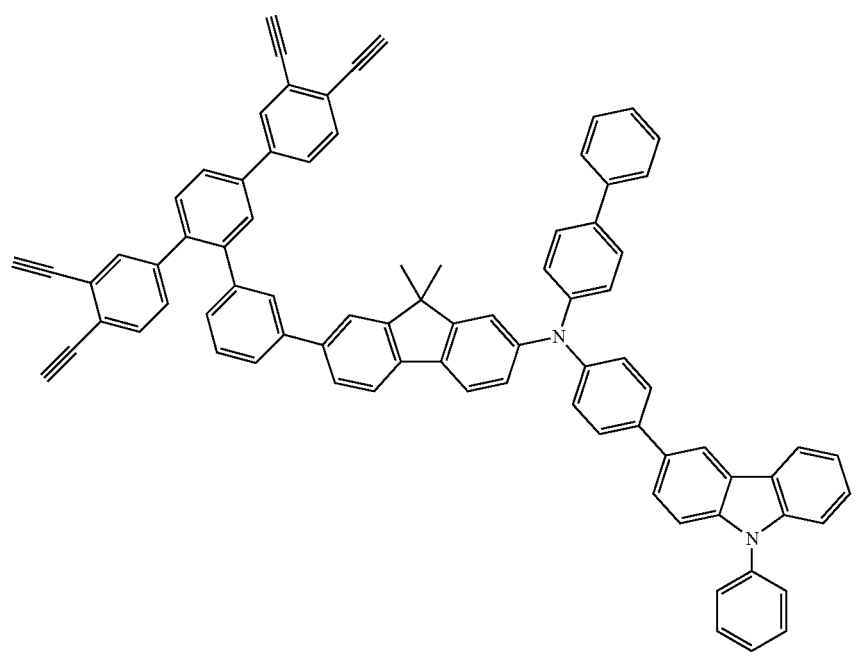

-continued
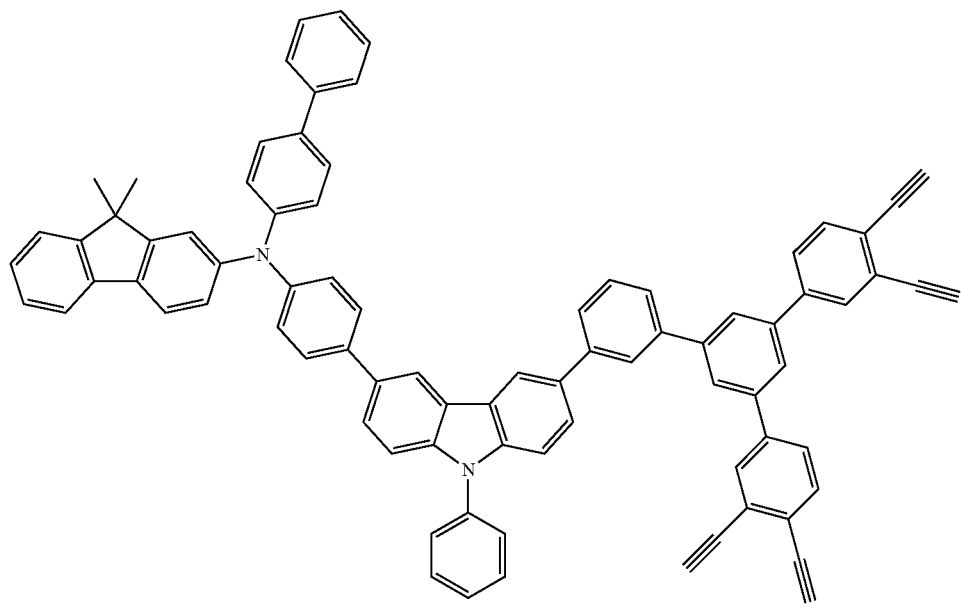
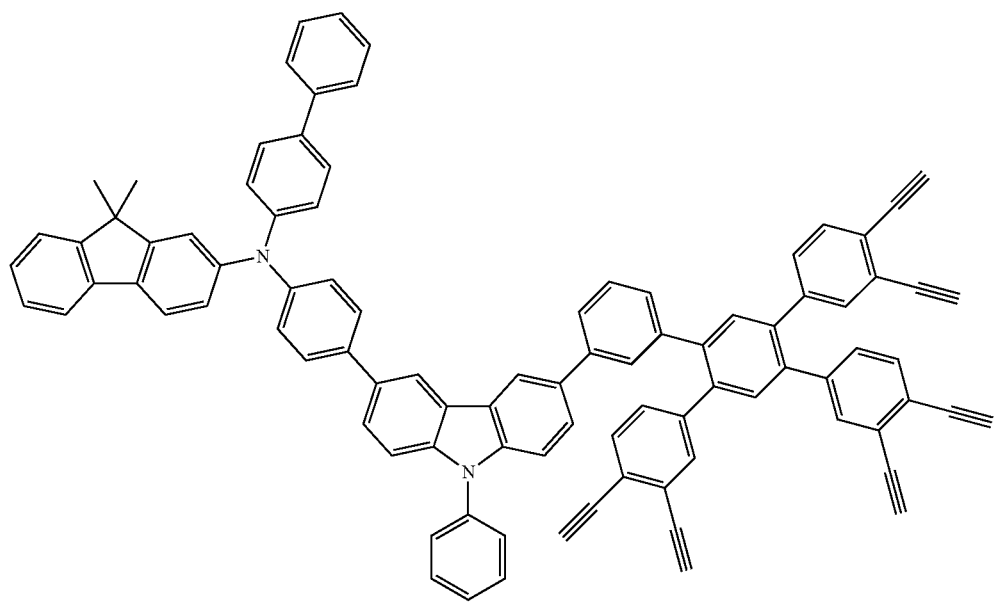

-continued
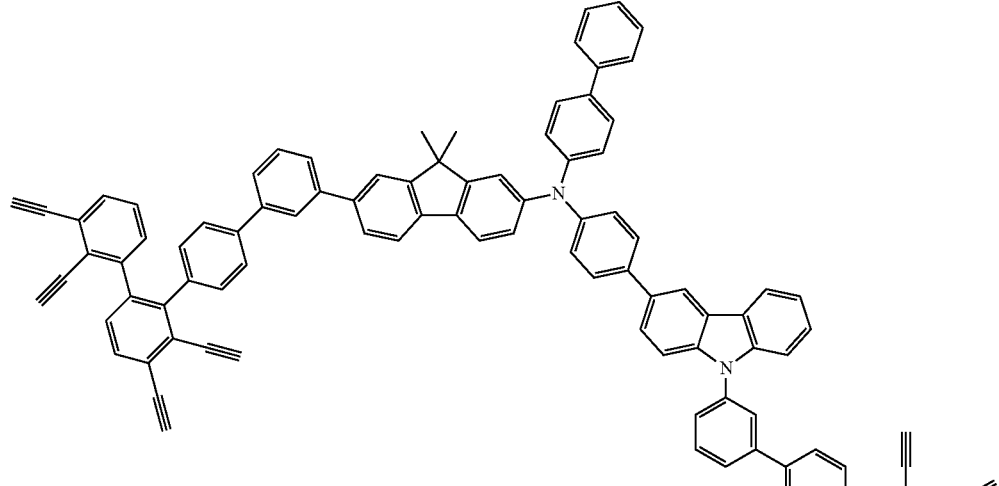
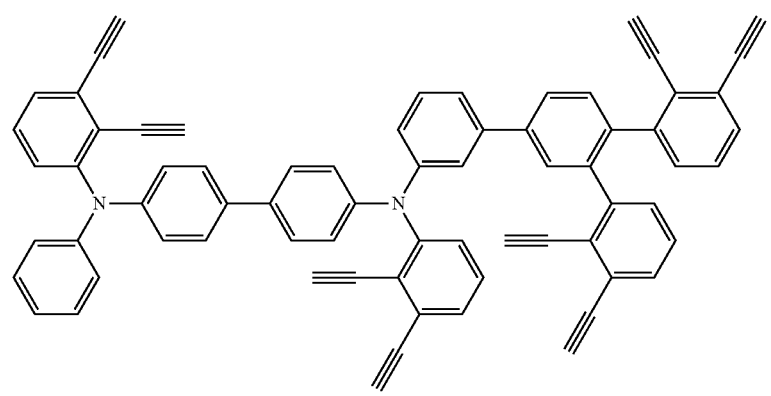
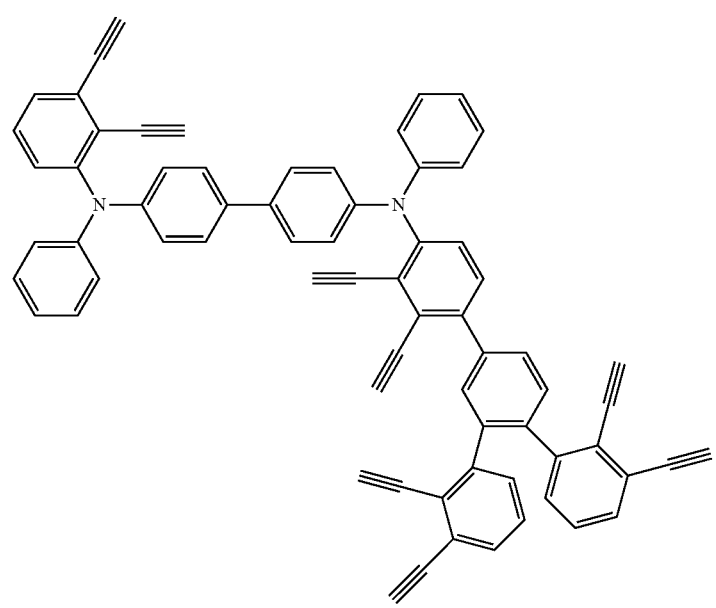

-continued
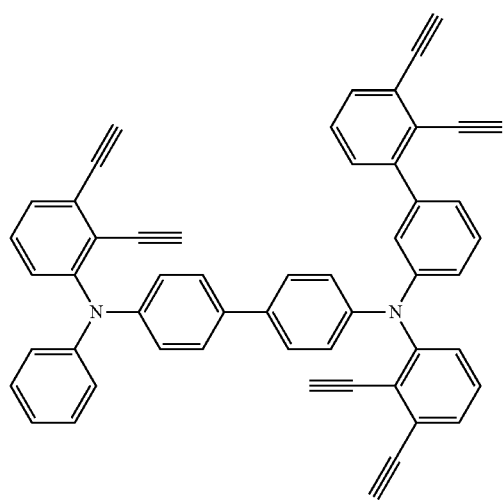
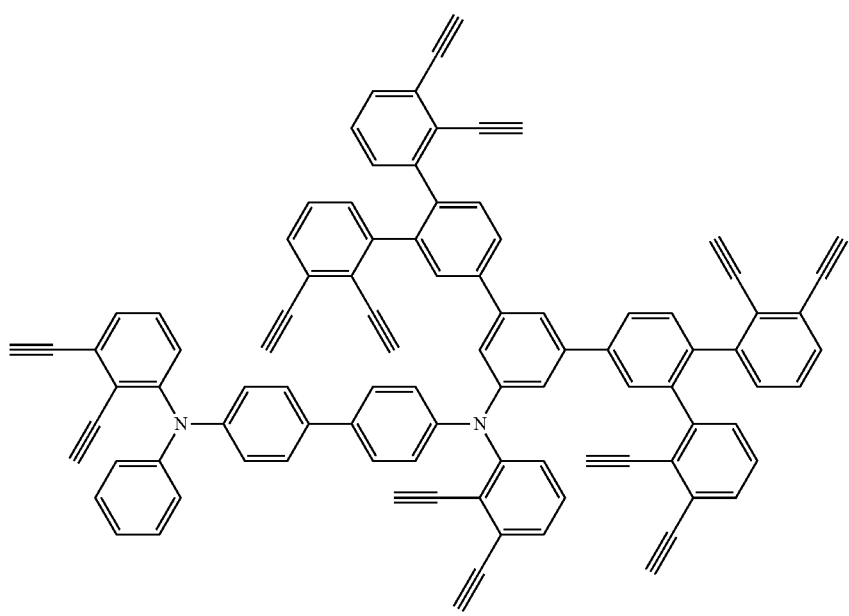
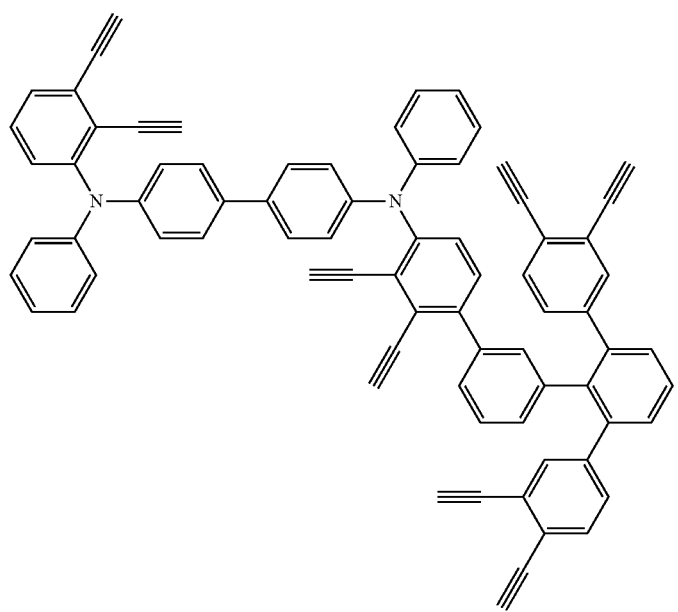

-continued
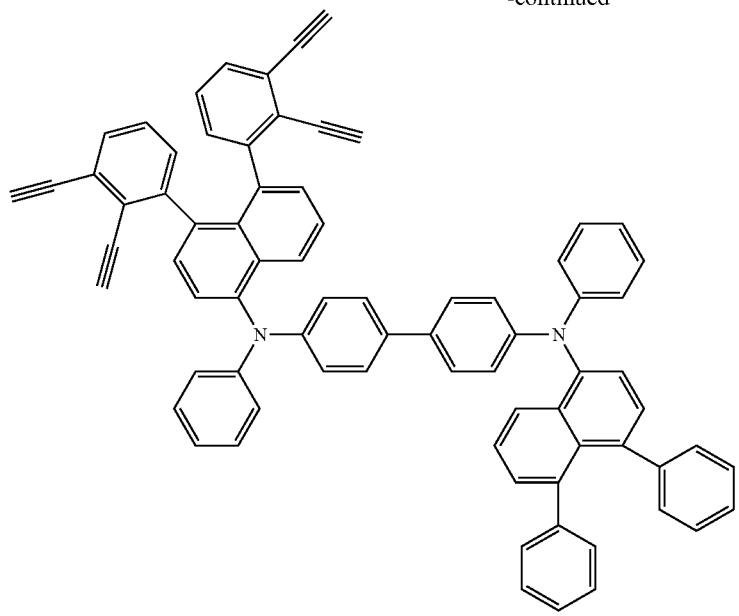
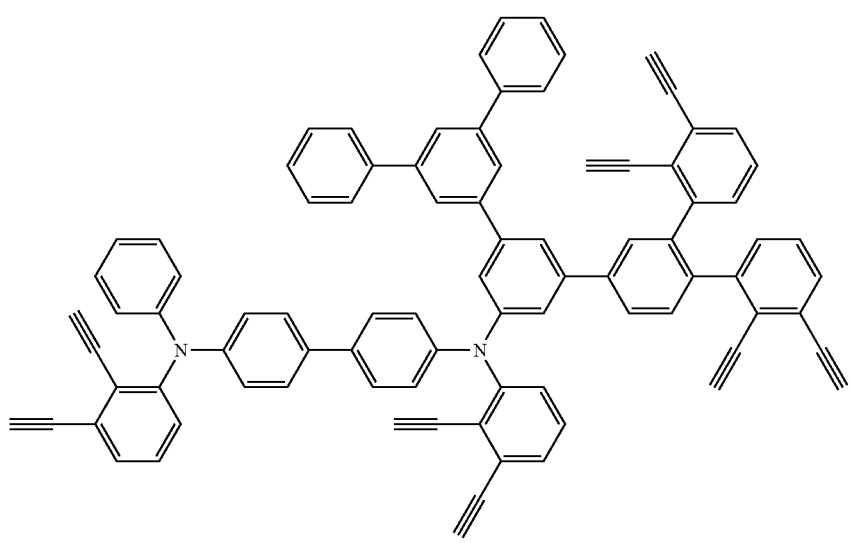
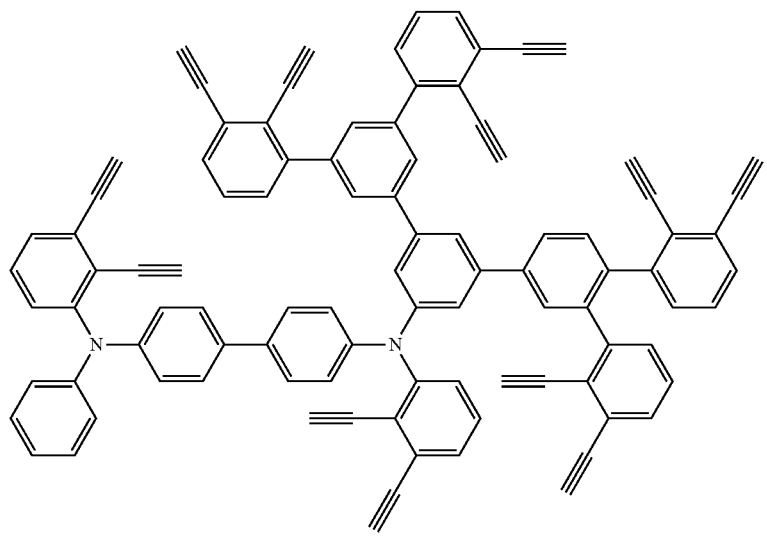

-continued
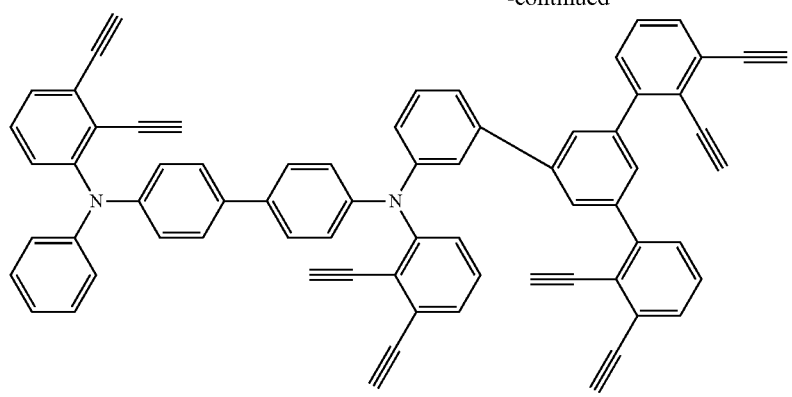
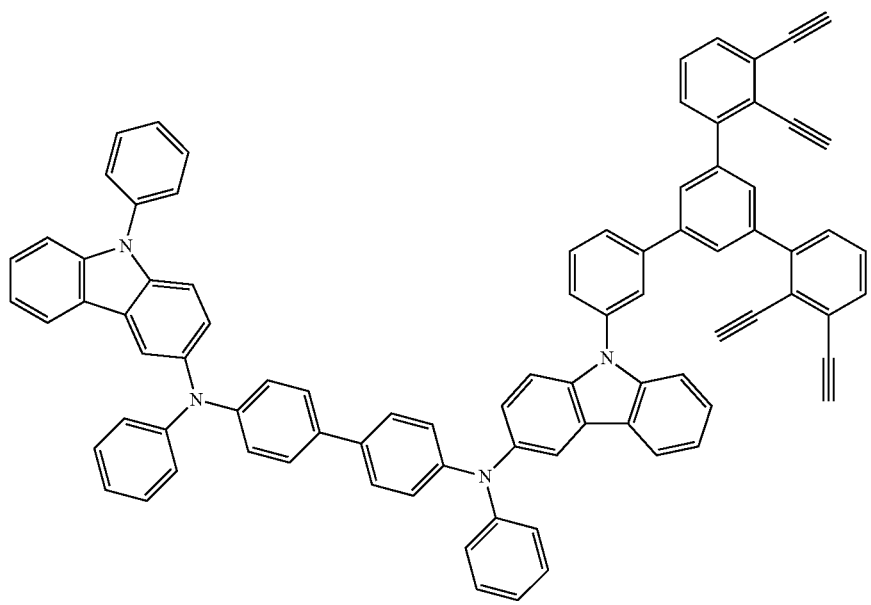
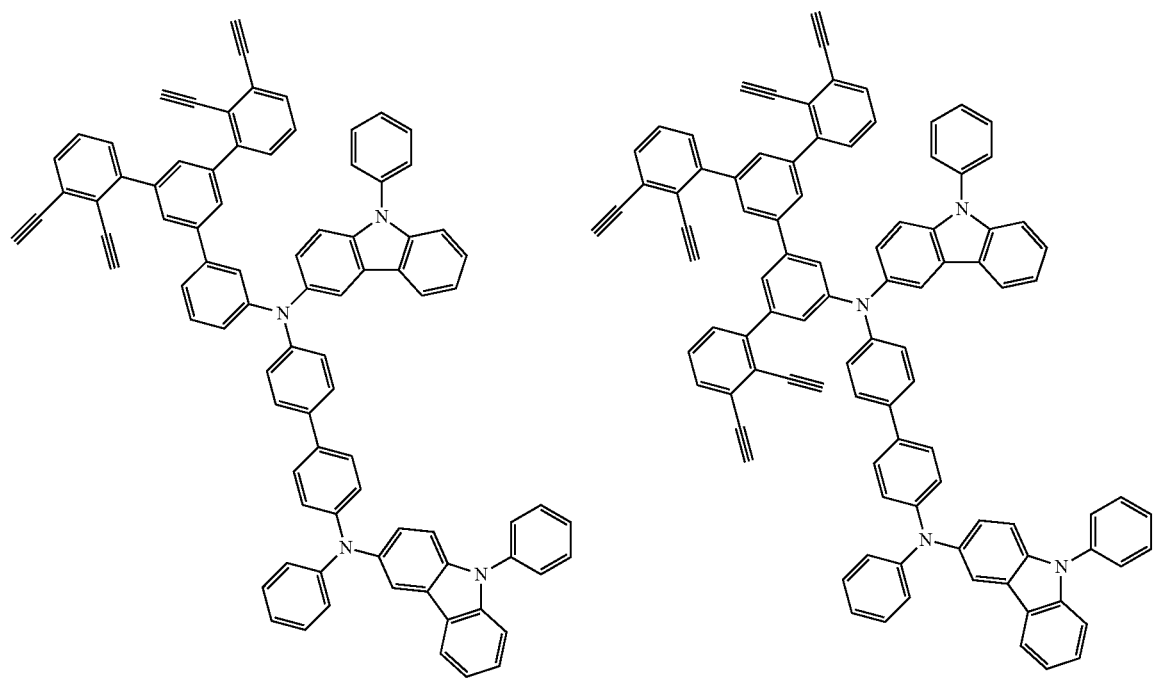 [SMILES: C#Cc1cccc(-c2cc(-c3cccc(N(c4ccc(-c5ccc(N(c6ccccc6)c6ccc7c(c6)c6ccccc6n7-c6ccccc6)cc5)cc4)c4ccc5c(c4)c4ccccc4n5-c4ccccc4)c3)cc(-c3cccc(C#C)c3C#C)c2)c1C#C ; C#Cc1cccc(-c2cc(-c3cc(-c4cccc(C#C)c4C#C)cc(N(c4ccc(-c5ccc(N(c6ccccc6)c6ccc7c(c6)c6ccccc6n7-c6ccccc6)cc5)cc4)c4ccc5c(c4)c4ccccc4n5-c4ccccc4)c3)cc(-c3cccc(C#C)c3C#C)c2)c1C#C]

-continued
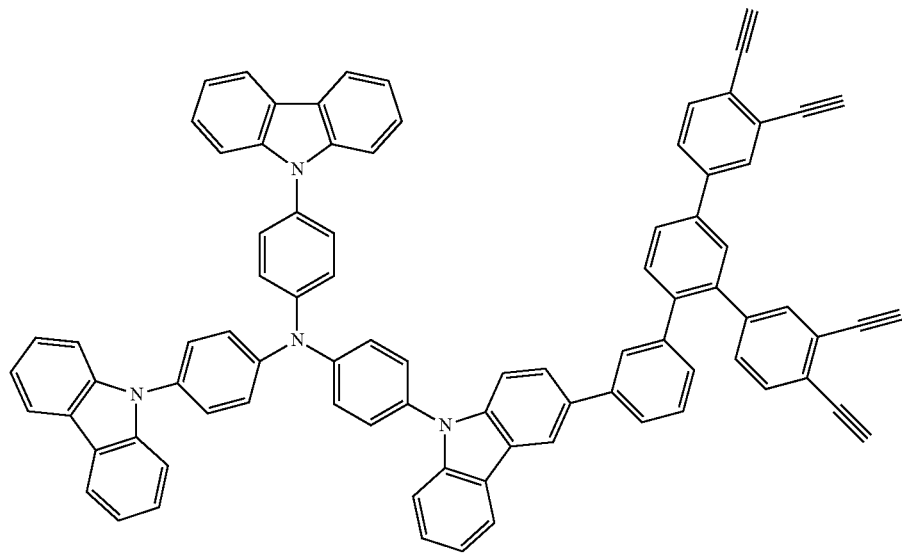
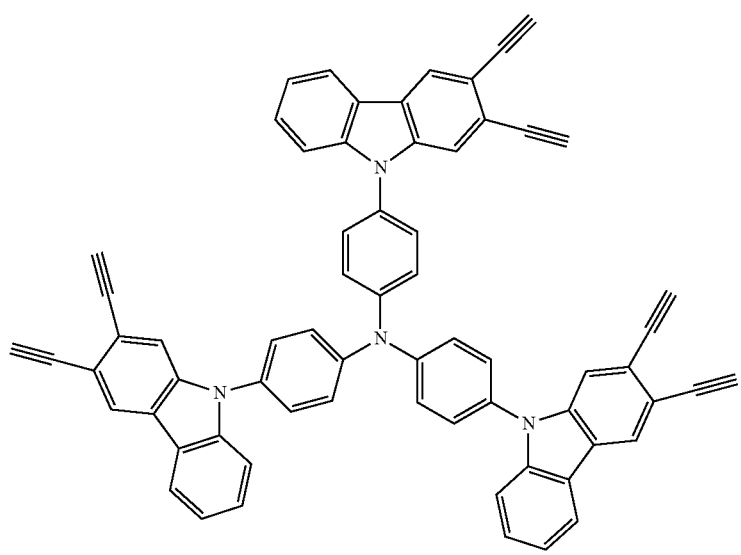
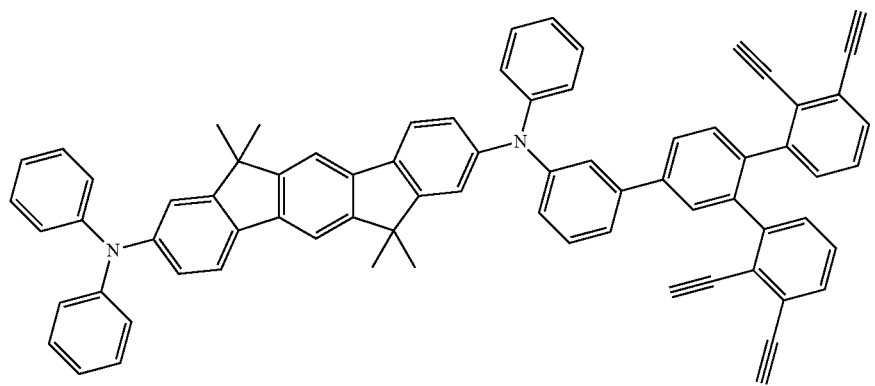

-continued
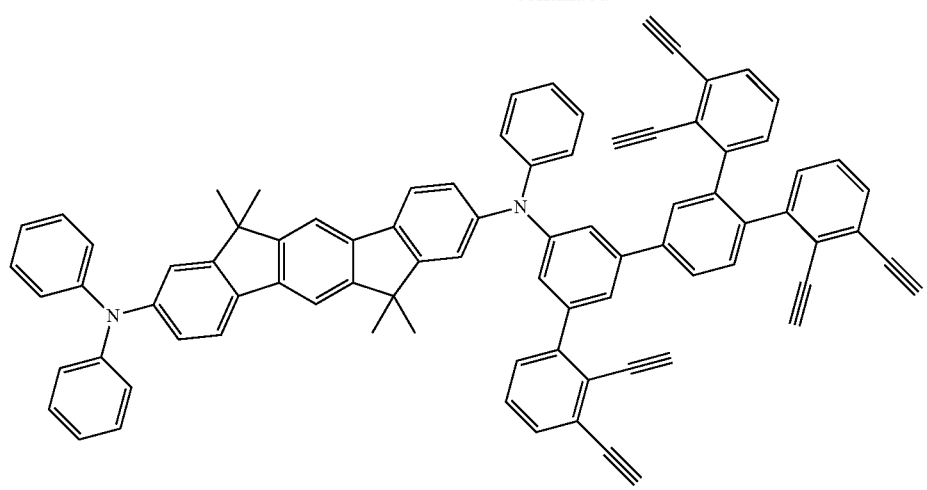
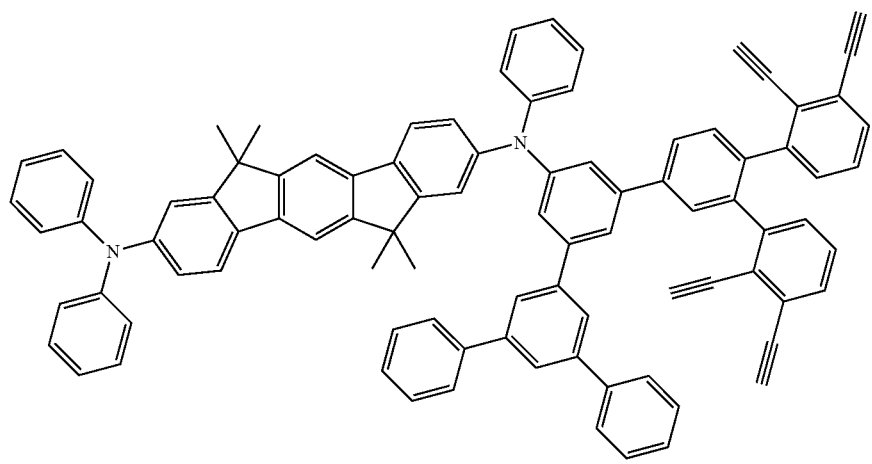
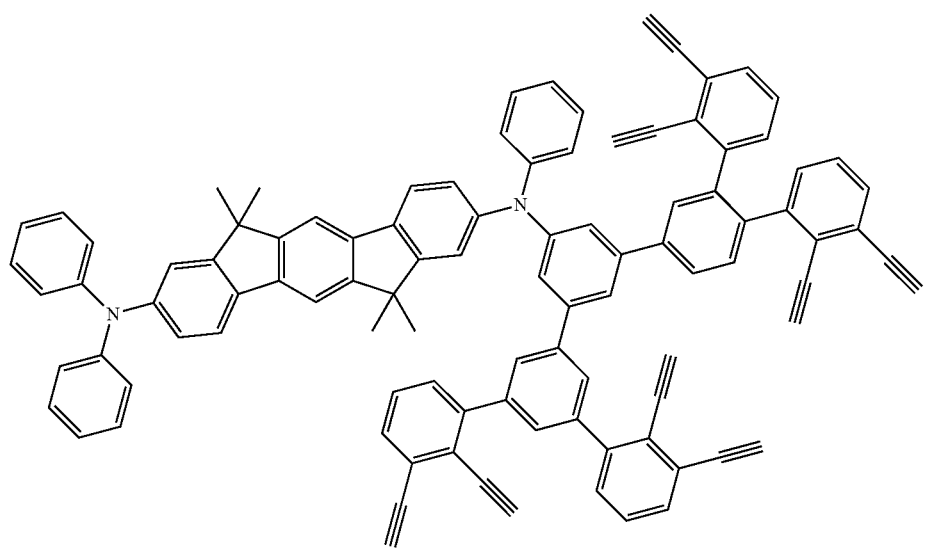

-continued
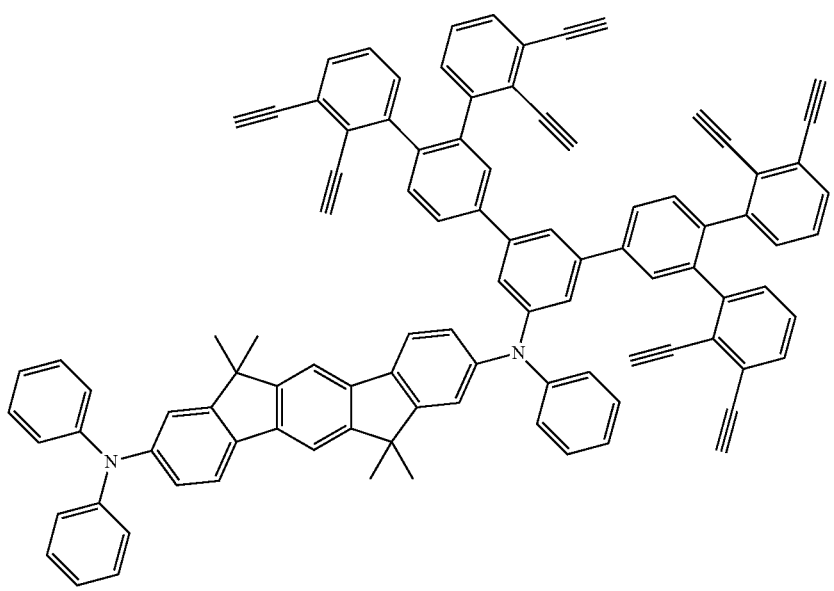
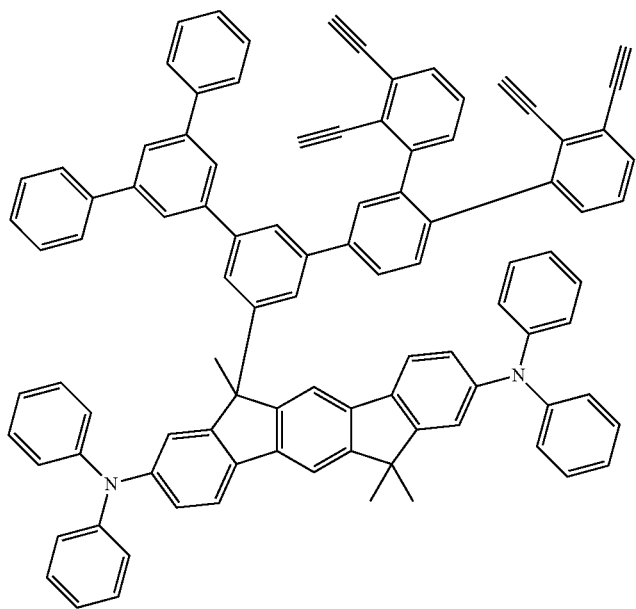

-continued
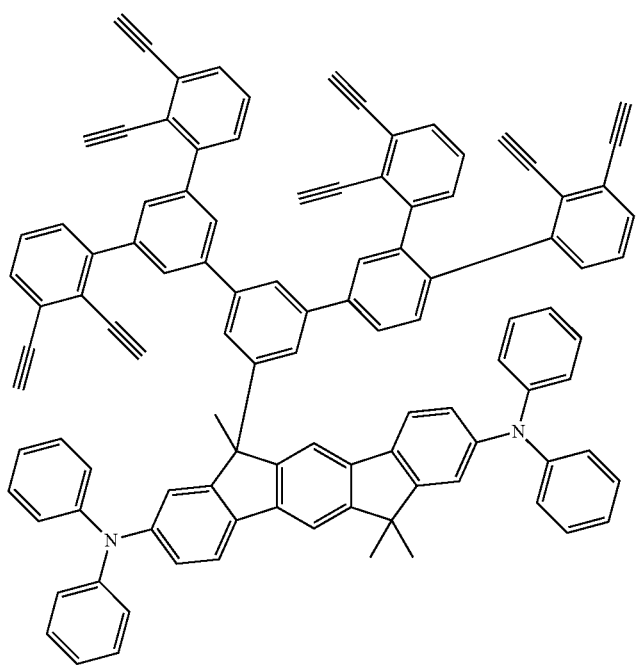
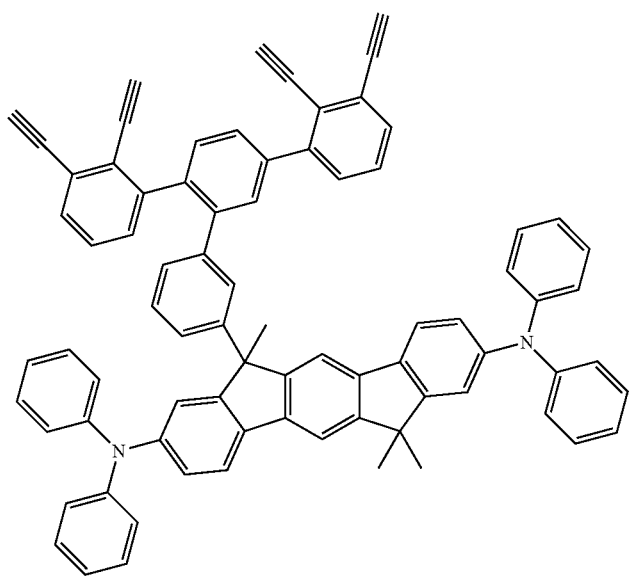

-continued
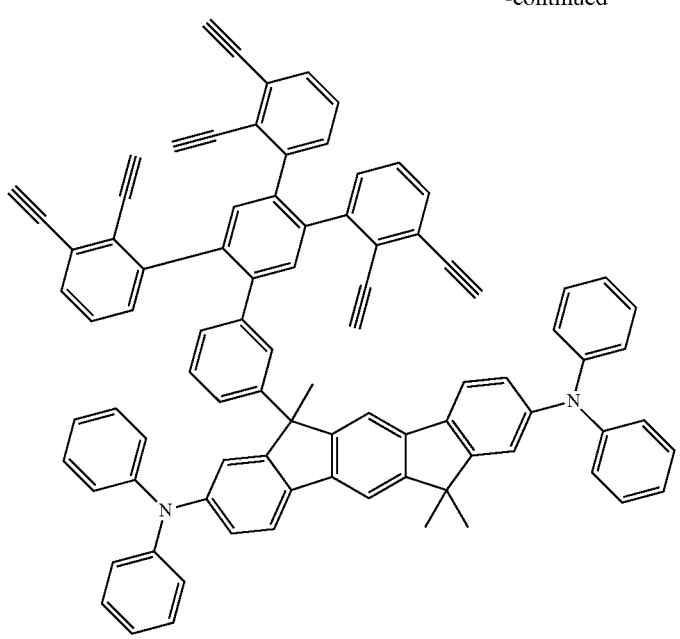
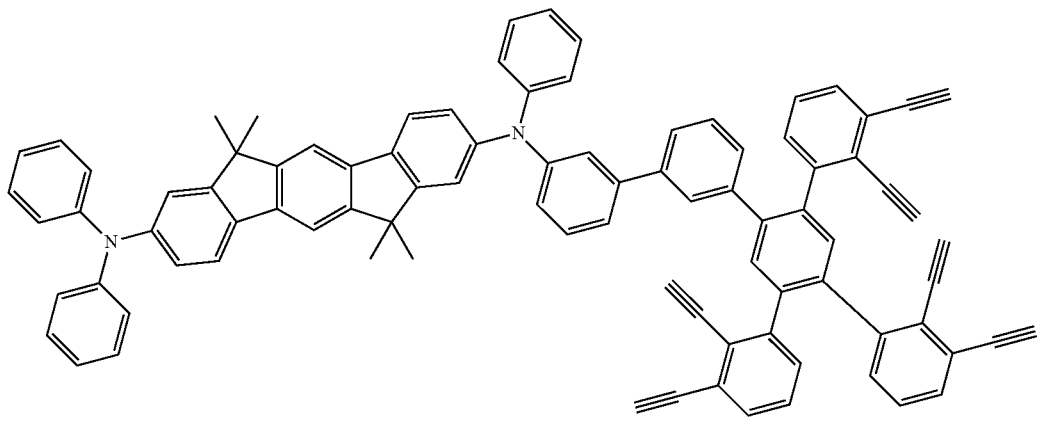
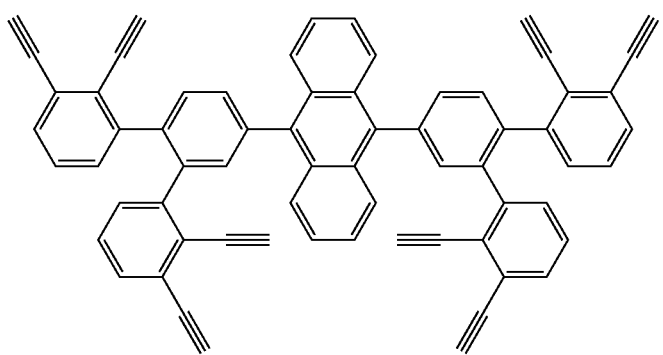

-continued
229
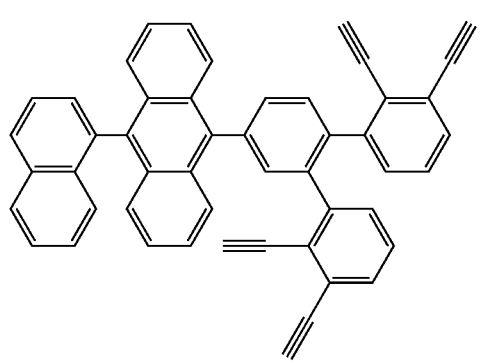
230
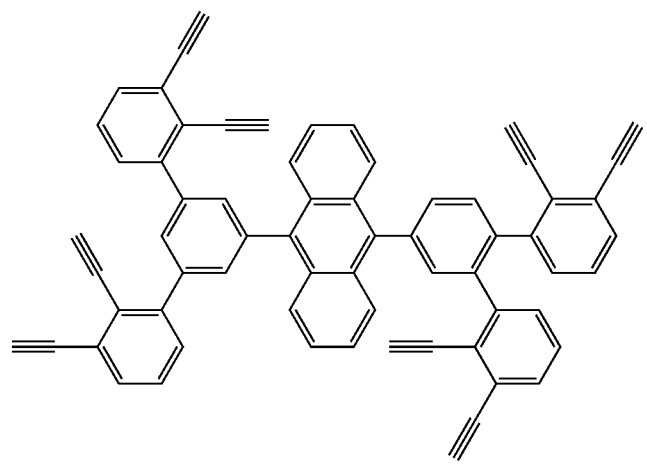
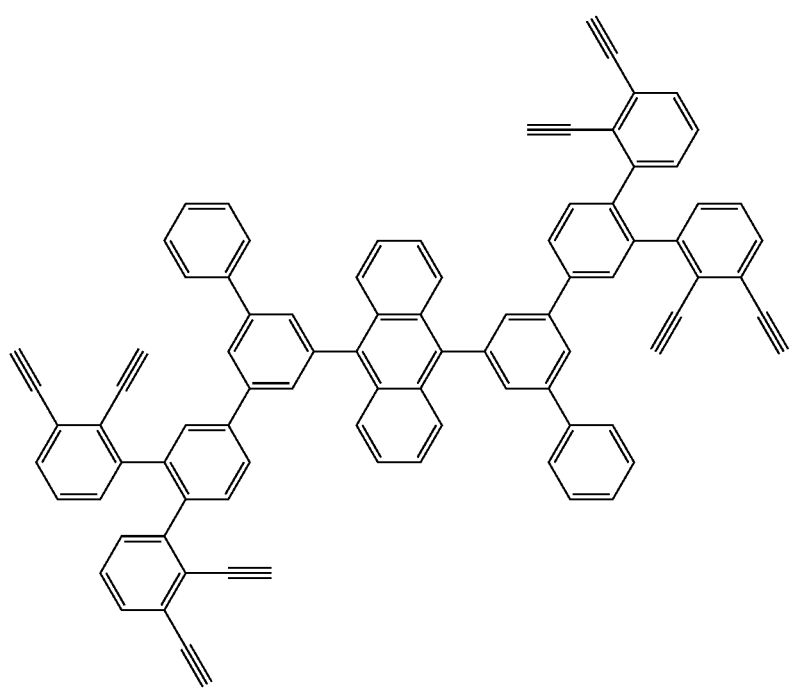

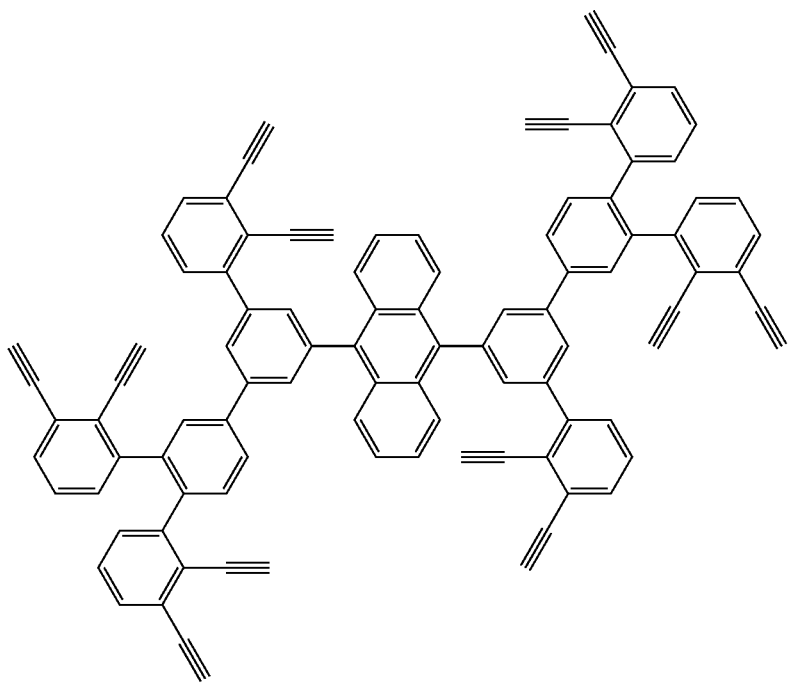
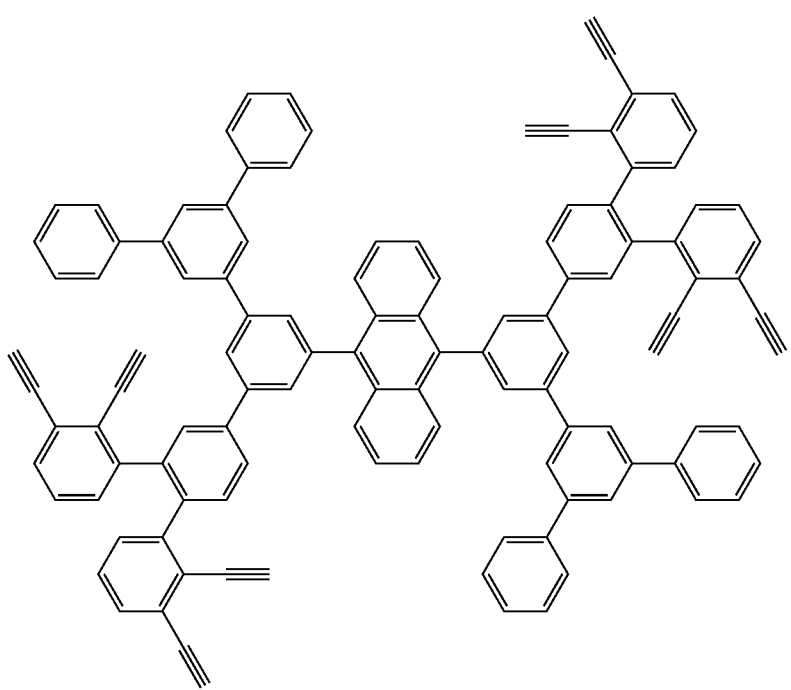

-continued
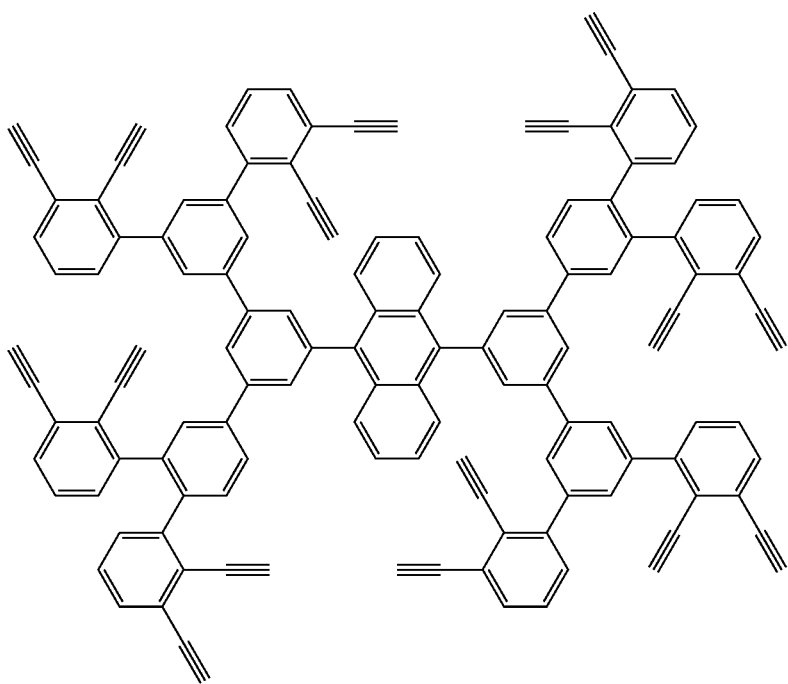
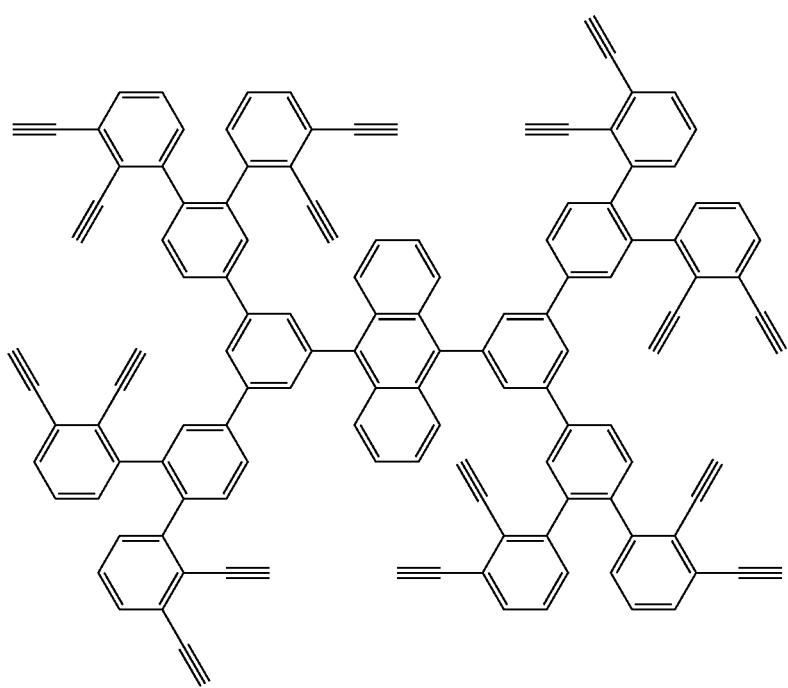

235
236
-continued
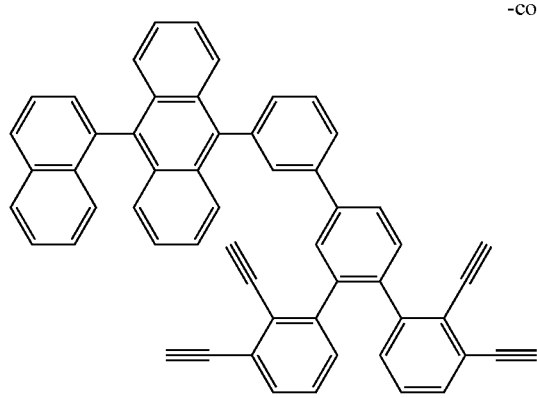
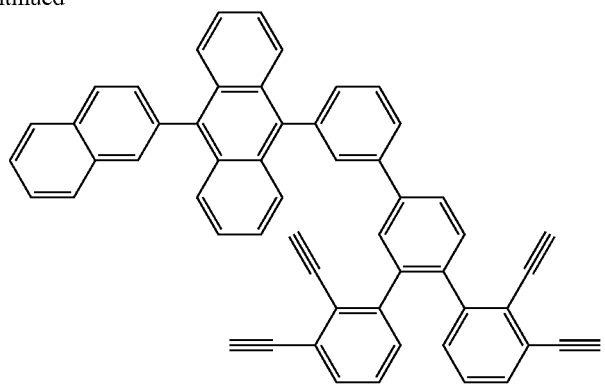
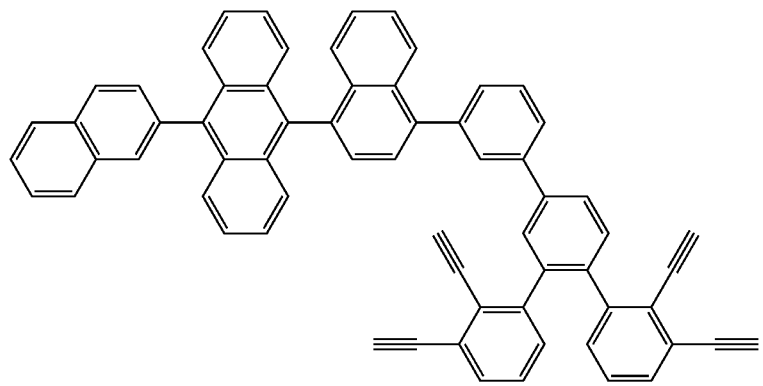
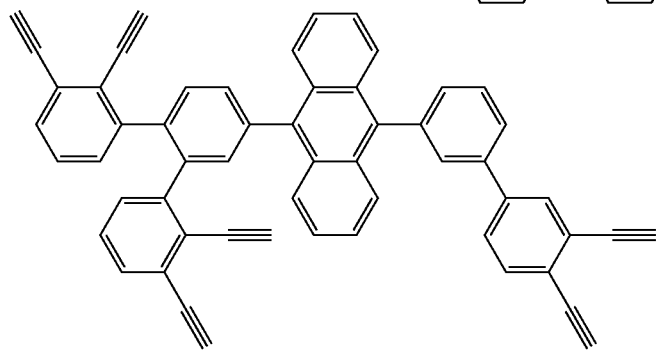
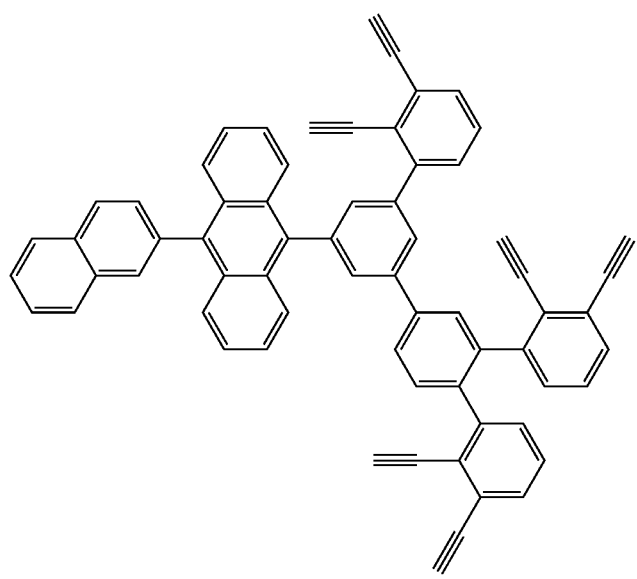

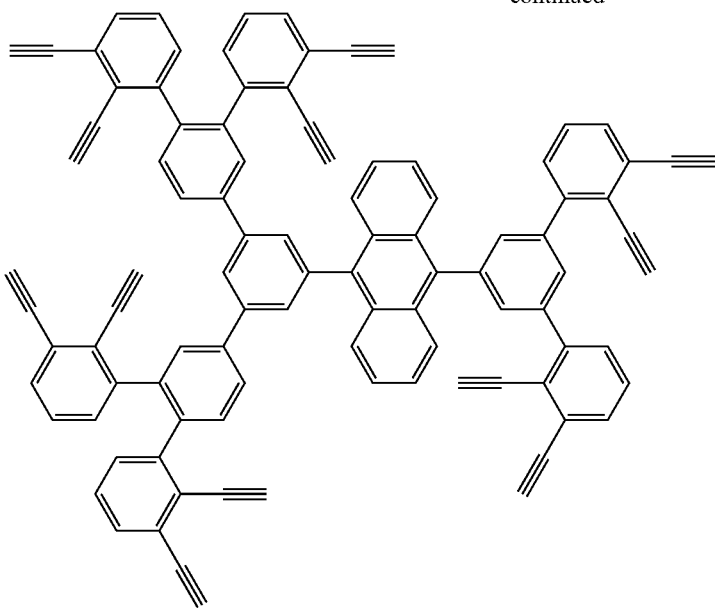
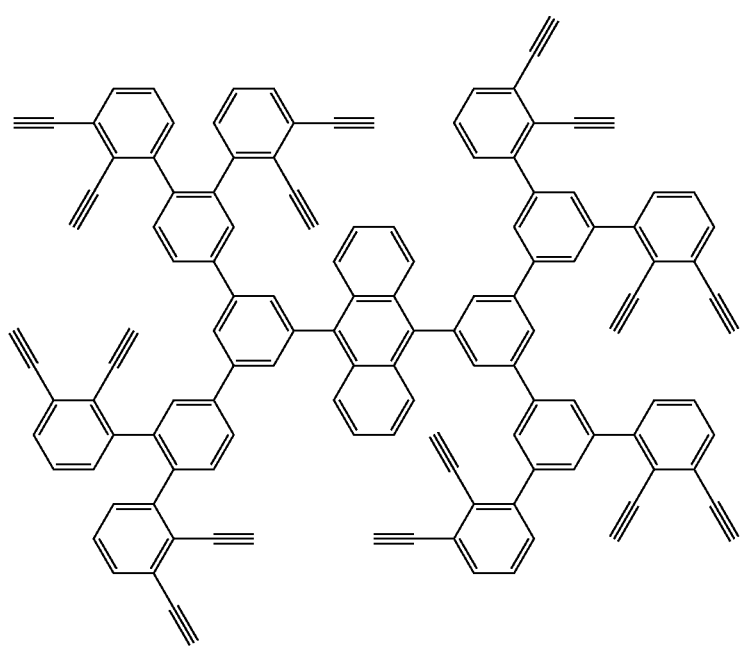

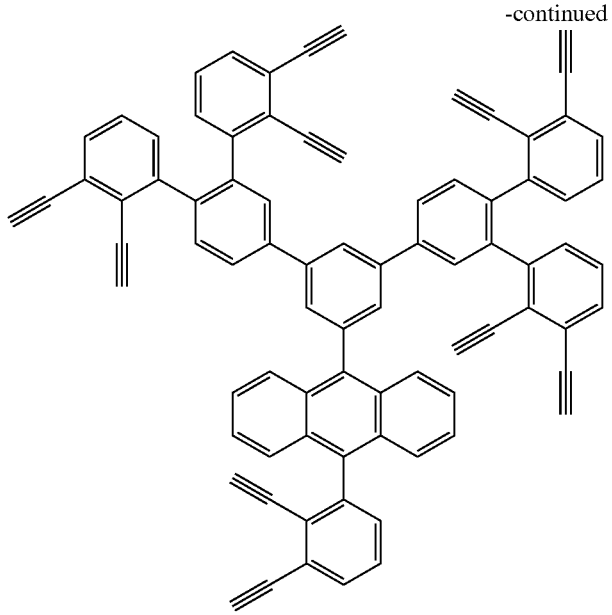
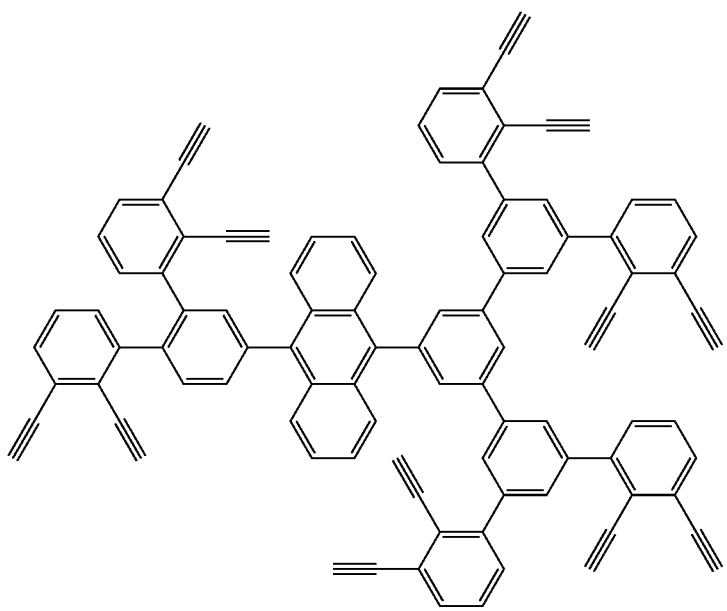
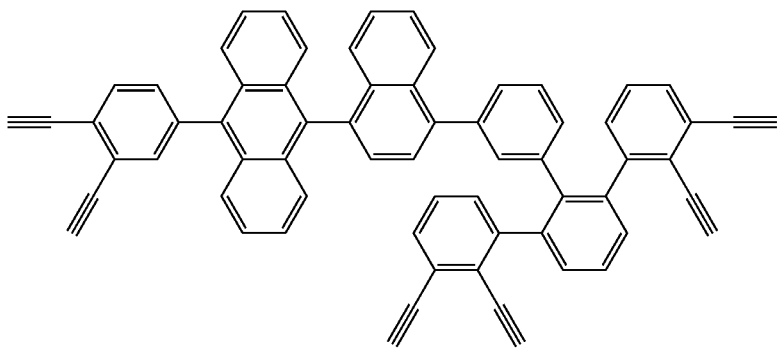

-continued
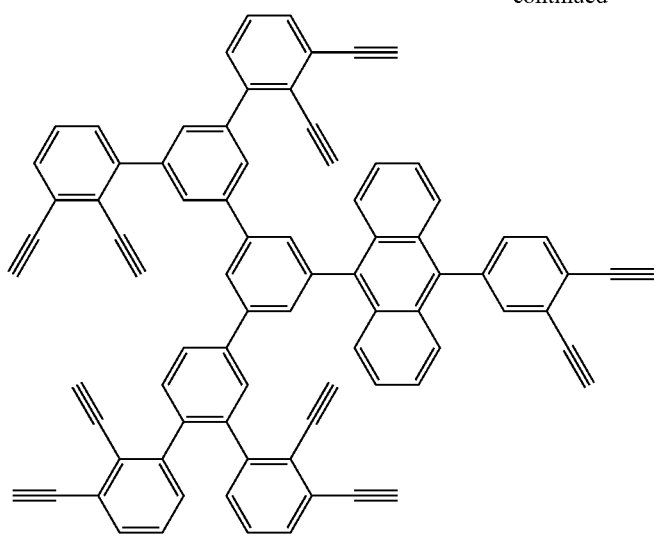
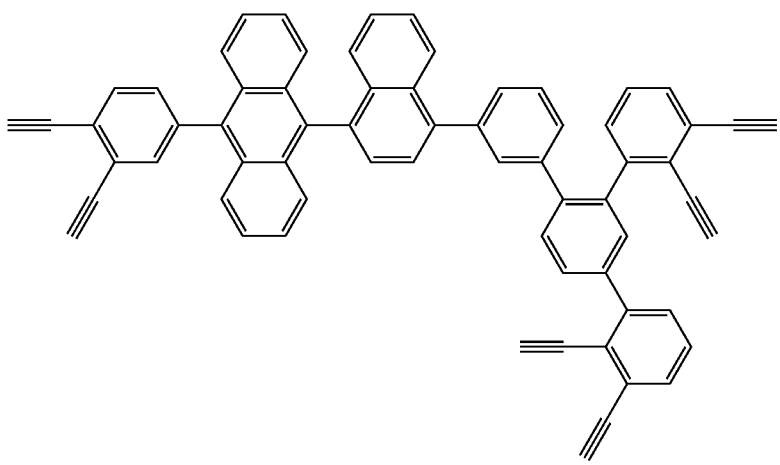
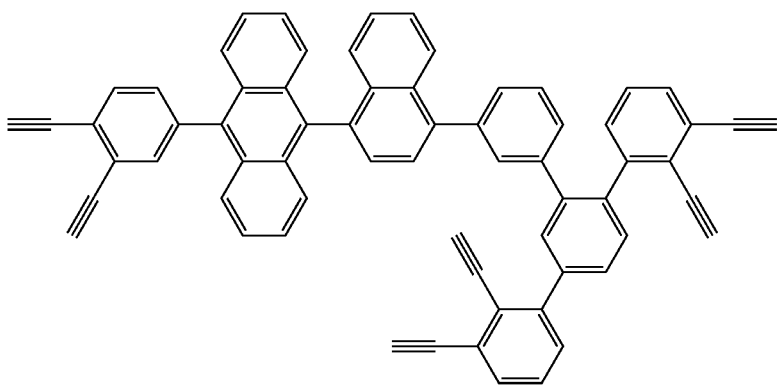

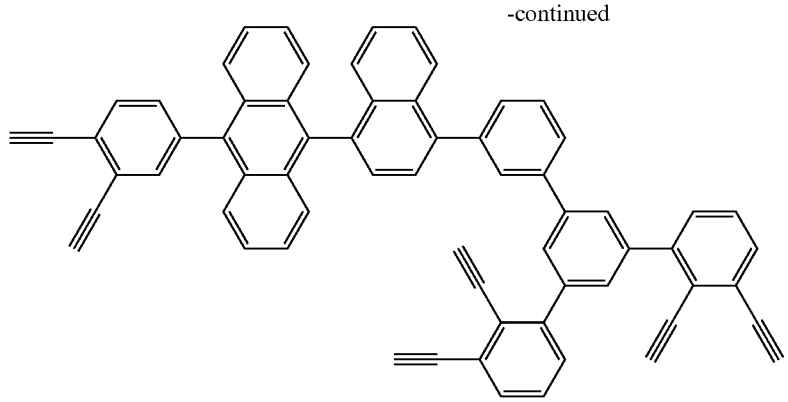
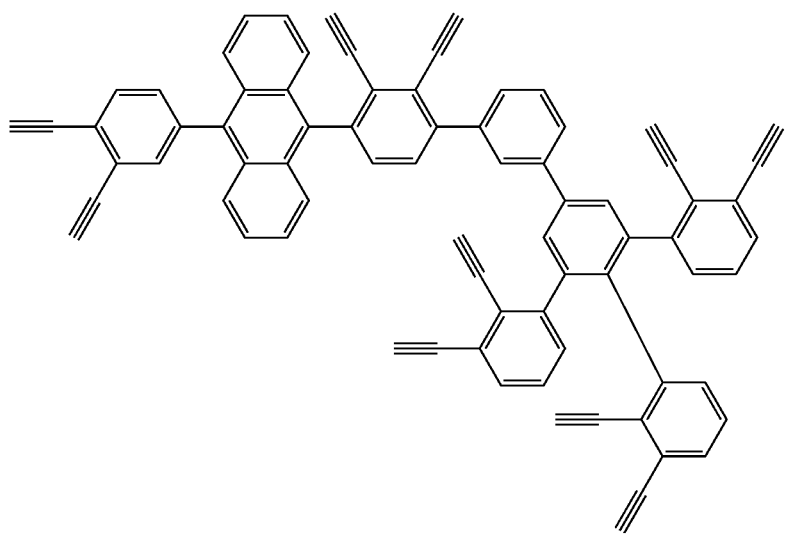
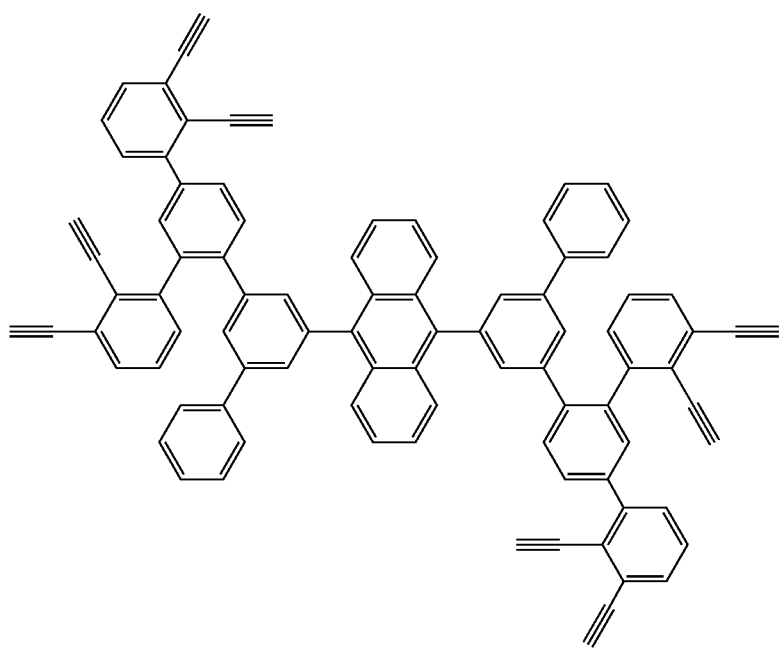

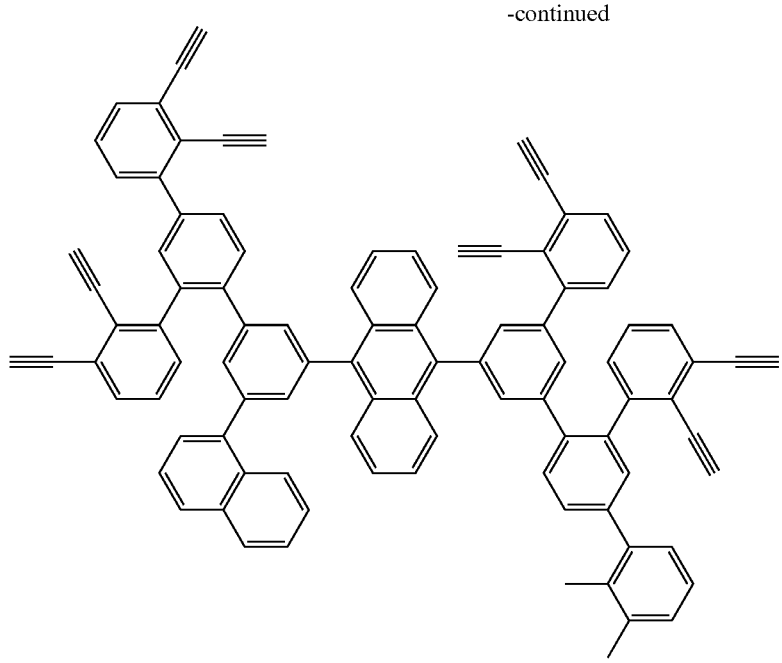
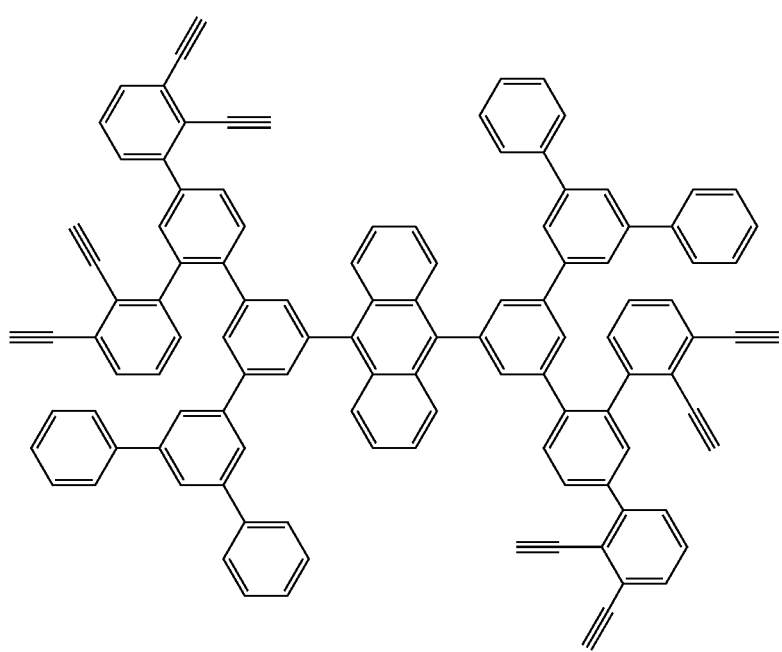

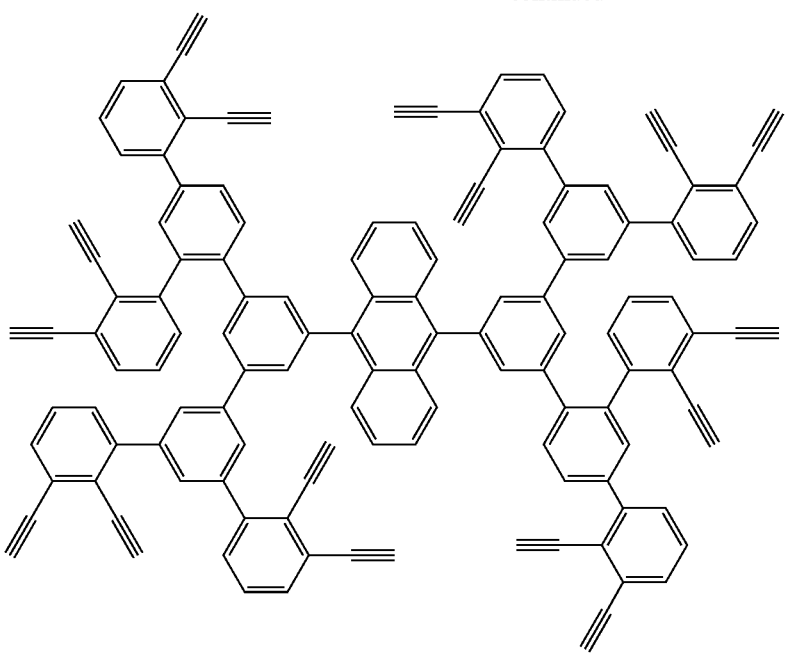
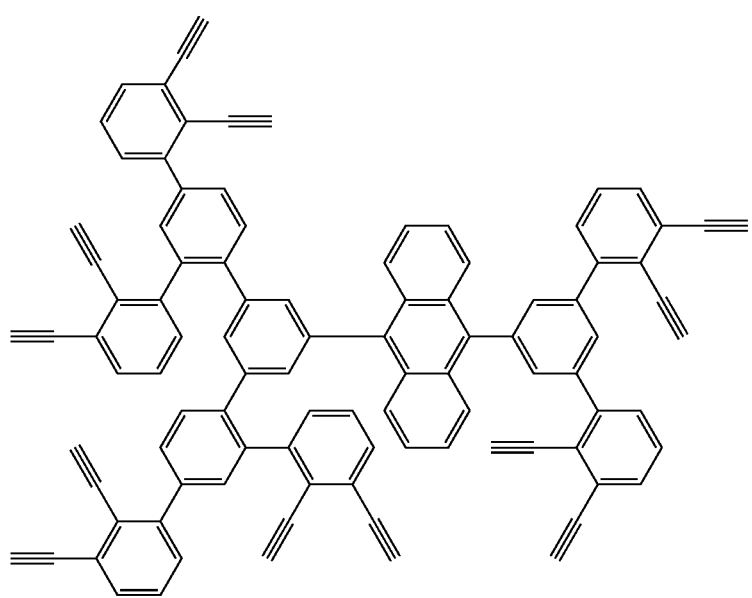

-continued
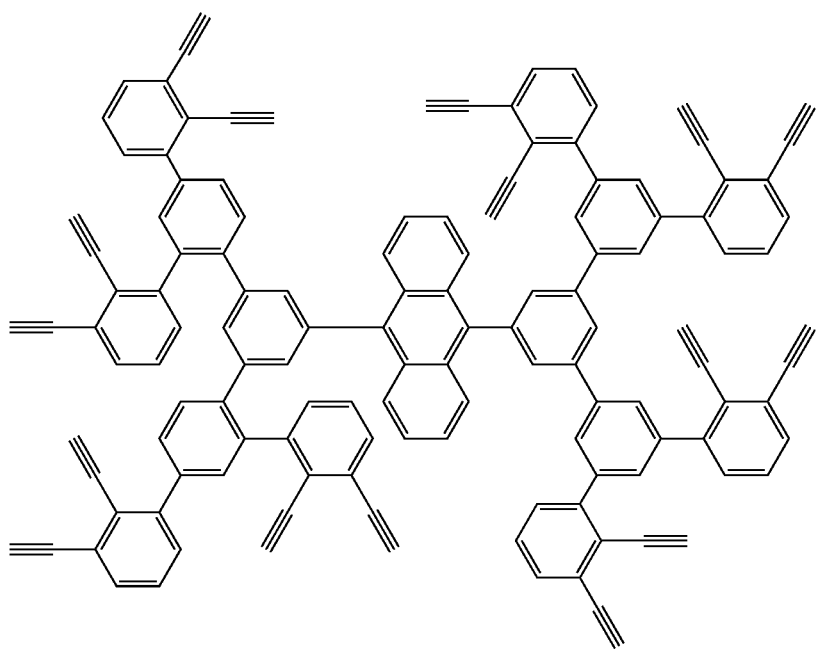
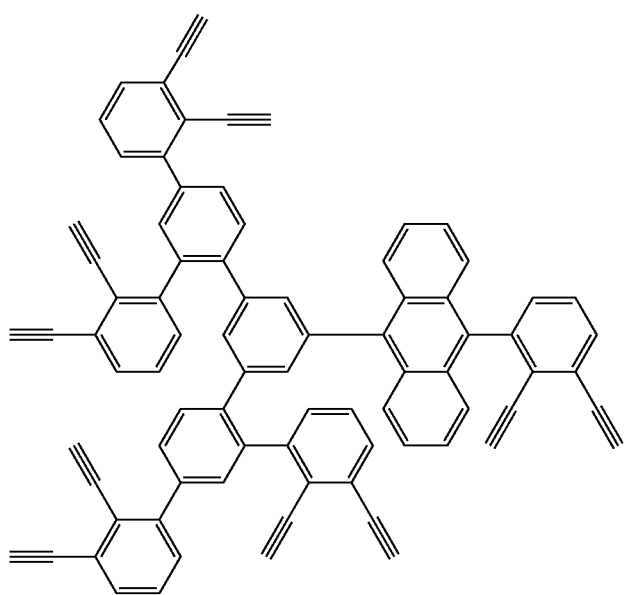

-continued
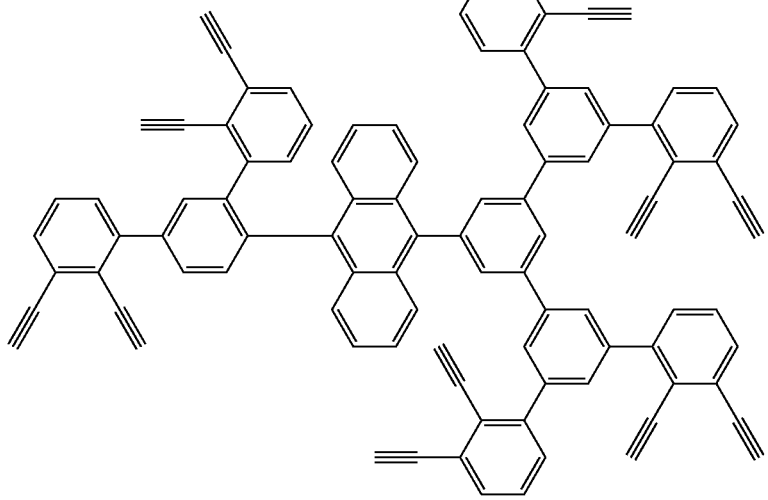
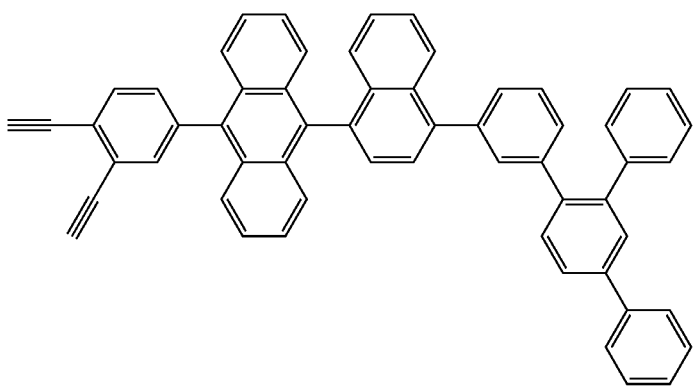
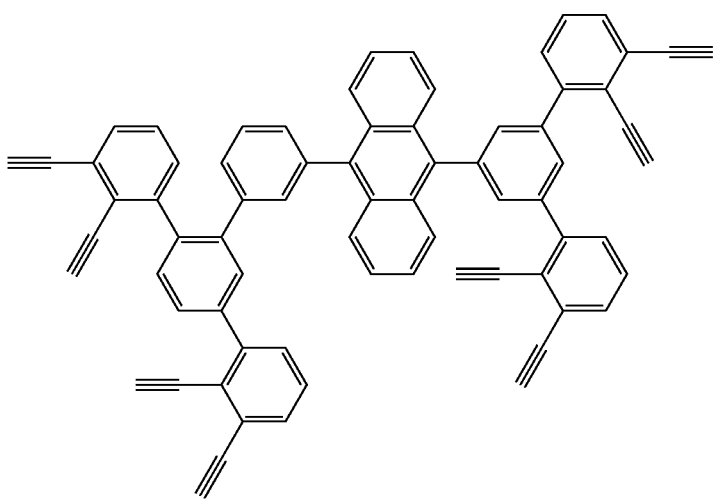

-continued
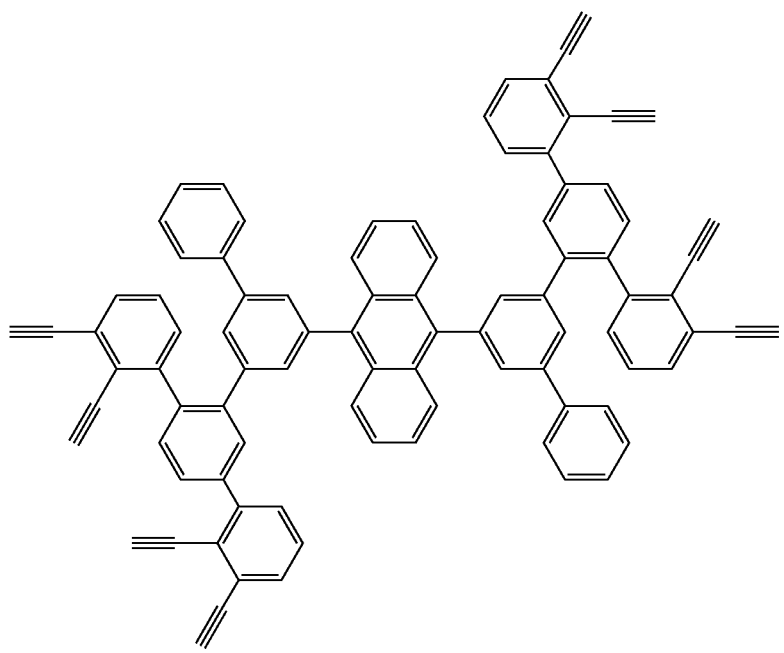
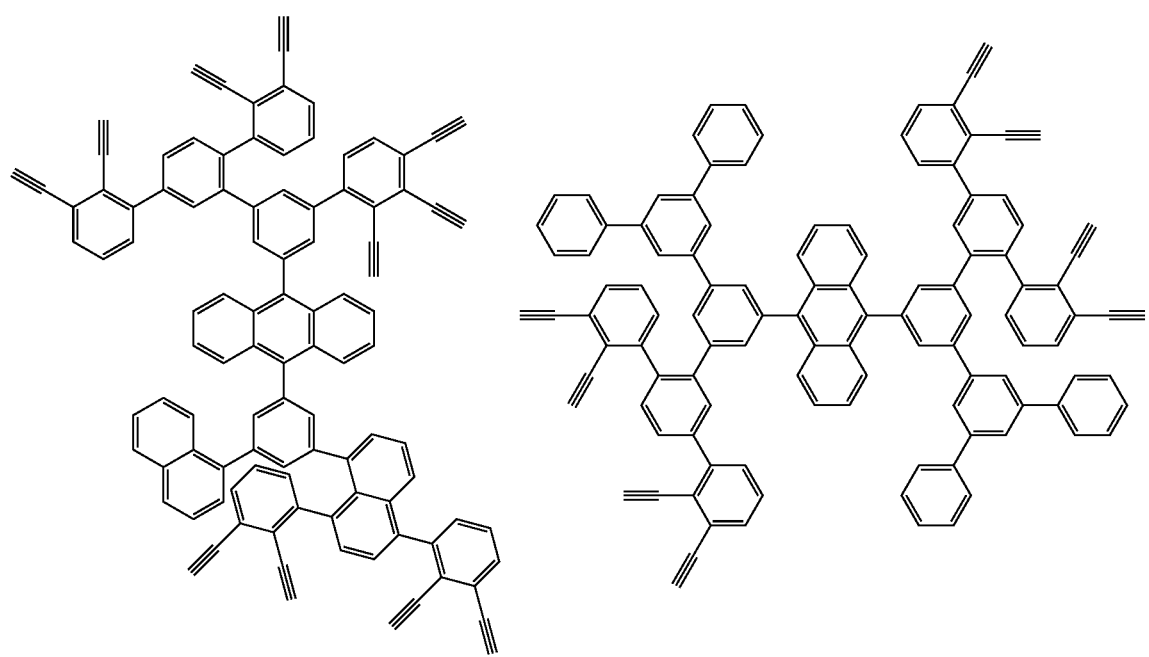

-continued
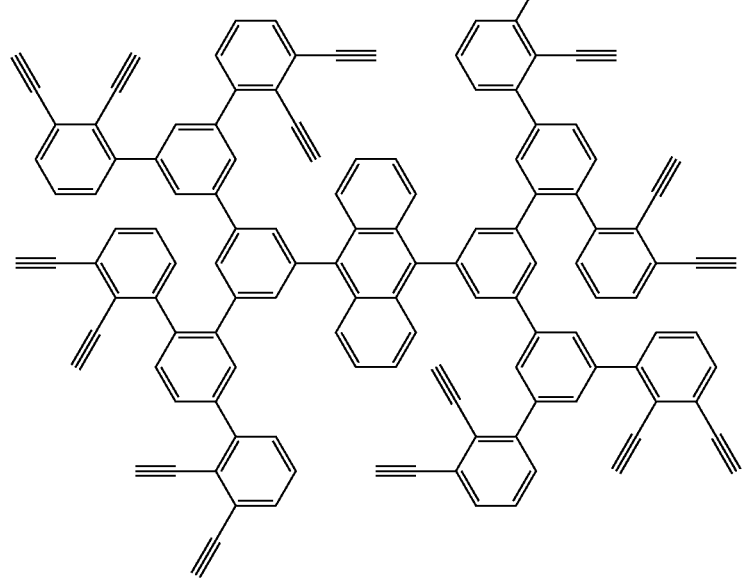
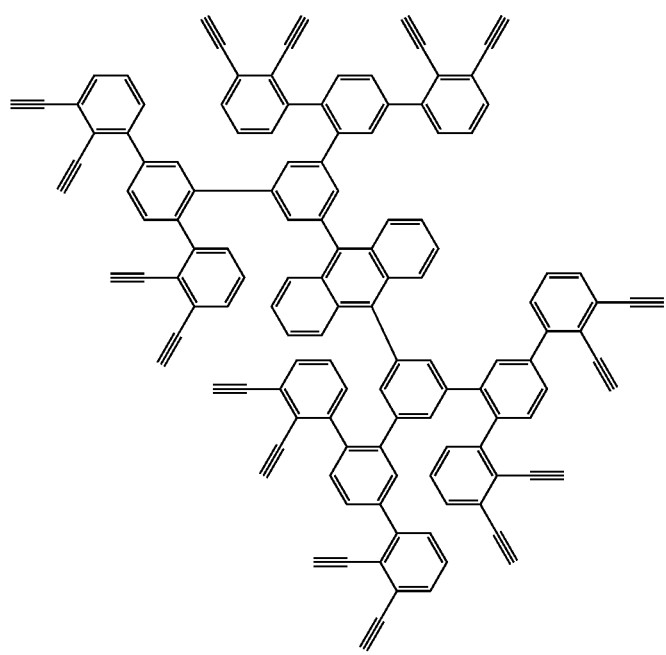

-continued
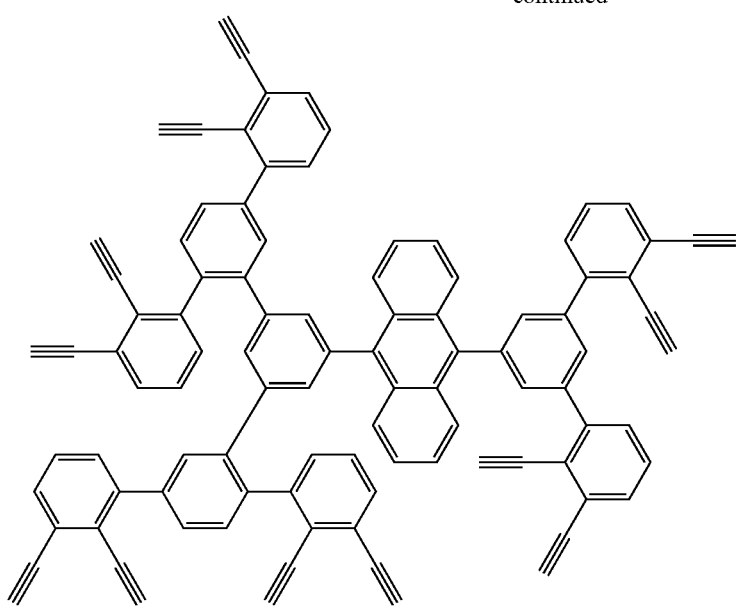
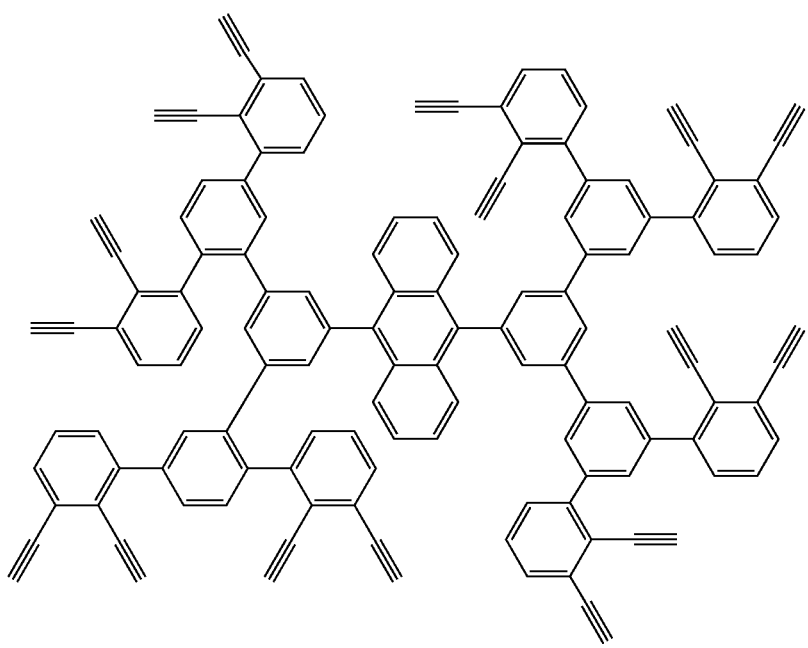

-continued
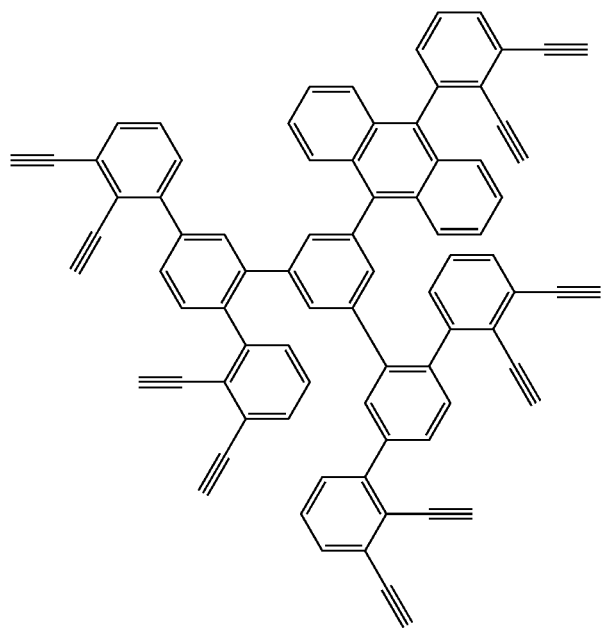
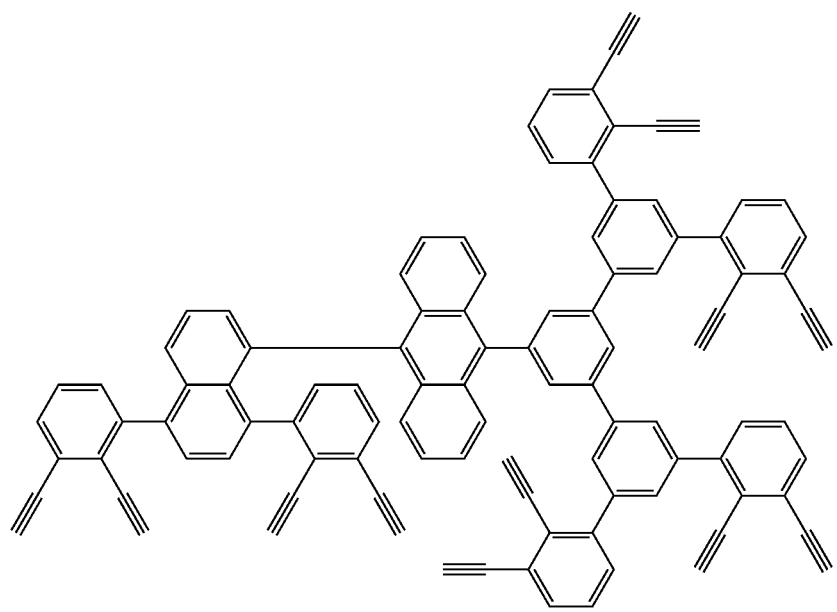
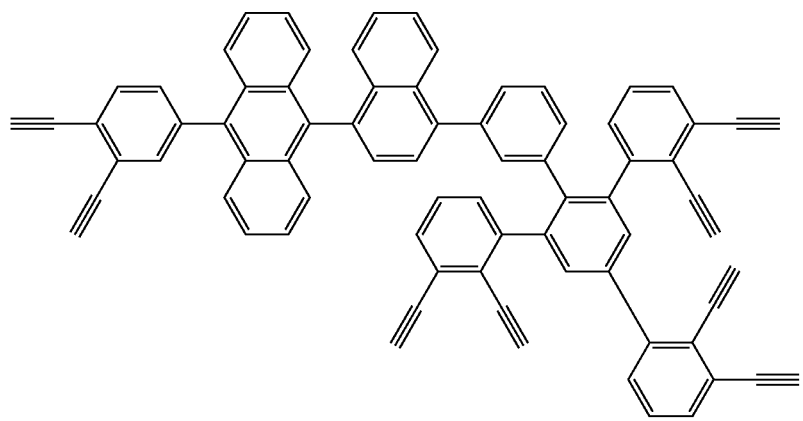

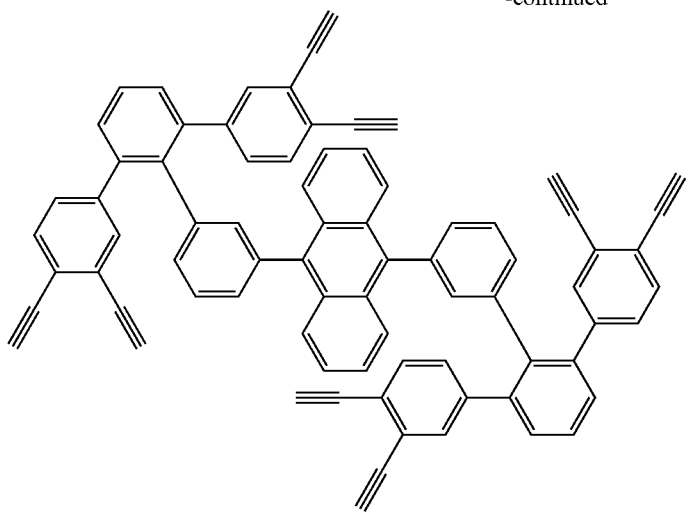
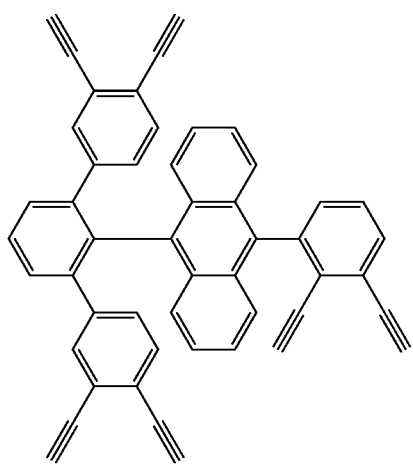
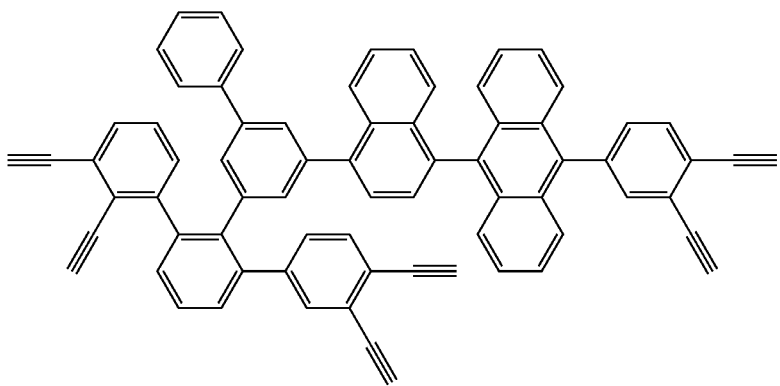

-continued
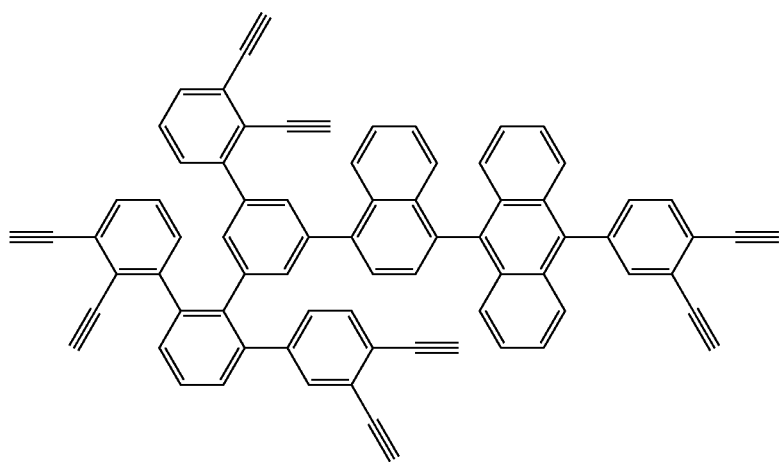
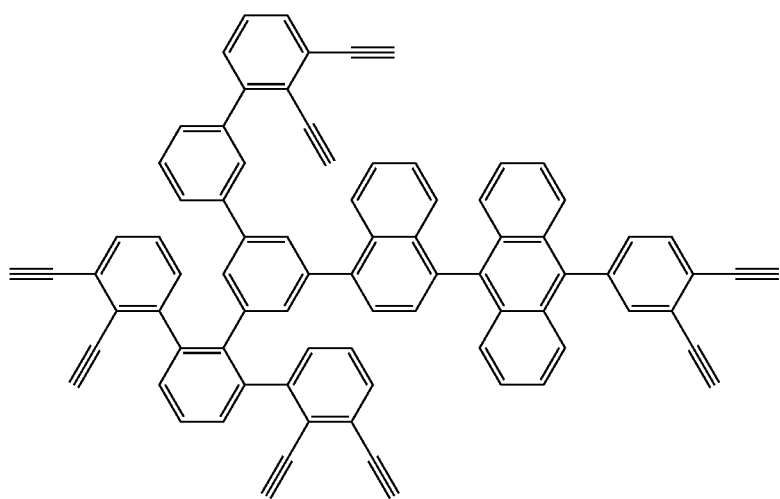
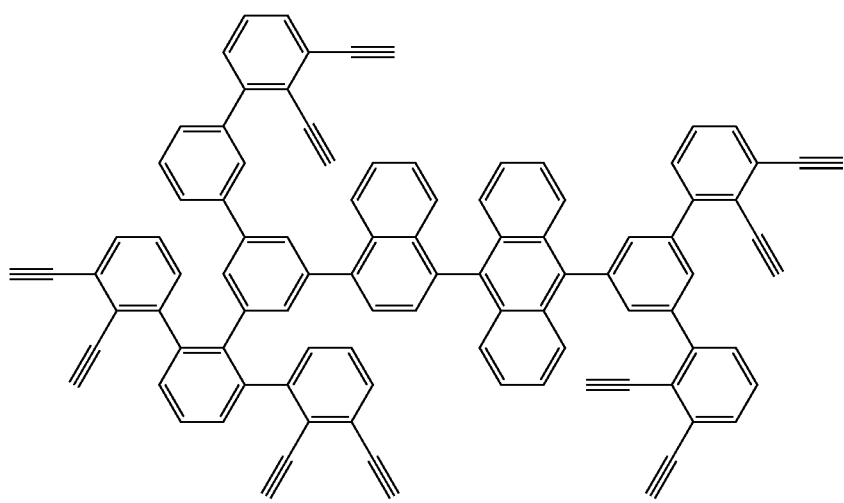

-continued
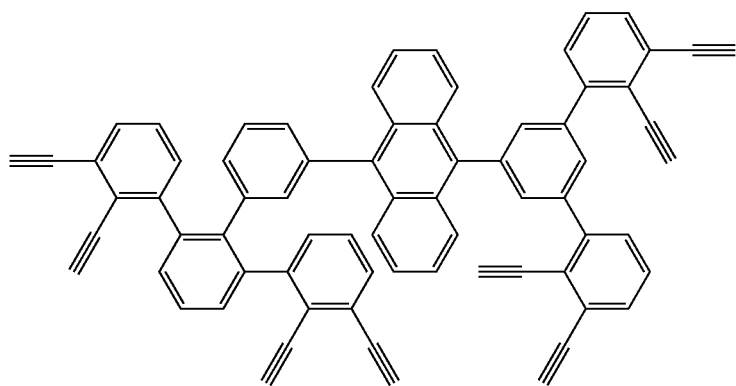

-continued
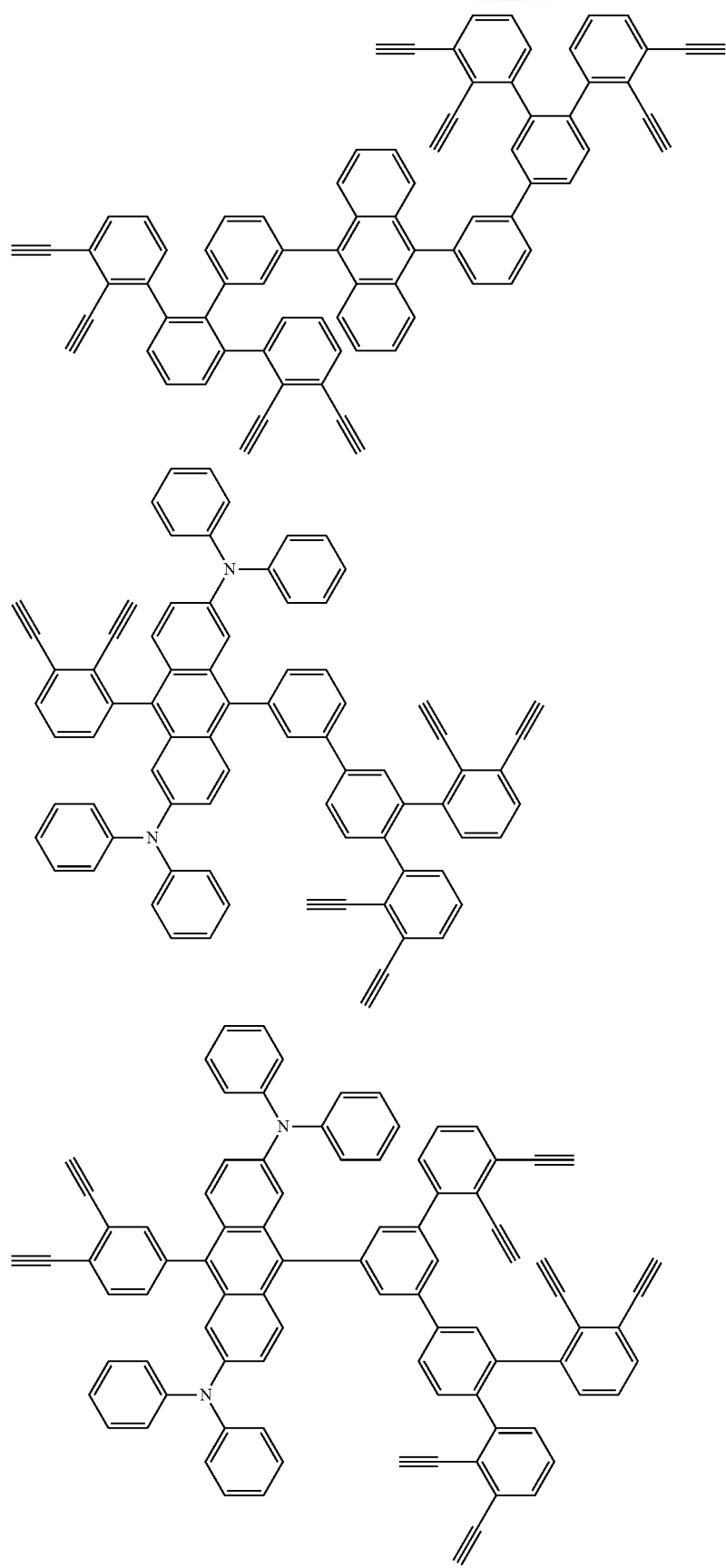

-continued
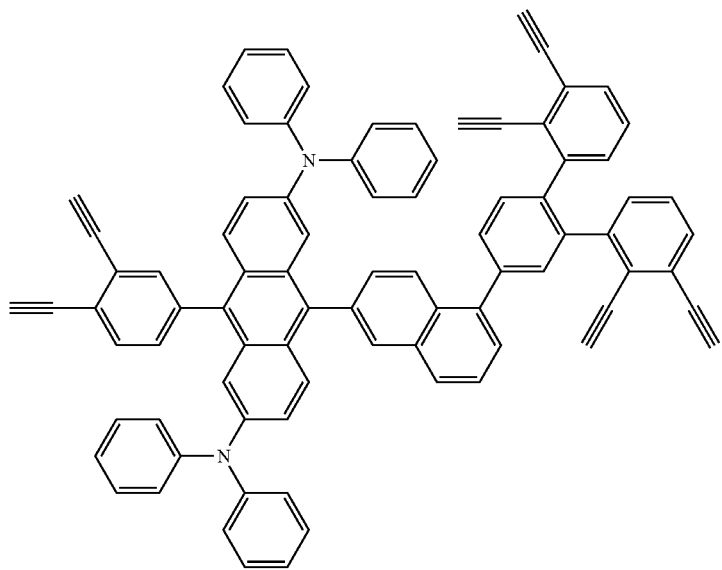
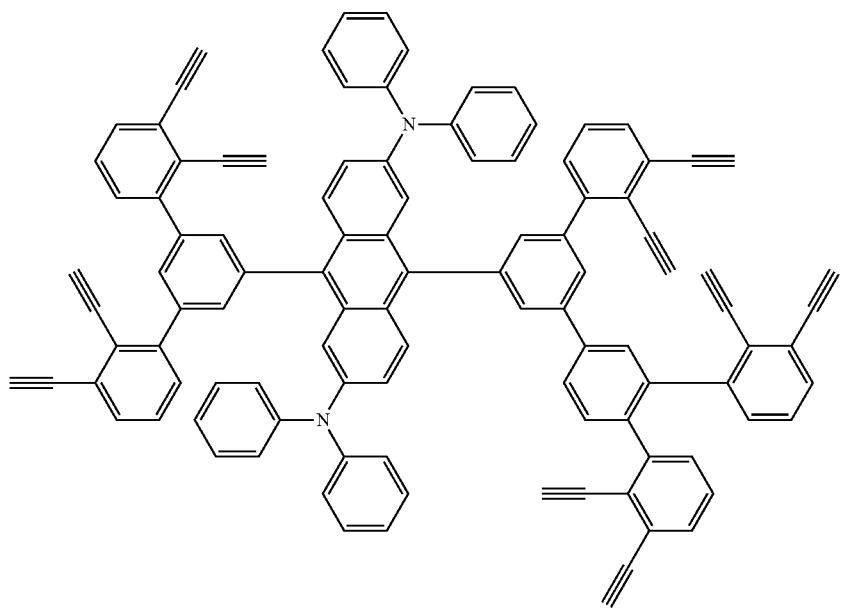
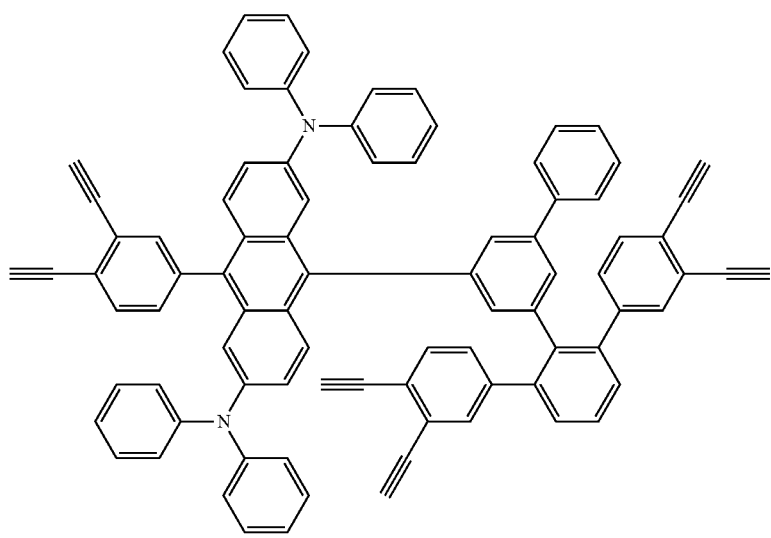

-continued
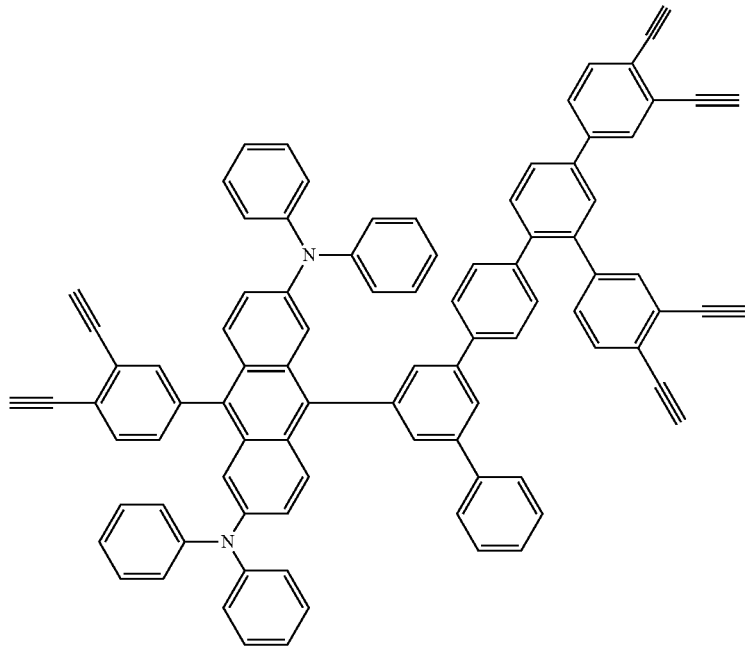
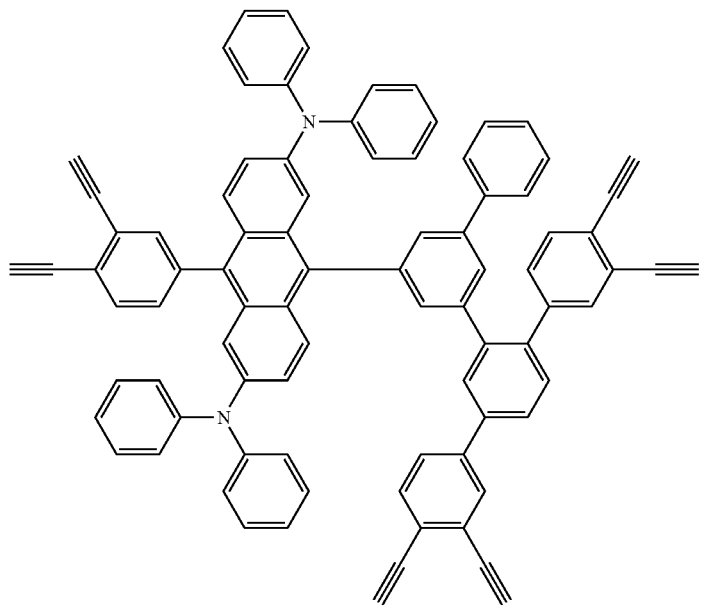
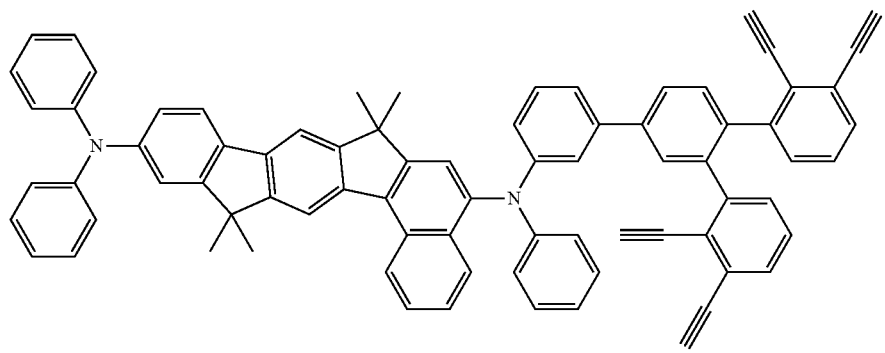

-continued
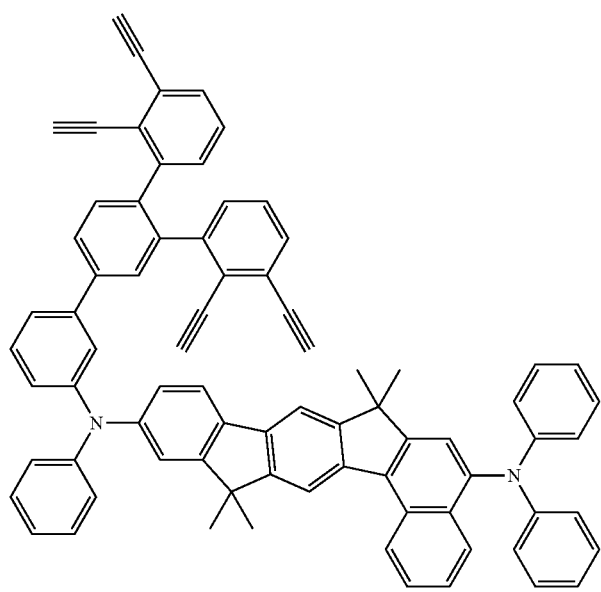
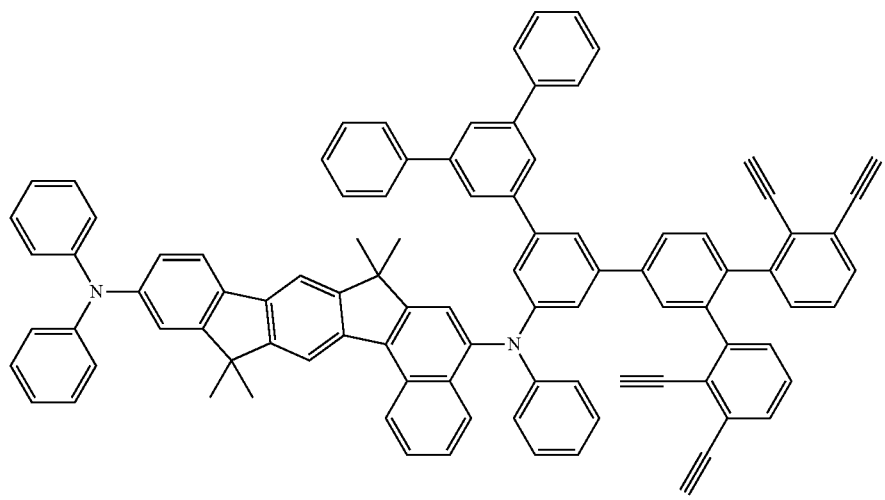
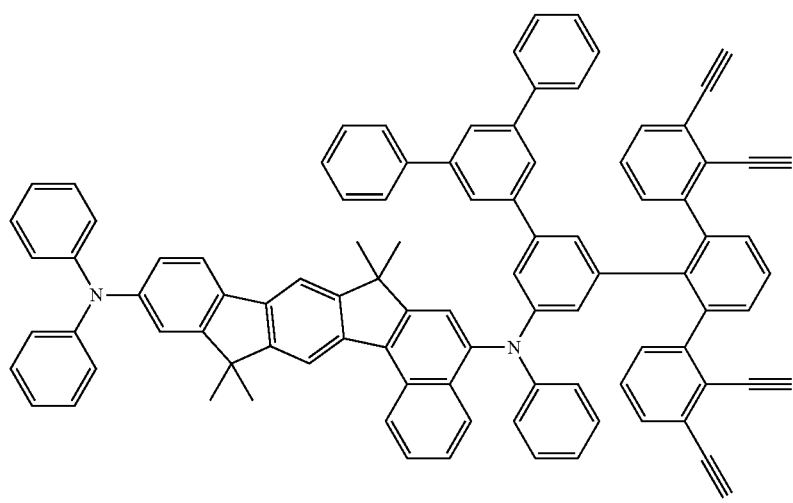

-continued
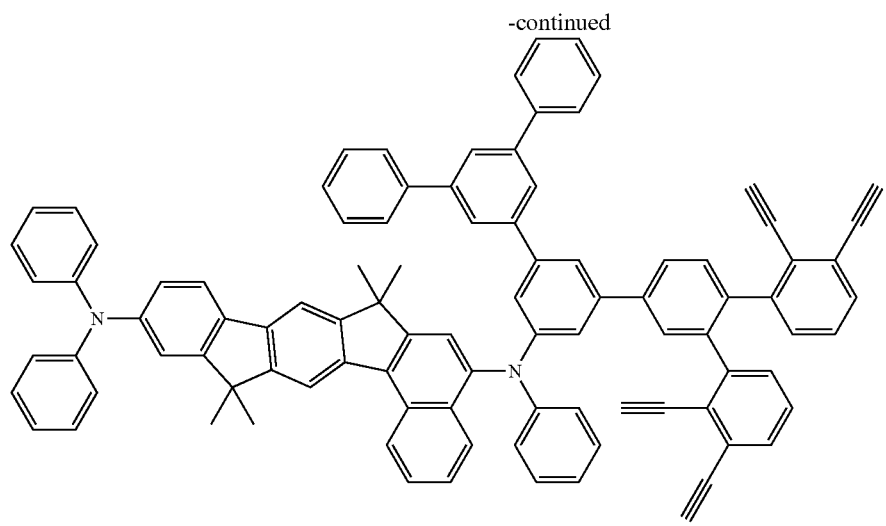
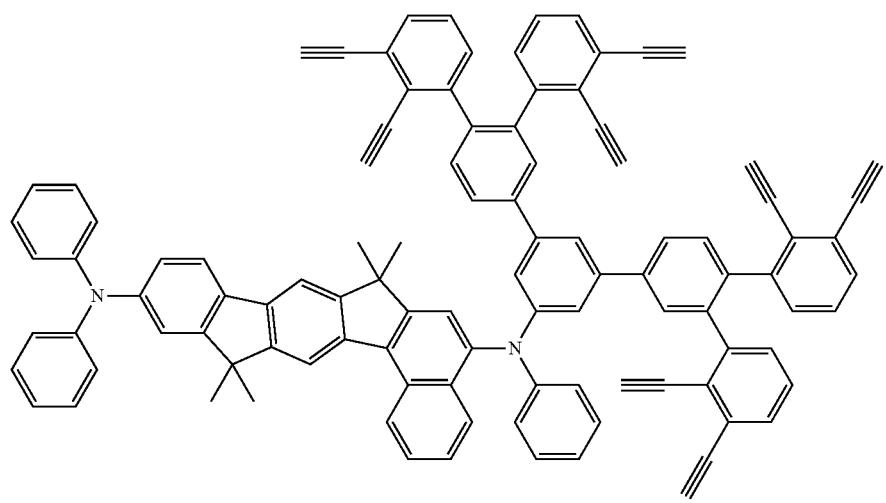
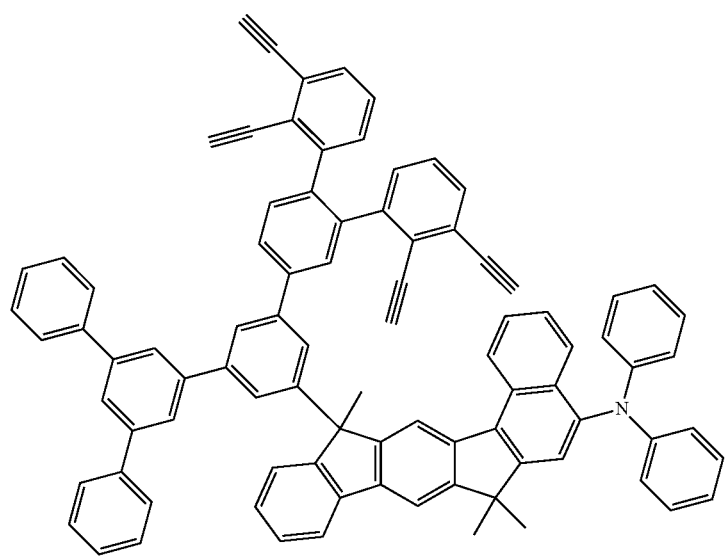

-continued
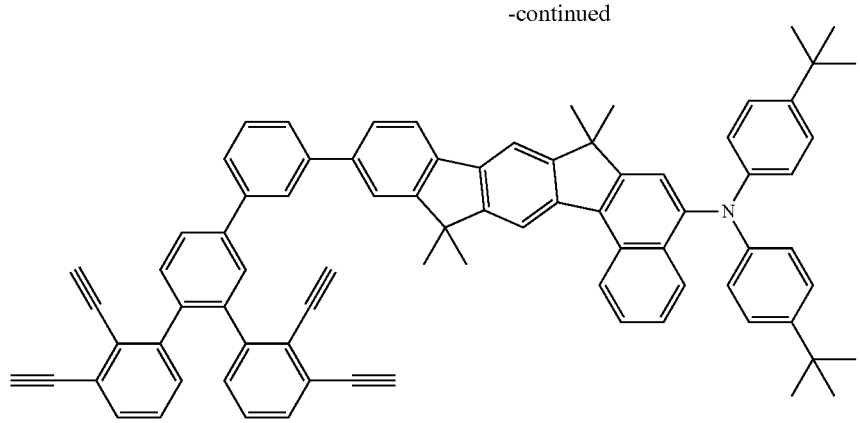
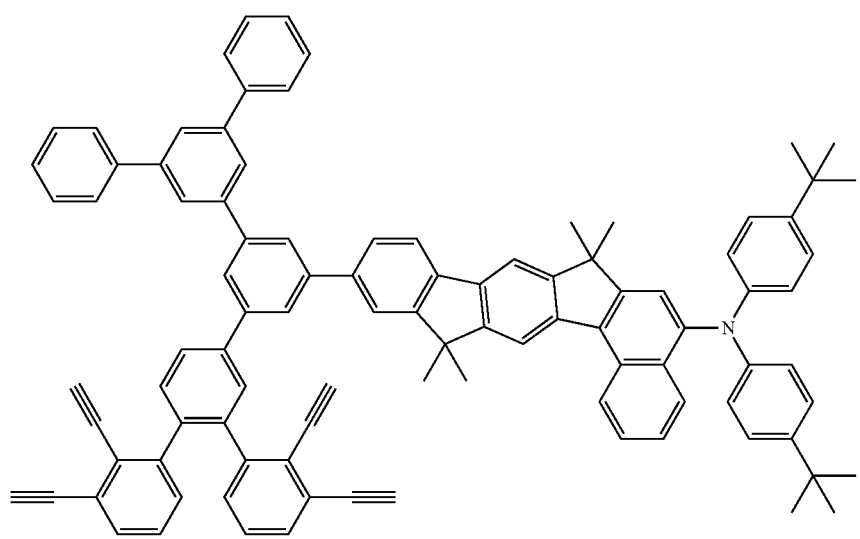
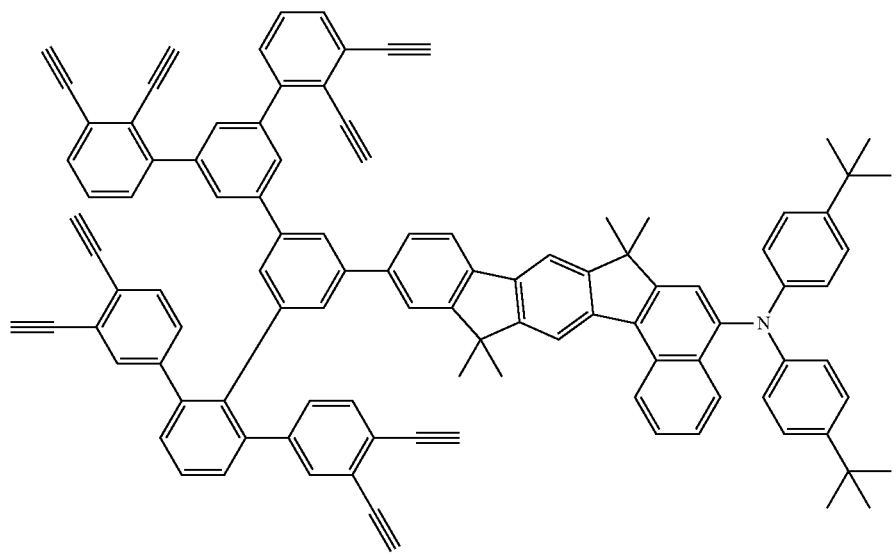

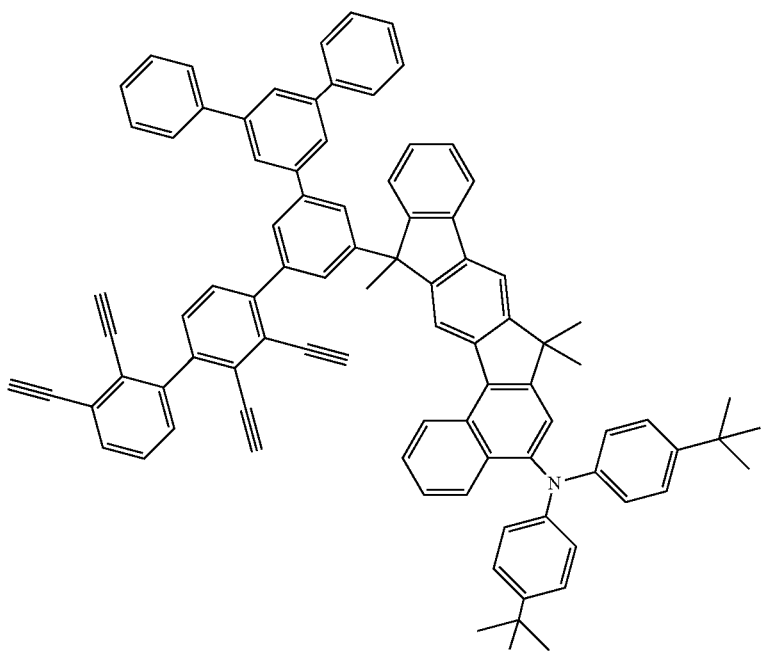
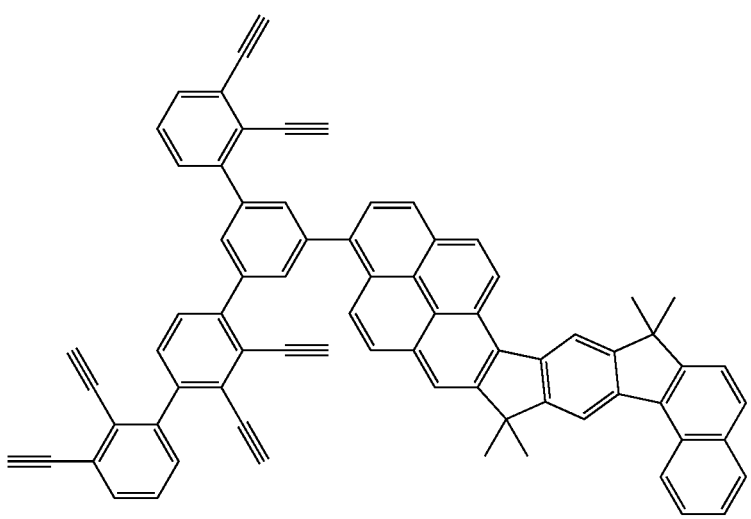

-continued
281 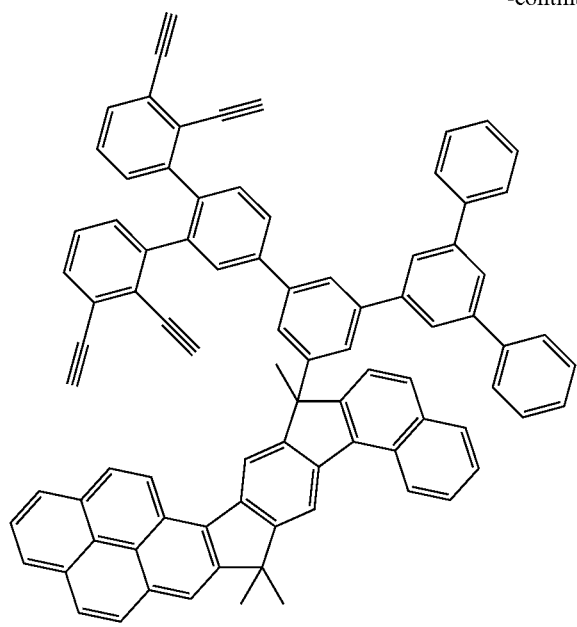
282 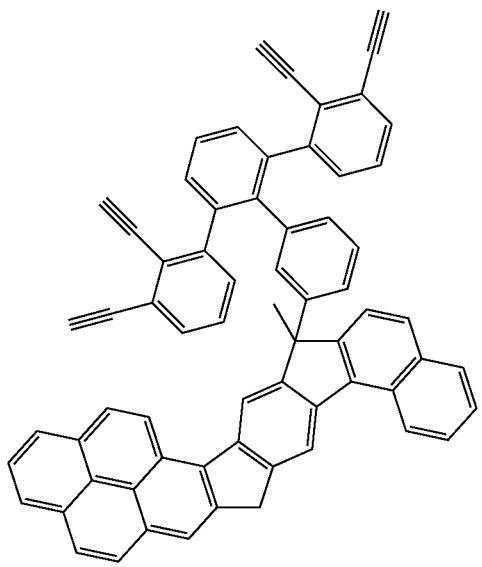
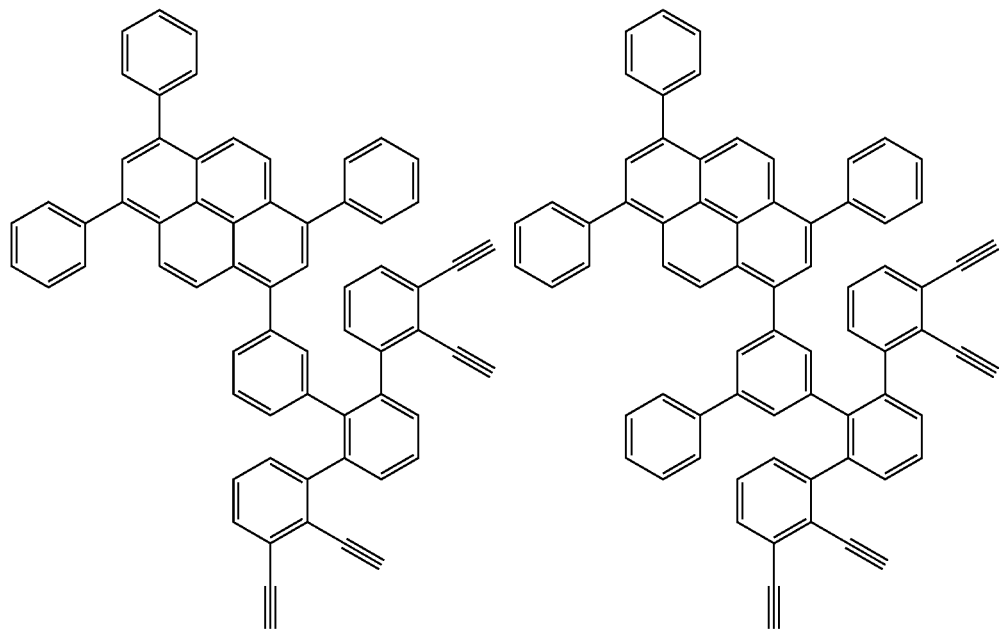

-continued
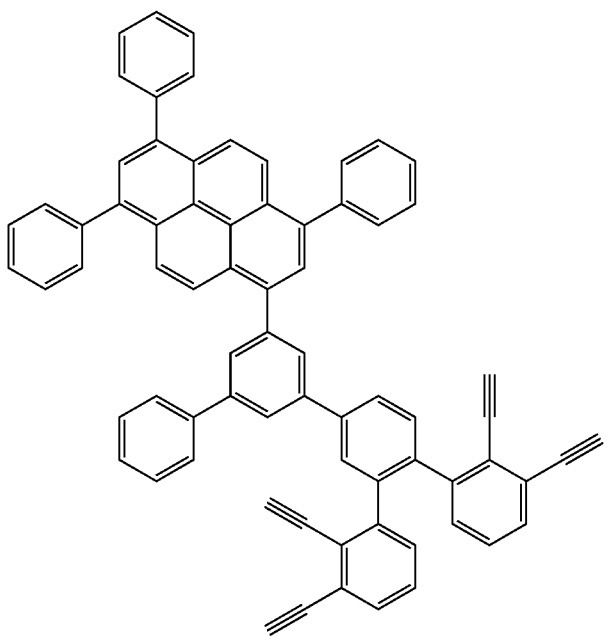
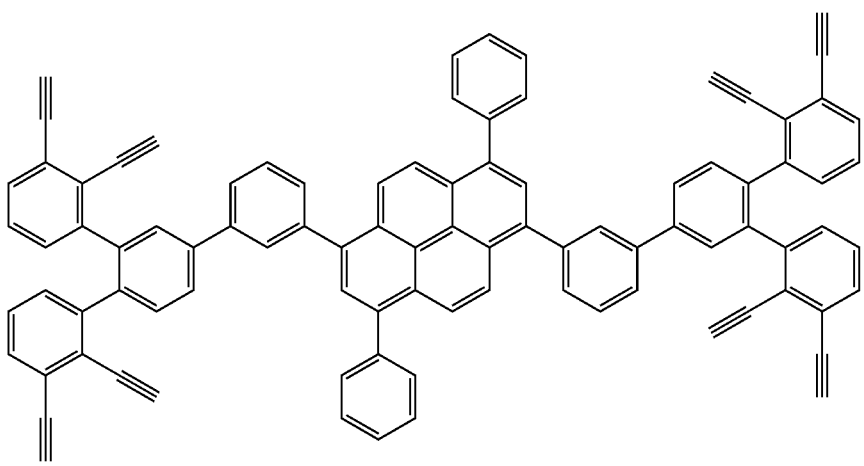
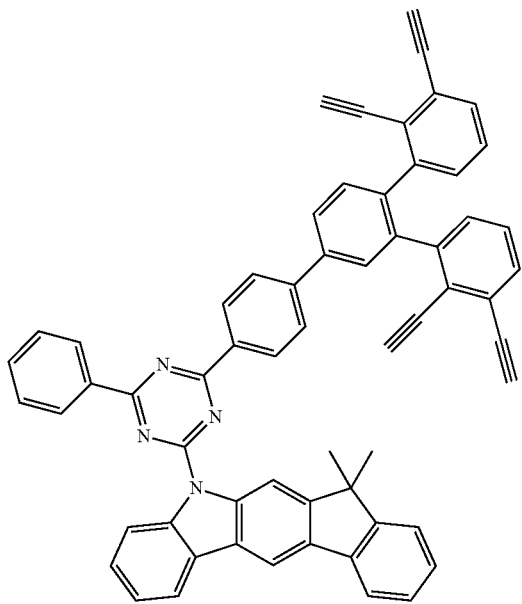

-continued
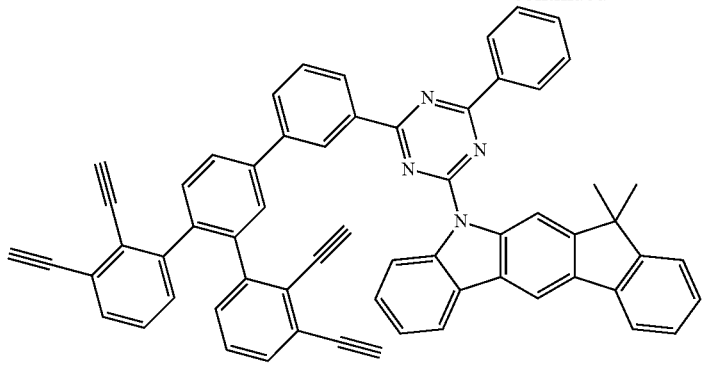
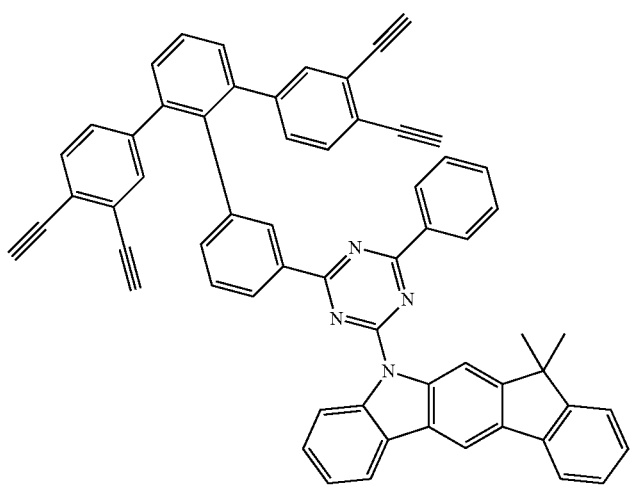
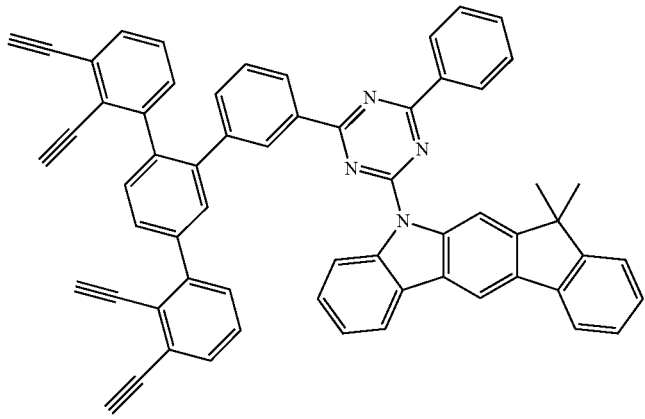
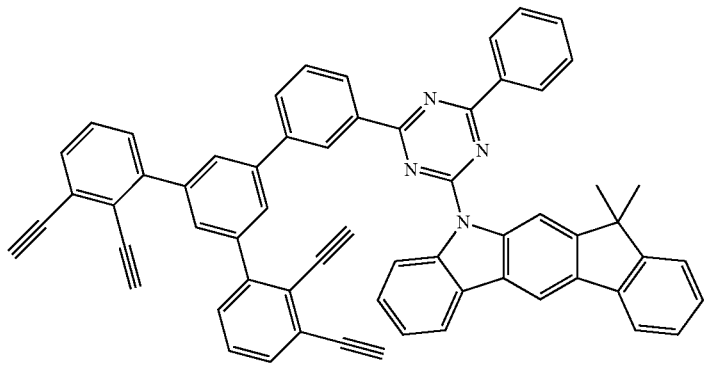

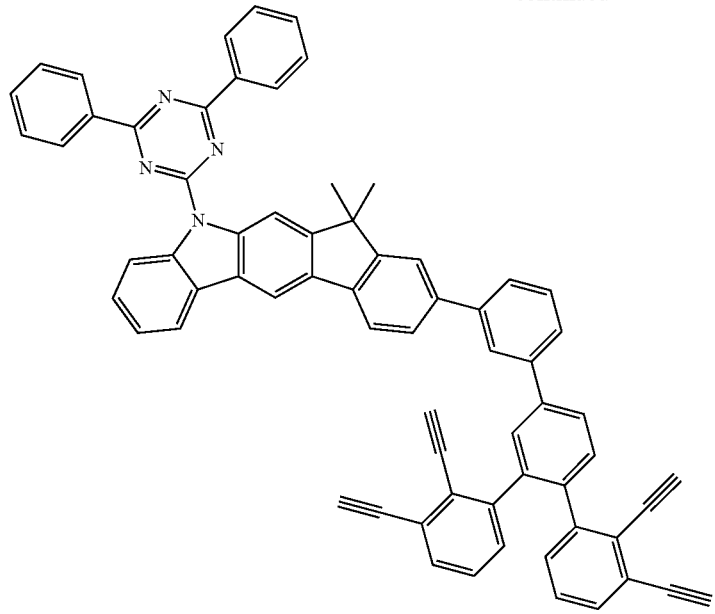
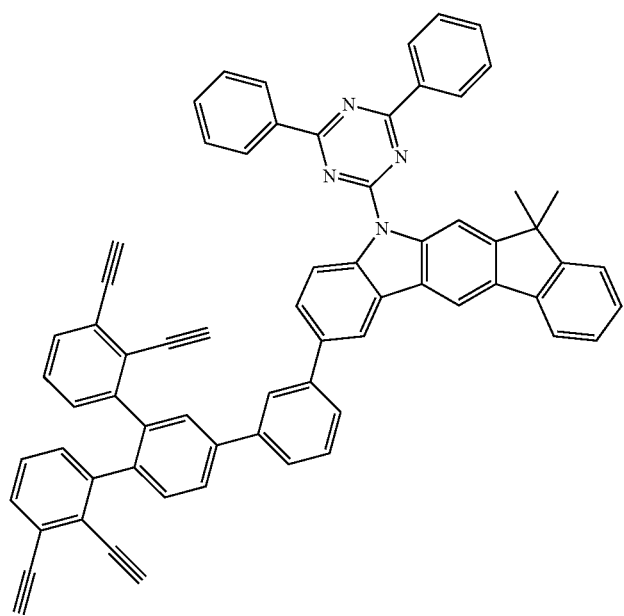

-continued
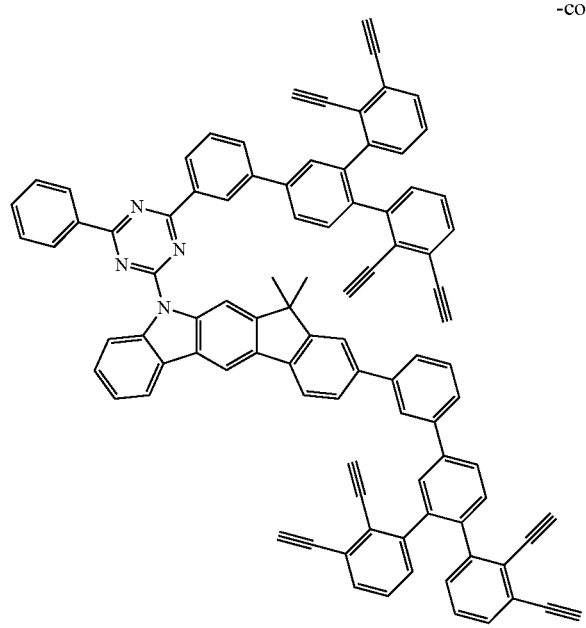
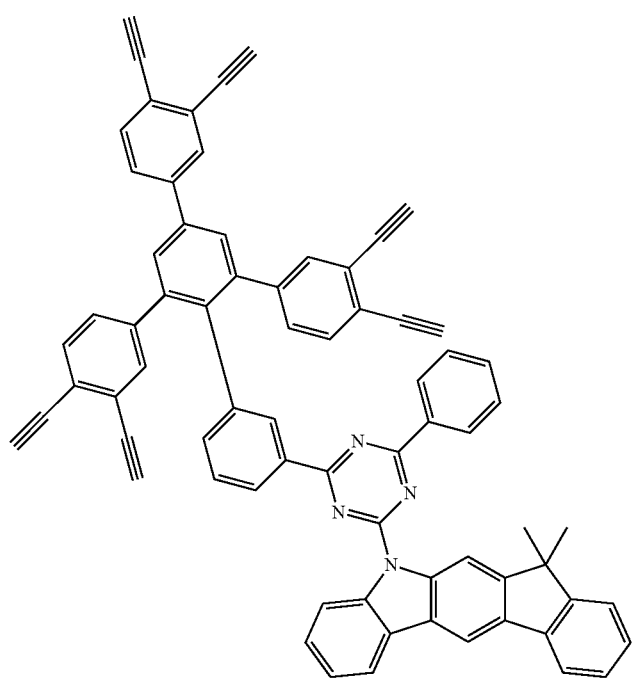

291 292
-continued
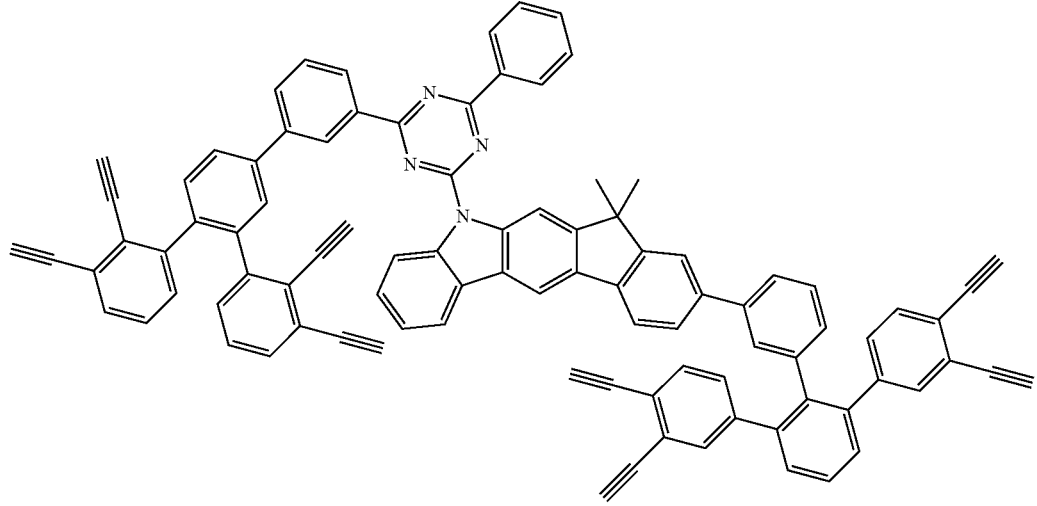
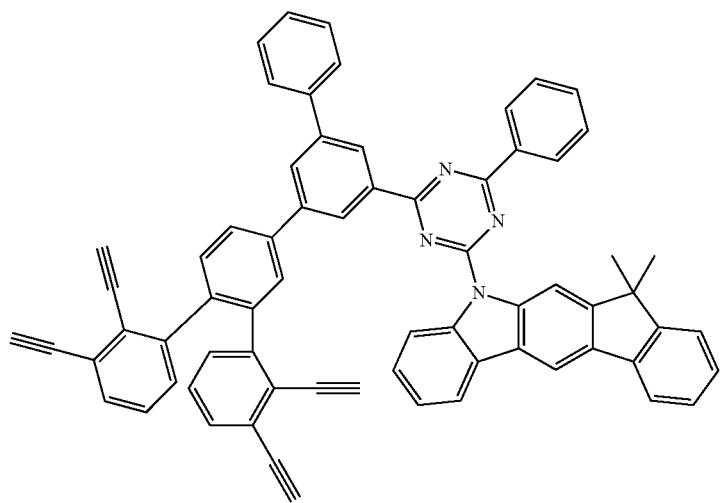
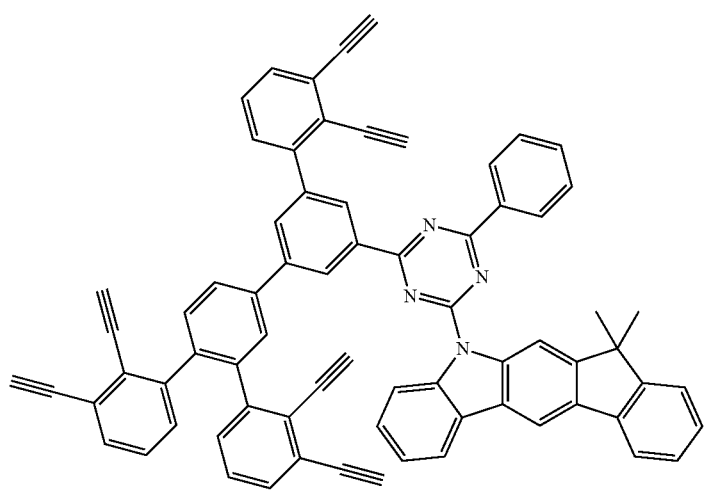

-continued
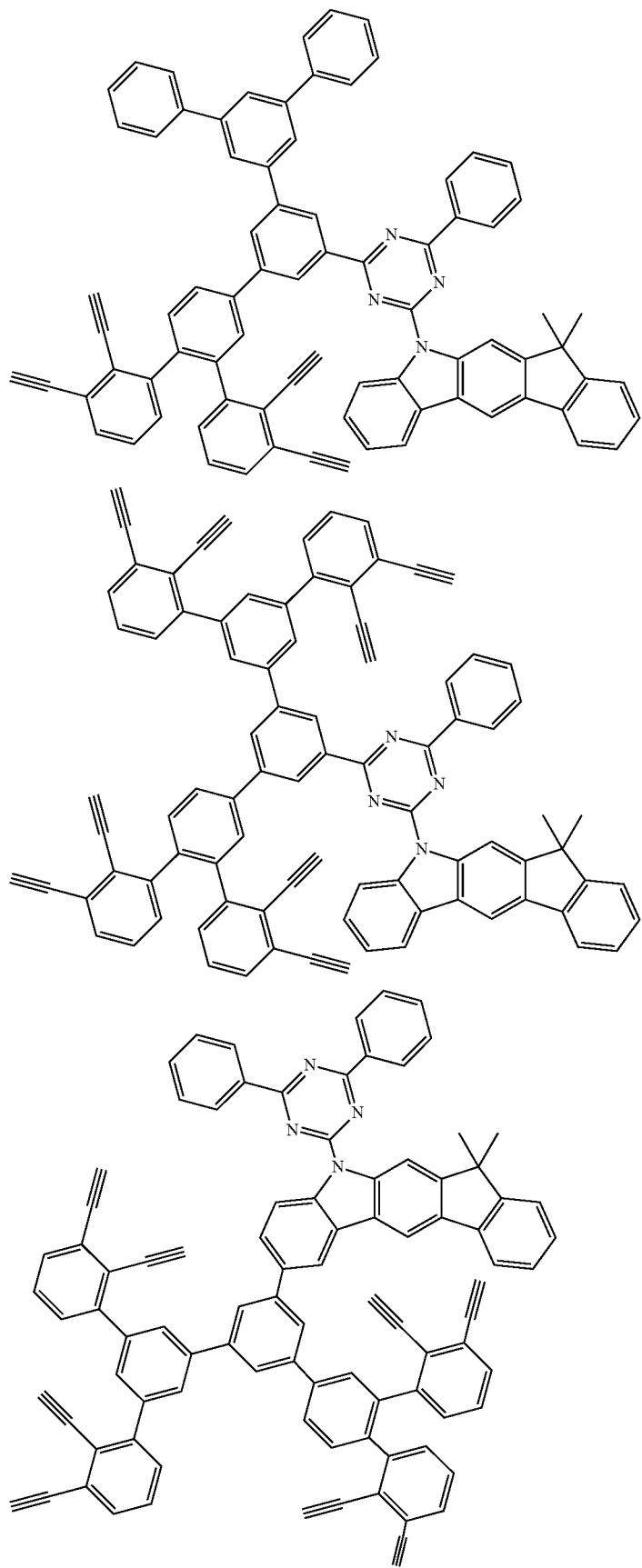

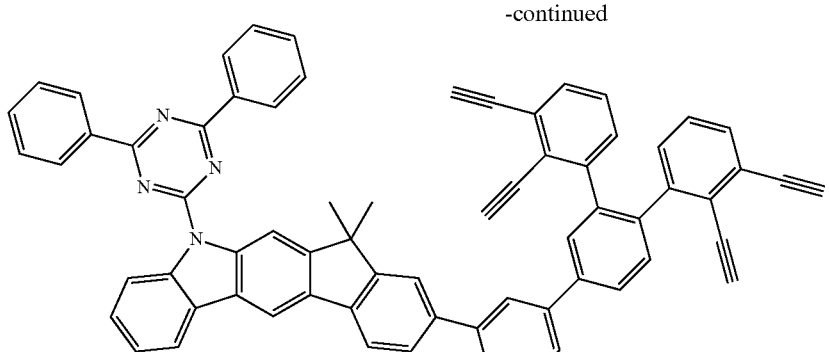
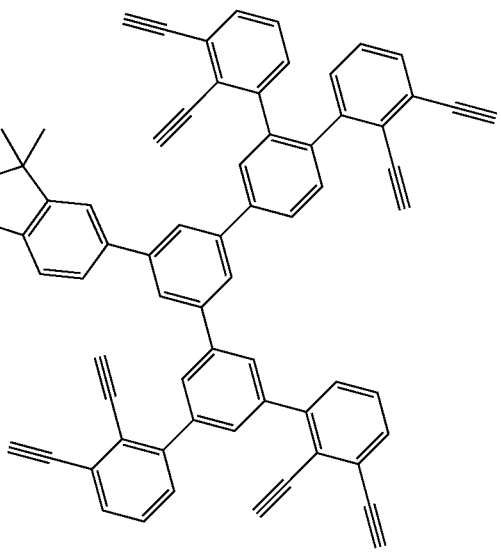
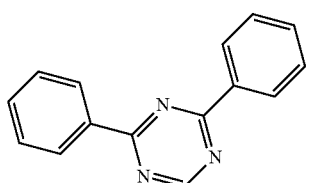
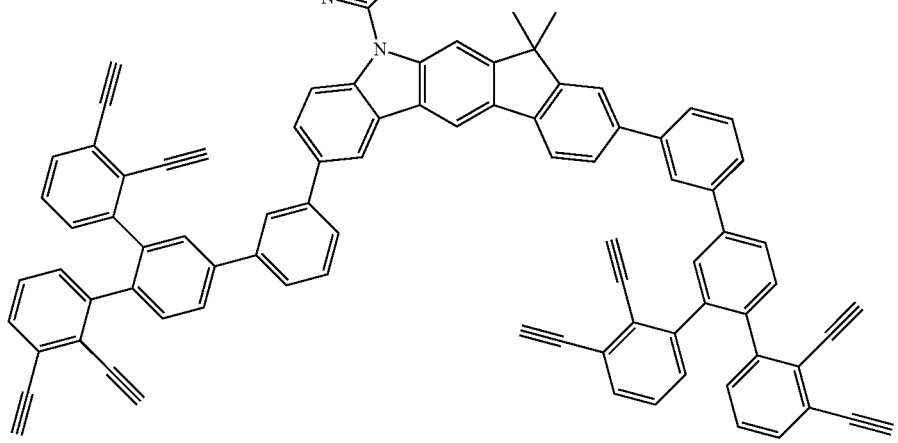
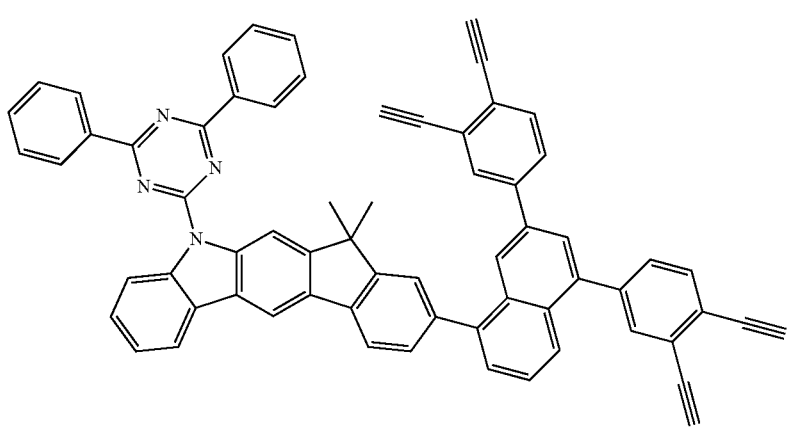

-continued
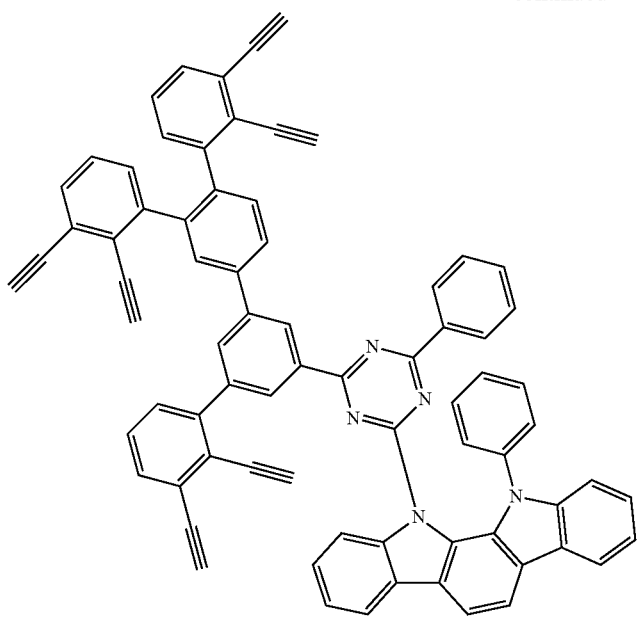
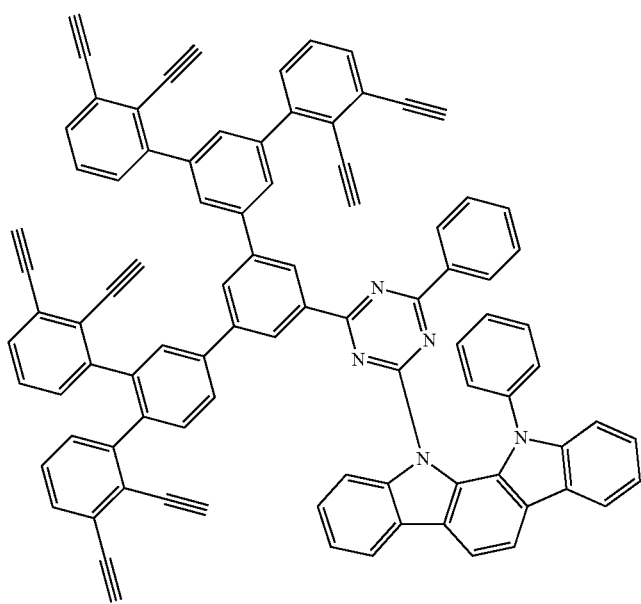

-continued
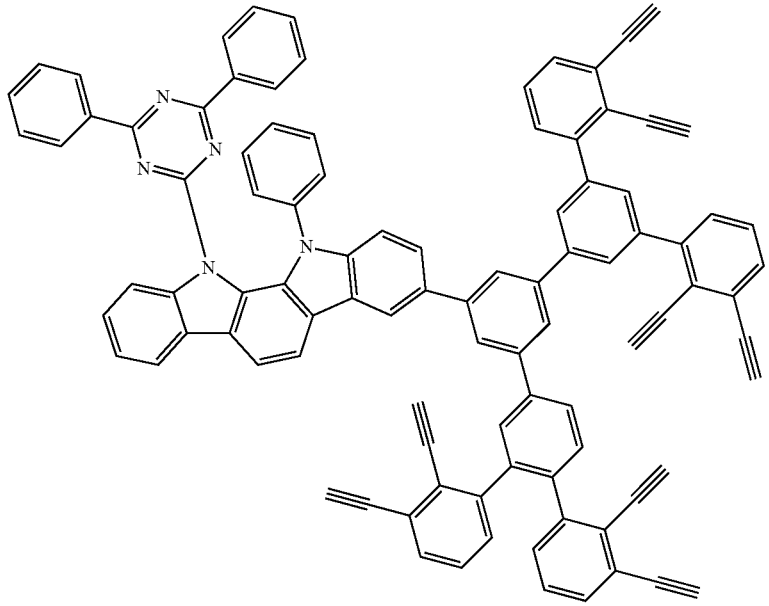
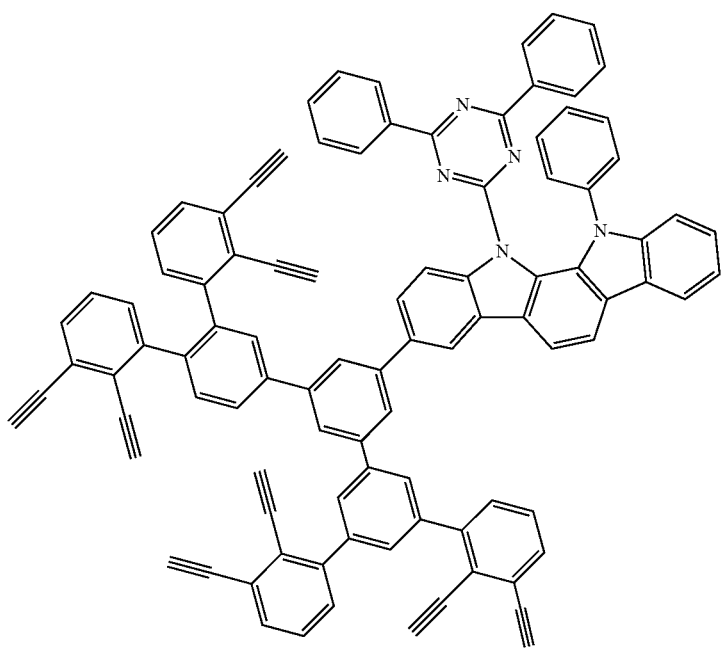

-continued
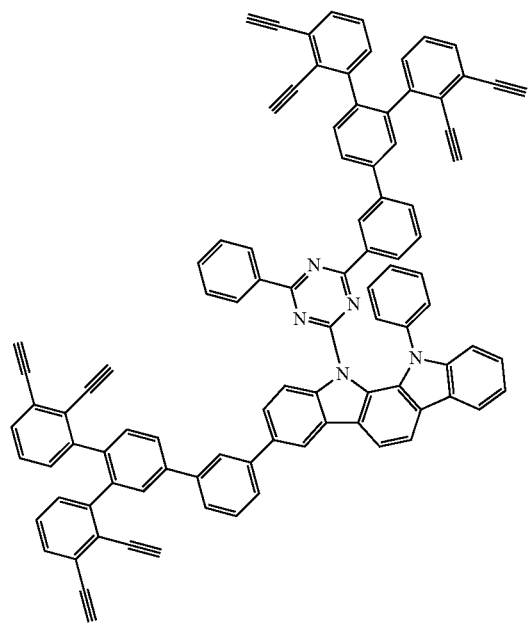
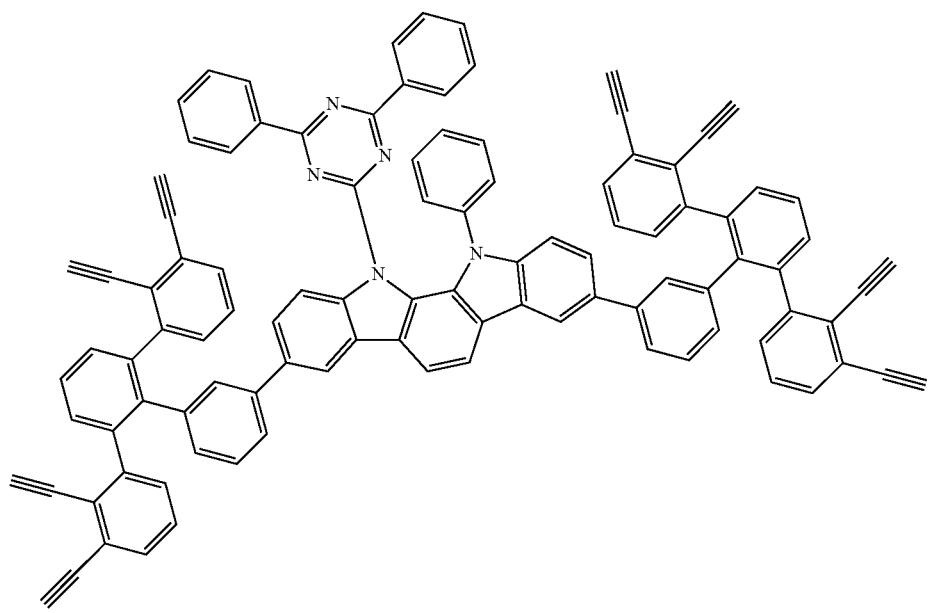

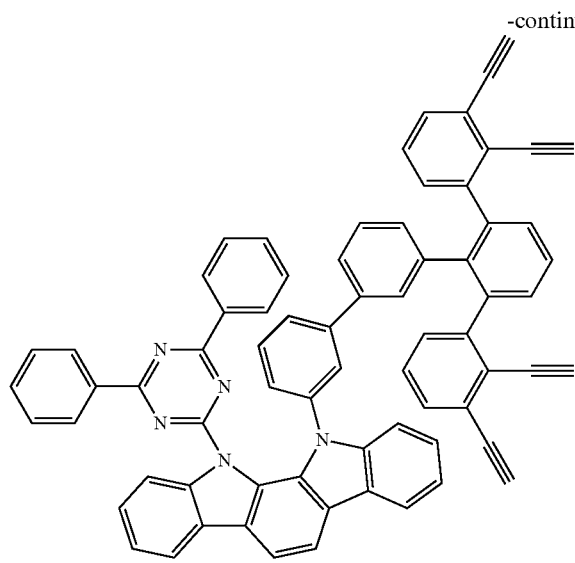
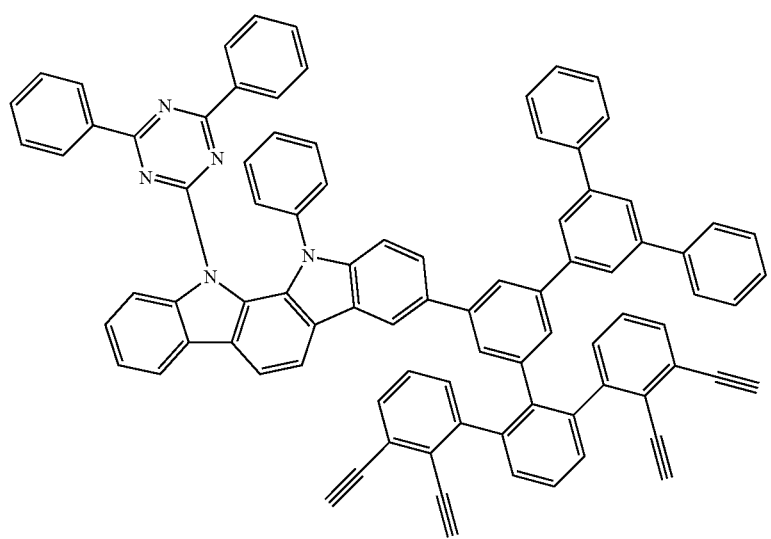
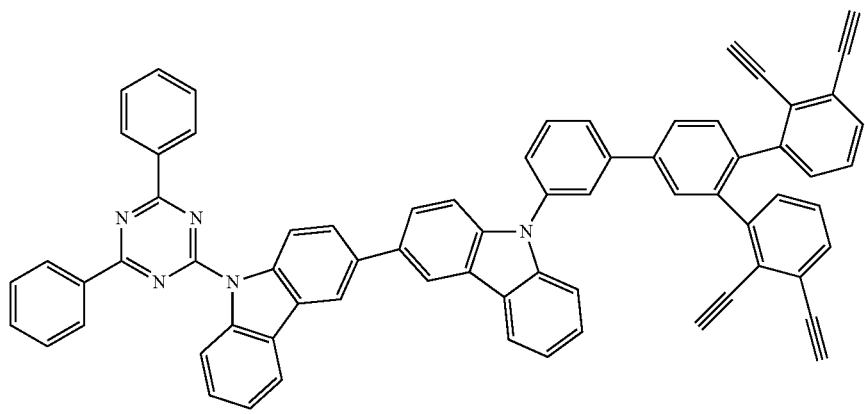

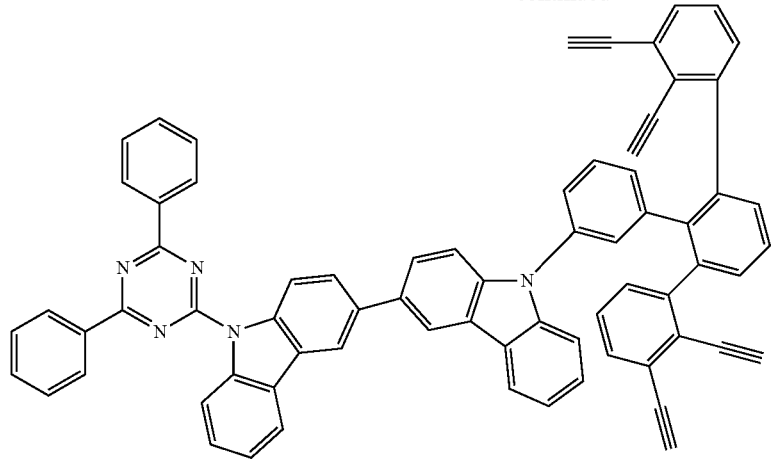
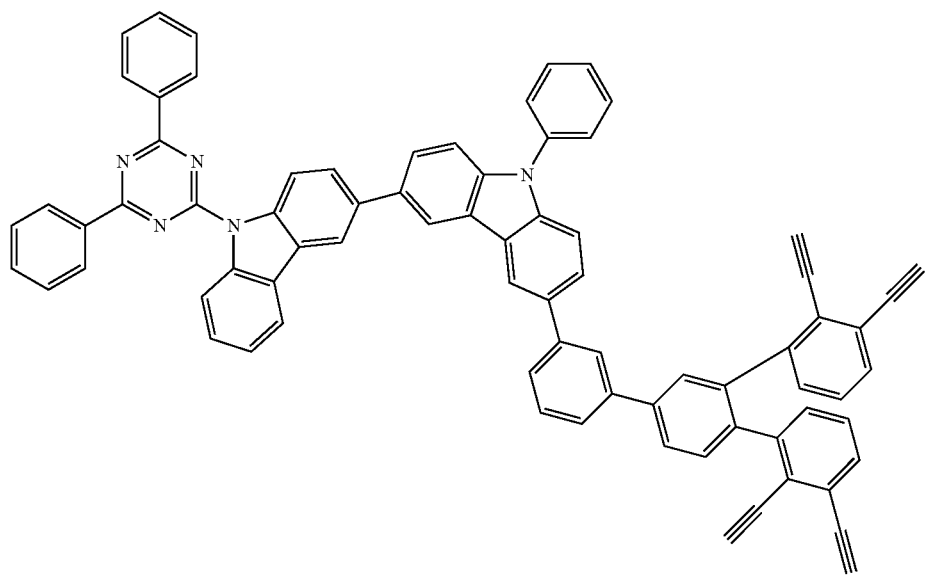
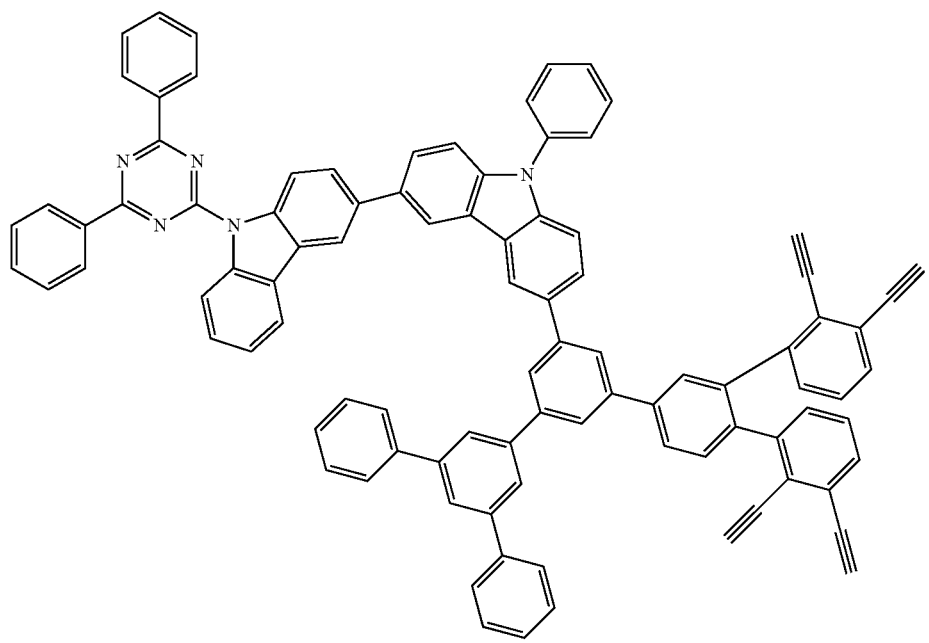

-continued
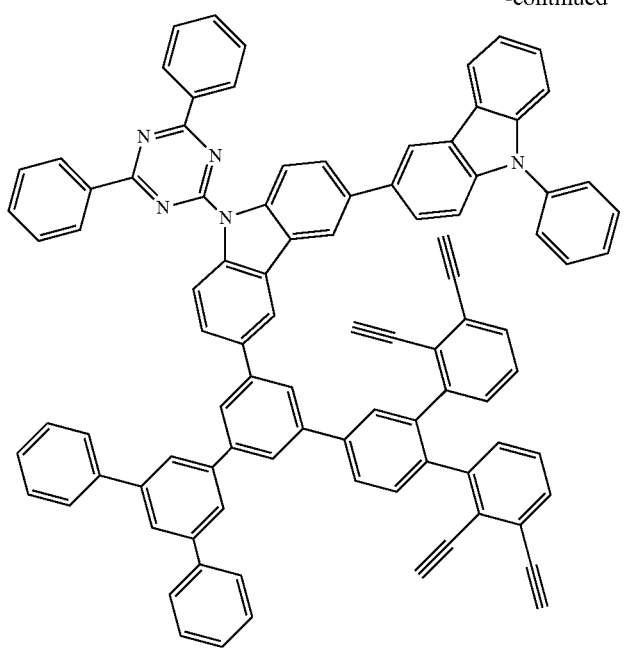
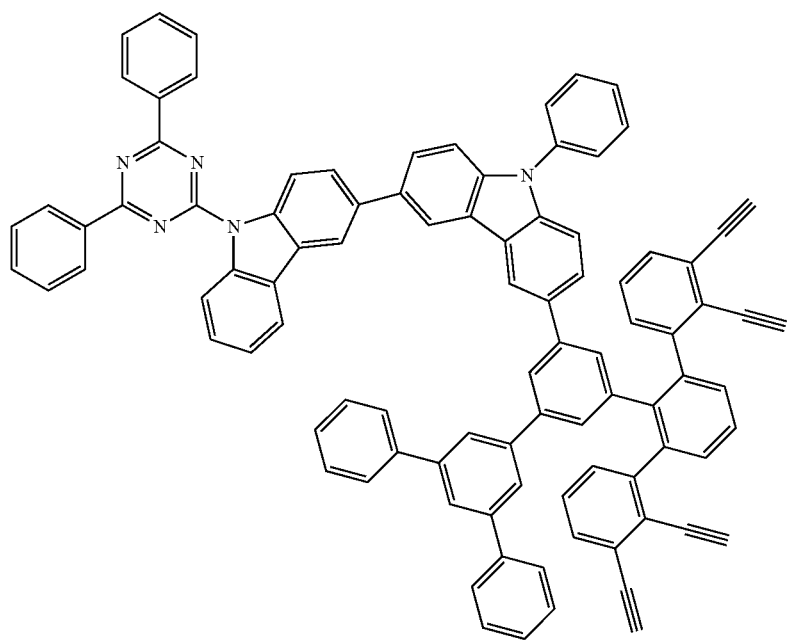

309
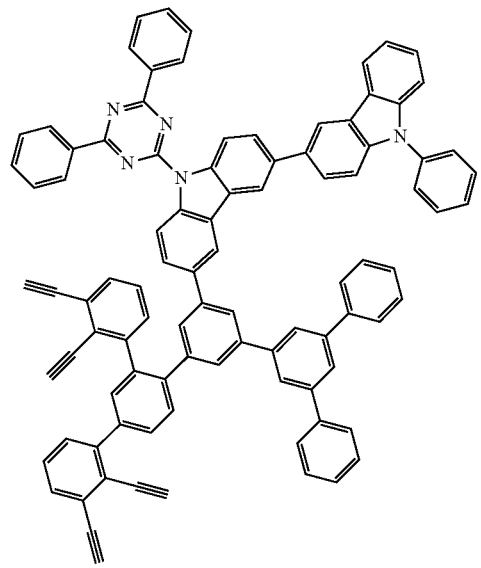
310
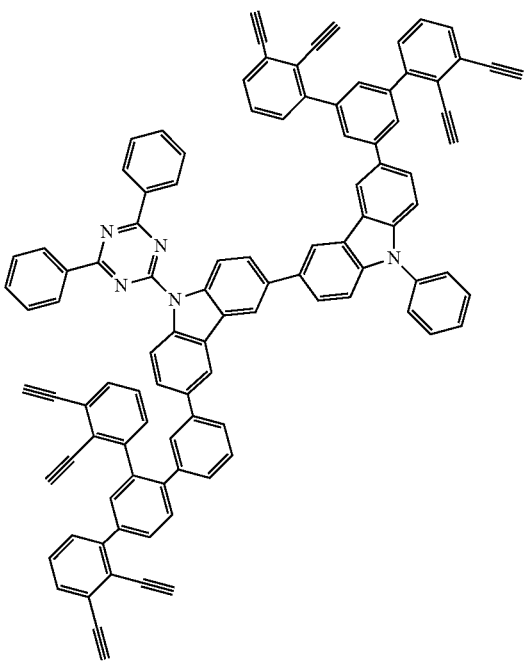
-continued
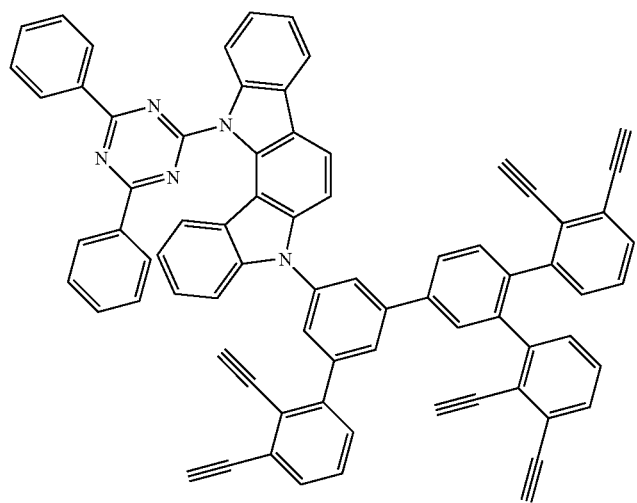

311
312
-continued
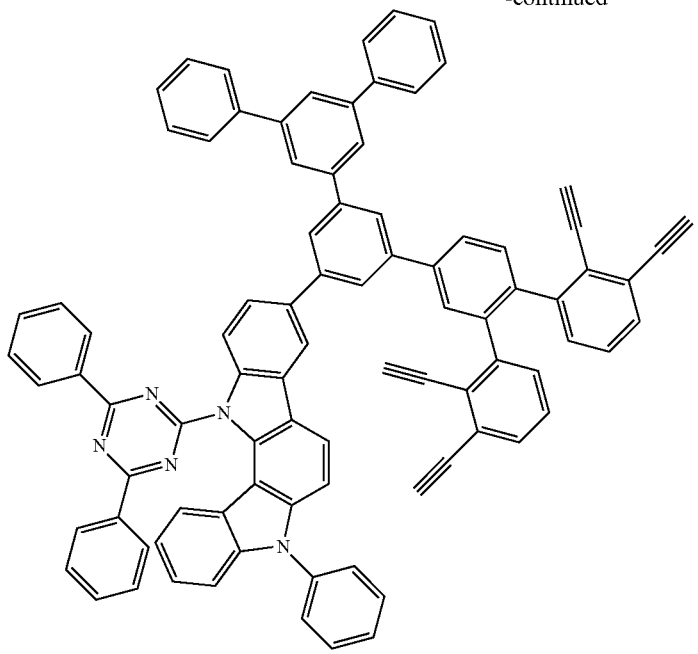
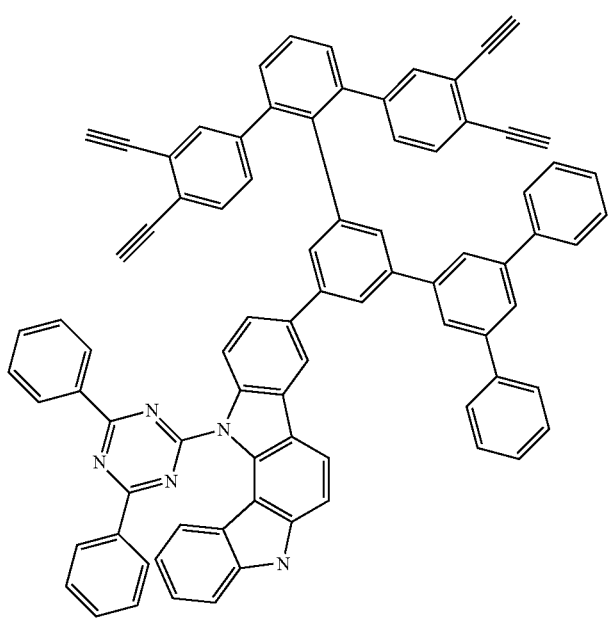

313
314
-continued
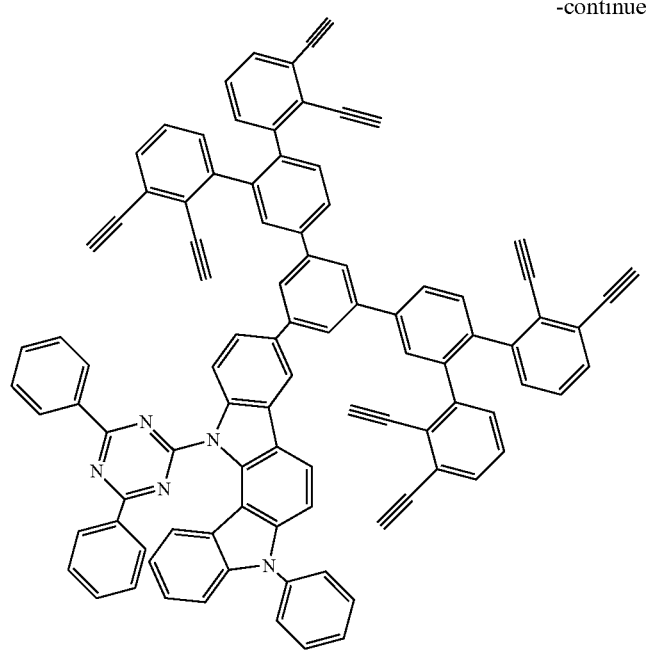
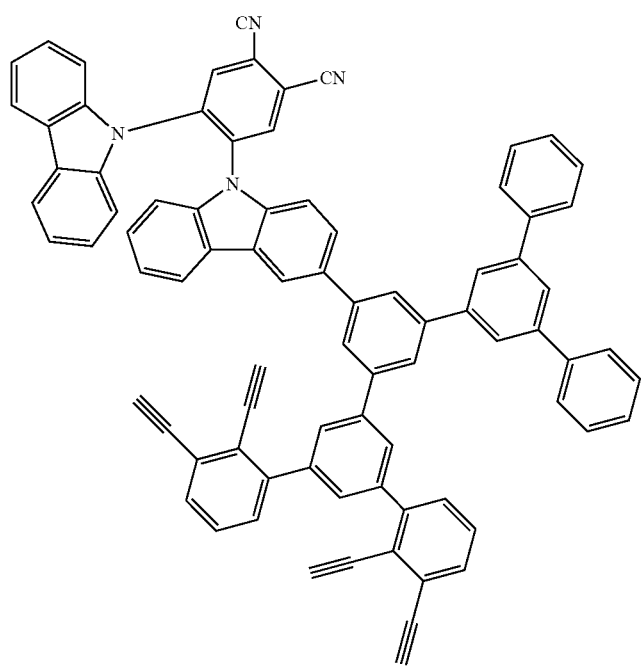

-continued
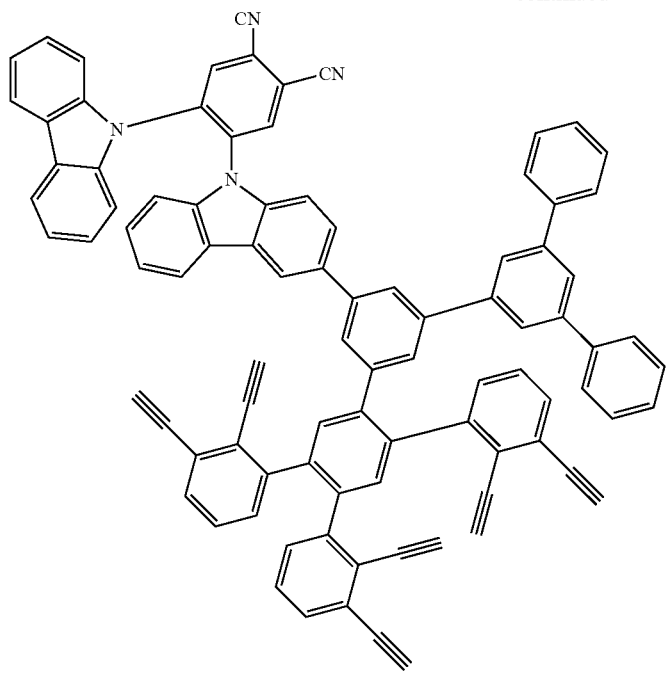
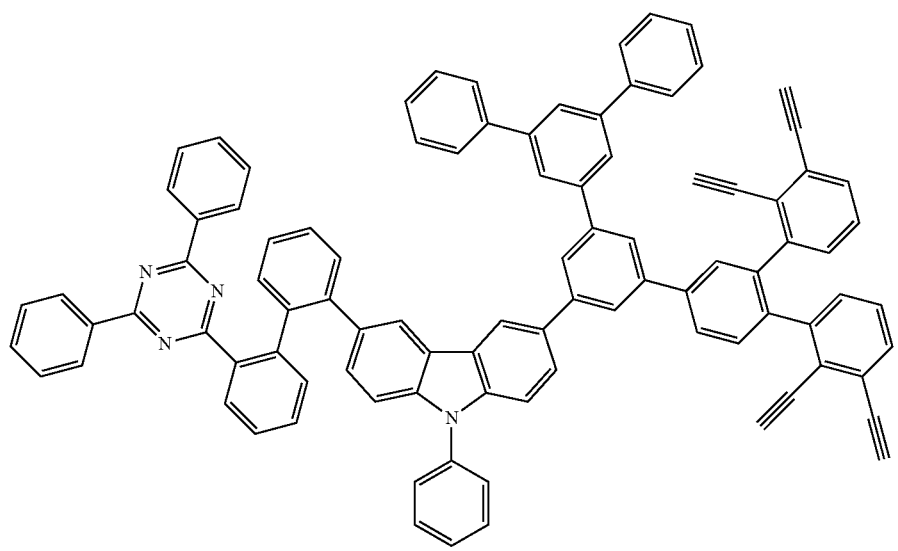
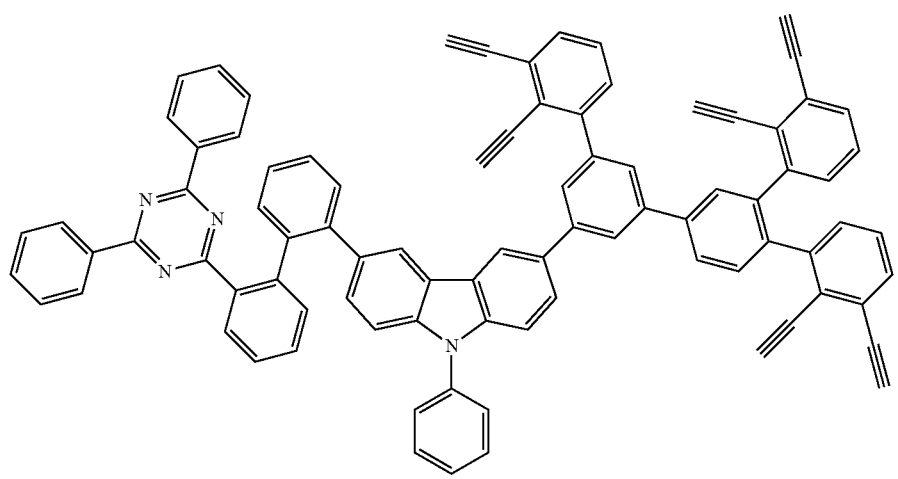

In the above method for synthesizing the organic functional compound of general formula (I), the reaction is carried out by using a raw material containing an active group. These active raw materials include at least one leaving group, for example, the leaving group is bromine, iodine, boric acid or borate ester. Appropriate reactions for forming C—C linkage are well known in the art and described in literatures, particularly appropriate and preferred coupling reactions are, for example, the SUZUKI, STILLE and HECK coupling reactions.

The above organic functional compound has at least the following advantages:

The above organic functional compound contains an organic functional structural unit and a solubilizing group, and has good solubility and film forming properties. At the same time, a larger conjugated group can be formed in molecule of the organic functional compound through the reaction as needed to deteriorate the solubility of the molecule, so that it has a property of being capable of undergoing controlled irreversible solubility reduction as needed, thereby avoiding problems such as interfacial miscibility and interface corrosion.

The mixture of one embodiment comprises the organic functional compound represented by the above general formula (I) and an organic functional material.

The organic functional material is at least one selected from the group consisting of a hole (also called electron hole) injection material (HIM), a hole transport material (HTM), a hole blocking material (HBM), an electron injection material (EIM), an electron transport material (ETM), an electron blocking material (EBM), an organic matrix material (Host), a light emitting material, and an organic dye. Wherein, the light emitting material is selected from a singlet emitter (fluorescent emitter), a triplet emitter (phosphorescent emitter) and a thermally activated delayed fluorescent material (TADF material). These organic functional materials have been described above. Specifically, the organic functional materials may be those disclosed in WO2010135519A1, US20090134784A1 and WO2011110277A1.

In one of the embodiments, the organic functional material is a fluorescent emitter (a singlet emitter), in which case the organic functional compound represented by the general formula (I) is used as a host or a co-host, and in the mixture, the weight percentage of the organic functional material is equal to or less than 15 wt %; further, the weight percentage of the organic functional material is equal to or less than 12 wt %; the weight percentage of the organic functional material is equal to or less than 9 wt %; the weight percentage of the organic functional material is equal to or less than 8 wt %; the weight percentage of the organic functional material is equal to or less than 7 wt %.

In another embodiment, the organic functional material is a TADF material.

In another embodiment, the organic functional material is a phosphorescent emitter (a triplet emitter), in which case the organic functional compound represented by the general formula (I) is used as a host or a co-host, and in the mixture, the weight percentage of the organic functional material is equal to or less than 30 wt %; further, the weight percentage of the organic functional material is equal to or less than 25 wt %; further, the weight percentage of the organic functional material is equal to or less than 20 wt %; further, the weight percentage of the organic functional material is equal to or less than 18 wt %.

In another embodiment, the organic functional material is a HTM material.

The formulation of an embodiment is a mixture containing solvent, and can be used as a coating or ink and can be applied in an organic electronic device as the material of functional layer. The organic electronic devices may be selected from the group consisting of an organic light emitting diode (OLED), an organic photovoltaic cell (OPV), an organic light emitting electrochemical cell (OLEEC), an organic field effect transistor (OFET), an organic light emitting field effect transistor, an organic laser, an organic spintronic device, an organic sensor and an organic plasmon emitting diode. The mixture may be a solution or a suspension.

The formulation includes one of the organic functional compound and the mixture, and an organic solvent. Wherein, the organic functional compound is an organic functional compound represented by the above general formula (1), and the mixture is the above mixture.

In the present embodiment, the molar mass of the organic functional compound is ≥700 g/mol, further, the molar mass of the organic functional compound is ≥800 g/mol; the molar mass of the organic functional compound is ≥900 g/mol; further, the molar mass of the organic functional compound is ≥1000 g/mol; further, the molar mass of the organic functional compound is ≥1100 g/mol.

Further, at 25° C., the solubility of the organic functional compound in toluene is equal to or greater than 10 mg/ml; further, the solubility of the organic functional compound in toluene is equal to or greater than 15 mg/ml; further, the solubility of the organic functional compound in toluene is equal to or greater than 20 mg/ml.

Since the mixture of the present embodiment is used as a printing material, the viscosity and surface tension of the formulation are important parameters. Only formulations with appropriate parameters can be suitable for specific substrates and specific printing methods.

Specifically, at the operating temperature or at 25° C., the formulation has a surface tension of about 19 dyne/cm to 50 dyne/cm; further, the formulation has a surface tension of 22 dyne/cm to 35 dyne/cm; further, the formulation has a surface tension of 25 dyne/cm to 33 dyne/cm.

Specifically, at the operating temperature or at 25° C., the formulation has a viscosity in a range from about 1 cps to 100 cps; further, the formulation has a viscosity in a range from 1 cps to 50 cps; further, the formulation has a viscosity in a range from 1.5 cps to 20 cps; further, the formulation has a viscosity in a range from 4.0 cps to 20 cps. In this case, the formulation can be used for inkjet printing.

Wherein, the viscosity of the formulation can be adjusted by various methods, such as by selecting a suitable concentration of the solvent, the organic functional compound or the mixture. Printing is carried out in accordance with a usual printing method by adjusting the viscosity of mixtures containing an organic functional compound or a mixture.

Specifically, in the formulation, the weight percentage of the organic functional compound or mixture is from 0.3% to 30%; further, the weight percentage of the organic functional compound or mixture is from 0.5% to 20%; further, the weight percentage of the organic functional compound or mixture is from 0.5% to 1%; further, the weight percentage of the organic functional compound or mixture is from 0.5% to 10%, further, the weight percentage of the organic functional compound or mixture is from 1% to 5%.

Specifically, the organic solvent includes a first solvent. The first solvent is at least one selected from the group consisting of an aromatic solvent, a heteroaromatic solvent, a ketone solvent, an ether solvent, and an ester solvent.

Further, the aromatic solvent is at least one selected from a chain aliphatic substituted aromatic, compound and a cyclic aliphatic substituted aromatic compound.

Specifically, the aromatic solvent and the heteroaromatic solvent are selected from the group consisting of p-diisopropylbenzene, pentyl benzene, tetrahydronaphthalene, cyclohexylbenzene, chloronaphthalene, 1,4-dimethylnaphthalene, 3-isopropylbiphenyl, p-methylisopropylbenzene, dipentylbenzene, tripentylbenzene, pentyltoluene, o-xylene, m-xylene, p-xylene, o-diethylbenzene, m-diethylbenzene, p-diethylbenzene, 1,2,3,4-tetramethylbenzene, 1,2,3,5-tetramethylbenzene, 1,2,4,5-tetramethylbenzene, butylbenzene, dodecylbenzene, dihexylbenzene, dibutylbenzene, p-diisopropylbenzene, 1-methoxynaphthalene, cyclohexylbenzene, dimethylnaphthalene, 3-isopropylbiphenyl, p-methylisopropylbenzene, 1-methylnaphthalene, 1,2,4-trichlorobenzene, 1,3-dipropoxybenzene, 4,4-difluorodiphenylmethane, 1,2-dimethoxy-4-(1-propenyl)benzene, diphenylmethane, 2-phenylpyridine, 3-phenylpyridine, N-methyldiphenylamine, 4-isopropylbiphenyl, α,α-dichlorodiphenylmethane, 4-(3-phenylpropyl)pyridine, benzyl benzoate, 1,1-bis(3,4-dimethylphenyl)ethane, 2-isopropylnaphthalene and dibenzyl ether.

Specifically, the ketone solvent is at least one selected from the group consisting of 1-tetralone, 2-tetralone, 2-(phenylepoxy)tetralone, 6-(methoxy)tetral one, acetophenone, phenylacetone, benzophenone, derivatives of 1-tetralone, derivatives of 2-tetralone, derivatives of 2-(phenylepoxy)tetralone, derivatives of 6-(methoxyl)tetralone, derivatives of acetophenone, derivatives of phenylacetone, and derivatives of benzophenone. Derivatives of 1-tetralone, derivatives of 2-tetralone, derivatives of 2-(phenylepoxy)tetralone, derivatives of 6-(methoxyl)tetralone, derivatives of acetophenone, derivatives of phenylacetone, and derivatives of benzophenone may be 4-methylacetophenone, 3-methylacetophenone, 2-methylacetophenone, 4-methylphenylacetone, 3-methylphenylacetone, 2-methylphenylacetone, isophorone, 2,6,8-trimethyl-4-nonanone, fenchone, 2-nonanone, 3-nanone, 5-nonanone, 2-decanone, 2,5-hexanedione, phorone, 6-undecanone, and the like.

Specifically, the ether solvent is at least one selected from the group consisting of 3-phenoxytoluene, butoxybenzene, benzylbutylbenzene, p-anisaldehyde dimethyl acetal, tetrahydro-2-phenoxy-2H-pyran, 1,2-dimethoxy-4-(1-propenyl) benzene, 1,4-benzodioxane, 1,3-dipropylbenzene, 2,5-dimethoxytoluene, 4-ethylphenetole, 1,2,4-trimethoxybenzene, 4-(1-propenyl)-1,2-dimethoxybenzene, 1,3-dimethoxybenzene, glycidyl phenyl ether, dibenzyl ether, 4-tert-butylanisole, trans-p-propenylanisole, 1,2-dimethoxybenzene, 1-methoxynaphthalene, diphenyl ether, 2-phenoxymethyl ether, 2-phenoxytetrahydrofuran, ethyl-2-naphthyl ether, pentyl ether, hexyl ether, dicaprylyl ether, ethylene glycol dibutyl ether, diethylene glycol diethyl ether, diethylene glycol butyl methyl ether, diethylene glycol dibutyl ether, triethylene glycol dimethyl ether, triethylene glycol ethyl methyl ether, triethyl ether butyl methyl ether, tripropylene glycol dimethyl ether, and tetraethylene glycol dimethyl ether.

Specifically, the ester solvent is at least one selected from the group consisting of alkyl octoate, alkyl sebacate, alkyl stearate, alkyl benzoate, alkyl phenylacetate, alkyl cinnamate, alkyl oxalate, alkyl maleate, alkyl lactone and alkyl oleate.

Further, the first solvent is at least one selected from an aliphatic ketone and an aliphatic ether. Specifically, the aliphatic ketone is at least one selected from the group consisting of 2-nonanone, 3-nonanone, 5-nonanone, 2-decanone, 2,5-hexanedione, 2,6,8-dimethyl-4-nonanone, phorone and 6-undecanone. The aliphatic ether is at least one selected from the group consisting of amyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethylene glycol ethyl methyl ether, triethylene glycol butyl methyl ether, tripropylene glycol dimethyl ether and tetraethylene glycol dimethyl ether.

Further, the organic solvent comprises a second solvent. The second solvent is at least one selected from the group consisting of methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methyl ethyl ketone, 1,2-dichloroethane, 3-phenoxy toluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, decalin and indene.

The mixture of the present embodiment can be used to prepare an organic electronic device by a printing or coating method.

The printing method may be inkjet printing or nozzle printing. The coating method may be typography, screen printing, dip coating, spin coating, blade coating, roller printing, twist roller printing, lithography, flexography, rotary printing, spray coating, brush coating or pad printing, slot die coating, etc. Further, the coating method is gravure printing, and the printing method is nozzle printing or inkjet printing.

Further, the formulation ay further include at least one of a surfactant, a lubricant, a wetting agent, a dispersant, a hydrophobic agent and a binder for adjusting the viscosity, film forming performance of the formulation and improving its adhesion. The printing technology, solvent, concentration and viscosity of the formulation may be adjusted according to Handbook of Print Media: Technologies and Production Methods, Helmut Kipphan, ISBN 3-540-67326-1.

The above formulation has at least the following advantages:

The above formulations have good printability and film forming property, and facilitate the realization of high-performance small-molecule organic electronic device, especially organic light emitting device, by solution processing, especially printing processes, thereby providing a low-cost, high-efficiency technology solution for preparation.

According to an embodiment, an organic functional film is prepared from one of the organic functional compound represented by the above formula (I), the mixture and the formulation. The organic functional film can be used in an organic electronic device.

According to an embodiment, a method for preparing an organic functional film includes at least the following steps:

Step S1: providing an ink.

The ink is the above formulation, or the ink is obtained by dissolving one of the organic functional compound of the above formula (I) and the above organic mixture in an organic solvent.

Step S2: forming a film layer on the substrate using the ink.

Specifically, the ink is applied to a substrate by a printing or coating method to form a film layer.

Wherein, the printing method may be inkjet printing or nozzle printing. The coating method may be typography, screen printing, dip coating, spin coating, blade coating, roller printing, twist roller printing, lithography, flexography, rotary printing, spray coating, brush coating or pad printing, slot die coating, etc.

Step S3: Subjecting the film layer to a Bergman cycloaromatization reaction at a temperature of 100° C. or higher under anhydrous and anaerobic conditions to obtain an organic functional film. Further, the film layer was treated for 2 hours at 190° C. in an environment of isolating water and oxygen for Bergman cycloaromatization reaction.

In some embodiments, the thickness of the resulting organic functional film (i.e., after the film layer is subjected to Bergman cycloaromatization reaction) is at least 50% of the thickness of the film layer, further, at least 60% of the thickness of the film layer; further, at least 70% of the thickness of the film layer; further, at least 85% of the thickness of the film layer.

The above organic functional film can be applied in an organic electronic device selected from an organic light emitting diode (OLED), an organic photovoltaic cell (OPV), an organic light emitting electrochemical cell (OLEEC), an organic field effect transistor (OFET), an organic light emitting field effect transistor, an organic laser, an organic spintronic device, organic sensor and an organic plasmon emitting diode. Further, the organic functional film is used in a hole transport layer, a hole injection layer or a light emitting layer of an OLED device; further, the organic functional film is used for a hole transport layer of an OLED device.

An organic electronic device according to an embodiment includes a functional layer, the material of which is the above organic functional film. Generally, the organic electronic device includes at least one cathode, one anode, and a functional layer is located between the cathode and the anode.

The organic electronic devices may be selected from the group consisting of an organic light emitting diode (OLED), an organic photovoltaic cell (OPV), an organic light emitting electrochemical cell (OLEEC), an organic field effect transistor (OFET), an organic light emitting field effect transistor, an organic laser, an organic spintronic device, an organic sensor and an organic plasmon emitting diode.

As shown in FIG. 1, the structure shown in FIG. 1 is an organic light emitting diode 100. The organic electronic device 100 includes a substrate 101, an anode 102, at least one light emitting layer 104, and a cathode 106.

Specifically, the substrate 101 may be opaque or transparent. A transparent substrate can be used to fabricate a transparent light emitting device. For example, the transparent substrate 101 may be disclosed in a document [Bulovic et al. *Nature* 1996, 380, p 29] and another document [Gu et al. *Appl. Phys. Lett.* 68, 68, p 2606]. The substrate 101 may be a rigid substrate 101 or an elastic substrate 101.

Specifically, the substrate 101 may be plastic, metal, semiconductor wafer or glass. Further, the substrate 101 has a smooth surface. A substrate 101 with no surface defects is an ideal option.

Further, the substrate 101 is flexible. The substrate 101 is a polymer thin film or a plastic; the substrate 101 has a glass transition temperature Tg of 150° C. or more, further larger than 200° C., further larger than 250° C., and further larger than 300° C. Specifically, the substrate 101 is selected from the group consisting of poly(ethylene terephthalate) (PET) and polyethylene(2,6-naphthalate) (PEN).

The material of the anode 102 comprises one of a conductive metal, a metallic oxide and a conductive polymer. The anode 102 can inject holes easily into the light emitting layer, hole injection layer, or the hole transport layer.

Specifically, the absolute value of the difference between the work function of the anode 102 and the HOMO energy level or the valence band energy level of the organic functional material (light emitting material) in the light emitting layer, p-type semiconductor material in the hole injection layer, p-type semiconductor material in the hole transport layer or p-type semiconductor material in the electron blocking layer is less than 0.5 eV, further less than 0.3 eV, and still further less than 0.2 eV.

Specifically, the material of the anode 102 is selected from the group consisting of Al, Cu, Au, Ag, Mg, Fe, Co, Ni, Mn, Pd, Pt, ITO and aluminum-doped zinc oxide (AZO). The material of the anode 102 may be prepared by physical vapor deposition. The physical vapor deposition specifically refers to radio frequency magnetron sputtering, vacuum thermal evaporation, electron beam (e-beam) evaporation, and the like.

It should be noted that the material of the anode 102 is not limited to the above materials and may also be patterned ITO.

The material of the light emitting layer 104 is the above-described organic functional film.

The material of the cathode 106 is selected from a conductive metal and a metal oxide. The material of the cathode 106 can inject electrons easily into the electron injection layer, the electron transport layer, or the light emitting layer.

Further, the absolute value of the difference between the work function of the cathode 106 and the HUMO energy level or the valence band energy level of the organic functional material (light emitting material) in the light emitting layer 104, n-type semiconductor material in the electron injection layer, n-type semiconductor material in the electron transport layer or n-type semiconductor material in the hole blocking layer is less than 0.5 eV, further less than 0.3 eV, and still further less than 0.2 eV. In principle, all materials that can be used as a cathode 106 for OLED are possibly used as the material of the cathode 106 of the present embodiment.

Further, the material of the cathode 106 is selected from the group consisting of Al, Au, Ag, Ca, Ba, Mg, LiF/Al, MgAg alloy, $BaF_2$/Al, Cu, Fe, Co, Ni, Mn, Pd, Pt and ITO. The material of the cathode 106 may be prepared by physical vapor deposition. Wherein, the physical vapor deposition specifically refers to radio frequency magnetron sputtering, vacuum thermal evaporation, electron beam (e-beam) evaporation, and the like.

Further, the organic light emitting diode 100 further includes other functional layers such as a hole injection layer (HIL), a hole transport layer (HTL), an electron blocking layer (EBL), an electron injection layer (EIL), and an electron transport layer (EFL). And at least one of a hole blocking layer (HBL). Suitable materials for use in these functional layers may be the materials disclosed in WO2010135519A1, US20090134784A1 and WO02011110277A1.

Specifically in the illustrated embodiment, the organic light emitting diode 100 further includes a hole injection layer or a hole transport layer 103. The material of the hole injection layer or the hole transport layer 103 is the above-described organic functional film.

Further, the organic light emitting diode 100 further includes an electron injection layer or an electron transport layer 105.

The organic light emitting diode 100 according to the present embodiment has an emission wavelength between 300 and 1000 nm, further between 350 and 900 nm, and further between 400 and 800 nm.

The above organic electronic device can be applied to various electronic devices, such as display equipments, lighting equipments, light sources or sensors.

The following are examples.

Example 1

The synthesis of the organic functional material of this embodiment is as follows:

13.6 g (0.018 mol) of intermediate a and 9.51 g (0.018 mol) of intermediate b are successively dissolved into 300 ml of toluene at room temperature, and then 1.2 g of tetrakis(triphenylphosphine)palladium, 10 g of potassium carbonate (0.74 mol), 60 ml of water, 60 ml of ethanol was successively added and heated to 110° C. to react for 15 hours. TLC plate showed that the reaction was completed. The reaction liquid was added to water and extracted three times with dichloromethane. The organic phase was then dried and concentrated to give a crude product. 12.6 g of solid compound 1 with a yield of 65% was obtained through a chromatography column.

The synthetic route is as follows:

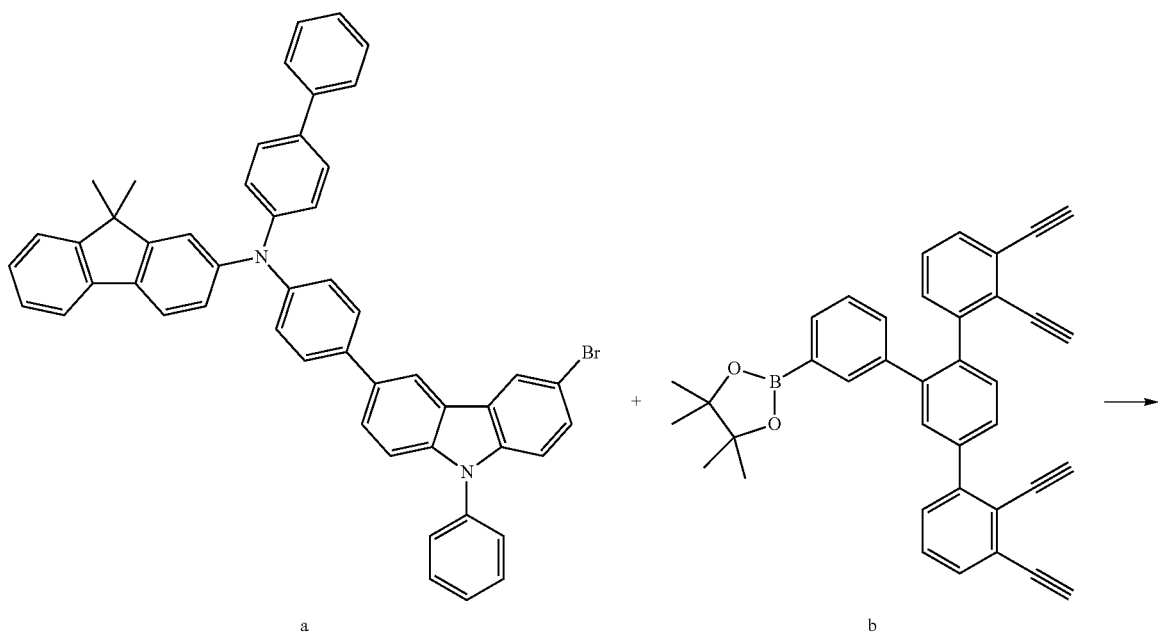

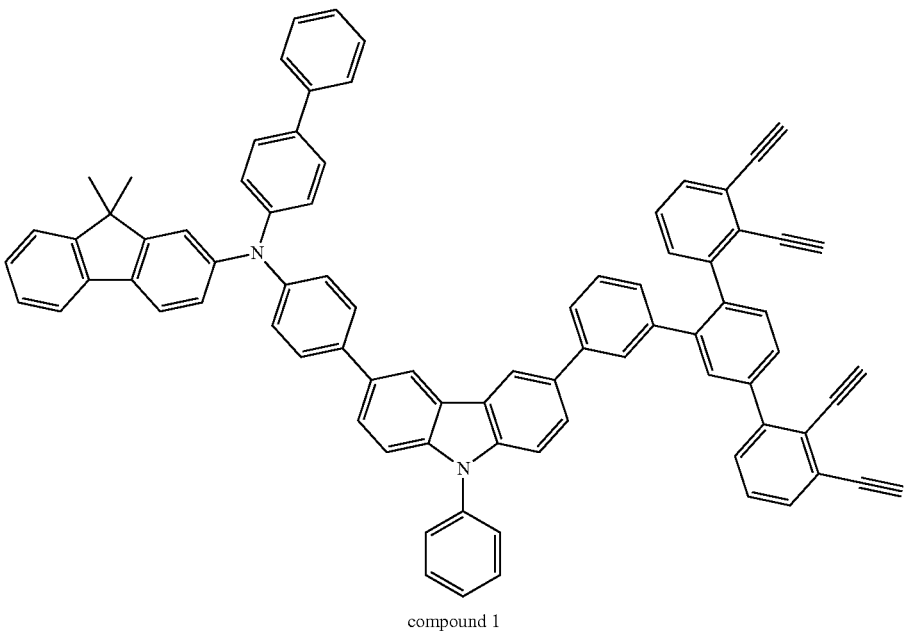

compound 1

Example 2

The synthesis of the organic functional material of this embodiment is as follows:

13.6 g (0.018 mol) of intermediate a and 13.6 g (0.018 mol) of intermediate b were successively dissolved into 300 ml of toluene at room temperature. And then 1.2 g of tetrakis(triphenylphosphine)palladium, 9.7 g (0.074 mol) of potassium carbonate, 60 ml of water, 60 ml of ethanol were added successively and heated to 110° C. to react for 15 hours. TLC plate showed that the reaction was completed. The reaction liquid was added to water and extracted three times with dichloromethane. The organic phase was then dried and concentrated to give a crude product 15.3 g of solid compound 2 with a yield of 65% was obtained through a chromatography column.

The synthetic route is as follows:

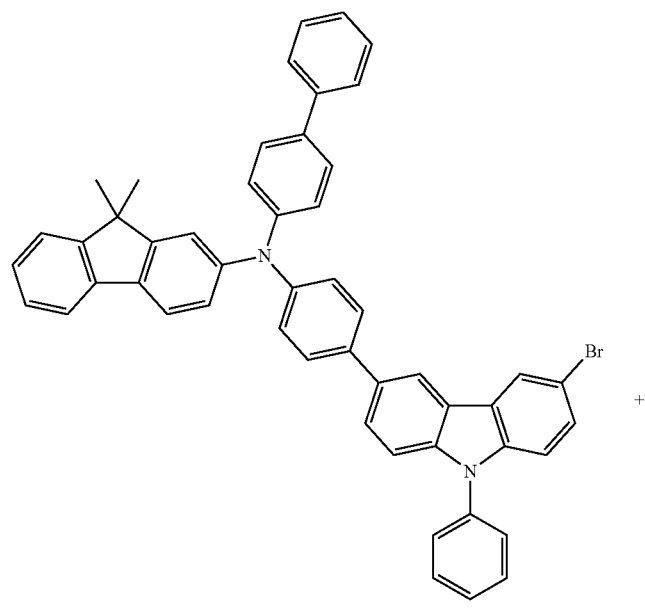

a

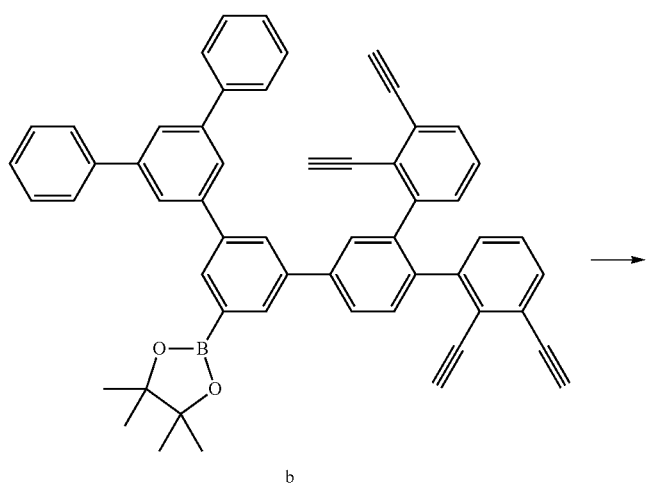

b

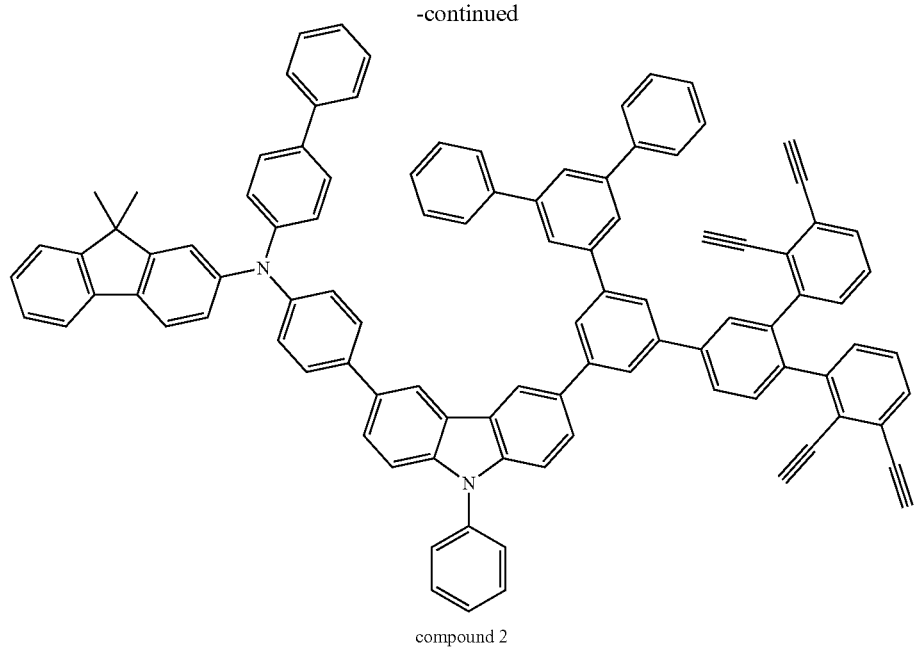

compound 2

Example 3

The synthesis of the organic functional material of this embodiment is as follows:

10.54 g (0.018 mol) of intermediate a and 8.14 g (0.018 mol) of intermediate b were successively dissolved into 300 ml of toluene at room temperature. And then 1.2 g of tetrakis(triphenylphosphine)palladium, 9.7 g (0.074 mol) of potassium carbonate, 60 ml of water, 60 ml of ethanol were added successively and heated to 110° C. to react for 15 hours. TLC plate showed that the reaction was completed. The reaction liquid was added to water and extracted three times with dichloromethane. The organic phase was then dried and concentrated to give a crude product. 8.98 g of solid compound 3 with a yield of 60% was obtained through a chromatography column.

The synthetic route is as follows:

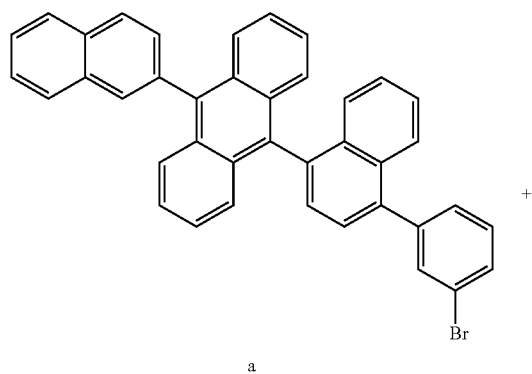

a

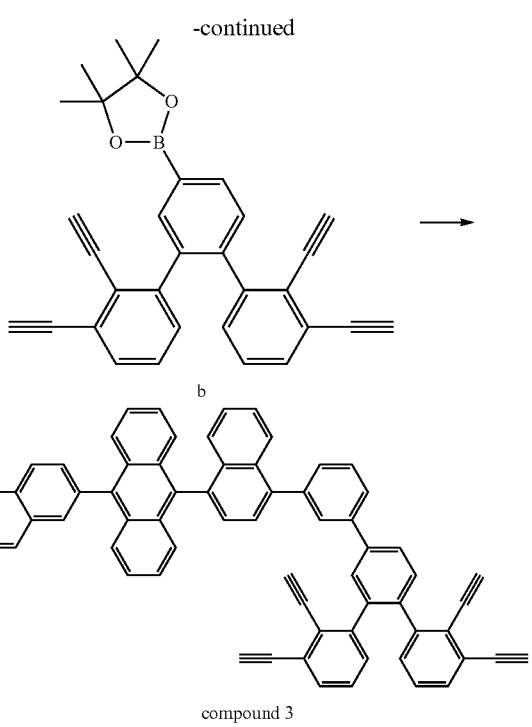

b compound 3

Example 4

The synthesis of the organic functional material of this embodiment is as follows:

10.54 g (0.018 mol) of intermediate a and 8.14 g (0.018 mol) of intermediate b were successively dissolved into 300 ml of toluene at room temperature. And then 1.2 g of tetrakis(triphenylphosphine)palladium, 9.7 g (0.074 mol) of potassium carbonate, 60 ml of water, 60 ml of ethanol were added successively and heated to 110° C. to react for 15 hours, TLC plate showed that the reaction was completed. The reaction liquid was added to water and extracted three times with dichloromethane. The organic phase was then dried and concentrated to give a crude product. 8.98 g of solid compound 4 with a yield of 60% was obtained through a chromatography column.

The synthetic route is as follows:

The reaction liquid was added to water and extracted three times with dichloromethane. The organic phase was then dried and concentrated to give a crude product. 9.79 g of solid compound 5 with a yield of 60% was obtained through a chromatography column.

The synthetic route is as follows:

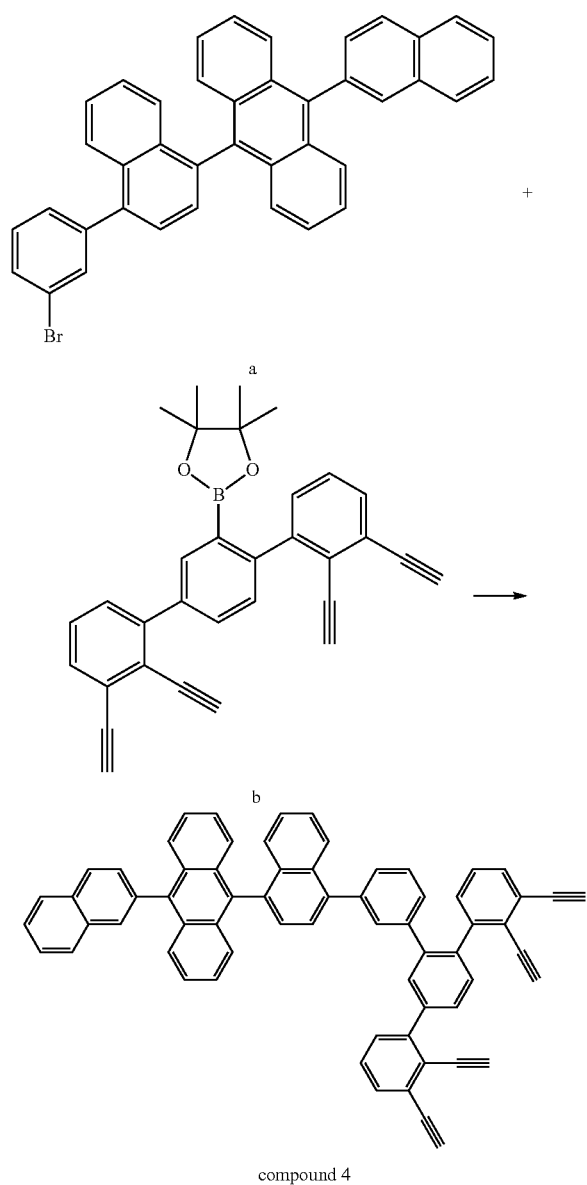

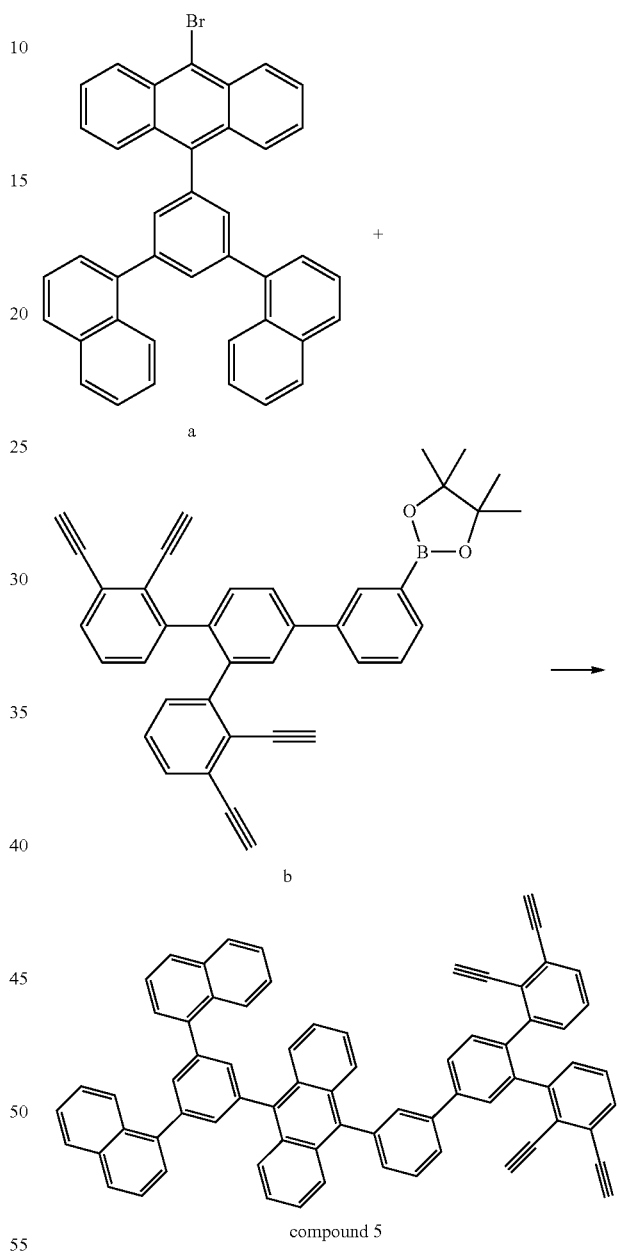

Example 5

The synthesis of the organic functional material of this embodiment is as follows:

10.54 g (0.018 mol) of intermediate a and 9.51 g (0.018 mol) of intermediate b were successively dissolved into 300 ml of toluene at room temperature. And then 1.2 g of tetrakis(triphenylphosphine)palladium, 9.7 g (0.074 mol) of potassium carbonate, 60 ml of water, 60 ml of ethanol were added successively and heated to 110° C. to react for 15 hours. TLC plate showed that the reaction was completed.

Examples 6 to 10

The preparation process of the organic functional films of Examples 6 to 10 was as follows:

(1) cleaning of glass substrate: ultrasonic treatment was conducted for 30 minutes using aqueous solution of 5% Decon90 cleaning solution, followed by ultrasonic cleaning with deionized water, then ultrasonic cleaning with isopropanol and blowing dry with nitrogen; the treatment under oxygen plasma was for 5 minutes;

(2) the organic functional compounds of Examples 1 to 5 were respectively dissolved in toluene at a concentration of 20 mg/mL, and the solution was spin-coated on a glass substrate in a nitrogen glove box to obtain a 60 nm film; the organic functional compound in Example 1 was used in Example 6; the organic functional compound in Example 2 was used in Example 7; the organic functional compound in Example 3 was used in Example 8; the organic functional compound in Example 4 was used in Example 9; the organic functional compound in Example 5 was used in Example 10;

(3) then annealing was carried out at 190° C. for 10 minutes to obtain the organic functional films of Examples 6 to 10, the thickness and surface roughness of which were measured;

(4) on the thin film toluene was added dropwise, drying, again measured in Example 6 to Example 10 thickness and surface roughness of the organic functional films.

The tests have shown that the thicknesses and surface roughness values of the organic functional films of Examples 6 to 10 are substantially unchanged, that is, the values of the thickness and the surface roughness of the organic functional films of Examples 6 to 10 before and after the dropwise addition of toluene in the step (4) were substantially unchanged, indicating that the organic functional compound produced in Examples 1 to 5 has a very low solubility in toluene after conversion.

The technical features of the above-described embodiments may be combined arbitrarily. To simplify the description, all the possible combinations of the technical features in the above embodiments are not described. However, all of the combinations of these technical features should be considered as within the scope of the present disclosure, as long as such combinations do not contradict with each other.

The above-described embodiments merely represent several embodiments of the present disclosure, and the description thereof is more specific and detailed, but it should not be construed as limiting the scope of the present disclosure. It should be noted that, for those skilled in the art, several variations and improvements may be made without departing from the concept of the present disclosure, and these are all within the protection scope of the present disclosure.

The invention claimed is:

1. An organic functional compound represented by a general formula below:
wherein,
A comprises one of structural formulas of

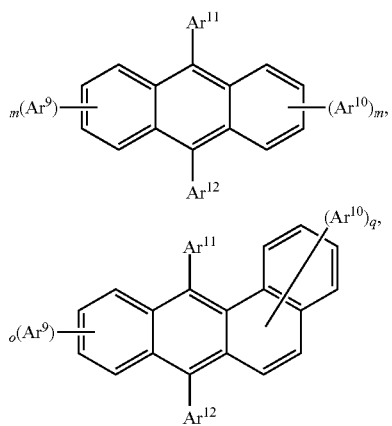

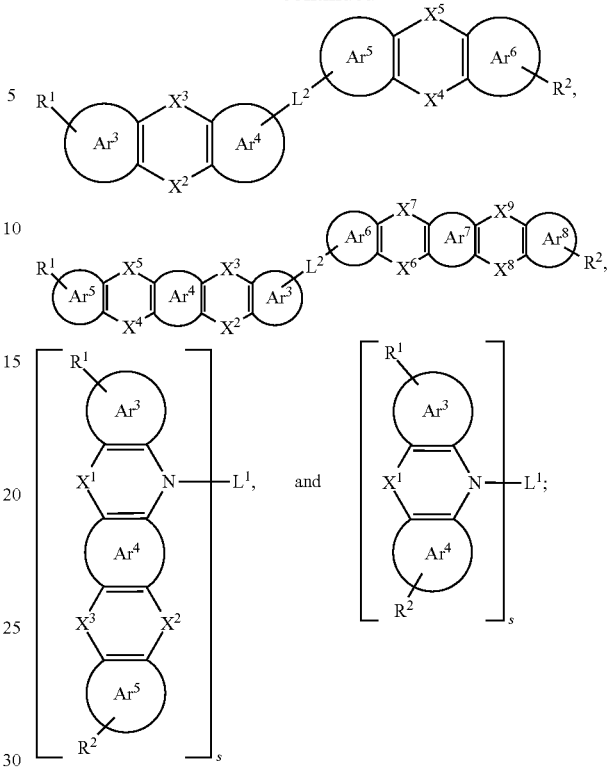

wherein, $Ar^{11}$ and $Ar^{12}$ are each independently selected from the group consisting of an aromatic group containing 6 to 60 carbon atoms, and an heteroaryl group containing 3 to 60 carbon atoms;

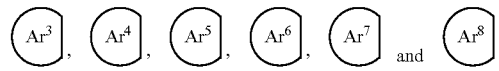

are each independently selected from the group consisting of an aromatic group containing 5 to 30 ring atoms, and an heteroaryl group containing 5 to 30 ring atoms;

$Ar^9$ and $Ar^{10}$ are each independently selected from the group consisting of H, D, F, CN, $NO_2$, $CF_3$, alkenyl, alkynyl, amine, acyl, amide, cyano, isocyano, alkoxy, hydroxy, carbonyl, sulfone, an alkyl group containing 1 to 60 carbon atoms, an aromatic group containing 6 to 60 carbon atoms, and a heterocyclic aryl group containing 3 to 60 carbon atoms;

$L^1$ is selected from an aromatic group containing 5 to 60 ring atoms and an heteroaryl group containing 5 to 60 ring atoms;

-$L^2$- is a single bond, or $L^2$ is selected from the group consisting of an aromatic group containing 5 to 30 ring atoms and an heteroaryl group containing 5 to 30 ring atoms;

—$X^1$— is a single bond, or $X^1$ is selected from the group consisting of N(R), C(R)$_2$, Si(R)$_2$, O, C=N(R), C=C(R)$_2$, P(R), P(=O)R, S, S=O and SO$_2$;

—$X^2$—, —$X^3$—, —$X^4$—, —$X^5$—, —$X^6$—, —$X^7$—, —$X^8$—, —$X^9$— are each independently selected from the group consisting of a single bond, —N(R)—, —C(R)$_2$—, —Si(R)$_2$—, —O—, —(C=N(R))—, —(C=C(R)$_2$), —P(R)—, —(P(=O)R)—, —S—, —(S=O)— and —(SO$_2$)—, and at most one of —X$^2$— and —X$^3$— is a single bond, at most one of —X$^4$— and —X$^5$— is a single bond, at most one of —X$^6$— and —X$^7$— is a single bond, and at most one of —X$^8$— and —X$^9$— is a single bond;

and, in the structural formula contained in the A, the number of carbon atoms on the ring attached to R$^1$, R$^2$ is at least one;

R is independently selected from the group consisting of H, D, F, CN, alkenyl, alkynyl, nitrile, amine, nitro, acyl, alkoxy, carbonyl, sulfone, an alkyl containing 1 to 30 carbon atoms, an aromatic hydrocarbon group containing 5 to 60 ring atoms, and an aromatic heterocyclic group containing 5 to 60 ring atoms;

R$^1$ and R$^2$ are each independently selected from the group consisting of H, D, F, CN, an alkyl group, an aromatic ring group, an aromatic heterocyclic group, an amino group, a silicon group, a germyl group, an alkoxy group, an aryloxy group, and a siloxy group; the alkyl group is selected from the group consisting of an unsubstituted alkyl group, an unsubstituted fluoroalkyl group, a deuterated alkyl group, and a deuterated fluoroalkyl group; the aromatic ring group is selected from the group consisting of an unsubstituted aromatic ring group and a deuterated aromatic ring group; the aromatic heterocyclic group is selected from the group consisting of an unsubstituted aromatic heterocyclic group and a deuterated aromatic heterocyclic group; the amino group is selected from the group consisting of an unsubstituted amino group and a deuterated amino group; the silicon group is selected from the group consisting of an unsubstituted silicon group and a deuterated silicon group; the germyl group is selected from the group consisting of an unsubstituted germyl group and a deuterated germyl group; the alkoxy group is selected from the group consisting of an unsubstituted alkoxy group, an unsubstituted silylalkoxy group, an unsubstituted fluoroalkoxy group, a deuterated alkoxy group, a deuterated fluoroalkoxy group, and a deuterated silylalkoxy group; the aryloxy group is selected from the group consisting of an unsubstituted aryloxy group and a deuterated aryloxy group; the siloxy group is selected from the group consisting of an unsubstituted siloxy group and a deuterated siloxy group;

m is any of integers from 0 to 4, o is any of integers from 0 to 4, q is any of integers from 0 to 6, and s is any of integers from 1 to 4;

—SG is selected from the group consisting of structural formulas as follows:

SG-01

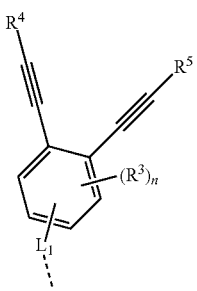

SG-02

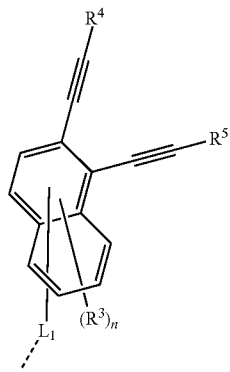

SG-03

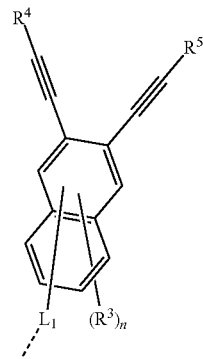

SG-04

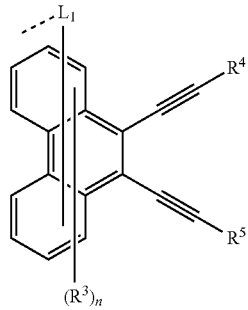

SG-05

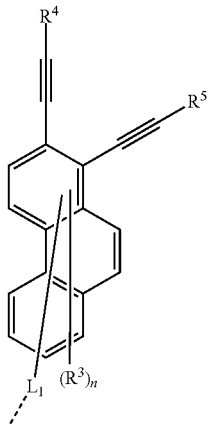

-continued
SG-06
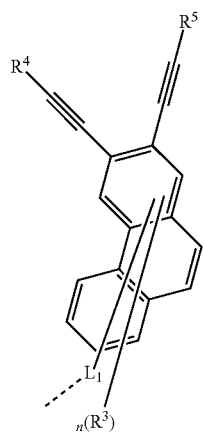
SG-07
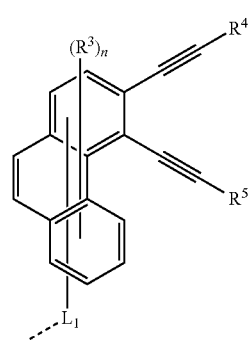
SG-08
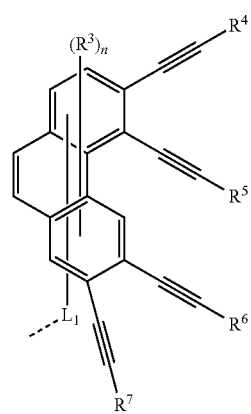
SG-09
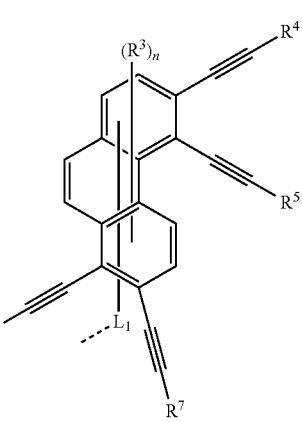
-continued
SG-10
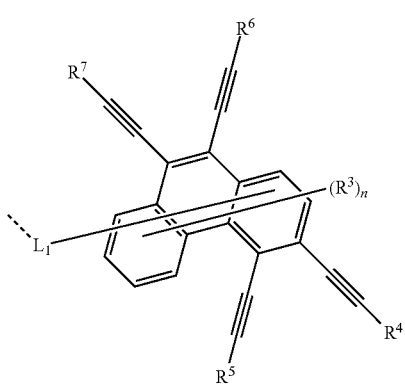
SG-11
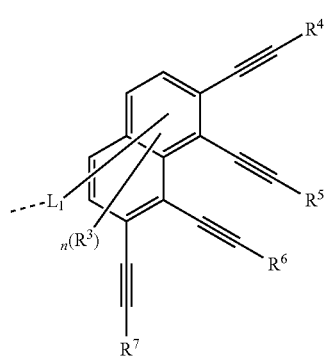
SG-12
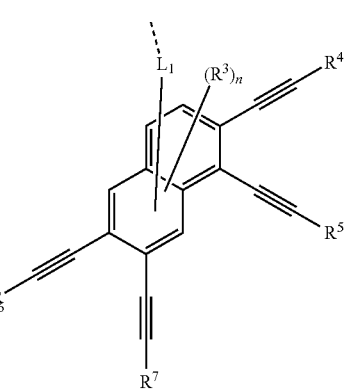
SG-13
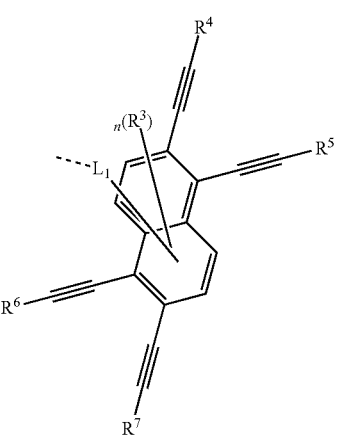

SG-14
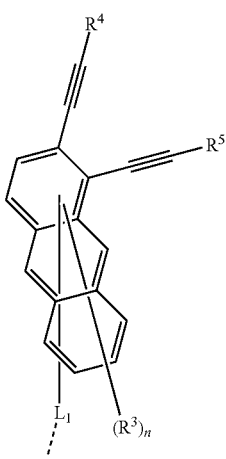
SG-15
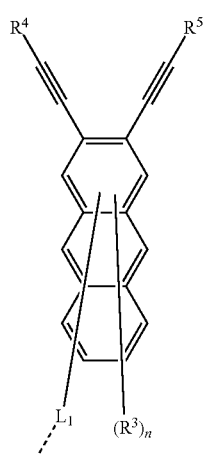
SG-16
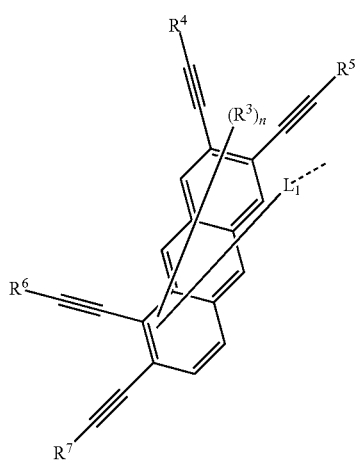
SG-17
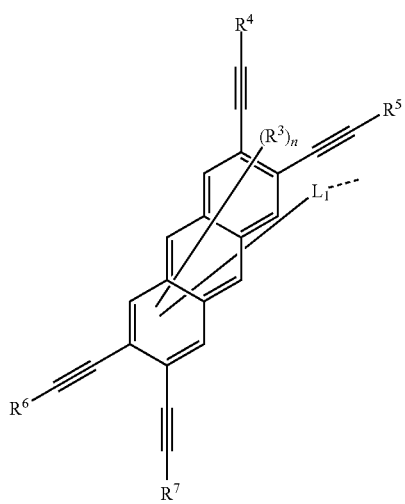
SG-18
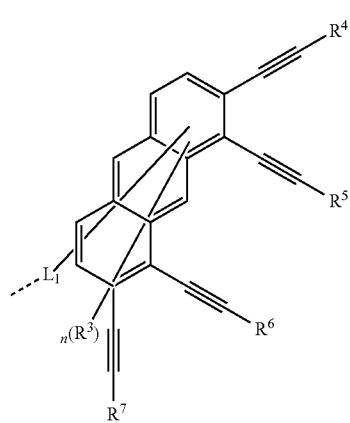
SG-19
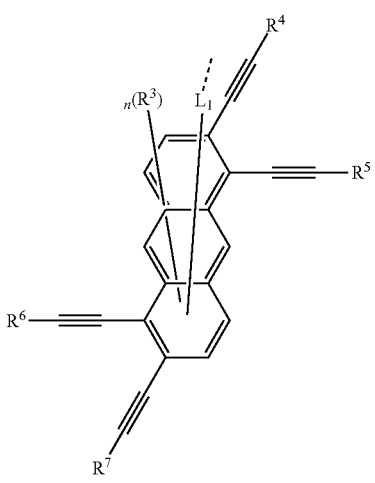

-continued

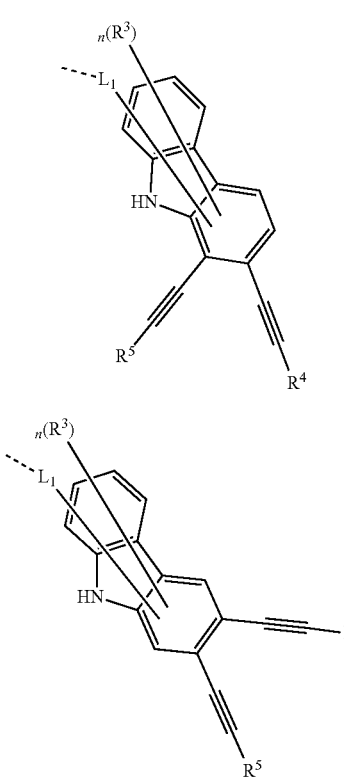

SG-20

SG-21 wherein $R^3$, $R^4$, $R^5$, $R^6$ and $R^7$ are each independently selected from the group consisting of H, D, F, CN, an alkyl group, an aromatic ring group, an aromatic heterocyclic group, an amino group, a silicon group, a germyl group, an alkoxy group, an aryloxy group, and a siloxy group; the alkyl group is selected from the group consisting of an unsubstituted alkyl group, an unsubstituted fluoroalkyl group, a deuterated alkyl group, and a deuterated fluoroalkyl group; the aromatic ring group is selected from the group consisting of an unsubstituted aromatic ring group and a deuterated aromatic ring group; the aromatic heterocyclic group is selected from the group consisting of an unsubstituted aromatic heterocyclic group and a deuterated aromatic heterocyclic group; the amino group is selected from the group consisting of an unsubstituted amino group and a deuterated amino group; the silicon group is selected from the group consisting of an unsubstituted silicon group and a deuterated silicon group; the germyl group is selected from the group consisting of an unsubstituted germyl group and a deuterated germyl group; the alkoxy group is selected from the group consisting of an unsubstituted alkoxy group, an unsubstituted silylalkoxy group, an unsubstituted fluoroalkoxy group, a deuterated alkoxy group, a deuterated fluoroalkoxy group, and a deuterated silylalkoxy group; the aryloxy group is selected from the group consisting of an unsubstituted aryloxy group and a deuterated aryloxy group; the siloxy group is selected from the group consisting of an unsubstituted siloxy group and a deuterated siloxy group;

n is an integer greater than 0;

-$L_1$- is a single bond, or $L_1$ is selected from the group consisting of an aryl group and a heteroaryl group;

p is an integer greater than or equal to 1.

2. The organic functional compound according to claim 1, wherein the A is selected from one of the following structural formulas:

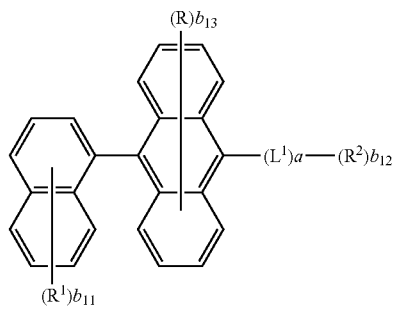
(1-1)

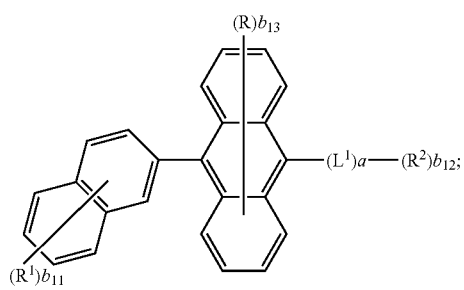
(1-2)

wherein a is any integer of 1 to 3; $b_{11}$ to $b_{13}$ are each independently selected from any integer of 0 to 6.

3. The organic functional compound according to claim 1, wherein the A is selected from one of the following structural formulas:

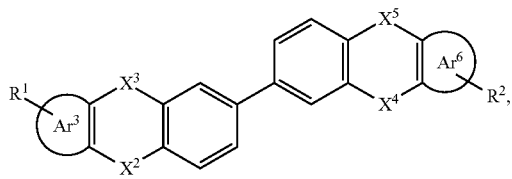

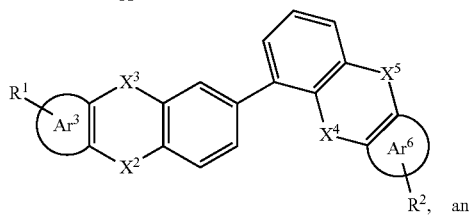
and

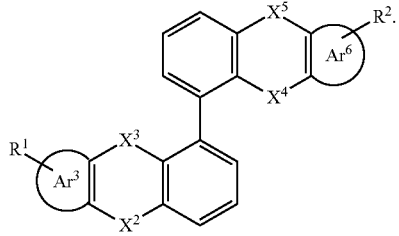

4. The organic functional compound according to claim 1, wherein the A is selected from one of the following structural formulas:

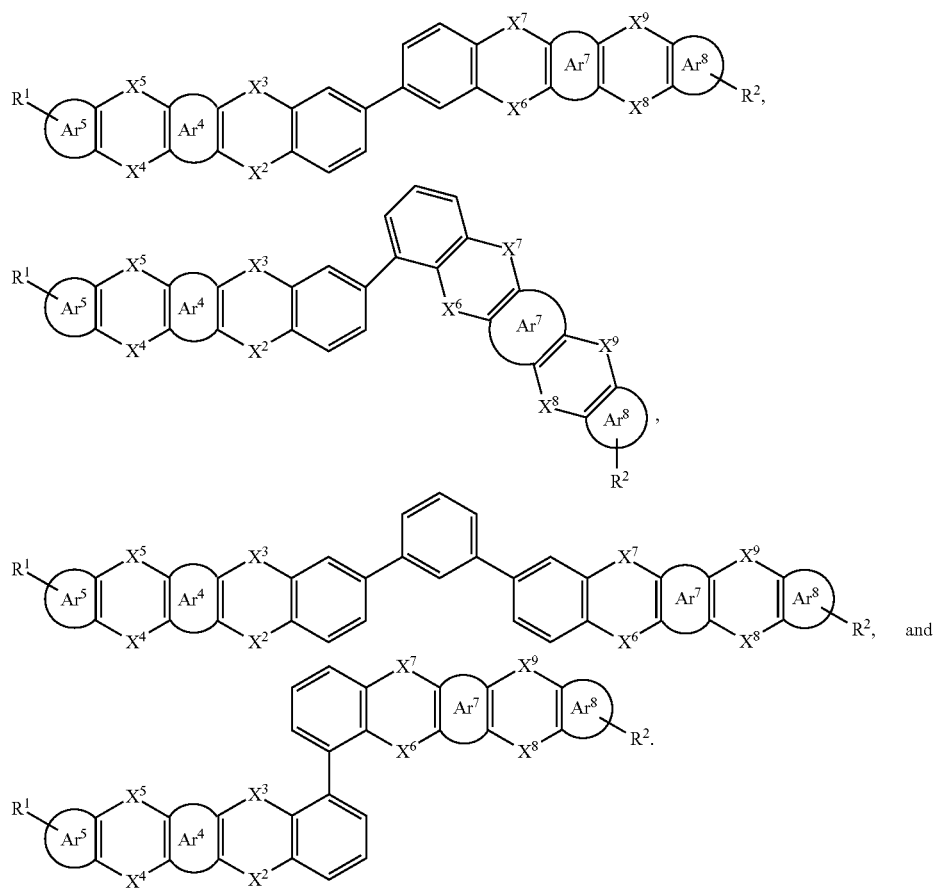
5. The organic functional compound according to claim 1, wherein the A has the following structural formula:
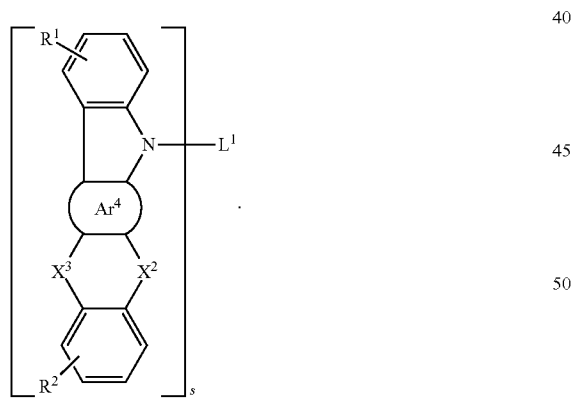
6. The organic functional compound according to claim 1, wherein the -$L_1$- is selected from the group consisting of the following single bond and structural formulas:
| single bond | 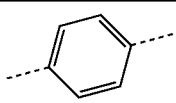 | 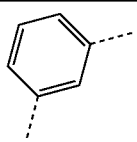 |
|---|---|---|
| $L_1$-1, | $L_1$-2, | $L_1$-3, |

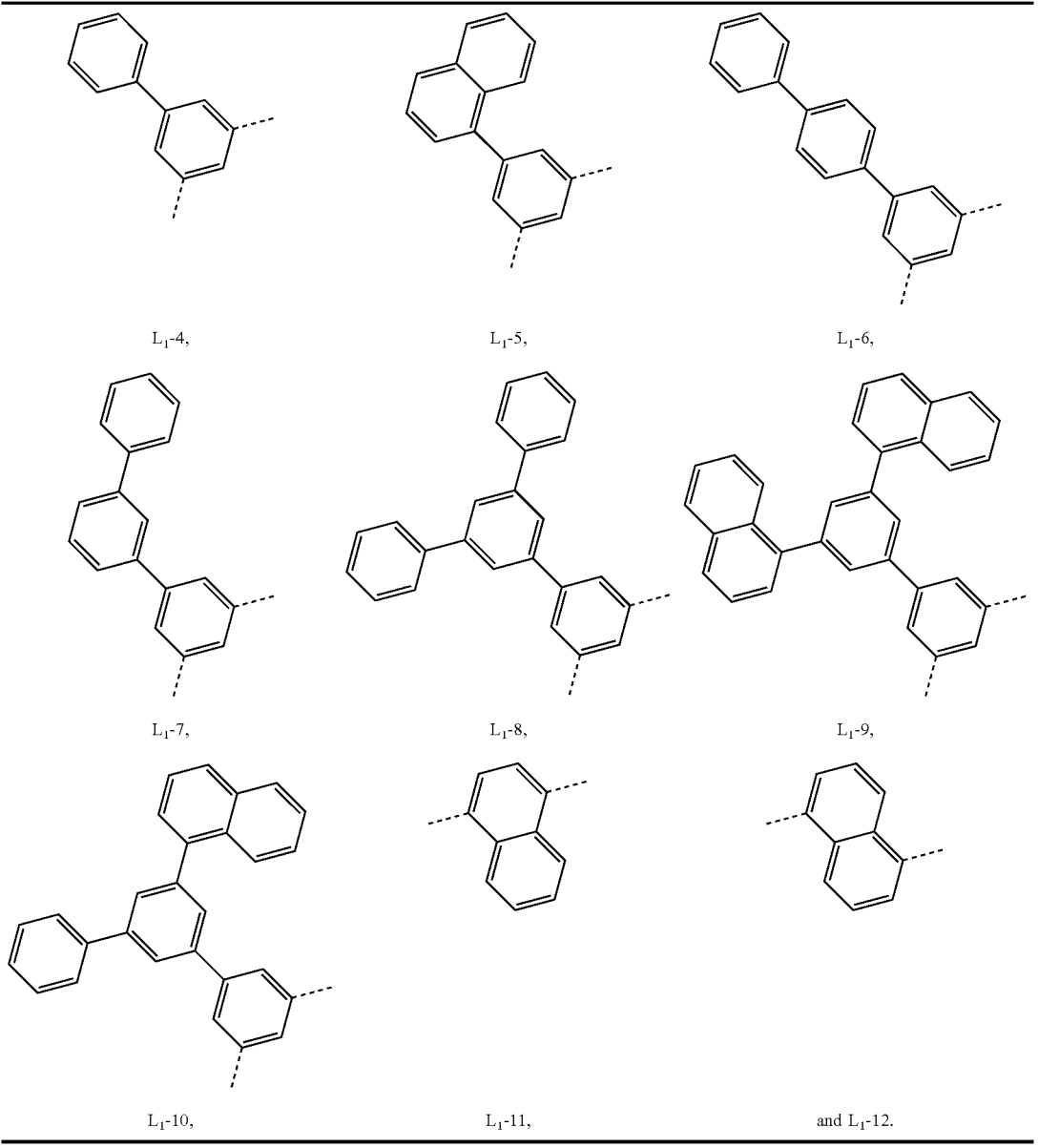

7. The organic functional compound according to claim 1, wherein the organic functional compound has a glass transition temperature of 100° C. or higher.

8. A mixture comprising the organic functional compound according to claim 1 and an organic solvent or an organic functional material which is selected from at least one selected from the group consisting of a hole injection material, a hole transport material, a hole blocking material, an electron injection material, an electron transport material, an electron blocking material, an organic matrix material, a light emitting material, and an organic dye.

9. An organic electronic device comprising a functional layer, wherein the functional layer is comprising the organic functional compound according to claim 1.

10. The organic electronic device according to claim 9, wherein the functional layer is a hole transport layer.

11. The organic electronic device according to claim 9, wherein the functional layer is a light emitting layer.

12. The organic electronic device according to claim 9, wherein the organic electronic device is selected from the group consisting of an organic light emitting diode, an organic photovoltaic cell, an organic light emitting electrochemical cell, an organic field effect transistor, an organic light emitting field effect transistor, an organic laser, an organic spintronic device, an organic sensor and an organic plasmon emitting diode.

* * * * *